United States Patent
Blundell et al.

(10) Patent No.: US 6,484,103 B1
(45) Date of Patent: Nov. 19, 2002

(54) CRYSTAL STRUCTURE

(75) Inventors: Tom L. Blundell, Royston (GB); Christopher Abell, Cambridge (GB); Frank Von Delft, La Jolla, CA (US)

(73) Assignee: Astex Technology Limited, Cambridge (GB)

( * ) Notice: Subject to any disclaimer, the term of this patent is extended or adjusted under 35 U.S.C. 154(b) by 2 days.

(21) Appl. No.: 09/659,759

(22) Filed: Sep. 11, 2000

(51) Int. Cl.$^7$ .................. G06F 19/00; G01N 33/48; C12Q 1/68

(52) U.S. Cl. .................. 702/19; 702/19; 435/6

(58) Field of Search .................. 435/6; 702/19, 702/27

(56) References Cited

PUBLICATIONS

Alexeev et al. The Crystal Structure of 8–Amino–7–oxononanoate Synthase: A Bacterial PLP–dependent, Acyl–CoA–condensing Enzyme. Journal of Molecular Biology,. Nov. 1998, vol. 284, No. 2, pp. 401–419.*

Fraser et al. Phosphorylated and Dephosphorylated Structures of Pig Heart, GTP–specific Succinyl–CoA Synthetase. Journal of Molecular Biology. Jun. 2000, vol. 299, No. 5, pp. 1325–1339.*

Barker et al., "Conserved cysteine and histidine residues in the structures of the tyrosyl and methionyl–tRNA synthetases", FEBS Letters, vol. 145, No. 2, Aug. 1982, pp. 191–193.

Bohacek et al., "The Art and Practice of Structure–Based Drug Design: A Molecular Modeling Perspective", Medicinal Research Reviews, vol. 16, (1996), pp. 3–50.

Brick et al., "Structure of Tyrosyl–tRNA Synthetase Refined at 2–3, A Resolution", J. Med. Biol. (1988), 208, pp. 83–98.

Greer et al., "Application of the Three–Dimensional Structures of Protein Target Molecules in Structure–Based Drug Design", Journal of Medicinal Chemistry, Apr. 15, 1994, vol. 37, No. 8, pp. 1035–1054.

Izard et al., "The crystal structure of a novel bacterial adenylyltransferase reveals half of sites reactivity", The EMBO Journal, vol. 18, No. 8, (1999), pp. 2021–2030.

Jones et al., "Docking small–molecule ligands into active sites", Current Opinion in Biotechnology, vol. 6, (1995), pp. 652–656.

Mechulam et al., "Crystal Structure of *Escherichia coli* Methionyl–tRNA synthetase Highlights Species–specific Features", J. Mol. Biol., (1999), 294, pp. 1287–1297.

Nureki et al., "Architectures of Class–Defining and Specific Domains of Glutamyl–tRNA Synthetase", Science, vol. 267, Mar. 31, 1995, p. 1958–1965.

Perona et al., "Structural Basis for Transfer RNA Aminoacylation of Escherichia coli Glutaminyl–tRNA Synthetase", Biochemistry, 1993, 32, pp. 8758–8771.

Shuker et al., "Discovering High–Affinity Ligands for Proteins: SAR by NMR", Science, vol. 274, Nov. 29, 1996, pp. 1531–1534.

Stout et al., "The additivity of substrate fragments in enzyme–ligand binding", Structure, 6, (1998), pp. 839–848 (Research Article).

Van Duyne et al., "Atomic Structures of the Human Immunophilin FKBP–12 Complexes with FK506 and Rapamycin", J. Mol. Biol. (1993), 229, pp. 105–124.

Verlinde et al., "In search of new lead compounds for trypanosomiasis drug design: A protein structure–based linked–fragment approach", Journal of Computer Aided Molecular Design, 6, (1992), pp. 131–147.

(List continued on next page.)

Primary Examiner—Michael Borin
Assistant Examiner—Nikolai Galitsky
(74) Attorney, Agent, or Firm—Nixon & Vanderhye P.C.

(57) ABSTRACT

A crystal of pantothenate synthetase (PS) has a monoclinic space group $P2_1$ and unit cell dimensions of $a=66.0\pm0.2$ Å, $b=78.1\pm0.2$ Å, $c=77.1\pm0.2$ Å and $\beta=103.7\pm0.2°$.

2 Claims, 6 Drawing Sheets

OTHER PUBLICATIONS

Weber et al., "A prototypical cytidylyltransferase: CTP:glycerol-3-phosphate cytidylyltransferase from *Bacillus subtilis*", Structure with Folding and Design, 7, (1999), pp. 1113–1124.

Delft et al, "The crystal structure of E. coli pantothenate synthetase confirms it as a member of the cytidylytransferase superfamily," Structure, vol. 9, May 2001, pp. 439–450; XP002187263.

Qoronfleh et al, "Production of selenomethionine–labeled recombinant . . . ", Journal of Biotechnology Elsevier Science Publishers, Amsterdam, NL, vol. 39, No. 2, Apr. 15, 1995, pp. 119–128; XP004036977.

Shao et al, "Accessibility of selenomethionine . . . ", FEBS Letters, Elsevier Science Publishers, Amsterdam, NL, vol. 441, No. 1, Dec. 11, 1998, pp. 77–82; XP004258875.

Jhoti, "High–throughput structural . . . ", Trends in Biology, Elsevier Publications, Cambridge, GB, vol. 19, No. 10, Oct. 1, 2001, pp. S67–S71; XP004310381.

* cited by examiner

CRYSTAL STRUCTURE

FIELD OF THE INVENTION

The present invention relates to the enzyme pantothenate synthetase, and in particular its crystal structure and the use of this structure in drug discovery.

BACKGROUND OF THE INVENTION

Pantothenic acid (vitamin $B_5$) is found in coenzyme A (CoA) and the acyl carrier protein (ACP), both of which are involved in fatty acid metabolism.

Pantothenic acid can be synthesised by plants and microorganisms but animals are apparently unable to make the vitamin, and require it in their diet. However, all organisms are able to convert pantothenic acid to its metabolically active form, coenzyme A.

The pathway for the synthesis of pantothenic acid is shown in FIG. 1. It provides a potential target for the treatment of infectious disease, since inhibitors of the pathway should be damaging to bacteria and fungi but not to human or animal subjects infected by bacteria.

Of specific interest is pantothenate synthetase (D-pantoate: β-alanine ligase (AMP-forming); EC 6.3.2.1) This enzyme catalyses the condensation between β-alanine and pantoic acid, the final steps in pantothenic acid biosynthesis. Inhibitors (whether competitive, non-competitive, uncompetitive or irreversible) of pantothenate synthetase would be of significant technical and commercial interest.

Purification of pantothenate synthetase (PS) to homogeneity was achieved by Miyatake et. al, (*J. Biochem.*, 79, (1976), 673–678). The enzyme was reported to require stoichiometric amounts of ATP as an energy source which is hydrolysed to AMP and inorganic pyrophosphate. The mechanism of the enzymic reaction involves pantoate adenylate as an intermediate.

However, until now no one has successfully determined the structure of PS. This has prevented PS inhibitors being developed via structure-based drug design methodologies. Knowledge of the structure of PS would significantly assist the rational design of novel therapeutics based on PS inhibitors.

SUMMARY OF THE INVENTION

The present invention is at least partly based on overcoming several technical hurdles: we have (i) produced PS crystals of suitable quality, including crystals of selenium atom PS derivatives, for performing X-ray diffraction analyses, (ii) collected X-ray diffraction data from the crystals, (iii) determined the three-dimensional structure of PS, and (iv) identified sites on the enzyme which are likely to be involved in the enzymic reaction.

In a first aspect, the present invention provides a crystal of PS having a monoclinic space group $P2_1$, and unit cell dimensions of a=66.0±0.2 Å, b=78.1±0.2 Å, c=77.1±0.2 Å and β=103.7±0.2°. Preferably the PS is a dimer.

In a second aspect, the invention also provides a crystal of PS having the three dimensional atomic coordinates of Table 1.

In a third aspect, the invention provides a method for crystallizing a selenium atom PS derivative which comprises producing PS by recombinant production in a bacterial host (e.g. *E. coli*) in the presence of selenomethionine, recovering a selenium atom PS derivative from the host and growing crystals from the recovered selenium atom PS derivative.

Thus, the selenium atom PS derivative and PS produced by crystallising native PS (see the detailed description below) are provided as crystallised proteins suitable for X-ray diffraction analysis.

The crystals may be grown by any suitable method, e.g. the hanging drop method.

In a fourth aspect, the present invention provides a method for identifying a potential inhibitor of PS comprising the steps of:

a. employing a three-dimensional structure of PS, or at least one sub-domain thereof, to characterise at least one PS active site, the three-dimensional structure being defined by atomic coordinate data according to Table 1; and b. identifying the potential inhibitor by designing or selecting a compound for interaction with the active site.

By "sub-domain" is meant at least one complete element of secondary structure, i.e. an alpha helix or a beta sheet, as described in the detailed description below.

If more than one PS active site is characterised and a plurality of respective compounds are designed or selected, the potential inhibitor may formed by linking the respective compounds into a larger compound which maintains the relative positions and orientations of the respective compounds at the active sites. The larger compound may be formed as a real molecule or by computer modelling.

In any event, the determination of the three-dimensional structure of PS provides a basis for the design of new and specific ligands for PS. For example, knowing the three-dimensional structure of PS, computer modelling programs may be used to design different molecules expected to interact with possible or confirmed active sites, such as binding sites or other structural or functional features of PS.

More specifically, a potential modulator of PS activity can be examined through the use of computer modelling using a docking program such as GRAM, DOCK, or AUTODOCK (see Walters et al., *Drug Discovery Today*, Vol.3, No.4, (1998), 160–178, and Dunbrack et al., *Folding and Design*, 2, (1997), 27–42) to identify potential inhibitors of PS. This procedure can include computer fitting of potential inhibitors to PS to ascertain how well the shape and the chemical structure of the potential inhibitor will bind to the enzyme.

Also computer-assisted, manual examination of the active site structure of PS may be performed. The use of programs such as GRID (Goodford, *J. Med. Chem.*, 28, (1985), 849–857)n—a program that determines probable interaction sites between molecules with various functional groups and the enzyme surface—may also be used to analyse the active site to predict partial structures of inhibiting compounds.

Computer programs can be employed to estimate the attraction, repulsion, and steric hindrance of the two binding partners (e.g. the PS and a potential inhibitor). Generally the tighter the fit, the fewer the steric hindrances, and the greater the attractive forces, the more potent the potential modulator since these properties are consistent with a tighter binding constant. Furthermore, the more specificity in the design of a potential drug, the more likely it is that the drug will not interact with other proteins as well. This will tend to minimise potential side-effects due to unwanted interactions with other proteins.

Alternatively, step b. may involve selecting the compound by computationally screening a database of compounds for interaction with the active site. For example, a 3-D descriptor for the potential inhibitor may be derived, the descriptor including geometric and functional constraints derived from the architecture and chemical nature of the active site. The descriptor may then be used to interrogate the compound database, a potential inhibitor being a compound that has a good match to the features of the descriptor. In effect, the descriptor is a type of virtual pharmacophore.

Having designed or selected possible binding partners, these can then be screened for activity. Consequently, the method preferably further comprises the further steps of:

c. obtaining or synthesising the potential inhibitor; and
d. contacting the potential inhibitor with PS to determine the ability of the potential inhibitor to interact with PS.

More preferably, in step d. the potential inhibitor is contacted with PS in the presence of a substrate, and typically a buffer, to determine the ability of said potential inhibitor to inhibit PS. The substrate may be e.g. pantoic acid (or a salt thereof), β-alanine (or a salt thereof), or ATP. So, for example, an assay mixture for PS may be produced which comprises the potential inhibitor, substrate and buffer.

Instead of, or in addition to, performing e.g. a chemical assay, the method may comprise the further steps of:

c. obtaining or synthesising said potential inhibitor;
d. forming a complex of PS and said potential inhibitor; and
e. analysing said complex by X-ray crystallography to determine the ability of said potential inhibitor to interact with PS. Detailed structural information can then be obtained about the binding of the potential inhibitor to PS, and in the light of this information adjustments can be made to the structure or functionality of the potential inhibitor, e.g. to improve binding to the active site. Steps c. to e. may be repeated and re-repeated as necessary.

In a fifth aspect, the invention includes a compound which is identified as an inhibitor of PS by the method of the fourth aspect.

In a sixth aspect, the invention provides a method of analysing a PS-ligand complex comprising the step of employing (i) X-ray crystallographic diffraction data from the PS-ligand complex and (ii) a three-dimensional structure of PS, or at least one subdomain thereof, to generate a difference Fourier electron density map of the complex, the three-dimensional structure being defined by atomic coordinate data according to Table 1.

Therefore, PS-ligand complexes can be crystallised and analysed using X-ray diffraction methods, e.g. according to the approach described by Greer et al., *J. of Medicinal Chemistry*, Vol. 37, (1994), 1035–1054, and difference Fourier electron density maps can be calculated based on X-ray diffraction patterns of soaked or co-crystallised PS and the solved structure of uncomplexed PS. These maps can then be used to determine whether and where a particular ligand binds to PS and/or changes the conformation of PS.

Electron density maps can be calculated using programs such as those from the CCP4 computing package (Collaborative Computational Project 4. The CCP4 Suite: Programs for Protein Crystallography, *Acta Crystallographica*, D50, (1994), 760–763.). For map visualisation and model building programs such as "O" (Jones et al., *Acta Crystallograhy*, A47, (1991), 110–119) can be used.

In a seventh aspect, the present invention provides computer readable media with either (a) atomic coordinate data according to Table 1 recorded thereon, said data defining the three-dimensional structure of PS or at least one sub-domain thereof, or (b) structure factor data for PS recorded thereon, the structure factor data being derivable from the atomic coordinate data of Table 1.

As used herein, "computer readable media" refers to any media which can be read and accessed directly by a computer. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

By providing such computer readable media, the atomic coordinate data can be routinely accessed to model PS or a sub-domain thereof. For example, RASMOL (Sayle et al., *TIBS*, Vol. 20, (1995), 374) is a publicly available computer software package which allows access and analysis of atomic coordinate data for structure determination and/or rational drug design.

On the other hand, structure factor data, which are derivable from atomic coordinate data (see e.g. Blundell et al., in *Protein Crystallography*, Academic Press, New York, London and San Francisco, (1976)), are particularly useful for calculating e.g. difference Fourier electron density maps.

In an eighth aspect, the present invention provides systems, particularly a computer systems, intended to generate structures and/or perform rational drug design for PS or PS ligand complexes, the systems containing either (a) atomic coordinate data according to Table 1, said data defining the three-dimensional structure of PS or at least one sub-domain thereof, or (b) structure factor data for PS, said structure factor data being derivable from the atomic coordinate data of Table 1.

Examples of such systems are microcomputer workstations available from Silicon Graphics Incorporated and Sun Microsystems running Unix based, Windows NT or IBM OS/2 operating systems.

As used herein, "a computer system" refers to the hardware means, software means and data storage means used to analyse the atomic coordinate data of the present invention. The minimum hardware means of the computer-based systems of the present invention comprises a central processing unit (CPU), input means, output means and data storage means. Desirably a monitor is provided to visualise structure data. The data storage means may be RAM or means for accessing computer readable media of the sixth aspect of the invention.

DETAILED DESCRIPTION OF THE INVENTION

The present invention is founded on the determination of the three dimensional atomic structure of PS.

The structure is defined in Table 1 which gives atomic coordinate data for PS, which we have crystallised as a dimer, and associated water molecules. In Table 1 "Atom type" refers to the respective element, the first letter defining the element; "X, Y, Z" define, with respect to the crystallographic axes, the atomic position (in Å) of the respective atom; "Occ." is the occupancy of the atom in the respective position; and "B" is a temperature factor (in Å$^2$) which accounts for movement of the atom around its atomic centre.

The atomic positions in Table 1 are given to three decimal places. However, for the avoidance of doubt it is hereby mentioned that varying the atomic positions of the atoms of the structure by up to about 0.2 Å in any direction will result in a structure which is substantially the same as the structure of Table 1 in terms of both its structural characteristics and utility e.g. for structure-based drug design.

PS Structural Characterization

Figure 1:
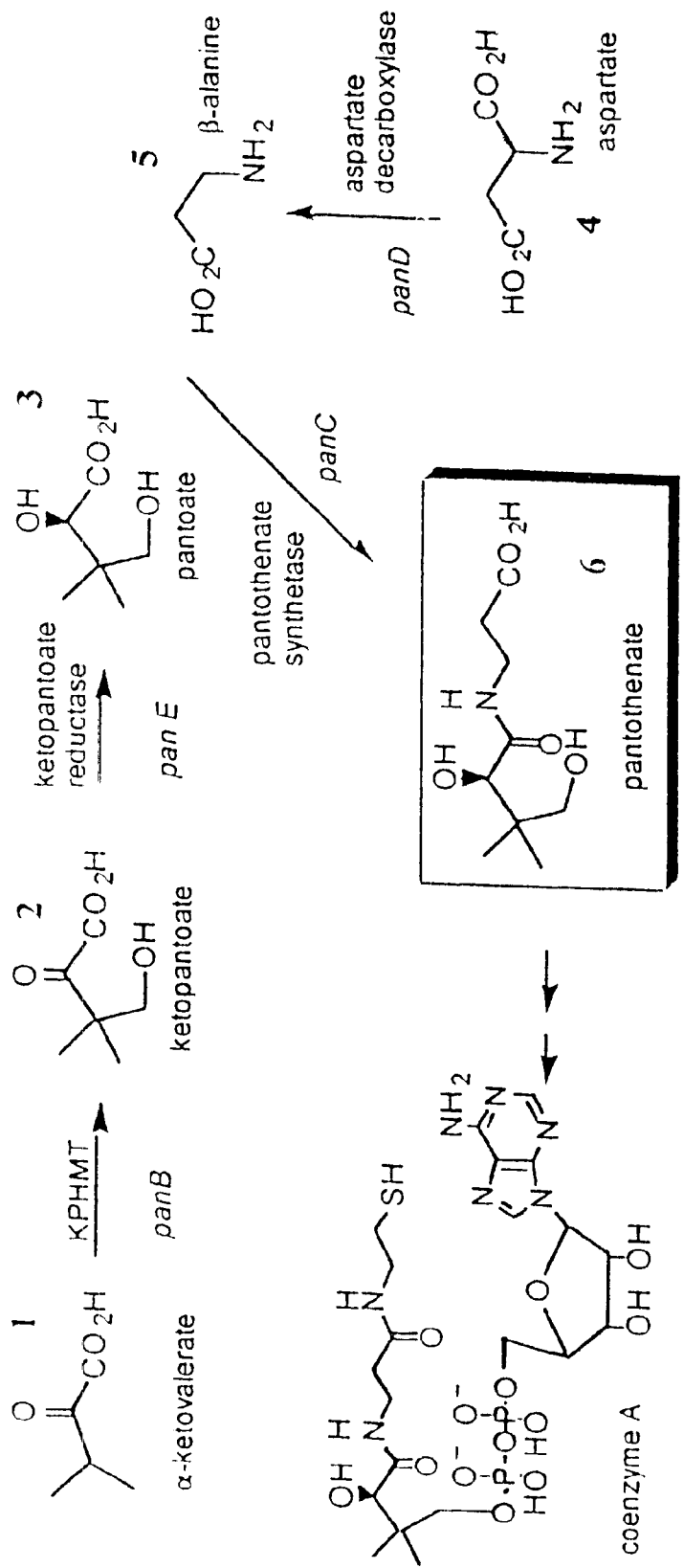
FIG. 1 shows schematically the pathway for the synthesis of pantothenic acid.
Figure 2A:
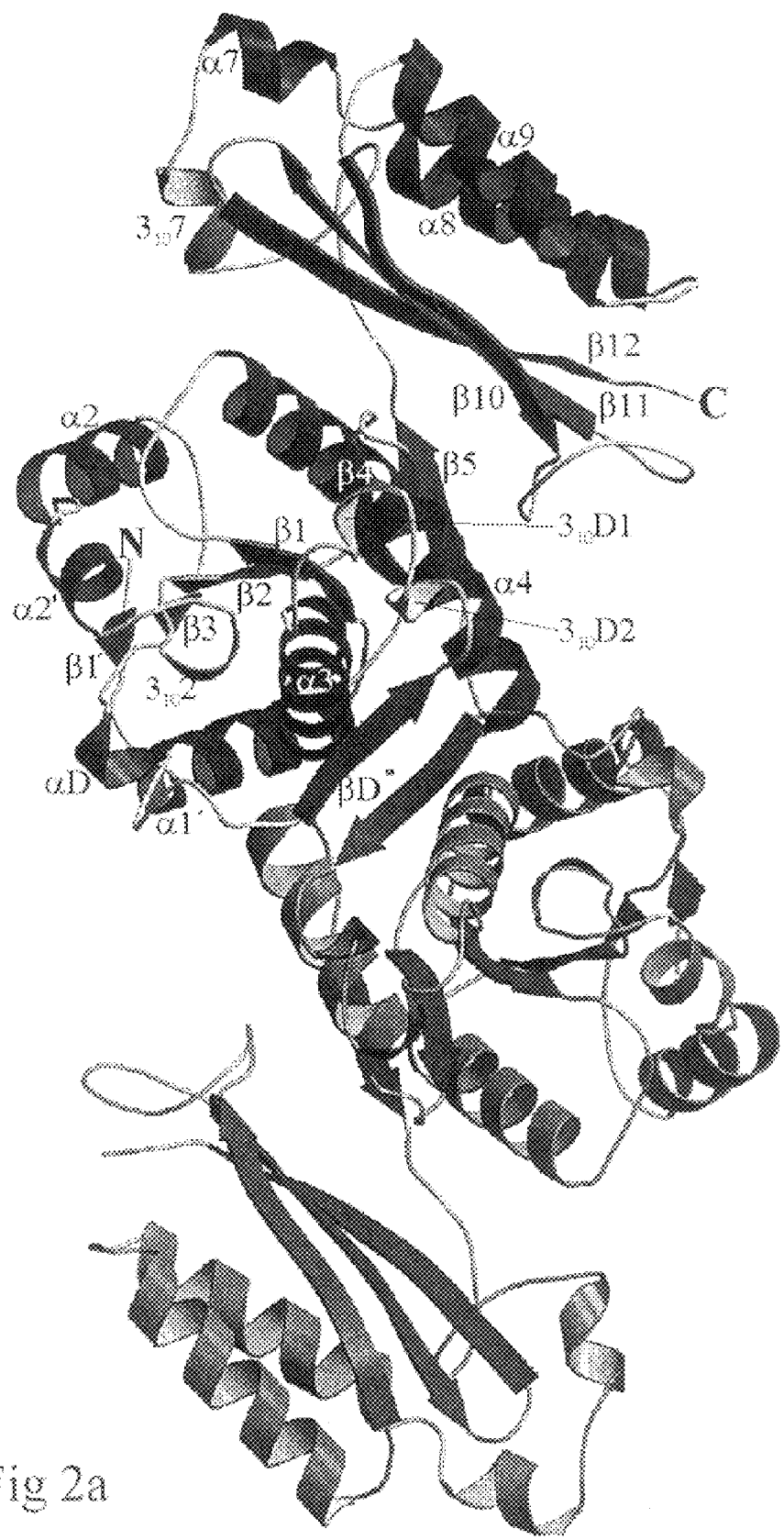
FIGS. 2a–c show the general structure of PS, being respectively (a) a "cartoon" of the dimer, (b) a schematic diagram of the monomer topology with numbering of secondary structures, and (c) a schematic plot of hydrogen bonding patterns between secondary structures.
Figure 2B:
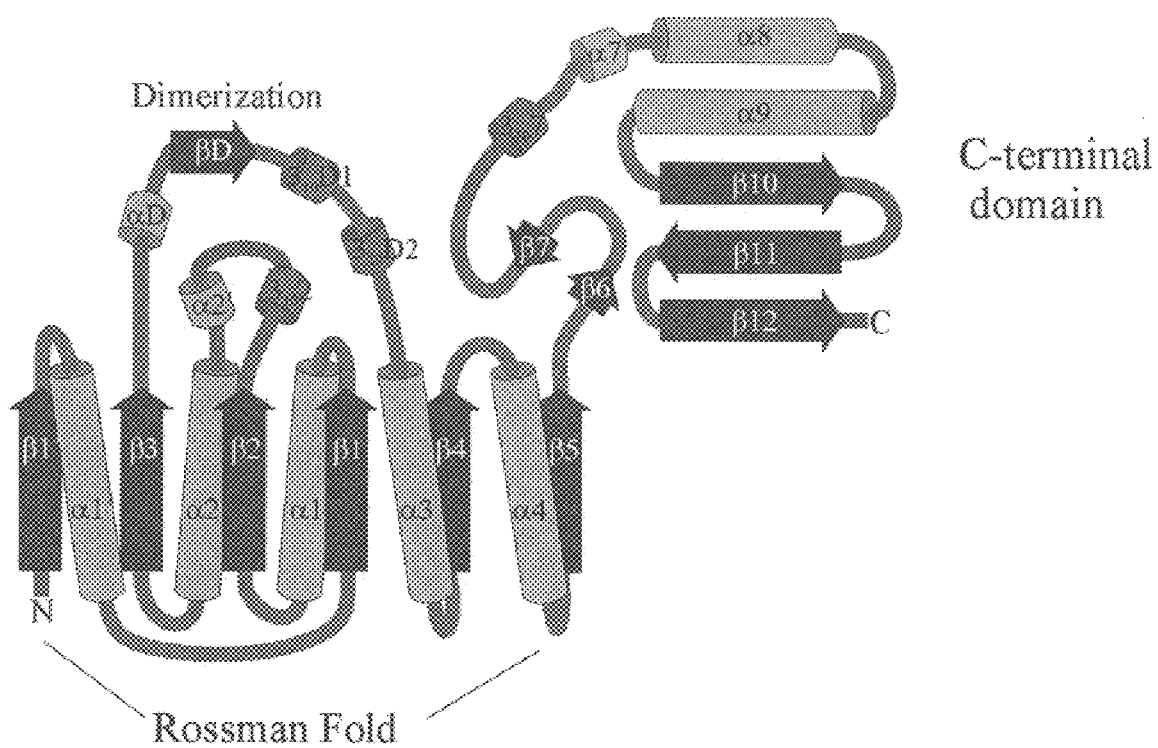
Figure 2C:
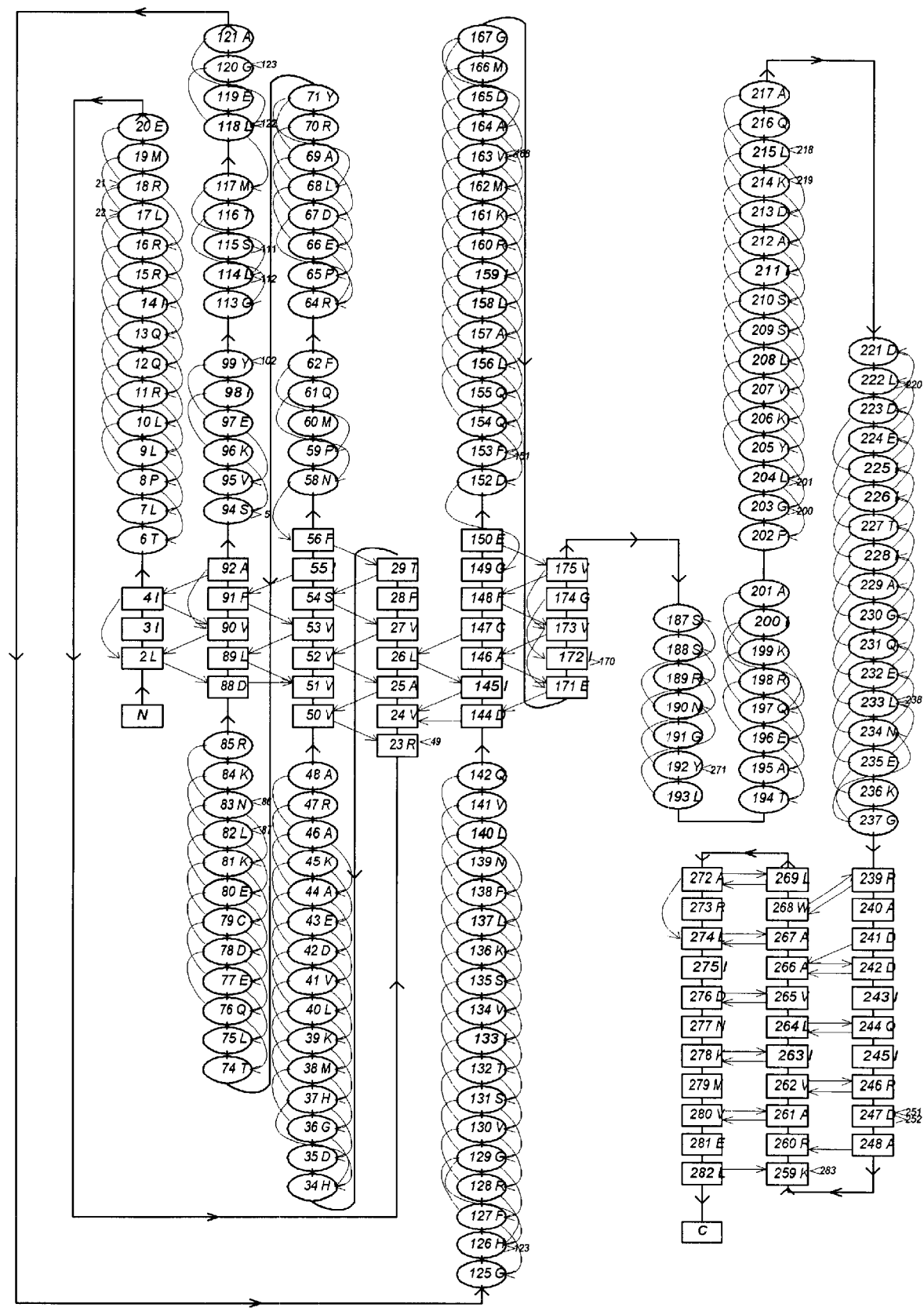

We have found that the structure of a PS monomer consists of two major domains, joined at about residue 176 (FIGS. 2a–c). Domain N (so called because it contains the N terminal) has an alpha-beta-alpha architecture; six parallel β-strands with 1'-3-2-1-4-5 topology alternate with α-helices to form a Rossman fold with central β-sheet sandwiched between two layers of α-helices (FIG. 2b). The helices (α1', 1, 2, 3 and 4) pack against the β-sheet in a right-handed way. The secondary structural elements have been numbered in FIGS. 2a and b, with elements that are insertions or additions to the "standard" nucleotide-binding Rossman fold (discussed below under "Identification of Likely Active Sites") denoted by primes. Strand β5 leads directly into the short β-hairpin and $3_{10}$ helix motif (β6, β7 and $\epsilon_{10}$7), which lies at the head of domain C (containing the C terminal) and is likely to be involved in phosphate binding (see below). The rest of the domain has a simple two-layer organisation: a helix-turn-helix layered above a flat sheet of three anti-parallel β-strands (α8 and 9, β10–12). This sheet faces a prominent cleft in domain N, the predicted catalytic region (see below), making the whole structure resemble somewhat a pot (domain N) with its lid (domain C) on a hinge, a common arrangement in two-domain enzymes.

Figure 3:
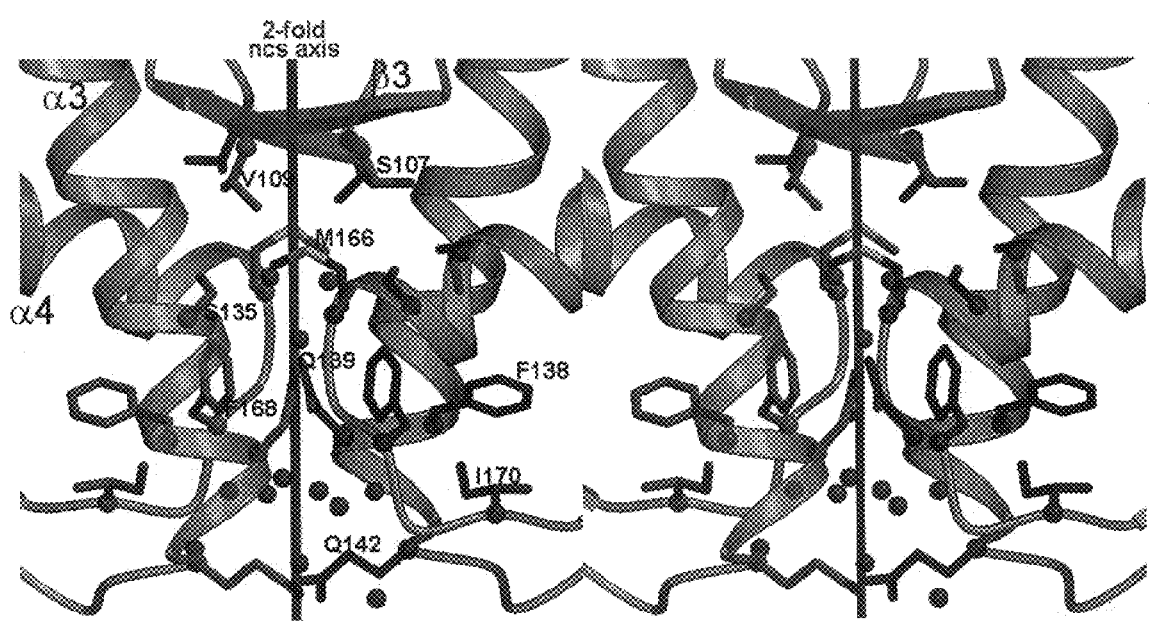
FIG. 3 is a stereo pair of images showing schematically the core of the dimerisation interface.

We have also found that the two monomers, A and B, of PS are related by a non-crystallographic quasi 2-fold rotational symmetry (NCS) axis. The dimerisation interface has a surface area of 1340 Å$^2$ and the core of the interface is shown in FIG. 3. The centre of the nearly symmetrical dimerisation interface is unusual: below a 2-strand β-sheet (βD from A and B) Val109, Met166 and Phe168 form a hydrophobic pocket around weakly H-bonded polar clusters of Ser135, conserved Asn139 and three water molecules, one of which lies on the NCS axis. Above the β-sheet Tyr108, Asp110 and Arg128 form a tight charged cluster, and the rest of the interface consists of salt bridges (His106 to Asp165; Arg11 to Asp169) and extensive water-mediated H-bonding interactions. The average B-factor of monomer B is about 4 Å$^2$ greater than that of A, which on the whole contains fewer disordered stretches. Also conformational differences between the monomers which can be explained by crystal packing arrangements are found at residues 173–180 and 187–193.

For residues B187–193, electron density was poor, and the apparent backbone connectivity could not be reconciled with stereochemical and Ramachandran constraints. The loop was eventually modelled using the same residues from monomer A (which are well ordered), and transformed by the operation that superimposes domain C of monomer A onto monomer B. However, it is likely that residues A187–193 are only ordered because the bottom of the dimerisation region is crystallographically packed tightly against this region and that the disordered seen in B is more realistic for the apo-enzyme in vivo.

Residues 239–244 also have entirely different but defined backbone conformations in the two monomers, and this difference is not readily explained by crystal packing. However, there appears to be no functional significance in the anomaly.

Solving the PS Crystal Structure

To solve the PS crystal structure, molecular replacement was not possible because prior to our determination of the PS structure similarities between the amino acid sequence of E. coli PS and that of proteins with known structures were not evident. Therefore, phase information needed to be obtained ab initio.

The phase problem was first approached by the Multiple Isomorphous Replacement technique, and crystals of PS were soaked with a range of heavy atom salts at a range of concentrations. However, the majority of these conditions resulted in crystal damage.

Eventually, production of selenomethionine PS (SeMet PS) was attempted, the selenium atoms being introduced into the protein prior to crystallisation by recombinant production of the protein in the presence of L-selenomethionine. This was successfully accomplished and is discussed in more detail below. X-ray analysis was performed on PS and SeMet PS crystals.

1. Production and Purification of PS

Native PS

DNA encoding the PanC gene was engineered into a pUC19 expression vector. E. coil cells were transformed using the plasmid.

Colonies of transformed cells were inoculated directly into LB medium containing ampicillin (100 mg/ml) and IPTG (70 mg/ml); induction of expression was continuous. The cultures were shaken (200 rpm on an orbital shaker) overnight at 37° C., when the cells were retrieved by centrifugation of the culture medium and the cell pellet stored frozen at −80° C.

Selenomethionine PS

The same E. coli strain was used as for native expression, but the methionine pathway inhibition system (see van Duyne et al., J. Mol. Biol., 229, (1993), 105–124) was used for selenomethionine incorporation. Cells were grown on a minimal, defined medium (see Table 2) containing selenomethionine as well as six other amino acids, whose presence inhibits the natural pathways for methionine synthesis. A starter culture (100 ml) of the same medium as above, but without selenomethionine or the inhibitory amino acids, was inoculated with transformed cells and grown at 37° C. to log growth phase. 1 ml of this culture was used to inoculate baffled 2/Erlemeyer flasks (250 ml complete medium per flask) which were shaken at 37° C. overnight and harvested as for native protein.

Purification

Harvested cells were suspended in 20–40 ml TD buffer (50 mM Tris/HCl pH 7.5±0.1 mM dithiothreitol) sonicated at maximum intensity for 8 times 15 seconds, with 15 second breaks, and cell debris removed by centrifugation (30 minutes, 15000×g).

The supernatant was stirred at 4° C. while $(NH_4)_2SO_4$ was added slowly over ca. 15 minutes to a final concentration of 29.1% (w/v); after a further 30 minutes of stirring, precipitated contaminants were removed by centrifugation (30 minutes, 15000×g). The solution was dialysed overnight against TD buffer (at least 21).

The dialysed protein solution was loaded at 4° C. onto an anion exchange column (Pharmacia Q-Sepharose, 16/10) and eluted with TD buffer against a NaCl gradient of 0 to 500 mM in 75 minutes, at a flow rate of 5 ml/min. The protein eluted between 0.21 and 0.24M NaCl. The protein-containing fractions were selected from SDS-PAGE analysis, and concentrated to ca 1 ml.

The concentrated fractions were loaded at 4° C. onto a size exclusion column (Pharmacia S200HR), and eluted with TD buffer containing NaCl at 500 mM. The fractions containing PS were confirmed by SDS-PAGE analysis. The fractions were pooled and dialysed overnight against TD buffer (at least 21).

The dialysed protein solution was loaded at room temperature onto an affinity column (Pharmacia Blue Sepharose HiLoad 16/10) and eluted with at least five column volumes of TD buffer containing 10 mM ATP. This effectively eluted all the protein, although this was not monitored directly.

ATP was removed from the eluant by repeated cycles (at least 5) of concentration (in a stirred cell concentrator (Amicon® Ultrafiltration Cell) under pressure in an $N_2$ atmosphere) and dilution with TD buffer; ATP content was monitored by the UV spectrum (220–300nm) of the solution. The protein was finally concentrated (Ultrafree® concentrator) to a concentration of between 20 and 30 mg/ml. At this concentration, the solution could be aliquoted and frozen directly at −80° C. without damage to the protein.

For the purification of the SeMet protein, some precautions were taken to minimise oxidation of the selenium in the protein. The DTT concentration in all buffers was raised to 5 mM, all buffers were thoroughly purged with $N_2$ gas before use, and the whole procedure was completed as fast as possible, within two days. The SeMet preparations of PS were subjected to Electrospray Mass Spectrometry (ESMS) to confirm the incorporation of selenomethionine during the expression.

2. Preparation of Crystals

Crystals of PS and SeMet PS were grown using the hanging drop vapour diffusion method. Protein (20 mg/ml) was mixed on a 1:1 ratio with crystallisation solution containing 4–7% (w/w) Polyethylene Glycol 4000 and 50 mM Tris/HCl buffer at pH8. Crystals formed within 2–4 days at 19° C. Crystallisation of SeMet PS, was performed using a nearly identical protocol, but additionally, 2 mM DTT was added to the crystallisation solution before mixing the drop.

Crystals ideally have approximate dimensions of 600× 200×50 µm. Under non-optimal conditions, crystals grow in clusters and are generally much thinner in the $3^{rd}$ dimension (10–20 µm).

Crystals of PS were cryo-protected using a protocol of gradual soaking in the cryo-protectant, glycerol. A crystal was placed in 20µl of crystallisation solution, and the concentration of glycerol is gradually increased to 28% (v/v) in 4% increments.

3. Structural Determination

Multi-wavelength data sets were collected from a cryo-cooled crystal of SeMet PS, on beam line X-25 of the NSLS at Brookhaven National Laboratories on Long Island, USA. This is a high-flux station with good intensity and wavelength stability. The presence of selenomethionine in the protein was confirmed independently by electrospray mass spectrometry. Before the experiment, a large number of crystals were extensively screened for highest resolution, low mosaicity and low background scatter.

Terminal radiation-induced diffraction decay was evident in the first crystal to be exposed, which influenced data collection from the second, final SeMet crystal.

In addition to the three data sets collected from SeMet crystals, a data set was collected from a large native crystal, which had been established to be nearly isomorphous with the SeMet crystals used. In order to have complete but also high resolution data, the same oscillation range was exposed twice, the first for measuring low resolution data (i.e. short exposures), and the second for the highest resolution possible (long exposures). All data were processed using MOSFLM (Leslie, *Joint CCP4 and EESF-EACMB Newsletter on Protein Crystallography*, Vol.26, Daresbury Laboratory, UK) and scaled with SCALA (Collaborative Computational Project 4. The CCP4 Suite: Programs for Protein Crystallography, *Acta Crystallographica*, D50, (1994), 760–763).

The selenium atoms were located using the program SnB (Weeks et al., *J. of Applied Crystallography*, 32, (1999), 120–124) and their positions refined using SHARP (LaFortelle et al., *Methods in Enzymology*, 276, (1997), 472–494 and LaFortelle et al., Maximum Likelihood Refinement in a Graphical environment, with SHARP, in CCP4 study week-end: *Recent Advances in Phasing*, ed. Wilson et al., Daresbury Laboratory, UK). The final model contained 19 selenium sites which were used to provide initial phasing. Solvent flattening and phase extension techniques were used to produce an interpretable electron density map.

The program O was used for model building. The experimental, solvent flattened electron density map was readily interpretable and secondary structural elements were clearly defined in the electron density bones (calculated with MAPMAN, see Kleywegt et al., *Acta Crystallographica*, D52, (1996b), 826–828). The main chain of one monomer could be traced nearly continuously, using the secondary structure template building functionality in O, and the selenium atoms identified using SHARP providing guidance for chain-tracing.

The complete main chain model of monomer A was manually rotated to correspond with the bones of the second monomer (B). Since the relative orientation of the two domains was slightly different in monomer B, it was optimised by rigid body refinement (using REFMAC, see Murshudov et al., *Acta Crystallographica*, D53, (1997), 24–255), keeping separate the two domains (residues 1–176 and 177–283).

The model was improved by three iterated cycles of restrained and individual isotropic maximum likelihood refinement with REFMAC (40–1.7 Å resolution) together with manual rebuilding in 0. $\sigma_A$-weighted $2F_{obs}-F_{calc}$ and $F_{obs}-F_{calc}$ maps were used (Read, *Acta Crystallographica*, A42, (1986), 140–149), the former frequently informative even when contoured at only 0.8–0.9 map standard deviations. For difficult parts of the model, maps and models resulting from simulated annealing in CNS (Brunger et al., *Acta Crystallographica*, D54, (1998), 905–921) were also considered. Ordered water molecules were modelled by automated cycles of water addition and removal by ARP (Perrakis et al., *Acta Crystallographica*, D55, (1999), 1765–1770) and refinement by REFMAC, with a final cycle of refinement with bulk solvent correction using CNS to ensure good geometry.

The final model consists of 4290 non-hydrogen protein atoms, and 384 water molecules. All residues were modelled, but electron density was poor for C-terminal residues (A283, B282–3), as well as residues B187–193; the B-factors of these residues are high, approaching 80 Å$^2$. Residues A251–259, B63–68 and B251–259, though visible, are also not well ordered and have B-factors approaching 60 Å$^2$. Two residues (A4 and A273) have alternative conformations, and 12 surface-exposed side chains are disordered and were modelled as the most common rotamer at zero occupancy.

Table 3 provides model parameters and refinement statistics for a version of the model which is essentially the same as that of Table 1 but contains more water molecules and also two ethanediol molecules and a Tris molecule. Residues B188–192 of this version of the model were reconstructed using BUSTER (Bricogne, *Methods in Enzymology*, 276, (1997), 361–423) in its implementation with TNT (Tronrud, *Methods in Enzymology*, 277, (1997), 306–319) instead of by the symmetry operation described above under "PS Structural Characterization". The program DDQ (van den Akker et al., *Acta Crystallographica*, D55, (1999), 206–218) was used to assess local and global accuracy and satisfactory completion of refinement, by considering difference density peaks arising from the final model. $\sigma_A$-weighted difference maps were calculated in REFMAC, excluding water molecules from the model. Quality of the model and its geometry were assessed by OOPS (Kleywegt et al., OOPS-a-daisy, *CCP4/ESF-EACBM Newsletter on Protein Crystallography*, 30, (1994), 20–24), PROCHECK (Laskowski et al., *J. Applied Crystallography*, 26, (1993), 283–291) and WHATCHECK (Hooft et al., *Nature*, 381, (1996), 272). No serious deviations from expected values are present, and warnings either correspond to well-defined justifiable features or else poorly-visible features that have high B-factors anyway. There are no Ramachandran outliers, and 92.2% of residues lie in most favoured regions of the plot.

Identification of Likely Active Sites

Having solved the PS crystal structure it is now evident that in terms of their $C_\alpha$ coordinates, the ATP-binding domains of (i) class I amino-acid tRNA synthetases (tRS) (i.e. EtRS from *Thermus thermophilus*, Nureki et al., *Science*, 267, (1995) 1958–1965; QtRS from *E. coli*, Perona et al., *Biochemistry*, 32, (1993) 8758–8771; MtRS from *Thermus aquaticus*, Mechulam et al., *J. of Molecular Biology*, 294, (1999), 1287–1297; and YtRS from *Bacillus stearothermophilus*, Brick et al., *J. of Molecular Biology*, 208, (1989), 83–98), (ii) phosphopantetheine adenylyltransferase (PPAT) from *E. coli* (Izard et al., *EMBO Journal*, 18, (1999), 2021–2030) and (iii) CTP:glycerol-3-phosphate cytidylyltransferase (CGT) from *B. subtilis* (Weber et al., *Structure with Folding and Design*, 7, (1999), 1113–1124) are structurally similar to domain N of PS.

More specifically, the particular class of Rossman fold which characterises tRS, CGT and PPAT consists of five $\beta$-strands in a central sheet and a cleft between $\beta$-strands $\beta1$ and $\beta4$ at the adenosine-binding site (see FIG. 2c). PS also has these features. In addition, in all four cases strand $\beta5$ is followed by catalytically important residues which form the KMSKS motif discussed below), and for both PS and tRS strand $\beta5$ leads directly into the next domain.

Furthermore, two sequence motifs, HIGH and KMSKS (Barker et al., *FEBS Letters*, 145, (1982), 191–193), are conserved in tRS proteins and also in the wider superfamily. From mutational studies (First et al., in *Biochemistry*, 32, (1993), 13644–13663) these motifs are known to be involved in ATP binding: the HIGH motif binds the adenine portion of ATP (cytidine in CGT) and the KMSKS motif stabilises the $\beta$- and $\gamma$-phosphate groups. These motifs are also found in PS and correspond respectively to residues 34–37 and 185–189.

The location of the bound ATP adenine in the structure of QtRS corresponds to within 2 to 3 Å of the positions of the bound nucleotides in YtRS, PPAT and CGT, i.e. in the cleft between strands $\beta1$ and $\beta4$ of the Rossman fold and against the top of helix $\alpha1$ (the location of the HIGH motif). When this domain of QtRS is aligned with domain N of PS the HIGH (actually HDGH in PS) residues line up very well and the QtRS-bound ATP fits nearly perfectly into the same cleft in PS. Despite this excellent match, there is a difference in the positions of the helices $\epsilon_{10}7$ (in PS) and $\alpha I$ (in QtRS) relative to the Rossman domain. This is the location of the KMSKS motif. However, by changing conservatively the $\phi/\phi$-angles of residues Val175, Pro176, Ile177 and Met178 which form the PS inter-domain linker main chain, domain C can be rotated sufficiently to align the KMSKS residues with their QtRS counterparts and thus involve them in phosphate binding.

Figure 4:
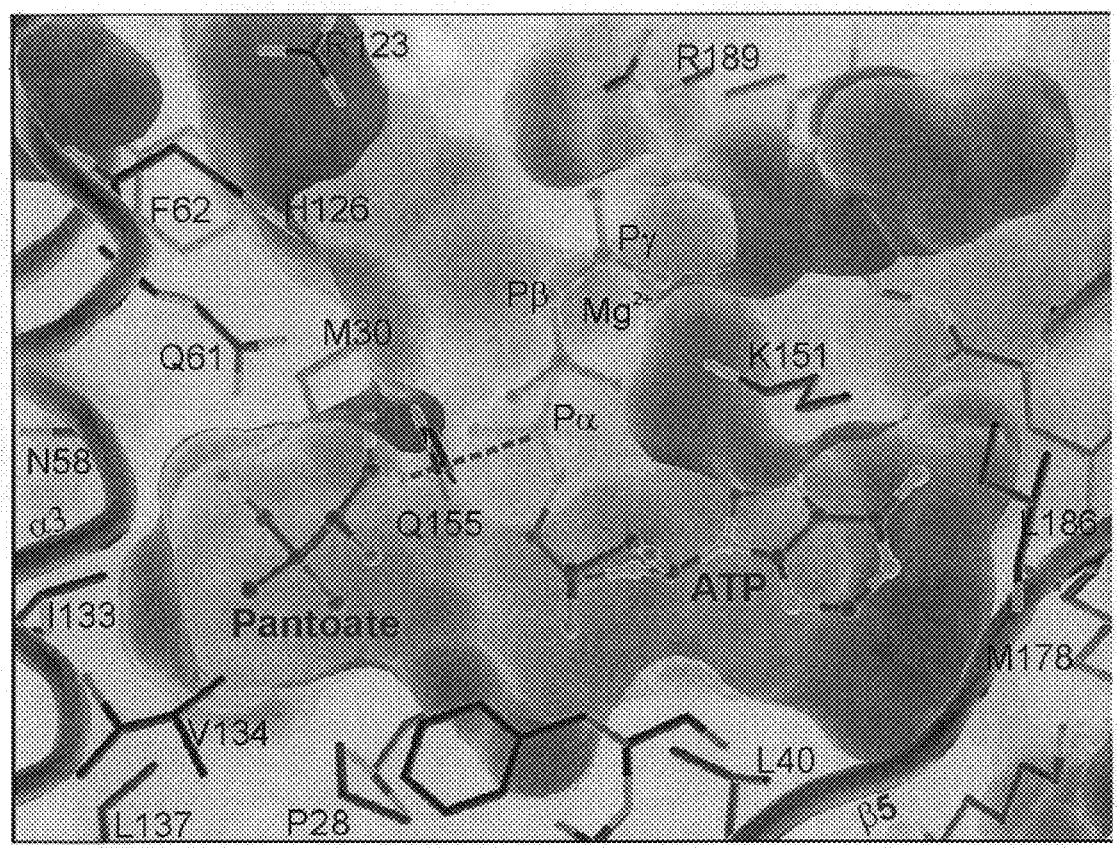
FIG. 4 shows a Connolly surface generated around the proposed PS active site.

FIG. 4 shows a Connolly surface generated around the proposed PS active site. It opens besides the ATP ribose group and the walls are formed by fully conserved residues, which are largely hydrophobic but include some polar groups. The catalytically essential $Mg^{2+}$ ion is shown at its most likely position where it is bound to $OG_{Ser188}$, $OH_{Tyr71}$, $O^{\alpha 1}{}_{ATP}$ and $O^{\gamma 1}{}_{ATP}$. This is also the proposed $Mg^{2+}$ binding position in PPAT. Slightly more speculatively, the most favourable conformer of pantoate is shown positioned in a cavity where it appears to satisfy the hydrophobic and hydrogen-bonding interactions of the substrate, as well as being suitably positioned for attack on ATP.

Binding positions for $\beta$-alanine may also be proposed, but with less certainty than the binding positions of ATP and pantoate. For example, the $\beta$-alanine carboxylate may bind in a conserved, positively charged pocket to Arg123, with Met30, Phe62 and Tyr71 providing a hydrophobic patch to accommodate the two $\beta$-alanine methylene groups, and His126 being suitably positioned to deprotonate the $NH_3^+$ group).

Structure-Based Drug Design

Determination of the 3D structure of PS provides important information about the likely active sites of PS, particularly when comparisons are made with similar enzymes. This information may then be used for rational design of PS inhibitors, e.g. by computational techniques which identify possible binding ligands for the active sites, by enabling linked-fragment approaches to drug design, and by enabling the identification and location of bound ligands using X-ray crystallographic analysis. These techniques are discussed in more detail below.

Greer et al. mentioned above describes an iterative approach to ligand design based on repeated sequences of computer modelling, protein-ligand complex formation and X-ray analysis. Thus novel thymidylate synthase inhibitor series were designed de novo by Greer et al., and PS inhibitors may also be designed in the this way. More specifically, using e.g. GRID on the solved 3D structure of PS, a ligand (e.g. a potential inhibitor) for PS may be designed that complements the functionalities of the PS active site(s). The ligand can then be synthesised, formed into a complex with PS, and the complex then analysed by X-ray crystallography to identify the actual position of the bound ligand. The structure and/or functional groups of the ligand can then be adjusted, if necessary, in view of the results of the X-ray analysis, and the synthesis and analysis sequence repeated until an optimised ligand is obtained. Related approaches to structure-based drug design are also discussed in Bohacek et al., *Medicinal Research Reviews*, Vol.16, (1996), 3–50.

As a result of the determination of the PS 3D structure, more purely computational techniques for rational drug design may also be used to design PS inhibitors (for an overview of these techniques see e.g. Walters et al. mentioned above). For example, automated ligand-receptor docking programs (discussed e.g. by Jones et al. in *Current Opinion in Biotechnology*, Vol.6, (1995), 652–656) which require accurate information on the atomic coordinates of target receptors may be used to design potential PS inhibitors.

Linked-fragment approaches to drug design also require accurate information on the atomic coordinates of target receptors. The basic idea behind these approaches is to determine (computationally or experimentally) the binding locations of plural ligands to a target molecule, and then construct a molecular scaffold to connect the ligands together in such a way that their relative binding positions are preserved. The connected ligands thus form a potential lead compound that can be further refined using e.g. the iterative technique of Greer et al. For a virtual linked-fragment approach see Verlinde et al., *J. of Computer-Aided Molecular Design*, 6, (1992), 131–147, and for NMR and X-ray approaches see Shuker et al., *Science*, 274, (1996), 1531–1534 and Stout et al., *Structure*, 6, (1998), 839–848. The use of these approaches to design PS inhibitors is made possible by the determination of the PS structure.

Many of the techniques and approaches to structure-based drug design described above rely at some stage on X-ray analysis to identify the binding position of a ligand in a ligand-protein complex. A common way of doing this is to perform X-ray crystallography on the complex, produce a difference Fourier electron density map, and associate a particular pattern of electron density with the ligand. However, in order to produce the map (as explained e.g. by Blundell et al. mentioned above) it is necessary to know beforehand the protein 3D structure (or at least the protein structure factors). Therefore, determination of the PS structure also allows difference Fourier electron density maps of PS-ligand complexes to be produced, which can greatly assist the process of rational drug design.

The approaches to structure-based drug design described above all require initial identification of possible compounds for interaction with target bio-molecule (in this case PS). Sometimes these compounds are known e.g. from the research literature. However, when they are not, or when novel compounds are wanted, a first stage of the drug design program may involve computer-based in silico screening of compound databases (such as the Cambridge Structural Database) with the aim of identifying compounds which interact with the active site or sites of the target bio-molecule. Screening selection criteria may be based on pharmacokinetic properties such as metabolic stability and toxicity. However, determination of the PS structure allows the architecture and chemical nature of each PS active site to be identified, which in turn allows the geometric and functional constraints of a descriptor for the potential inhibitor to be derived. The descriptor is, therefore, a type of virtual 3-D pharmacophore, which can also be used as selection criteria or filter for database screening.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention.

References

The references listed below are incorporated by reference.
Barker et al., *FEBS Letters*, 145, (1982), 191–193.
Bohacek et al., *Medicinal Research Reviews*, Vol.16, (1996), 3–50.
Brick et al., *J. of Molecular Biology*, 208, (1989), 83–98.
Bricogne, *Methods in Enzymology*, 276, (1997), 361–423.
Brunger et al., *Acta Crystallographica*, D54, (1998), 905–921.
Blundell et al., in *Protein Crystallography*, Academic Press, New York, London and San Francisco, (1976).
Collaborative Computational Project 4. The CCP4 Suite: Programs for Protein Crystallography, *Acta Crystallographica*, D50, (1994), 760–763.
Dunbrack et al., *Folding and Design*, 2, (1997), 27–42.
First et al., in *Biochemistry*, 32, (1993), 13644–13663.
Goodford, *J. Med. Chem.*, 28, (1985), 849–857.
Greer et al., *J. of Medicinal Chemistry*, Vol. 37, (1994), 1035–1054.
Hooft et al., *Nature*, 381, (1996), 272.
Izard et al., *EMBO Journal*, 18, (1999), 2021–2030.
Jones et al., *Acta Crystallograhy*, A47, (1991), 110–119.
Jones et al. in *Current Opinion in Biotechnology*, Vol.6, (1995), 652–656.
Kleywegt et al., OOPS-a-daisy, *CCP4/ESF-EACBM Newsletter on Protein Crystallography*, 30, (1994), 20–24.
Kleywegt et al., *Acta Crystallographica*, D52, (1996b), 826–828.
LaFortelle et al., *Methods in Enzymology*, 276, (1997), 472–494.
LaFortelle et al., Maximum Likelihood Refinement in a Graphical environment, with SHARP, in CCP4 study week-end: *Recent Advances in Phasing*, ed. Wilson et al., Daresbury Laboratory, UK.
Leslie, *Joint CCP4 and EESF-EACMB Newsletter on Protein Crystallography*, Vol.26, Daresbury Laboratory, UK.
Laskowski et al., *J. Applied Crystallography*, 26, (1993), 283–291.
Mechulam et al., *J. of Molecular Biology*, 294, (1999), 1287–1297.
Miyatake et. al, *J. Biochem.*, 79, (1976), 673–678.
Murshudov et al., *Acta Crystallographica*, D53, (1997), 24–255.
Nureki et al., *Science*, 267, (1995) 1958–1965.
Perona et al., *Biochemistry*, 32, (1993) 8758–8771.
Perrakis et al., *Acta Crystallographica*, D55, (1999), 1765–1770.
Read, Acta Crystallographica, A42, (1986), 140–149.
Sayle et al., *TIBS*, Vol. 20, (1995), 374.
Shuker et al., *Science*, 274, (1996), 1531–1534.
Stout et al., *Structure*, 6, (1998), 839–848.
Tronrud, *Methods in Enzymology*, 277, (1997), 306–319.
van den Akker et al., *Acta Crystallographica*, D55, (1999), 206–218.
van Duyne et al., *J. Mol. Biol.*, 229, (1993), 105–124.
Verlinde et al., *J. of Computer-Aided Molecular Design*, 6, (1992), 131–147.
Walters et al., *Drug Discovery Today*, Vol.3, No.4, (1998), 160–178.
Weber et al., *Structure with Folding and Design*, 7, (1999), 1113–1124.
Weeks et al., *J. of Applied Crystallography*, 32, (1999), 120–124.

TABLE 1

| REMARK Written by O version 6.2.1 | | | | | | | | | |
|---|---|---|---|---|---|---|---|---|---|
| REMARK Sun Dec 19 17:28:32 1999 | | | | | | | | | |
| CRYST1/ | 66.031 | 78.075 | 77.126 | 90.00 | 103.71 | 90.00 | | | |
| ORIGX1 | 1.000000 | 0.000000 | 0.000000 | 0.00000 | | | | | |
| ORIGX2 | 0.000000 | 1.000000 | 0.000000 | 0.00000 | | | | | |
| ORIGX3 | 0.000000 | 0.000000 | 1.000000 | 0.00000 | | | | | |
| SCALE1 | 0.015144 | 0.000000 | 0.003694 | 0.00000 | | | | | |
| SCALE2 | 0.000000 | 0.012808 | 0.000000 | 0.00000 | | | | | |
| SCALE3 | 0.000000 | 0.000000 | 0.013346 | 0.00000 | | | | | |
| | Atom type | | | | X | Y | Z | Occ. | B | Atomic No. |

Monomer A

| | | | | | | X | Y | Z | Occ. | B | Atomic No. |
|---|---|---|---|---|---|---|---|---|---|---|---|
| ATOM | 1 | N | MET | A | 1 | 21.480 | 5.652 | 9.350 | 1.00 | 40.77 | 7 |
| ATOM | 2 | CA | MET | A | 1 | 22.828 | 6.214 | 9.115 | 1.00 | 37.51 | 6 |
| ATOM | 3 | C | MET | A | 1 | 23.471 | 6.721 | 10.394 | 1.00 | 37.12 | 6 |
| ATOM | 4 | O | MET | A | 1 | 22.954 | 7.659 | 10.999 | 1.00 | 37.52 | 8 |
| ATOM | 5 | CB | MET | A | 1 | 22.777 | 7.385 | 8.130 | 1.00 | 35.78 | 6 |
| ATOM | 6 | CG | MET | A | 1 | 24.222 | 7.748 | 7.741 | 1.00 | 33.60 | 6 |
| ATOM | 7 | SD | MET | A | 1 | 24.158 | 8.882 | 6.335 | 1.00 | 30.36 | 16 |
| ATOM | 8 | CE | MET | A | 1 | 23.874 | 10.429 | 7.197 | 1.00 | 27.91 | 6 |
| ATOM | 9 | N | LEU | A | 2 | 24.565 | 6.125 | 10.835 | 1.00 | 33.76 | 7 |
| ATOM | 10 | CA | LEU | A | 2 | 25.238 | 6.573 | 12.014 | 1.00 | 33.24 | 6 |
| ATOM | 11 | C | LEU | A | 2 | 26.150 | 7.745 | 11.696 | 1.00 | 32.31 | 6 |
| ATOM | 12 | O | LEU | A | 2 | 26.856 | 7.637 | 10.679 | 1.00 | 31.54 | 8 |
| ATOM | 13 | CB | LEU | A | 2 | 26.138 | 5.467 | 12.571 | 1.00 | 36.11 | 6 |
| ATOM | 14 | CG | LEU | A | 2 | 25.578 | 4.098 | 12.886 | 1.00 | 40.23 | 6 |
| ATOM | 15 | CD1 | LEU | A | 2 | 26.741 | 3.164 | 13.253 | 1.00 | 39.01 | 6 |
| ATOM | 16 | CD2 | LEU | A | 2 | 24.566 | 4.121 | 14.018 | 1.00 | 40.87 | 6 |
| ATOM | 17 | N | ILE | A | 3 | 26.233 | 8.778 | 12.481 | 1.00 | 30.54 | 7 |
| ATOM | 18 | CA | ILE | A | 3 | 27.148 | 9.869 | 12.303 | 1.00 | 30.81 | 6 |
| ATOM | 19 | C | ILE | A | 3 | 28.090 | 9.801 | 13.509 | 1.00 | 31.50 | 6 |
| ATOM | 20 | O | ILE | A | 3 | 27.616 | 9.918 | 14.642 | 1.00 | 31.89 | 8 |
| ATOM | 21 | CB | ILE | A | 3 | 26.523 | 11.280 | 12.249 | 1.00 | 31.52 | 6 |
| ATOM | 22 | CG1 | ILE | A | 3 | 25.579 | 11.383 | 11.041 | 1.00 | 34.35 | 6 |
| ATOM | 23 | CG2 | ILE | A | 3 | 27.610 | 12.348 | 12.227 | 1.00 | 33.27 | 6 |
| ATOM | 24 | CD1 | ILE | A | 3 | 24.913 | 12.769 | 11.018 | 1.00 | 34.98 | 6 |
| ATOM | 25 | N | ILE | A | 4 | 29.350 | 9.493 | 13.296 | 1.00 | 26.66 | 7 |
| ATOM | 26 | CA | ILE | A | 4 | 30.352 | 9.345 | 14.340 | 1.00 | 27.86 | 6 |
| ATOM | 27 | C | ILE | A | 4 | 31.314 | 10.510 | 14.337 | 1.00 | 28.36 | 6 |
| ATOM | 28 | O | ILE | A | 4 | 31.896 | 10.956 | 13.322 | 1.00 | 26.38 | 8 |
| ATOM | 29 | CB | ILE | A | 4 | 31.105 | 7.998 | 14.143 | 1.00 | 27.57 | 6 |
| ATOM | 30 | CG1 | ILE | A | 4 | 30.125 | 6.847 | 13.972 | 0.50 | 27.40 | 6 |
| ATOM | 31 | CG2 | ILE | A | 4 | 32.067 | 7.779 | 15.312 | 0.50 | 26.53 | 6 |
| ATOM | 32 | CD1 | ILE | A | 4 | 29.201 | 6.526 | 15.113 | 0.50 | 28.00 | 6 |
| ATOM | 33 | N | GLU | A | 5 | 31.633 | 11.053 | 15.537 | 1.00 | 25.12 | 7 |
| ATOM | 34 | CA | GLU | A | 5 | 32.526 | 12.186 | 15.655 | 1.00 | 28.91 | 6 |
| ATOM | 35 | C | GLU | A | 5 | 33.843 | 11.934 | 16.357 | 1.00 | 26.18 | 6 |
| ATOM | 36 | O | GLU | A | 5 | 34.724 | 12.779 | 16.300 | 1.00 | 27.45 | 8 |
| ATOM | 37 | CB | GLU | A | 5 | 31.769 | 13.303 | 16.441 | 1.00 | 31.10 | 6 |
| ATOM | 38 | CG | GLU | A | 5 | 30.611 | 13.871 | 15.627 | 1.00 | 34.62 | 6 |
| ATOM | 39 | CD | GLU | A | 5 | 29.795 | 14.929 | 16.355 | 1.00 | 40.38 | 6 |
| ATOM | 40 | OE1 | GLU | A | 5 | 30.263 | 15.579 | 17.306 | 1.00 | 41.78 | 8 |
| ATOM | 41 | OE2 | GLU | A | 5 | 28.625 | 15.153 | 15.971 | 1.00 | 43.11 | 8 |
| ATOM | 42 | N | THR | A | 6 | 33.976 | 10.823 | 17.094 | 1.00 | 27.41 | 7 |
| ATOM | 43 | CA | THR | A | 6 | 35.188 | 10.587 | 17.848 | 1.00 | 27.21 | 6 |
| ATOM | 44 | C | THR | A | 6 | 35.969 | 9.345 | 17.384 | 1.00 | 26.94 | 6 |
| ATOM | 45 | O | THR | A | 6 | 35.294 | 8.397 | 16.960 | 1.00 | 25.74 | 8 |
| ATOM | 46 | CB | THR | A | 6 | 34.867 | 10.400 | 19.351 | 1.00 | 29.81 | 6 |
| ATOM | 47 | OG1 | THR | A | 6 | 34.175 | 9.170 | 19.608 | 1.00 | 30.13 | 8 |
| ATOM | 48 | CG2 | THR | A | 6 | 33.967 | 11.528 | 19.852 | 1.00 | 29.59 | 6 |
| ATOM | 49 | N | LEU | A | 7 | 37.249 | 9.359 | 17.679 | 1.00 | 27.76 | 7 |
| ATOM | 50 | CA | LEU | A | 7 | 38.052 | 8.175 | 17.280 | 1.00 | 27.99 | 6 |
| ATOM | 51 | C | LEU | A | 7 | 37.684 | 6.899 | 18.006 | 1.00 | 29.61 | 6 |
| ATOM | 52 | O | LEU | A | 7 | 37.546 | 5.845 | 17.381 | 1.00 | 26.94 | 8 |
| ATOM | 53 | CB | LEU | A | 7 | 39.526 | 8.515 | 17.460 | 1.00 | 28.02 | 6 |
| ATOM | 54 | CG | LEU | A | 7 | 40.011 | 9.725 | 16.678 | 1.00 | 31.71 | 6 |
| ATOM | 55 | CD1 | LEU | A | 7 | 41.523 | 9.840 | 16.799 | 1.00 | 34.04 | 6 |
| ATOM | 56 | CD2 | LEU | A | 7 | 39.612 | 9.641 | 15.219 | 1.00 | 32.76 | 6 |
| ATOM | 57 | N | PRO | A | 8 | 37.434 | 6.913 | 19.313 | 1.00 | 30.58 | 7 |
| ATOM | 58 | CA | PRO | A | 8 | 37.081 | 5.687 | 20.013 | 1.00 | 29.86 | 6 |
| ATOM | 59 | C | PRO | A | 8 | 35.814 | 5.062 | 19.505 | 1.00 | 28.23 | 6 |
| ATOM | 60 | O | PRO | A | 8 | 35.701 | 3.845 | 19.394 | 1.00 | 25.90 | 8 |
| ATOM | 61 | CB | PRO | A | 8 | 37.001 | 6.107 | 21.485 | 1.00 | 31.83 | 6 |
| ATOM | 62 | CG | PRO | A | 8 | 37.816 | 7.345 | 21.593 | 1.00 | 31.44 | 6 |
| ATOM | 63 | CD | PRO | A | 8 | 37.601 | 8.053 | 20.243 | 1.00 | 30.62 | 6 |
| ATOM | 64 | N | LEU | A | 9 | 34.754 | 5.838 | 19.239 | 1.00 | 27.49 | 7 |
| ATOM | 65 | CA | LEU | A | 9 | 33.489 | 5.349 | 18.746 | 1.00 | 28.03 | 6 |

TABLE 1-continued

| | | | | | | | | | | |
|---|---|---|---|---|---|---|---|---|---|---|
| ATOM | 66 | C | LEU | A | 9 | 33.625 | 4.896 | 17.281 | 1.00 | 25.69 | 6 |
| ATOM | 67 | O | LEU | A | 9 | 32.960 | 3.907 | 16.978 | 1.00 | 26.00 | 8 |
| ATOM | 68 | CB | LEU | A | 9 | 32.376 | 6.393 | 18.920 | 1.00 | 31.67 | 6 |
| ATOM | 69 | CG | LEU | A | 9 | 32.089 | 6.741 | 20.400 | 1.00 | 35.64 | 6 |
| ATOM | 70 | CD1 | LEU | A | 9 | 31.037 | 7.824 | 20.573 | 1.00 | 35.73 | 6 |
| ATOM | 71 | CD2 | LEU | A | 9 | 31.636 | 5.493 | 21.154 | 1.00 | 37.26 | 6 |
| ATOM | 72 | N | LEU | A | 10 | 34.532 | 5.512 | 16.526 | 1.00 | 25.45 | 7 |
| ATOM | 73 | CA | LEU | A | 10 | 34.763 | 5.045 | 15.154 | 1.00 | 23.19 | 6 |
| ATOM | 74 | C | LEU | A | 18 | 35.461 | 3.678 | 15.228 | 1.00 | 23.87 | 6 |
| ATOM | 75 | O | LEU | A | 10 | 35.017 | 2.730 | 14.592 | 1.00 | 23.85 | 8 |
| ATOM | 76 | CB | LEU | A | 10 | 35.577 | 6.082 | 14.350 | 1.00 | 21.87 | 6 |
| ATOM | 77 | CG | LEU | A | 10 | 36.012 | 5.560 | 12.953 | 1.00 | 22.51 | 6 |
| ATOM | 78 | CD1 | LEU | A | 10 | 34.829 | 5.397 | 12.007 | 1.00 | 22.75 | 6 |
| ATOM | 79 | CD2 | LEU | A | 10 | 37.072 | 6.488 | 12.337 | 1.00 | 23.02 | 6 |
| ATOM | 80 | N | ARG | A | 11 | 36.423 | 3.571 | 16.150 | 1.00 | 25.14 | 7 |
| ATOM | 81 | CA | ARG | A | 11 | 37.191 | 2.304 | 16.232 | 1.00 | 28.37 | 6 |
| ATOM | 82 | C | ARG | A | 11 | 36.236 | 1.209 | 16.642 | 1.00 | 29.20 | 6 |
| ATOM | 83 | O | ARG | A | 11 | 36.288 | 0.113 | 16.066 | 1.00 | 27.74 | 8 |
| ATOM | 84 | CB | ARG | A | 11 | 38.399 | 2.556 | 17.142 | 1.00 | 31.48 | 6 |
| ATOM | 85 | CG | ARG | A | 11 | 39.141 | 1.279 | 17.544 | 1.00 | 36.42 | 6 |
| ATOM | 86 | CD | ARG | A | 11 | 40.384 | 1.586 | 18.401 | 1.00 | 40.76 | 6 |
| ATOM | 87 | NE | ARG | A | 11 | 40.948 | 0.327 | 18.857 | 1.00 | 44.29 | 7 |
| ATOM | 88 | CZ | ARG | A | 11 | 40.627 | −0.524 | 19.819 | 1.00 | 45.48 | 6 |
| ATOM | 89 | NH1 | ARG | A | 11 | 39.610 | −0.297 | 20.644 | 1.00 | 47.34 | 7 |
| ATOM | 90 | NH2 | ARG | A | 11 | 41.306 | −1.656 | 20.008 | 1.00 | 45.04 | 7 |
| ATOM | 91 | N | GLN | A | 12 | 35.347 | 1.474 | 17.591 | 1.00 | 26.32 | 7 |
| ATOM | 92 | CA | GLN | A | 12 | 34.364 | 0.453 | 17.968 | 1.00 | 28.52 | 6 |
| ATOM | 93 | C | GLN | A | 12 | 33.550 | −0.050 | 16.798 | 1.00 | 27.48 | 6 |
| ATOM | 94 | O | GLN | A | 12 | 33.340 | −1.248 | 16.579 | 1.00 | 25.61 | 8 |
| ATOM | 95 | CB | GLN | A | 12 | 33.450 | 1.032 | 19.051 | 1.00 | 30.81 | 6 |
| ATOM | 96 | CG | GLN | A | 12 | 32.364 | 0.022 | 19.483 | 1.00 | 34.43 | 6 |
| ATOM | 97 | CD | GLN | A | 12 | 31.513 | 0.662 | 20.570 | 1.00 | 37.80 | 6 |
| ATOM | 98 | OE1 | GLN | A | 12 | 31.804 | 0.354 | 21.743 | 1.00 | 43.75 | 8 |
| ATOM | 99 | NE2 | GLN | A | 12 | 30.545 | 1.495 | 20.293 | 1.00 | 38.11 | 7 |
| ATOM | 100 | N | GLN | A | 13 | 32.938 | 0.879 | 16.025 | 1.00 | 25.56 | 7 |
| ATOM | 101 | CA | GLN | A | 13 | 32.110 | 0.497 | 14.901 | 1.00 | 24.82 | 6 |
| ATOM | 102 | C | GLN | A | 13 | 32.889 | −0.235 | 13.804 | 1.00 | 23.46 | 6 |
| ATOM | 103 | O | GLN | A | 13 | 32.360 | −1.209 | 13.326 | 1.00 | 24.23 | 8 |
| ATOM | 104 | CB | GLN | A | 13 | 31.427 | 1.706 | 14.213 | 1.00 | 28.90 | 6 |
| ATOM | 105 | CG | GLN | A | 13 | 30.471 | 2.397 | 15.154 | 1.00 | 34.73 | 6 |
| ATOM | 106 | CD | GLN | A | 13 | 29.201 | 1.611 | 15.405 | 1.00 | 37.69 | 6 |
| ATOM | 107 | OE1 | GLN | A | 13 | 28.697 | 0.913 | 14.519 | 1.00 | 40.12 | 8 |
| ATOM | 108 | NE2 | GLN | A | 13 | 28.765 | 1.760 | 16.646 | 1.00 | 39.64 | 7 |
| ATOM | 109 | N | ILE | A | 14 | 34.075 | 0.258 | 13.493 | 1.00 | 21.48 | 7 |
| ATOM | 110 | CA | ILE | A | 14 | 34.904 | −0.413 | 12.482 | 1.00 | 23.36 | 6 |
| ATOM | 111 | C | ILE | A | 14 | 35.252 | −1.833 | 12.978 | 1.00 | 23.78 | 6 |
| ATOM | 112 | O | ILE | A | 14 | 35.100 | −2.754 | 12.163 | 1.00 | 24.98 | 8 |
| ATOM | 113 | CB | ILE | A | 14 | 36.157 | 0.388 | 12.154 | 1.00 | 24.05 | 6 |
| ATOM | 114 | CG1 | ILE | A | 14 | 35.752 | 1.756 | 11.492 | 1.00 | 23.68 | 6 |
| ATOM | 115 | CG2 | ILE | A | 14 | 37.152 | −0.372 | 11.258 | 1.00 | 23.44 | 6 |
| ATOM | 116 | CD1 | ILE | A | 14 | 34.981 | 1.571 | 10.185 | 1.00 | 22.33 | 6 |
| ATOM | 117 | N | ARG | A | 15 | 35.691 | −1.946 | 14.210 | 1.00 | 24.68 | 7 |
| ATOM | 118 | CA | ARG | A | 15 | 36.062 | −3.331 | 14.658 | 1.00 | 24.36 | 6 |
| ATOM | 119 | C | ARG | A | 15 | 34.868 | −4.230 | 14.500 | 1.00 | 24.62 | 6 |
| ATOM | 120 | O | ARG | A | 15 | 34.925 | −5.358 | 13.991 | 1.00 | 26.61 | 8 |
| ATOM | 121 | CB | ARG | A | 15 | 36.618 | −3.304 | 16.087 | 1.00 | 24.77 | 6 |
| ATOM | 122 | CG | ARG | A | 15 | 38.037 | −2.760 | 16.169 | 1.00 | 29.78 | 6 |
| ATOM | 123 | CD | ARG | A | 15 | 38.488 | −2.556 | 17.609 | 1.00 | 31.54 | 6 |
| ATOM | 124 | NE | ARG | A | 15 | 38.632 | −3.872 | 18.241 | 1.00 | 34.58 | 7 |
| ATOM | 125 | CZ | ARG | A | 15 | 39.603 | −4.741 | 17.996 | 1.00 | 36.36 | 6 |
| ATOM | 126 | NH1 | ARG | A | 15 | 48.588 | −4.484 | 17.142 | 1.00 | 37.87 | 7 |
| ATOM | 127 | NH2 | ARG | A | 15 | 39.609 | −5.896 | 18.638 | 1.00 | 37.41 | 7 |
| ATOM | 128 | N | ARG | A | 16 | 33.681 | −3.788 | 14.925 | 1.00 | 23.16 | 7 |
| ATOM | 129 | CA | ARG | A | 16 | 32.495 | −4.643 | 14.843 | 1.00 | 24.97 | 6 |
| ATOM | 130 | C | ARG | A | 16 | 32.091 | −5.007 | 13.453 | 1.00 | 26.58 | 6 |
| ATOM | 131 | O | ARG | A | 16 | 31.688 | −6.112 | 13.134 | 1.00 | 25.54 | 8 |
| ATOM | 132 | CB | ARG | A | 16 | 31.335 | −3.905 | 15.565 | 1.00 | 26.81 | 6 |
| ATOM | 133 | CG | ARG | A | 16 | 31.739 | −3.858 | 17.037 | 1.00 | 30.82 | 6 |
| ATOM | 134 | CD | ARG | A | 16 | 30.609 | −3.393 | 17.953 | 1.00 | 35.27 | 6 |
| ATOM | 135 | NE | ARG | A | 16 | 31.145 | −3.440 | 19.331 | 1.00 | 38.72 | 7 |
| ATOM | 136 | CZ | ARG | A | 16 | 30.380 | −3.407 | 20.431 | 1.00 | 41.50 | 6 |
| ATOM | 137 | NH1 | ARG | A | 16 | 29.057 | −3.350 | 20.279 | 1.00 | 41.64 | 7 |
| ATOM | 138 | NH2 | ARG | A | 16 | 30.986 | −3.478 | 21.616 | 1.00 | 40.81 | 7 |
| ATOM | 139 | N | LEU | A | 17 | 32.236 | −4.016 | 12.503 | 1.00 | 25.60 | 7 |
| ATOM | 140 | CA | LEU | A | 17 | 31.869 | −4.342 | 11.148 | 1.00 | 25.51 | 6 |
| ATOM | 141 | C | LEU | A | 17 | 32.796 | −5.382 | 10.547 | 1.00 | 25.77 | 6 |
| ATOM | 142 | O | LEU | A | 17 | 32.287 | −6.296 | 9.882 | 1.00 | 27.72 | 8 |
| ATOM | 143 | CB | LEU | A | 17 | 31.929 | −3.067 | 10.251 | 1.00 | 26.53 | 6 |
| ATOM | 144 | CG | LEU | A | 17 | 30.763 | −2.131 | 10.574 | 1.00 | 28.03 | 6 |

TABLE 1-continued

| | | | | | | | | | | |
|---|---|---|---|---|---|---|---|---|---|---|
| ATOM | 145 | CD1 | LEU | A | 17 | 31.127 | −0.707 | 10.125 | 1.00 | 29.84 | 6 |
| ATOM | 146 | CD2 | LEU | A | 17 | 29.455 | −2.554 | 9.941 | 1.00 | 30.48 | 6 |
| ATOM | 147 | N | ARG | A | 18 | 34.062 | −5.187 | 10.811 | 1.00 | 25.72 | 7 |
| ATOM | 148 | CA | ARG | A | 18 | 35.021 | −6.172 | 10.278 | 1.00 | 26.50 | 6 |
| ATOM | 149 | C | ARG | A | 18 | 34.894 | −7.544 | 10.989 | 1.00 | 27.79 | 6 |
| ATOM | 150 | O | ARG | A | 18 | 34.993 | −8.564 | 10.329 | 1.00 | 26.32 | 8 |
| ATOM | 151 | CB | ARG | A | 18 | 36.436 | −5.665 | 10.405 | 1.00 | 28.86 | 6 |
| ATOM | 152 | CG | ARG | A | 18 | 36.506 | −4.291 | 9.685 | 1.00 | 31.17 | 6 |
| ATOM | 153 | CD | ARG | A | 18 | 37.972 | −4.010 | 9.471 | 1.00 | 36.04 | 6 |
| ATOM | 154 | NE | ARG | A | 18 | 38.502 | −4.834 | 8.364 | 1.00 | 39.73 | 7 |
| ATOM | 155 | CZ | ARG | A | 18 | 39.788 | −5.197 | 8.409 | 1.00 | 41.34 | 6 |
| ATOM | 156 | NH1 | ARG | A | 18 | 40.523 | −4.806 | 9.456 | 1.00 | 42.67 | 7 |
| ATOM | 157 | NH2 | ARG | A | 18 | 40.324 | −5.921 | 7.432 | 1.00 | 41.84 | 7 |
| ATOM | 158 | N | MET | A | 19 | 34.537 | −7.458 | 12.259 | 1.00 | 25.78 | 7 |
| ATOM | 159 | CA | MET | A | 19 | 34.344 | −8.735 | 13.010 | 1.00 | 27.53 | 6 |
| ATOM | 160 | C | MET | A | 19 | 33.230 | −9.524 | 12.371 | 1.00 | 26.64 | 6 |
| ATOM | 161 | O | MET | A | 19 | 33.236 | −10.747 | 12.181 | 1.00 | 25.81 | 8 |
| ATOM | 162 | CB | MET | A | 19 | 34.097 | −8.377 | 14.473 | 1.00 | 24.76 | 6 |
| ATOM | 163 | CG | MET | A | 19 | 33.680 | −9.547 | 15.350 | 1.00 | 26.87 | 6 |
| ATOM | 164 | SD | MET | A | 19 | 31.960 | −10.075 | 15.286 | 1.00 | 24.59 | 16 |
| ATOM | 165 | CE | MET | A | 19 | 31.123 | −8.581 | 15.796 | 1.00 | 28.15 | 6 |
| ATOM | 166 | N | GLU | A | 20 | 32.202 | −8.844 | 11.855 | 1.00 | 28.38 | 7 |
| ATOM | 167 | CA | GLU | A | 20 | 31.083 | −9.471 | 11.156 | 1.00 | 28.35 | 6 |
| ATOM | 168 | C | GLU | A | 20 | 31.345 | −9.875 | 9.720 | 1.00 | 31.76 | 6 |
| ATOM | 169 | O | GLU | A | 20 | 30.395 | −10.362 | 9.077 | 1.00 | 32.53 | 8 |
| ATOM | 170 | CB | GLU | A | 20 | 29.874 | −8.502 | 11.103 | 1.00 | 30.90 | 6 |
| ATOM | 171 | CG | GLU | A | 20 | 29.474 | −8.103 | 12.493 | 1.00 | 31.14 | 6 |
| ATOM | 172 | N | GLY | A | 21 | 32.531 | −9.676 | 9.217 | 1.00 | 29.46 | 7 |
| ATOM | 173 | CA | GLY | A | 21 | 32.968 | −10.045 | 7.901 | 1.00 | 30.44 | 6 |
| ATOM | 174 | C | GLY | A | 21 | 32.503 | −9.016 | 6.844 | 1.00 | 28.10 | 6 |
| ATOM | 175 | O | GLY | A | 21 | 32.465 | −9.457 | 5.705 | 1.00 | 30.38 | 8 |
| ATOM | 176 | N | LYS | A | 22 | 32.195 | −7.815 | 7.269 | 1.00 | 27.01 | 7 |
| ATOM | 177 | CA | LYS | A | 22 | 31.684 | −6.909 | 6.184 | 1.00 | 26.80 | 6 |
| ATOM | 178 | C | LYS | A | 22 | 32.855 | −6.293 | 5.441 | 1.00 | 26.41 | 6 |
| ATOM | 179 | O | LYS | A | 22 | 33.844 | −5.944 | 6.097 | 1.00 | 27.41 | 8 |
| ATOM | 180 | CB | LYS | A | 22 | 30.773 | −5.883 | 6.825 | 1.00 | 27.50 | 6 |
| ATOM | 181 | CG | LYS | A | 22 | 29.392 | −6.529 | 7.152 | 1.00 | 32.21 | 6 |
| ATOM | 182 | CD | LYS | A | 22 | 28.721 | −5.570 | 8.118 | 1.00 | 37.87 | 6 |
| ATOM | 183 | CE | LYS | A | 22 | 27.207 | −5.752 | 8.159 | 1.00 | 42.38 | 6 |
| ATOM | 184 | NZ | LYS | A | 22 | 26.574 | −4.400 | 8.447 | 1.00 | 46.00 | 7 |
| ATOM | 185 | N | ARG | A | 23 | 32.737 | −6.159 | 4.128 | 1.00 | 26.60 | 7 |
| ATOM | 186 | CA | ARG | A | 23 | 33.781 | −5.503 | 3.325 | 1.00 | 27.62 | 6 |
| ATOM | 187 | C | ARG | A | 23 | 33.468 | −4.008 | 3.350 | 1.00 | 25.54 | 6 |
| ATOM | 188 | O | ARG | A | 23 | 32.293 | −3.677 | 3.209 | 1.00 | 25.62 | 8 |
| ATOM | 189 | CB | ARG | A | 23 | 33.784 | −6.101 | 1.934 | 1.00 | 31.46 | 6 |
| ATOM | 190 | CG | ARG | A | 23 | 34.506 | −5.433 | 0.801 | 1.00 | 39.27 | 6 |
| ATOM | 191 | CD | ARG | A | 23 | 34.206 | −5.965 | −0.610 | 1.00 | 43.15 | 6 |
| ATOM | 192 | NE | ARG | A | 23 | 35.366 | −5.731 | −1.466 | 1.00 | 45.63 | 7 |
| ATOM | 193 | CZ | ARG | A | 23 | 36.577 | −6.268 | −1.262 | 1.00 | 46.18 | 6 |
| ATOM | 194 | NH1 | ARG | A | 23 | 36.841 | −7.101 | −0.272 | 1.00 | 47.31 | 7 |
| ATOM | 195 | NH2 | ARG | A | 23 | 37.537 | −5.954 | −2.117 | 1.00 | 48.28 | 7 |
| ATOM | 196 | N | VAL | A | 24 | 34.412 | −3.165 | 3.697 | 1.00 | 23.62 | 7 |
| ATOM | 197 | CA | VAL | A | 24 | 34.196 | −1.743 | 3.900 | 1.00 | 22.06 | 6 |
| ATOM | 198 | C | VAL | A | 24 | 34.785 | −0.891 | 2.782 | 1.00 | 17.49 | 6 |
| ATOM | 199 | O | VAL | A | 24 | 35.924 | −1.166 | 2.392 | 1.00 | 18.13 | 8 |
| ATOM | 200 | CB | VAL | A | 24 | 34.830 | −1.279 | 5.218 | 1.00 | 22.91 | 6 |
| ATOM | 201 | CG1 | VAL | A | 24 | 34.677 | 0.198 | 5.452 | 1.00 | 24.86 | 6 |
| ATOM | 202 | CG2 | VAL | A | 24 | 34.173 | −2.010 | 6.405 | 1.00 | 24.10 | 6 |
| ATOM | 203 | N | ALA | A | 25 | 34.023 | 0.099 | 2.315 | 1.00 | 17.82 | 7 |
| ATOM | 204 | CA | ALA | A | 25 | 34.597 | 0.939 | 1.279 | 1.00 | 18.16 | 6 |
| ATOM | 205 | C | ALA | A | 25 | 34.593 | 2.272 | 2.004 | 1.00 | 18.48 | 6 |
| ATOM | 206 | O | ALA | A | 25 | 33.673 | 2.667 | 2.768 | 1.00 | 22.08 | 8 |
| ATOM | 207 | CB | ALA | A | 25 | 33.863 | 1.032 | −0.030 | 1.00 | 20.30 | 6 |
| ATOM | 208 | N | LEU | A | 26 | 35.579 | 3.142 | 1.726 | 1.00 | 16.71 | 7 |
| ATOM | 209 | CA | LEU | A | 26 | 35.791 | 4.438 | 2.266 | 1.00 | 16.65 | 6 |
| ATOM | 210 | C | LEU | A | 26 | 35.819 | 5.507 | 1.152 | 1.00 | 17.57 | 6 |
| ATOM | 211 | O | LEU | A | 26 | 36.497 | 5.321 | 0.146 | 1.00 | 18.90 | 8 |
| ATOM | 212 | CB | LEU | A | 26 | 37.120 | 4.628 | 3.038 | 1.00 | 18.22 | 6 |
| ATOM | 213 | CG | LEU | A | 26 | 37.458 | 6.066 | 3.461 | 1.00 | 18.69 | 6 |
| ATOM | 214 | CD1 | LEU | A | 26 | 36.500 | 6.657 | 4.511 | 1.00 | 20.43 | 6 |
| ATOM | 215 | CD2 | LEU | A | 26 | 38.B87 | 6.061 | 4.006 | 1.00 | 20.45 | 6 |
| ATOM | 216 | N | VAL | A | 27 | 35.065 | 6.569 | 1.318 | 1.00 | 16.54 | 7 |
| ATOM | 217 | CA | VAL | A | 27 | 35.028 | 7.712 | 0.418 | 1.00 | 16.69 | 6 |
| ATOM | 218 | C | VAL | A | 27 | 35.493 | 8.915 | 1.208 | 1.00 | 15.96 | 6 |
| ATOM | 219 | O | VAL | A | 27 | 34.643 | 9.495 | 1.891 | 1.00 | 17.62 | 8 |
| ATOM | 220 | CB | VAL | A | 27 | 33.636 | 8.038 | −0.196 | 1.00 | 18.00 | 6 |
| ATOM | 221 | CG1 | VAL | A | 27 | 33.738 | 9.238 | −1.157 | 1.00 | 21.63 | 6 |
| ATOM | 222 | CG2 | VAL | A | 27 | 33.057 | 6.801 | −0.869 | 1.00 | 20.05 | 6 |
| ATOM | 223 | N | PRO | A | 28 | 36.728 | 9.403 | 1.100 | 1.00 | 18.63 | 7 |

TABLE 1-continued

| | | | | | | | | | | |
|---|---|---|---|---|---|---|---|---|---|---|
| ATOM | 224 | CA | PRO | A | 28 | 37.265 | 10.543 | 1.776 | 1.00 | 19.42 | 6 |
| ATOM | 225 | C | PRO | A | 28 | 36.814 | 11.864 | 1.198 | 1.00 | 20.36 | 6 |
| ATOM | 226 | O | PRO | A | 28 | 36.941 | 11.994 | −0.024 | 1.00 | 21.38 | 8 |
| ATOM | 227 | CB | PRO | A | 28 | 38.775 | 10.466 | 1.589 | 1.00 | 23.04 | 6 |
| ATOM | 228 | CG | PRO | A | 28 | 39.036 | 9.147 | 0.945 | 1.00 | 23.71 | 6 |
| ATOM | 229 | CD | PRO | A | 28 | 37.765 | 8.641 | 0.309 | 1.00 | 19.69 | 6 |
| ATOM | 230 | N | THR | A | 29 | 36.209 | 12.765 | 1.957 | 1.00 | 20.05 | 7 |
| ATOM | 231 | CA | THR | A | 29 | 35.752 | 14.046 | 1.426 | 1.00 | 20.41 | 6 |
| ATOM | 232 | C | THR | A | 29 | 36.036 | 15.159 | 2.439 | 1.00 | 18.55 | 6 |
| ATOM | 233 | O | THR | A | 29 | 36.271 | 14.922 | 3.618 | 1.00 | 19.34 | 8 |
| ATOM | 234 | CB | THR | A | 29 | 34.254 | 14.069 | 1.053 | 1.00 | 21.16 | 6 |
| ATOM | 235 | OG1 | THR | A | 29 | 33.512 | 14.439 | 2.242 | 1.00 | 19.82 | 8 |
| ATOM | 236 | CG2 | THR | A | 29 | 33.658 | 12.762 | 0.537 | 1.00 | 20.33 | 6 |
| ATOM | 237 | N | MET | A | 30 | 35.897 | 16.391 | 2.003 | 1.00 | 20.47 | 7 |
| ATOM | 238 | CA | MET | A | 30 | 35.998 | 17.616 | 2.811 | 1.00 | 20.82 | 6 |
| ATOM | 239 | C | MET | A | 30 | 34.587 | 18.281 | 2.815 | 1.00 | 23.33 | 6 |
| ATOM | 240 | O | MET | A | 30 | 34.465 | 19.488 | 3.115 | 1.00 | 23.42 | 8 |
| ATOM | 241 | CB | MET | A | 30 | 37.065 | 18.623 | 2.375 | 1.00 | 21.06 | 6 |
| ATOM | 242 | CG | MET | A | 30 | 38.446 | 17.925 | 2.357 | 1.00 | 21.02 | 6 |
| ATOM | 243 | SD | MET | A | 30 | 39.740 | 19.108 | 2.816 | 1.00 | 24.24 | 16 |
| ATOM | 244 | CE | MET | A | 30 | 39.431 | 20.461 | 1.687 | 1.00 | 26.95 | 6 |
| ATOM | 245 | N | GLY | A | 31 | 33.576 | 17.477 | 2.616 | 1.00 | 21.21 | 7 |
| ATOM | 246 | CA | GLY | A | 31 | 32.189 | 17.985 | 2.705 | 1.00 | 24.38 | 6 |
| ATOM | 247 | C | GLY | A | 31 | 31.835 | 18.946 | 1.563 | 1.00 | 24.71 | 6 |
| ATOM | 248 | O | GLY | A | 31 | 32.498 | 18.909 | 0.524 | 1.00 | 22.94 | 8 |
| ATOM | 249 | N | ASN | A | 32 | 30.712 | 19.650 | 1.637 | 1.00 | 24.08 | 7 |
| ATOM | 250 | CA | ASN | A | 32 | 30.269 | 20.550 | 0.552 | 1.00 | 22.88 | 6 |
| ATOM | 251 | C | ASN | A | 32 | 29.995 | 19.636 | −0.655 | 1.00 | 22.70 | 6 |
| ATOM | 252 | O | ASN | A | 32 | 30.519 | 19.801 | −1.762 | 1.00 | 25.35 | 8 |
| ATOM | 253 | CB | ASN | A | 32 | 31.269 | 21.654 | 0.253 | 1.00 | 27.38 | 6 |
| ATOM | 254 | CG | ASN | A | 32 | 30.612 | 22.708 | −0.658 | 1.00 | 31.01 | 6 |
| ATOM | 255 | OD1 | ASN | A | 32 | 29.390 | 22.842 | −0.531 | 1.00 | 33.26 | 8 |
| ATOM | 256 | ND2 | ASN | A | 32 | 31.392 | 23.283 | −1.538 | 1.00 | 31.51 | 7 |
| ATOM | 257 | N | LEU | A | 33 | 29.250 | 18.551 | −0.428 | 1.00 | 22.17 | 7 |
| ATOM | 258 | CA | LEU | A | 33 | 29.111 | 17.438 | −1.343 | 1.00 | 20.92 | 6 |
| ATOM | 259 | C | LEU | A | 33 | 28.300 | 17.796 | −2.594 | 1.00 | 23.49 | 6 |
| ATOM | 260 | O | LEU | A | 33 | 27.325 | 18.519 | −2.397 | 1.00 | 25.06 | 8 |
| ATOM | 261 | CB | LEU | A | 33 | 28.479 | 16.200 | −0.668 | 1.00 | 21.06 | 6 |
| ATOM | 262 | CG | LEU | A | 33 | 29.372 | 15.713 | 0.501 | 1.00 | 21.76 | 6 |
| ATOM | 263 | CD1 | LEU | A | 33 | 28.821 | 14.431 | 1.108 | 1.00 | 24.92 | 6 |
| ATOM | 264 | CD2 | LEU | A | 33 | 30.834 | 15.495 | 0.073 | 1.00 | 21.13 | 6 |
| ATOM | 265 | N | HIS | A | 34 | 28.691 | 17.217 | −3.706 | 1.00 | 21.31 | 7 |
| ATOM | 266 | CA | HIS | A | 34 | 27.929 | 17.454 | −4.953 | 1.00 | 19.68 | 6 |
| ATOM | 267 | C | HIS | A | 34 | 27.793 | 16.165 | −5.698 | 1.00 | 21.69 | 6 |
| ATOM | 268 | O | HIS | A | 34 | 28.073 | 15.035 | −5.218 | 1.00 | 21.01 | 8 |
| ATOM | 269 | CB | HIS | A | 34 | 28.648 | 18.575 | −5.722 | 1.00 | 20.00 | 6 |
| ATOM | 270 | CG | HIS | A | 34 | 30.062 | 18.267 | −6.078 | 1.00 | 23.69 | 6 |
| ATOM | 271 | ND1 | HIS | A | 34 | 30.449 | 17.170 | −6.770 | 1.00 | 26.07 | 7 |
| ATOM | 272 | CD2 | HIS | A | 34 | 31.211 | 18.953 | −5.778 | 1.00 | 26.19 | 6 |
| ATOM | 273 | CE1 | HIS | A | 34 | 31.776 | 17.161 | −6.890 | 1.00 | 27.03 | 6 |
| ATOM | 274 | NE2 | HIS | A | 34 | 32.262 | 18.221 | −6.296 | 1.00 | 27.65 | 7 |
| ATOM | 275 | N | ASP | A | 35 | 27.277 | 16.218 | −6.957 | 1.00 | 20.96 | 7 |
| ATOM | 276 | CA | ASP | A | 35 | 26.992 | 15.008 | −7.685 | 1.00 | 21.21 | 6 |
| ATOM | 277 | C | ASP | A | 35 | 28.213 | 14.132 | −7.962 | 1.00 | 20.16 | 6 |
| ATOM | 278 | O | ASP | A | 35 | 28.006 | 12.921 | −8.079 | 1.00 | 22.17 | 8 |
| ATOM | 279 | CB | ASP | A | 35 | 26.386 | 15.393 | −9.061 | 1.00 | 23.09 | 6 |
| ATON | 280 | CG | ASP | A | 35 | 24.959 | 15.842 | −8.957 | 1.00 | 26.28 | 6 |
| ATOM | 281 | OD1 | ASP | A | 35 | 24.273 | 15.662 | −7.929 | 1.00 | 27.10 | 8 |
| ATOM | 282 | OD2 | ASP | A | 35 | 24.439 | 16.326 | −10.018 | 1.00 | 25.60 | 8 |
| ATOM | 283 | N | GLY | A | 36 | 29.375 | 14.766 | −8.056 | 1.00 | 21.98 | 7 |
| ATOM | 284 | CA | GLY | A | 36 | 30.620 | 14.030 | −8.244 | 1.00 | 21.77 | 6 |
| ATOM | 285 | C | GLY | A | 36 | 30.786 | 13.041 | −7.065 | 1.00 | 22.77 | 6 |
| ATOM | 286 | O | GLY | A | 36 | 31.157 | 11.870 | −7.245 | 1.00 | 22.33 | 8 |
| ATOM | 287 | N | HIS | A | 37 | 30.620 | 13.573 | −5.849 | 1.00 | 22.48 | 7 |
| ATOM | 288 | CA | HIS | A | 37 | 30.753 | 12.759 | −4.642 | 1.00 | 19.90 | 6 |
| ATOM | 289 | C | HIS | A | 37 | 29.688 | 11.715 | −4.564 | 1.00 | 20.48 | 6 |
| ATOM | 290 | O | HIS | A | 37 | 29.886 | 10.568 | −4.111 | 1.00 | 20.51 | 8 |
| ATOM | 291 | CB | HIS | A | 37 | 30.659 | 13.645 | −3.371 | 1.00 | 20.77 | 6 |
| ATOM | 292 | CG | HIS | A | 37 | 31.604 | 14.773 | −3.310 | 1.00 | 23.28 | 6 |
| ATOM | 293 | ND1 | HIS | A | 37 | 32.947 | 14.667 | −2.929 | 1.00 | 28.53 | 7 |
| ATOM | 294 | CD2 | HIS | A | 37 | 31.407 | 16.089 | −3.544 | 1.00 | 19.82 | 6 |
| ATOM | 295 | CE1 | HIS | A | 37 | 33.536 | 15.843 | −2.870 | 1.00 | 23.53 | 6 |
| ATOM | 296 | NE2 | HIS | A | 37 | 32.585 | 16.736 | −3.250 | 1.00 | 26.84 | 7 |
| ATOM | 297 | N | MET | A | 38 | 28.469 | 11.976 | −5.080 | 1.00 | 19.18 | 7 |
| ATOM | 298 | CA | MET | A | 38 | 27.409 | 10.961 | −5.035 | 1.00 | 19.76 | 6 |
| ATOM | 299 | C | MET | A | 38 | 27.795 | 9.798 | −5.955 | 1.00 | 22.39 | 6 |
| ATOM | 300 | O | MET | A | 38 | 27.476 | 8.670 | −5.614 | 1.00 | 21.94 | 8 |
| ATOM | 301 | CB | MET | A | 38 | 26.038 | 11.520 | −5.422 | 1.00 | 23.14 | 6 |
| ATOM | 302 | CG | MET | A | 38 | 25.482 | 12.594 | −4.447 | 1.00 | 25.87 | 6 |

TABLE 1-continued

| | | | | | | | | | | |
|---|---|---|---|---|---|---|---|---|---|---|
| ATOM | 303 | SD | MET | A | 38 | 25.332 | 11.996 | −2.726 | 1.00 | 28.93 | 16 |
| ATOM | 304 | CE | MET | A | 38 | 26.690 | 12.846 | −1.980 | 1.00 | 25.74 | 6 |
| ATOM | 305 | N | LYS | A | 39 | 28.493 | 10.034 | −7.069 | 1.00 | 19.54 | 7 |
| ATOM | 306 | CA | LYS | A | 39 | 28.943 | 8.945 | −7.921 | 1.00 | 21.23 | 6 |
| ATOM | 307 | C | LYS | A | 39 | 29.995 | 8.090 | −7.205 | 1.00 | 19.48 | 6 |
| ATOM | 308 | O | LYS | A | 39 | 29.947 | 6.878 | −7.283 | 1.00 | 19.63 | 8 |
| ATOM | 309 | CB | LYS | A | 39 | 29.524 | 9.474 | −9.236 | 1.00 | 23.04 | 6 |
| ATOM | 310 | CG | LYS | A | 39 | 29.977 | 8.354 | −10.200 | 1.00 | 23.73 | 6 |
| ATOM | 311 | CD | LYS | A | 39 | 28.831 | 7.464 | −10.663 | 1.00 | 29.69 | 6 |
| ATOM | 312 | CE | LYS | A | 39 | 29.392 | 6.340 | −11.576 | 1.00 | 32.23 | 6 |
| ATOM | 313 | NZ | LYS | A | 39 | 28.207 | 5.549 | −12.095 | 1.00 | 35.95 | 7 |
| ATOM | 314 | N | LEU | A | 40 | 30.869 | 8.716 | −6.387 | 1.00 | 18.59 | 7 |
| ATOM | 315 | CA | LEU | A | 40 | 31.829 | 7.935 | −5.587 | 1.00 | 19.30 | 6 |
| ATOM | 316 | C | LEU | A | 40 | 31.065 | 7.001 | −4.652 | 1.00 | 17.32 | 6 |
| ATOM | 317 | O | LEU | A | 40 | 31.433 | 5.818 | −4.467 | 1.00 | 19.58 | 8 |
| ATOM | 318 | CB | LEU | A | 40 | 32.725 | 8.865 | −4.822 | 1.00 | 20.84 | 6 |
| ATOM | 319 | CG | LEU | A | 40 | 33.577 | 9.868 | −5.641 | 1.00 | 21.98 | 6 |
| ATOM | 320 | CD1 | LEU | A | 40 | 34.510 | 10.649 | −4.714 | 1.00 | 19.78 | 6 |
| ATOM | 321 | CD2 | LEU | A | 40 | 34.368 | 9.211 | −6.759 | 1.00 | 22.47 | 6 |
| ATOM | 322 | N | VAL | A | 41 | 30.079 | 7.532 | −3.957 | 1.00 | 19.06 | 7 |
| ATOM | 323 | CA | VAL | A | 41 | 29.260 | 6.732 | −3.016 | 1.00 | 18.09 | 6 |
| ATOM | 324 | C | VAL | A | 41 | 28.598 | 5.614 | −3.736 | 1.00 | 17.62 | 6 |
| ATOM | 325 | O | VAL | A | 41 | 28.537 | 4.470 | −3.258 | 1.00 | 19.88 | 8 |
| ATOM | 326 | CB | VAL | A | 41 | 28.253 | 7.674 | −2.265 | 1.00 | 20.51 | 6 |
| ATOM | 327 | CG1 | VAL | A | 41 | 27.211 | 6.841 | −1.514 | 1.00 | 21.02 | 6 |
| ATOM | 328 | CG2 | VAL | A | 41 | 29.010 | 8.629 | −1.336 | 1.00 | 19.99 | 6 |
| ATOM | 329 | N | ASP | A | 42 | 28.010 | 5.882 | −4.952 | 1.00 | 18.32 | 7 |
| ATOM | 330 | CA | ASP | A | 42 | 27.355 | 4.768 | −5.614 | 1.00 | 20.18 | 6 |
| ATOM | 331 | C | ASP | A | 42 | 28.312 | 3.653 | −5.995 | 1.00 | 20.77 | 6 |
| ATOM | 332 | O | ASP | A | 42 | 27.977 | 2.483 | −5.943 | 1.00 | 22.32 | 8 |
| ATOM | 333 | CB | ASP | A | 42 | 26.667 | 5.238 | −6.920 | 1.00 | 22.54 | 6 |
| ATOM | 334 | CG | ASP | A | 42 | 25.531 | 6.164 | −6.652 | 1.00 | 24.06 | 6 |
| ATOM | 335 | OD1 | ASP | A | 42 | 24.908 | 6.188 | −5.570 | 1.00 | 27.49 | 8 |
| ATOM | 336 | OD2 | ASP | A | 42 | 25.140 | 6.976 | −7.558 | 1.00 | 30.83 | 8 |
| ATOM | 337 | N | GLU | A | 43 | 29.539 | 4.041 | −6.419 | 1.00 | 20.92 | 7 |
| ATOM | 338 | CA | GLU | A | 43 | 30.528 | 3.015 | −6.753 | 1.00 | 22.39 | 6 |
| ATOM | 339 | C | GLU | A | 43 | 30.924 | 2.224 | −5.512 | 1.00 | 21.74 | 6 |
| ATOM | 340 | O | GLU | A | 43 | 31.185 | 1.036 | −5.623 | 1.00 | 23.66 | 8 |
| ATOM | 341 | CB | GLU | A | 43 | 31.816 | 3.583 | −7.342 | 1.00 | 23.36 | 6 |
| ATOM | 342 | CG | GLU | A | 43 | 31.560 | 4.030 | −8.792 | 1.00 | 32.68 | 6 |
| ATOM | 343 | CD | GLU | A | 43 | 31.450 | 2.806 | −9.705 | 1.00 | 34.94 | 6 |
| ATOM | 344 | OE1 | GLU | A | 43 | 32.113 | 1.776 | −9.517 | 1.00 | 39.24 | 8 |
| ATOM | 345 | OE2 | GLU | A | 43 | 30.590 | 2.908 | −10.606 | 1.00 | 42.50 | 8 |
| ATOM | 346 | N | ALA | A | 44 | 31.103 | 2.914 | −4.372 | 1.00 | 21.59 | 7 |
| ATOM | 347 | CA | ALA | A | 44 | 31.413 | 2.228 | −3.131 | 1.00 | 20.24 | 6 |
| ATOM | 348 | C | ALA | A | 44 | 30.241 | 1.299 | −2.736 | 1.00 | 22.05 | 6 |
| ATOM | 349 | O | ALA | A | 44 | 30.575 | 0.162 | −2.324 | 1.00 | 23.77 | 8 |
| ATOM | 350 | CB | ALA | A | 44 | 31.698 | 3.226 | −2.025 | 1.00 | 19.63 | 6 |
| ATOM | 351 | N | LYS | A | 45 | 29.033 | 1.800 | −2.843 | 1.00 | 24.11 | 7 |
| ATOM | 352 | CA | LYS | A | 45 | 27.888 | 0.912 | −2.499 | 1.00 | 26.00 | 6 |
| ATOM | 353 | C | LYS | A | 45 | 27.912 | −0.215 | −3.471 | 1.00 | 27.19 | 6 |
| ATOM | 354 | O | LYS | A | 45 | 27.573 | −1.297 | −2.970 | 1.00 | 28.01 | 8 |
| ATOM | 355 | CB | LYS | A | 45 | 26.550 | 1.612 | −2.555 | 1.00 | 28.17 | 6 |
| ATOM | 356 | CG | LYS | A | 45 | 26.331 | 2.723 | −1.544 | 1.00 | 33.53 | 6 |
| ATOM | 357 | CD | LYS | A | 45 | 25.613 | 2.271 | −0.277 | 1.00 | 40.20 | 6 |
| ATOM | 358 | CE | LYS | A | 45 | 24.365 | 1.437 | −0.586 | 1.00 | 42.16 | 6 |
| ATOM | 359 | NZ | LYS | A | 45 | 23.332 | 1.467 | 0.475 | 1.00 | 47.05 | 7 |
| ATOM | 360 | N | ALA | A | 46 | 28.221 | −0.250 | −4.714 | 1.00 | 25.90 | 7 |
| ATOM | 361 | CA | ALA | A | 46 | 28.227 | −1.457 | −5.529 | 1.00 | 26.79 | 6 |
| ATOM | 362 | C | ALA | A | 46 | 29.360 | −2.424 | −5.183 | 1.00 | 29.75 | 6 |
| ATOM | 363 | O | ALA | A | 46 | 29.233 | −3.661 | −5.395 | 1.00 | 28.75 | 8 |
| ATOM | 364 | CB | ALA | A | 46 | 28.360 | −1.038 | −6.984 | 1.00 | 28.50 | 6 |
| ATOM | 365 | N | ARG | A | 47 | 30.492 | −1.922 | −4.680 | 1.00 | 26.27 | 7 |
| ATOM | 366 | CA | ARG | A | 47 | 31.649 | −2.782 | −4.511 | 1.00 | 25.06 | 6 |
| ATOM | 367 | C | ARG | A | 47 | 31.816 | −3.283 | −3.103 | 1.00 | 25.85 | 6 |
| ATOM | 368 | O | ARG | A | 47 | 32.669 | −4.158 | −2.954 | 1.00 | 29.00 | 8 |
| ATOM | 369 | CB | ARG | A | 47 | 32.921 | −1.993 | −4.921 | 1.00 | 26.64 | 6 |
| ATOM | 370 | CG | ARG | A | 47 | 32.973 | −1.664 | −6.407 | 1.00 | 30.45 | 6 |
| ATOM | 371 | CD | ARG | A | 47 | 34.079 | −0.626 | −6.688 | 1.00 | 30.96 | 6 |
| ATOM | 372 | NE | ARG | A | 47 | 33.831 | −0.063 | −8.068 | 1.00 | 36.09 | 7 |
| ATOM | 373 | CZ | ARG | A | 47 | 34.612 | −0.526 | −9.051 | 1.00 | 37.23 | 6 |
| ATOM | 374 | NH1 | ARG | A | 47 | 35.552 | −1.422 | −8.779 | 1.00 | 37.53 | 7 |
| ATOM | 375 | NH2 | ARG | A | 47 | 34.458 | −0.076 | −10.277 | 1.00 | 38.83 | 7 |
| ATOM | 376 | N | ALA | A | 48 | 31.118 | −2.729 | −2.117 | 1.00 | 23.59 | 7 |
| ATOM | 377 | CA | ALA | A | 48 | 31.382 | −3.211 | −0.762 | 1.00 | 23.32 | 6 |
| ATOM | 378 | C | ALA | A | 48 | 30.099 | −3.421 | 0.008 | 1.00 | 23.85 | 6 |
| ATOM | 379 | O | ALA | A | 48 | 29.048 | −2.891 | −0.355 | 1.00 | 26.50 | 8 |
| ATOM | 380 | CB | ALA | A | 48 | 32.316 | −2.196 | −0.069 | 1.00 | 24.37 | 6 |
| ATOM | 381 | N | ASP | A | 49 | 30.163 | −4.115 | 1.146 | 1.00 | 22.20 | 7 |

TABLE 1-continued

| | | | | | | | | | | |
|---|---|---|---|---|---|---|---|---|---|---|
| ATOM | 382 | CA | ASP | A | 49 | 28.925 | −4.271 | 1.916 | 1.00 | 26.00 | 6 |
| ATOM | 383 | C | ASP | A | 49 | 28.562 | −3.133 | 2.803 | 1.00 | 26.80 | 6 |
| ATOM | 384 | O | ASP | A | 49 | 27.400 | −2.841 | 3.120 | 1.00 | 28.51 | 8 |
| ATOM | 385 | CB | ASP | A | 49 | 29.066 | −5.563 | 2.775 | 1.00 | 31.27 | 6 |
| ATOM | 386 | CG | ASP | A | 49 | 29.809 | −6.700 | 2.149 | 1.00 | 35.17 | 6 |
| ATOM | 387 | OD1 | ASP | A | 49 | 30.741 | −7.285 | 2.759 | 1.00 | 35.30 | 8 |
| ATOM | 388 | OD2 | ASP | A | 49 | 29.459 | −7.142 | 1.032 | 1.00 | 39.32 | 8 |
| ATOM | 389 | N | VAL | A | 50 | 29.551 | −2.305 | 3.185 | 1.00 | 21.71 | 7 |
| ATOM | 390 | CA | VAL | A | 50 | 29.379 | −1.186 | 4.072 | 1.00 | 24.23 | 6 |
| ATOM | 391 | C | VAL | A | 50 | 30.120 | 0.032 | 3.514 | 1.00 | 22.66 | 6 |
| ATOM | 392 | O | VAL | A | 50 | 31.259 | −0.150 | 3.088 | 1.00 | 23.46 | 8 |
| ATOM | 393 | CB | VAL | A | 50 | 29.980 | −1.492 | 5.460 | 1.00 | 28.04 | 6 |
| ATOM | 394 | CG1 | VAL | A | 50 | 29.862 | −0.274 | 6.353 | 1.00 | 30.12 | 6 |
| ATOM | 395 | CG2 | VAL | A | 50 | 29.310 | −2.723 | 6.087 | 1.00 | 31.57 | 6 |
| ATOM | 396 | N | VAL | A | 51 | 29.462 | 1.181 | 3.484 | 1.00 | 20.55 | 7 |
| ATOM | 397 | CA | VAL | A | 51 | 30.124 | 2.367 | 2.940 | 1.00 | 18.63 | 6 |
| ATOM | 398 | C | VAL | A | 51 | 30.317 | 3.377 | 4.038 | 1.00 | 19.83 | 6 |
| ATOM | 399 | O | VAL | A | 51 | 29.382 | 3.743 | 4.754 | 1.00 | 19.84 | 8 |
| ATOM | 400 | CB | VAL | A | 51 | 29.292 | 3.029 | 1.830 | 1.00 | 21.12 | 6 |
| ATOM | 401 | CG1 | VAL | A | 51 | 29.993 | 4.288 | 1.310 | 1.00 | 22.56 | 6 |
| ATOM | 402 | CG2 | VAL | A | 51 | 29.015 | 2.098 | 0.666 | 1.00 | 23.68 | 6 |
| ATOM | 403 | N | VAL | A | 52 | 31.527 | 3.878 | 4.198 | 1.00 | 18.34 | 7 |
| ATOM | 404 | CA | VAL | A | 52 | 31.884 | 4.890 | 5.151 | 1.00 | 18.76 | 6 |
| ATOM | 405 | C | VAL | A | 52 | 32.298 | 6.183 | 4.450 | 1.00 | 20.80 | 6 |
| ATOM | 406 | O | VAL | A | 52 | 33.147 | 6.104 | 3.559 | 1.00 | 21.14 | 8 |
| ATOM | 407 | CB | VAL | A | 52 | 33.088 | 4.473 | 6.034 | 1.00 | 20.37 | 6 |
| ATOM | 408 | CG1 | VAL | A | 52 | 33.539 | 5.585 | 6.978 | 1.00 | 19.87 | 6 |
| ATOM | 409 | CG2 | VAL | A | 52 | 32.719 | 3.217 | 6.820 | 1.00 | 21.14 | 6 |
| ATOM | 410 | N | VAL | A | 53 | 31.712 | 7.325 | 4.777 | 1.00 | 18.75 | 7 |
| ATOM | 411 | CA | VAL | A | 53 | 32.134 | 8.568 | 4.131 | 1.06 | 18.32 | 6 |
| ATOM | 412 | C | VAL | A | 53 | 32.759 | 9.411 | 5.215 | 1.00 | 18.55 | 6 |
| ATOM | 413 | O | VAL | A | 53 | 32.055 | 9.630 | 6.225 | 1.00 | 19.86 | 8 |
| ATOM | 414 | CB | VAL | A | 53 | 30.949 | 9.327 | 3.473 | 1.00 | 18.40 | 6 |
| ATOM | 415 | CG1 | VAL | A | 53 | 31.462 | 10.680 | 2.967 | 1.00 | 20.65 | 6 |
| ATOM | 416 | CG2 | VAL | A | 53 | 30.322 | 8.469 | 2.396 | 1.00 | 17.69 | 6 |
| ATOM | 417 | N | SER | A | 54 | 33.913 | 9.963 | 4.996 | 1.00 | 16.45 | 7 |
| ATOM | 418 | CA | SER | A | 54 | 34.482 | 10.911 | 5.946 | 1.00 | 20.30 | 6 |
| ATOM | 419 | C | SER | A | 54 | 34.280 | 12.349 | 5.478 | 1.00 | 21.22 | 6 |
| ATOM | 420 | O | SER | A | 54 | 34.281 | 12.545 | 4.254 | 1.00 | 18.83 | 8 |
| ATOM | 421 | CB | SER | A | 54 | 35.971 | 10.631 | 6.156 | 1.00 | 21.31 | 6 |
| ATOM | 422 | OG | SER | A | 54 | 36.695 | 10.788 | 4.949 | 1.00 | 21.56 | 8 |
| ATOM | 423 | N | ILE | A | 55 | 33.909 | 13.223 | 6.394 | 1.00 | 21.28 | 7 |
| ATOM | 424 | CA | ILE | A | 55 | 33.699 | 14.621 | 6.108 | 1.00 | 19.86 | 6 |
| ATOM | 425 | C | ILE | A | 55 | 34.649 | 15.356 | 7.100 | 1.00 | 20.76 | 6 |
| ATOM | 426 | O | ILE | A | 55 | 34.344 | 15.342 | 8.300 | 1.00 | 22.84 | 8 |
| ATOM | 427 | CB | ILE | A | 55 | 32.273 | 15.102 | 6.291 | 1.00 | 21.61 | 6 |
| ATOM | 428 | CG1 | ILE | A | 55 | 31.333 | 14.422 | 5.255 | 1.00 | 21.20 | 6 |
| ATOM | 429 | CG2 | ILE | A | 55 | 32.222 | 16.614 | 6.139 | 1.00 | 22.98 | 6 |
| ATOM | 430 | CD1 | ILE | A | 55 | 29.854 | 14.691 | 5.584 | 1.00 | 24.15 | 6 |
| ATOM | 431 | N | PHE | A | 56 | 35.723 | 15.883 | 6.577 | 1.00 | 17.70 | 7 |
| ATOM | 432 | CA | PHE | A | 56 | 36.699 | 16.589 | 7.404 | 1.00 | 18.93 | 6 |
| ATOM | 433 | C | PHE | A | 56 | 37.459 | 17.589 | 6.579 | 1.00 | 20.83 | 6 |
| ATOM | 434 | O | PHE | A | 56 | 38.263 | 17.314 | 5.680 | 1.00 | 21.50 | 8 |
| ATOM | 435 | CB | PHE | A | 56 | 37.671 | 15.557 | 8.060 | 1.00 | 17.73 | 6 |
| ATOM | 436 | CG | PHE | A | 56 | 38.721 | 16.209 | 8.950 | 1.00 | 19.66 | 6 |
| ATOM | 437 | CD1 | PHE | A | 56 | 38.297 | 16.881 | 10.098 | 1.00 | 20.08 | 6 |
| ATOM | 438 | CD2 | PHE | A | 56 | 40.059 | 16.144 | 8.616 | 1.00 | 20.24 | 6 |
| ATOM | 439 | CE1 | PHE | A | 56 | 39.261 | 17.479 | 10.909 | 1.00 | 19.99 | 6 |
| ATOM | 440 | CE2 | PHE | A | 56 | 41.029 | 16.743 | 9.433 | 1.00 | 20.35 | 6 |
| ATOM | 441 | CZ | PHE | A | 56 | 40.591 | 17.409 | 10.573 | 1.00 | 21.50 | 6 |
| ATOM | 442 | N | VAL | A | 57 | 37.284 | 18.883 | 6.949 | 1.00 | 21.60 | 7 |
| ATOM | 443 | CA | VAL | A | 57 | 38.009 | 19.978 | 6.334 | 1.00 | 23.17 | 6 |
| ATOM | 444 | C | VAL | A | 57 | 39.362 | 20.006 | 7.039 | 1.00 | 25.23 | 6 |
| ATOM | 445 | O | VAL | A | 57 | 39.473 | 20.469 | 8.172 | 1.00 | 24.88 | 8 |
| ATOM | 446 | CB | VAL | A | 57 | 37.247 | 21.325 | 6.458 | 1.00 | 23.78 | 6 |
| ATOM | 447 | CG1 | VAL | A | 57 | 38.051 | 22.403 | 5.763 | 1.00 | 24.08 | 6 |
| ATOM | 448 | CG2 | VAL | A | 57 | 35.853 | 21.178 | 5.874 | 1.00 | 23.56 | 6 |
| ATOM | 449 | N | ASN | A | 58 | 40.343 | 19.429 | 6.377 | 1.00 | 24.28 | 7 |
| ATOM | 450 | CA | ASN | A | 58 | 41.667 | 19.181 | 6.907 | 1.00 | 22.31 | 6 |
| ATOM | 451 | C | ASN | A | 58 | 42.545 | 20.385 | 6.858 | 1.00 | 23.05 | 6 |
| ATOM | 452 | O | ASN | A | 58 | 43.072 | 20.747 | 5.806 | 1.00 | 24.44 | 8 |
| ATOM | 453 | CB | ASN | A | 58 | 42.250 | 18.045 | 6.040 | 1.00 | 21.07 | 6 |
| ATOM | 454 | CG | ASN | A | 58 | 43.684 | 17.738 | 6.385 | 1.00 | 22.18 | 6 |
| ATOM | 455 | OD1 | ASN | A | 58 | 44.133 | 17.942 | 7.521 | 1.00 | 23.39 | 8 |
| ATOM | 456 | ND2 | ASN | A | 58 | 44.431 | 17.254 | 5.415 | 1.00 | 20.86 | 7 |
| ATOM | 457 | N | PRO | A | 59 | 42.863 | 21.002 | 8.000 | 1.00 | 24.30 | 7 |
| ATOM | 458 | CA | PRO | A | 59 | 43.727 | 22.187 | 7.996 | 1.00 | 25.81 | 6 |
| ATOM | 459 | C | PRO | A | 59 | 45.060 | 22.042 | 7.348 | 1.00 | 26.27 | 6 |
| ATOM | 460 | O | PRO | A | 59 | 45.679 | 22.957 | 6.784 | 1.00 | 27.28 | 8 |

TABLE 1-continued

| | | | | | | | | | | |
|---|---|---|---|---|---|---|---|---|---|---|
| ATOM | 461 | CB | PRO | A | 59 | 43.869 | 22.509 | 9.493 | 1.00 | 24.50 | 6 |
| ATOM | 462 | CG | PRO | A | 59 | 42.719 | 21.834 | 10.171 | 1.00 | 26.42 | 6 |
| ATOM | 463 | CD | PRO | A | 59 | 42.427 | 20.600 | 9.337 | 1.00 | 24.44 | 6 |
| ATOM | 464 | N | MET | A | 60 | 45.602 | 20.784 | 7.391 | 1.00 | 27.24 | 7 |
| ATOM | 465 | CA | MET | A | 60 | 46.952 | 20.529 | 6.856 | 1.00 | 28.64 | 6 |
| ATOM | 466 | C | MET | A | 60 | 47.008 | 20.656 | 5.361 | 1.00 | 31.51 | 6 |
| ATOM | 467 | O | MET | A | 60 | 48.101 | 20.868 | 4.822 | 1.00 | 31.68 | 8 |
| ATOM | 468 | CB | MET | A | 60 | 47.374 | 19.171 | 7.462 | 1.00 | 28.13 | 6 |
| ATOM | 469 | CG | MET | A | 60 | 48.810 | 18.867 | 7.264 | 1.00 | 32.00 | 6 |
| ATOM | 470 | SD | MET | A | 60 | 49.373 | 17.277 | 7.999 | 1.00 | 31.44 | 16 |
| ATOM | 471 | CE | MET | A | 60 | 50.665 | 17.068 | 6.848 | 1.00 | 31.98 | 6 |
| ATOM | 472 | N | GLN | A | 61 | 45.847 | 20.601 | 4.648 | 1.00 | 30.53 | 7 |
| ATOM | 473 | CA | GLN | A | 61 | 45.972 | 20.8D0 | 3.202 | 1.00 | 33.22 | 6 |
| ATOM | 474 | C | GLN | A | 61 | 45.492 | 22.174 | 2.780 | 1.00 | 35.82 | 6 |
| ATON | 475 | O | GLN | A | 61 | 45.183 | 22.463 | 1.611 | 1.00 | 39.20 | 8 |
| ATOM | 476 | CB | GLN | A | 61 | 45.264 | 19.567 | 2.566 | 1.00 | 31.83 | 6 |
| ATOM | 477 | CG | GLN | A | 61 | 43.747 | 19.745 | 2.433 | 1.00 | 29.02 | 6 |
| ATOM | 478 | CD | GLN | A | 61 | 43.189 | 18.320 | 2.094 | 1.00 | 28.13 | 6 |
| ATOM | 479 | OE1 | GLN | A | 61 | 43.302 | 17.290 | 2.731 | 1.00 | 24.18 | 8 |
| ATOM | 480 | NE2 | GLN | A | 61 | 42.486 | 18.326 | 0.963 | 1.00 | 28.14 | 7 |
| ATOM | 481 | N | PHE | A | 62 | 45.576 | 23.209 | 3.658 | 1.00 | 33.24 | 7 |
| ATOM | 482 | CA | PHE | A | 62 | 45.219 | 24.574 | 3.275 | 1.00 | 33.76 | 6 |
| ATOM | 483 | C | PHE | A | 62 | 46.434 | 25.502 | 3.390 | 1.00 | 35.21 | 6 |
| ATOM | 484 | O | PHE | A | 62 | 47.120 | 25.382 | 4.405 | 1.00 | 33.54 | 8 |
| ATOM | 485 | CB | PHE | A | 62 | 44.138 | 25.218 | 4.136 | 1.00 | 31.27 | 6 |
| ATOM | 486 | CG | PHE | A | 62 | 42.754 | 24.742 | 3.809 | 1.00 | 30.27 | 6 |
| ATOM | 487 | CD1 | PHE | A | 62 | 42.301 | 23.528 | 4.291 | 1.00 | 29.03 | 6 |
| ATOM | 488 | CD2 | PHE | A | 62 | 41.930 | 25.486 | 2.975 | 1.00 | 29.79 | 6 |
| ATOM | 489 | CE1 | PHE | A | 62 | 41.037 | 23.065 | 3.956 | 1.00 | 28.62 | 6 |
| ATOM | 490 | CE2 | PHE | A | 62 | 40.682 | 25.043 | 2.637 | 1.00 | 28.83 | 6 |
| ATOM | 491 | CZ | PHE | A | 62 | 40.223 | 23.823 | 3.112 | 1.00 | 28.44 | 6 |
| ATOM | 492 | N | ASP | A | 63 | 46.598 | 26.394 | 2.439 | 1.00 | 40.06 | 7 |
| ATOM | 493 | CA | ASP | A | 63 | 47.689 | 27.339 | 2.350 | 1.00 | 42.93 | 6 |
| ATOM | 494 | C | ASP | A | 63 | 47.787 | 28.342 | 3.485 | 1.00 | 44.06 | 6 |
| ATOM | 495 | O | ASP | A | 63 | 48.906 | 28.726 | 3.827 | 1.00 | 43.96 | 8 |
| ATOM | 496 | CB | ASP | A | 63 | 47.575 | 28.206 | 1.085 | 1.00 | 47.09 | 6 |
| ATOM | 497 | CG | ASP | A | 63 | 47.423 | 27.434 | −0.198 | 1.00 | 51.39 | 6 |
| ATOM | 498 | OD1 | ASP | A | 63 | 47.397 | 26.169 | −0.162 | 1.00 | 54.46 | 8 |
| ATOM | 499 | OD2 | ASP | A | 63 | 47.317 | 28.098 | −1.257 | 1.00 | 52.58 | 8 |
| ATOM | 500 | N | ARG | A | 64 | 46.669 | 28.845 | 3.990 | 1.00 | 43.31 | 7 |
| ATOM | 501 | CA | ARG | A | 64 | 46.717 | 29.795 | 5.095 | 1.00 | 44.44 | 6 |
| ATOM | 502 | C | ARG | A | 64 | 45.451 | 29.635 | 5.923 | 1.00 | 41.86 | 6 |
| ATOM | 503 | O | ARG | A | 64 | 44.424 | 29.201 | 5.428 | 1.00 | 38.21 | 8 |
| ATOM | 504 | CB | ARG | A | 64 | 46.808 | 31.240 | 4.660 | 1.00 | 47.55 | 6 |
| ATOM | 505 | CG | ARG | A | 64 | 48.161 | 31.803 | 4.295 | 1.00 | 52.46 | 6 |
| ATOM | 506 | CD | ARG | A | 64 | 47.938 | 33.125 | 3.520 | 1.00 | 55.58 | 6 |
| ATOM | 507 | NE | ARG | A | 64 | 47.067 | 32.875 | 2.441 | 1.00 | 58.62 | 7 |
| ATOM | 508 | CZ | ARG | A | 64 | 46.215 | 32.846 | 1.486 | 1.00 | 60.36 | 6 |
| ATOM | 509 | NH1 | ARG | A | 64 | 45.436 | 33.900 | 1.230 | 1.00 | 62.10 | 7 |
| ATOM | 510 | NH2 | ARG | A | 64 | 46.118 | 31.748 | 0.742 | 1.00 | 60.56 | 7 |
| ATOM | 511 | N | PRO | A | 65 | 45.506 | 30.080 | 7.169 | 1.00 | 41.07 | 7 |
| ATOM | 512 | CA | PRO | A | 65 | 44.375 | 30.002 | 8.068 | 1.00 | 41.23 | 6 |
| ATOM | 513 | C | PRG | A | 65 | 43.127 | 30.709 | 7.584 | 1.00 | 41.03 | 6 |
| ATOM | 514 | O | PRO | A | 65 | 42.000 | 30.258 | 7.847 | 1.00 | 39.31 | 8 |
| ATOM | 515 | CB | PRO | A | 65 | 44.911 | 30.622 | 9.356 | 1.00 | 42.70 | 6 |
| ATOM | 516 | CG | PRO | A | 65 | 46.398 | 30.368 | 9.281 | 1.00 | 43.00 | 6 |
| ATOM | 517 | CD | PRO | A | 65 | 46.709 | 30.642 | 7.823 | 1.00 | 42.34 | 6 |
| ATOM | 518 | N | GLU | A | 66 | 43.274 | 31.789 | 6.810 | 1.00 | 41.59 | 7 |
| ATOM | 519 | CA | GLU | A | 66 | 42.070 | 32.514 | 6.362 | 1.00 | 42.96 | 6 |
| ATOM | 520 | C | GLU | A | 66 | 41.347 | 31.757 | 5.259 | 1.00 | 40.61 | 6 |
| ATOM | 521 | O | GLU | A | 66 | 40.120 | 31.853 | 5.153 | 1.00 | 38.18 | 8 |
| ATOM | 522 | CB | GLU | A | 66 | 42.463 | 33.934 | 5.932 | 1.00 | 48.02 | 6 |
| ATOM | 523 | CG | GLU | A | 66 | 43.670 | 33.931 | 5.016 | 1.00 | 54.67 | 6 |
| ATOM | 524 | CD | GLU | A | 66 | 44.083 | 35.290 | 4.503 | 1.00 | 59.02 | 6 |
| ATOM | 525 | OE1 | GLU | A | 66 | 44.156 | 36.244 | 5.323 | 1.00 | 62.04 | 8 |
| ATOM | 526 | OE2 | GLU | A | 66 | 44.334 | 35.389 | 3.276 | 1.00 | 60.81 | 8 |
| ATOM | 527 | N | ASP | A | 67 | 42.108 | 30.969 | 4.481 | 1.00 | 38.50 | 7 |
| ATOM | 528 | CA | ASP | A | 67 | 41.447 | 30.178 | 3.439 | 1.00 | 37.14 | 6 |
| ATOM | 529 | C | ASP | A | 67 | 40.655 | 29.082 | 4.122 | 1.00 | 34.07 | 6 |
| ATOM | 530 | O | ASP | A | 67 | 39.529 | 28.761 | 3.792 | 1.00 | 30.58 | 8 |
| ATOM | 531 | CB | ASP | A | 67 | 42.413 | 29.550 | 2.449 | 1.00 | 41.16 | 6 |
| ATOM | 532 | CG | ASP | A | 67 | 43.388 | 30.540 | 1.846 | 1.00 | 44.61 | 6 |
| ATOM | 533 | OD1 | ASP | A | 67 | 43.068 | 31.742 | 1.741 | 1.00 | 46.57 | 8 |
| ATOM | 534 | OD2 | ASP | A | 67 | 44.487 | 30.073 | 1.482 | 1.00 | 47.46 | 8 |
| ATOM | 535 | N | LEU | A | 68 | 41.286 | 28.452 | 5.142 | 1.00 | 31.94 | 7 |
| ATOM | 536 | CA | LEU | A | 68 | 40.581 | 27.433 | 5.887 | 1.00 | 30.62 | 6 |
| ATOM | 537 | C | LEU | A | 68 | 39.303 | 27.981 | 6.477 | 1.00 | 30.54 | 6 |
| ATOM | 538 | O | LEU | A | 68 | 38.243 | 27.345 | 6.533 | 1.00 | 30.35 | 8 |
| ATOM | 539 | CB | LEU | A | 68 | 41.523 | 26.893 | 7.001 | 1.00 | 29.74 | 6 |

TABLE 1-continued

| ATOM | 540 | CG | LEU | A | 68 | 40.908 | 25.958 | 8.016 | 1.00 | 30.11 | 6 |
|---|---|---|---|---|---|---|---|---|---|---|---|
| ATOM | 541 | CD1 | LEU | A | 68 | 40.510 | 24.577 | 7.474 | 1.00 | 30.95 | 6 |
| ATOM | 542 | CD2 | LEU | A | 68 | 41.899 | 25.712 | 9.149 | 1.00 | 31.60 | 6 |
| ATOM | 543 | N | ALA | A | 69 | 39.345 | 29.225 | 7.012 | 1.00 | 29.90 | 7 |
| ATOM | 544 | CA | ALA | A | 69 | 38.146 | 29.740 | 7.662 | 1.00 | 32.87 | 6 |
| ATOM | 545 | C | ALA | A | 69 | 37.021 | 29.993 | 6.663 | 1.00 | 34.82 | 6 |
| ATOM | 546 | O | ALA | A | 69 | 35.855 | 29.854 | 7.018 | 1.00 | 35.59 | 8 |
| ATOM | 547 | CB | ALA | A | 69 | 38.487 | 31.030 | 8.425 | 1.00 | 32.66 | 6 |
| ATOM | 548 | N | ARG | A | 70 | 37.345 | 30.321 | 5.431 | 1.00 | 34.63 | 7 |
| ATOM | 549 | CA | ARG | A | 70 | 36.337 | 30.625 | 4.423 | 1.00 | 37.34 | 6 |
| ATOM | 550 | C | ARG | A | 70 | 35.777 | 29.350 | 3.803 | 1.00 | 36.74 | 6 |
| ATOM | 551 | O | ARG | A | 70 | 34.726 | 29.502 | 3.165 | 1.00 | 35.73 | 8 |
| ATOM | 552 | CB | ARG | A | 70 | 36.923 | 31.526 | 3.334 | 1.00 | 38.93 | 6 |
| ATOM | 553 | CG | ARG | A | 70 | 37.284 | 32.923 | 3.813 | 1.00 | 41.54 | 6 |
| ATOM | 554 | CD | ARG | A | 70 | 37.555 | 33.855 | 2.643 | 1.00 | 43.19 | 6 |
| ATOM | 555 | NE | ARG | A | 70 | 38.731 | 33.447 | 1.880 | 1.00 | 47.13 | 7 |
| ATOM | 556 | CZ | ARG | A | 70 | 39.977 | 33.789 | 2.190 | 1.00 | 47.82 | 6 |
| ATOM | 557 | NH1 | ARG | A | 70 | 40.213 | 34.544 | 3.252 | 1.00 | 51.37 | 7 |
| ATOM | 558 | NH2 | ARG | A | 70 | 40.984 | 33.371 | 1.435 | 1.00 | 48.98 | 7 |
| ATOM | 559 | N | TYR | A | 71 | 36.419 | 28.197 | 3.875 | 1.00 | 32.87 | 7 |
| ATOM | 560 | CA | TYR | A | 71 | 35.941 | 26.999 | 3.187 | 1.00 | 31.99 | 6 |
| ATOM | 561 | C | TYR | A | 71 | 34.522 | 26.700 | 3.578 | 1.00 | 30.54 | 6 |
| ATOM | 562 | O | TYR | A | 71 | 34.125 | 26.714 | 4.739 | 1.00 | 30.28 | 8 |
| ATOM | 563 | CB | TYR | A | 71 | 36.927 | 25.840 | 3.502 | 1.00 | 29.15 | 6 |
| ATOM | 564 | CG | TYR | A | 71 | 36.753 | 24.730 | 2.482 | 1.00 | 29.96 | 6 |
| ATOM | 565 | CD1 | TYR | A | 71 | 37.363 | 24.753 | 1.233 | 1.00 | 30.99 | 6 |
| ATOM | 566 | CD2 | TYR | A | 71 | 35.931 | 23.658 | 2.815 | 1.00 | 29.82 | 6 |
| ATOM | 567 | CE1 | TYR | A | 71 | 37.166 | 23.667 | 0.356 | 1.00 | 33.09 | 6 |
| ATOM | 568 | CE2 | TYR | A | 71 | 35.713 | 22.625 | 1.927 | 1.00 | 31.04 | 6 |
| ATOM | 569 | CZ | TYR | A | 71 | 36.332 | 22.650 | 0.702 | 1.00 | 31.47 | 6 |
| ATOM | 570 | OH | TYR | A | 71 | 36.163 | 21.647 | −0.214 | 1.00 | 34.74 | 8 |
| ATOM | 571 | N | PRO | A | 72 | 33.687 | 26.356 | 2.591 | 1.00 | 33.76 | 7 |
| ATOM | 572 | CA | PRO | A | 72 | 32.271 | 26.095 | 2.809 | 1.00 | 35.62 | 6 |
| ATOM | 573 | C | PRO | A | 72 | 31.987 | 24.932 | 3.712 | 1.00 | 36.23 | 6 |
| ATOM | 574 | O | PRO | A | 72 | 32.552 | 23.855 | 3.521 | 1.00 | 37.45 | 8 |
| ATOM | 575 | CB | PRO | A | 72 | 31.695 | 25.904 | 1.408 | 1.00 | 36.05 | 6 |
| ATOM | 576 | CG | PRO | A | 72 | 32.853 | 25.628 | 0.524 | 1.00 | 36.68 | 6 |
| ATOM | 577 | CD | PRO | A | 72 | 34.044 | 26.284 | 1.155 | 1.00 | 35.26 | 6 |
| ATOM | 578 | N | ARG | A | 73 | 31.114 | 25.089 | 4.705 | 1.00 | 35.24 | 7 |
| ATOM | 579 | CA | ARG | A | 73 | 30.752 | 23.978 | 5.580 | 1.00 | 35.44 | 6 |
| ATOM | 580 | C | ARG | A | 73 | 29.254 | 23.808 | 5.446 | 1.00 | 36.32 | 6 |
| ATOM | 581 | O | ARG | A | 73 | 28.544 | 24.827 | 5.569 | 1.00 | 36.64 | 8 |
| ATOM | 582 | CB | ARG | A | 73 | 31.232 | 24.214 | 7.012 | 1.00 | 37.96 | 6 |
| ATOM | 583 | CG | ARG | A | 73 | 32.778 | 24.055 | 6.985 | 1.00 | 38.27 | 6 |
| ATOM | 584 | CD | ARG | A | 73 | 33.433 | 24.599 | 8.180 | 1.00 | 39.86 | 6 |
| ATOM | 585 | NE | ARG | A | 73 | 34.854 | 24.417 | 8.347 | 1.00 | 37.69 | 7 |
| ATOM | 586 | CZ | ARG | A | 73 | 35.799 | 25.216 | 7.876 | 1.00 | 38.63 | 6 |
| ATOM | 587 | NH1 | ARG | A | 73 | 37.047 | 24.918 | 8.212 | 1.00 | 36.16 | 7 |
| ATOM | 588 | NH2 | ARG | A | 73 | 35.534 | 26.279 | 7.132 | 1.00 | 38.20 | 7 |
| ATOM | 589 | N | THR | A | 74 | 28.763 | 22.645 | 5.057 | 1.00 | 34.43 | 7 |
| ATOM | 590 | CA | THR | A | 74 | 27.358 | 22.363 | 4.859 | 1.00 | 34.04 | 6 |
| ATOM | 591 | C | THR | A | 74 | 27.033 | 20.953 | 5.354 | 1.00 | 32.80 | 6 |
| ATOM | 592 | O | THR | A | 74 | 26.421 | 20.107 | 4.689 | 1.00 | 31.08 | 8 |
| ATOM | 593 | CB | THR | A | 74 | 26.856 | 22.409 | 3.403 | 1.00 | 36.39 | 6 |
| ATOM | 594 | OG1 | THR | A | 74 | 27.567 | 21.394 | 2.652 | 1.00 | 38.24 | 8 |
| ATOM | 595 | CG2 | THR | A | 74 | 27.020 | 23.800 | 2.776 | 1.00 | 37.30 | 6 |
| ATOM | 596 | N | LEU | A | 75 | 27.405 | 20.714 | 6.616 | 1.00 | 31.90 | 7 |
| ATOM | 597 | CA | LEU | A | 75 | 27.234 | 19.377 | 7.168 | 1.00 | 30.80 | 6 |
| ATOM | 598 | C | LEU | A | 75 | 25.818 | 18.900 | 7.129 | 1.00 | 30.32 | 6 |
| ATOM | 599 | O | LEU | A | 75 | 25.595 | 17.716 | 6.815 | 1.00 | 29.31 | 8 |
| ATOM | 600 | CB | LEU | A | 75 | 27.865 | 19.401 | 8.605 | 1.00 | 32.17 | 6 |
| ATOM | 601 | CG | LEU | A | 75 | 27.986 | 18.001 | 9.219 | 1.00 | 33.15 | 6 |
| ATOM | 602 | CD1 | LEU | A | 75 | 28.985 | 17.154 | 8.420 | 1.00 | 33.59 | 6 |
| ATOM | 603 | CD2 | LEU | A | 75 | 28.401 | 18.093 | 10.663 | 1.00 | 32.87 | 6 |
| ATOM | 604 | N | GLN | A | 76 | 24.793 | 19.692 | 7.502 | 1.00 | 29.90 | 7 |
| ATOM | 605 | CA | GLN | A | 76 | 23.429 | 19.175 | 7.436 | 1.00 | 31.72 | 6 |
| ATOM | 606 | C | GLN | A | 76 | 23.040 | 18.695 | 6.054 | 1.00 | 28.82 | 6 |
| ATOM | 607 | O | GLN | A | 76 | 22.449 | 17.626 | 5.924 | 1.00 | 30.69 | 8 |
| ATOM | 608 | CB | GLN | A | 76 | 22.423 | 20.270 | 7.881 | 1.00 | 34.78 | 6 |
| ATOM | 609 | CG | GLN | A | 76 | 21.016 | 19.720 | 8.042 | 1.00 | 40.38 | 6 |
| ATOM | 610 | CD | GLN | A | 76 | 20.095 | 20.836 | 8.524 | 1.00 | 45.28 | 6 |
| ATOM | 611 | OE1 | GLN | A | 76 | 19.111 | 21.196 | 7.859 | 1.00 | 48.24 | 8 |
| ATOM | 612 | NE2 | GLN | A | 76 | 20.453 | 21.402 | 9.677 | 1.00 | 47.35 | 7 |
| ATOM | 613 | N | GLU | A | 77 | 23.274 | 19.493 | 5.023 | 1.00 | 26.49 | 7 |
| ATOM | 614 | CA | GLU | A | 77 | 22.946 | 19.111 | 3.656 | 1.00 | 27.35 | 6 |
| ATOM | 615 | C | GLU | A | 77 | 23.777 | 17.906 | 3.193 | 1.00 | 27.59 | 6 |
| ATOM | 616 | O | GLU | A | 77 | 23.263 | 17.064 | 2.463 | 1.00 | 27.03 | 8 |
| ATOM | 617 | CB | GLU | A | 77 | 23.227 | 20.280 | 2.718 | 1.00 | 28.83 | 6 |
| ATOM | 618 | CG | GLU | A | 77 | 22.722 | 19.997 | 1.302 | 1.00 | 32.09 | 6 |

TABLE 1-continued

| | | | | | | | | | | |
|---|---|---|---|---|---|---|---|---|---|---|
| ATOM | 619 | N | ASP | A | 78 | 25.048 | 17.886 | 3.617 | 1.00 | 26.66 | 7 |
| ATOM | 620 | CA | ASP | A | 78 | 25.875 | 16.706 | 3.239 | 1.00 | 26.91 | 6 |
| ATOM | 621 | C | ASP | A | 78 | 25.226 | 15.431 | 3.735 | 1.00 | 26.68 | 6 |
| ATOM | 622 | O | ASP | A | 78 | 25.042 | 14.448 | 3.018 | 1.00 | 24.38 | 8 |
| ATOM | 623 | CB | ASP | A | 78 | 27.275 | 16.820 | 3.796 | 1.00 | 25.18 | 6 |
| ATOM | 624 | CG | ASP | A | 78 | 28.116 | 17.931 | 3.332 | 1.00 | 28.50 | 6 |
| ATOM | 625 | OD1 | ASP | A | 78 | 27.681 | 18.573 | 2.312 | 1.00 | 28.92 | 8 |
| ATOM | 626 | OD2 | ASP | A | 78 | 29.179 | 18.397 | 3.774 | 1.00 | 29.90 | 8 |
| ATOM | 627 | N | CYS | A | 79 | 24.883 | 15.488 | 5.051 | 1.00 | 27.85 | 7 |
| ATOM | 628 | CA | CYS | A | 79 | 24.304 | 14.292 | 5.666 | 1.00 | 30.04 | 6 |
| ATOM | 629 | C | CYS | A | 79 | 22.949 | 13.894 | 5.111 | 1.00 | 29.71 | 6 |
| ATOM | 630 | O | CYS | A | 79 | 22.684 | 12.715 | 4.944 | 1.00 | 29.58 | 8 |
| ATOM | 631 | CB | CYS | A | 79 | 24.188 | 14.507 | 7.183 | 1.00 | 31.67 | 6 |
| ATOM | 632 | SG | CYS | A | 79 | 25.844 | 14.386 | 7.916 | 1.00 | 33.92 | 16 |
| ATOM | 633 | N | GLU | A | 80 | 22.134 | 14.874 | 4.734 | 1.00 | 30.93 | 7 |
| ATOM | 634 | CA | GLU | A | 80 | 20.899 | 14.555 | 4.007 | 1.00 | 32.01 | 6 |
| ATOM | 635 | C | GLU | A | 80 | 21.197 | 13.812 | 2.705 | 1.00 | 29.17 | 6 |
| ATOM | 636 | O | GLU | A | 80 | 20.524 | 12.822 | 2.413 | 1.00 | 29.08 | 8 |
| ATOM | 637 | CB | GLU | A | 80 | 20.135 | 15.852 | 3.756 | 1.00 | 36.34 | 6 |
| ATOM | 638 | CG | GLU | A | 80 | 19.379 | 16.349 | 4.985 | 1.00 | 43.73 | 6 |
| ATOM | 639 | CD | GLU | A | 80 | 18.700 | 17.700 | 4.818 | 1.00 | 48.86 | 6 |
| ATOM | 640 | OE1 | GLU | A | 80 | 18.432 | 18.156 | 3.670 | 1.00 | 51.62 | 8 |
| ATOM | 641 | OE2 | GLU | A | 80 | 18.442 | 18.338 | 5.884 | 1.00 | 51.33 | 8 |
| ATOM | 642 | N | LYS | A | 81 | 22.175 | 14.264 | 1.921 | 1.00 | 26.79 | 7 |
| ATOM | 643 | CA | LYS | A | 81 | 22.522 | 13.581 | 0.676 | 1.00 | 27.73 | 6 |
| ATOM | 644 | C | LYS | A | 81 | 23.067 | 12.161 | 0.921 | 1.00 | 27.62 | 6 |
| ATOM | 645 | O | LYS | A | 81 | 22.686 | 11.291 | 0.147 | 1.00 | 25.90 | 8 |
| ATOM | 646 | CB | LYS | A | 81 | 23.541 | 14.390 | −0.112 | 1.00 | 27.61 | 6 |
| ATOM | 647 | CG | LYS | A | 81 | 23.036 | 15.708 | −0.702 | 1.00 | 27.05 | 6 |
| ATOM | 648 | CD | LYS | A | 81 | 24.149 | 16.381 | −1.485 | 1.00 | 29.23 | 6 |
| ATOM | 649 | CE | LYS | A | 81 | 23.586 | 17.726 | −1.958 | 1.00 | 31.40 | 6 |
| ATOM | 650 | NZ | LYS | A | 81 | 24.290 | 18.189 | −3.180 | 1.00 | 33.21 | 7 |
| ATOM | 651 | N | LEU | A | 82 | 23.941 | 12.067 | 1.932 | 1.00 | 25.01 | 7 |
| ATOM | 652 | CA | LEU | A | 82 | 24.428 | 10.653 | 2.208 | 1.00 | 25.50 | 6 |
| ATOM | 653 | C | LEU | A | 82 | 23.359 | 9.729 | 2.719 | 1.00 | 24.46 | 6 |
| ATOM | 654 | O | LEU | A | 82 | 23.296 | 8.571 | 2.335 | 1.00 | 25.35 | 8 |
| ATOM | 655 | CB | LEU | A | 82 | 25.616 | 10.767 | 3.179 | 1.00 | 24.87 | 6 |
| ATOM | 656 | CG | LEU | A | 82 | 26.765 | 11.600 | 2.627 | 1.00 | 25.74 | 6 |
| ATOM | 657 | CD1 | LEU | A | 82 | 27.854 | 11.923 | 3.663 | 1.00 | 24.08 | 6 |
| ATOM | 658 | CD2 | LEU | A | 82 | 27.412 | 10.853 | 1.463 | 1.00 | 24.64 | 6 |
| ATOM | 659 | N | ASN | A | 83 | 22.437 | 10.262 | 3.549 | 1.00 | 27.59 | 7 |
| ATOM | 660 | CA | ASN | A | 83 | 21.352 | 9.467 | 4.081 | 1.00 | 29.62 | 6 |
| ATOM | 661 | C | ASN | A | 83 | 20.400 | 9.086 | 2.941 | 1.00 | 31.66 | 6 |
| ATOM | 662 | O | ASN | A | 83 | 20.066 | 7.899 | 2.966 | 1.00 | 31.60 | 8 |
| ATOM | 663 | CB | ASN | A | 83 | 20.649 | 10.212 | 5.205 | 1.00 | 32.77 | 6 |
| ATOM | 664 | CG | ASN | A | 83 | 19.718 | 9.324 | 6.010 | 1.00 | 37.49 | 6 |
| ATOM | 665 | OD1 | ASN | A | 83 | 18.788 | 9.898 | 6.588 | 1.00 | 42.54 | 8 |
| ATOM | 666 | ND2 | ASN | A | 83 | 19.899 | 8.019 | 6.093 | 1.00 | 37.69 | 7 |
| ATOM | 667 | N | LYS | A | 84 | 20.176 | 9.954 | 1.933 | 1.00 | 31.56 | 7 |
| ATOM | 668 | CA | LYS | A | 84 | 19.397 | 9.440 | 0.781 | 1.00 | 33.04 | 6 |
| ATOM | 669 | C | LYS | A | 84 | 20.155 | 8.440 | −0.069 | 1.00 | 34.14 | 6 |
| ATOM | 670 | O | LYS | A | 84 | 19.531 | 7.661 | −0.824 | 1.00 | 34.69 | 8 |
| ATOM | 671 | CB | LYS | A | 84 | 18.915 | 10.637 | −0.071 | 1.00 | 36.71 | 6 |
| ATOM | 672 | CG | LYS | A | 84 | 17.639 | 11.350 | 0.339 | 1.00 | 42.14 | 6 |
| ATOM | 673 | CD | LYS | A | 84 | 17.457 | 12.707 | −0.355 | 1.00 | 45.16 | 6 |
| ATOM | 674 | CE | LYS | A | 84 | 16.334 | 13.494 | 0.303 | 1.00 | 48.19 | 6 |
| ATOM | 675 | NZ | LYS | A | 84 | 16.337 | 14.928 | −0.105 | 1.00 | 50.51 | 7 |
| ATOM | 676 | N | ARG | A | 85 | 21.483 | 8.305 | 0.021 | 1.00 | 34.32 | 7 |
| ATOM | 677 | CA | ARG | A | 85 | 22.276 | 7.344 | −0.773 | 1.00 | 33.70 | 6 |
| ATOM | 678 | C | ARG | A | 85 | 22.620 | 6.057 | −0.050 | 1.00 | 34.60 | 6 |
| ATOM | 679 | O | ARG | A | 85 | 23.358 | 5.112 | −0.377 | 1.00 | 36.33 | 8 |
| ATOM | 680 | CB | ARG | A | 85 | 23.529 | 8.099 | −1.166 | 1.00 | 34.84 | 6 |
| ATOM | 681 | CG | ARG | A | 85 | 24.040 | 7.946 | −2.583 | 1.00 | 36.24 | 6 |
| ATOM | 682 | CD | ARG | A | 85 | 23.177 | 8.780 | −3.502 | 1.00 | 37.79 | 6 |
| ATOM | 683 | NE | ARG | A | 85 | 23.549 | 8.555 | −4.891 | 1.00 | 36.63 | 7 |
| ATOM | 684 | CZ | ARG | A | 85 | 23.122 | 9.364 | −5.853 | 1.00 | 37.76 | 6 |
| ATOM | 685 | NH1 | ARG | A | 85 | 22.368 | 10.397 | −5.507 | 1.00 | 38.88 | 7 |
| ATOM | 686 | NH2 | ARG | A | 85 | 23.473 | 9.117 | −7.100 | 1.00 | 37.39 | 7 |
| ATOM | 687 | N | LYS | A | 86 | 21.948 | 5.940 | 1.093 | 1.00 | 33.51 | 7 |
| ATOM | 688 | CA | LYS | A | 86 | 21.983 | 4.881 | 2.059 | 1.00 | 34.48 | 6 |
| ATOM | 689 | C | LYS | A | 86 | 23.404 | 4.563 | 2.503 | 1.00 | 32.25 | 6 |
| ATOM | 690 | O | LYS | A | 86 | 23.823 | 3.405 | 2.516 | 1.00 | 34.37 | 8 |
| ATOM | 691 | CB | LYS | A | 86 | 21.290 | 3.624 | 1.477 | 1.00 | 37.47 | 6 |
| ATOM | 692 | CG | LYS | A | 86 | 19.862 | 3.957 | 1.034 | 1.00 | 42.40 | 6 |
| ATON | 693 | CD | LYS | A | 86 | 18.990 | 4.373 | 2.205 | 1.00 | 46.88 | 6 |
| ATOM | 694 | CE | LYS | A | 86 | 18.857 | 3.256 | 3.233 | 1.00 | 50.03 | 6 |
| ATOM | 695 | NZ | LYS | A | 86 | 18.397 | 3.827 | 4.543 | 1.00 | 52.47 | 7 |
| ATOM | 696 | N | VAL | A | 87 | 24.138 | 5.595 | 2.885 | 1.00 | 29.97 | 7 |
| ATOM | 697 | CA | VAL | A | 87 | 25.490 | 5.405 | 3.428 | 1.00 | 26.05 | 6 |

TABLE 1-continued

| | | | | | | | | | | |
|---|---|---|---|---|---|---|---|---|---|---|
| ATOM | 698 | C | VAL | A | 87 | 25.390 | 4.849 | 4.829 | 1.00 | 28.43 | 6 |
| ATOM | 699 | O | VAL | A | 87 | 24.498 | 5.233 | 5.587 | 1.00 | 26.14 | 8 |
| ATOM | 700 | CB | VAL | A | 87 | 26.199 | 6.749 | 3.397 | 1.00 | 26.58 | 6 |
| ATOM | 701 | CG1 | VAL | A | 87 | 27.425 | 6.848 | 4.304 | 1.00 | 23.69 | 6 |
| ATOM | 702 | CG2 | VAL | A | 87 | 26.640 | 7.063 | 1.961 | 1.00 | 25.53 | 6 |
| ATOM | 703 | N | ASP | A | 88 | 26.274 | 3.947 | 5.231 | 1.00 | 25.06 | 7 |
| ATOM | 704 | CA | ASP | A | 88 | 26.163 | 3.320 | 6.552 | 1.00 | 27.11 | 6 |
| ATOM | 705 | C | ASP | A | 88 | 26.718 | 4.129 | 7.696 | 1.00 | 26.68 | 6 |
| ATOM | 706 | O | ASP | A | 88 | 26.108 | 4.221 | 8.763 | 1.00 | 27.00 | 8 |
| ATOM | 707 | CB | ASP | A | 88 | 26.899 | 1.986 | 6.461 | 1.00 | 29.00 | 6 |
| ATOM | 708 | CG | ASP | A | 88 | 26.332 | 1.114 | 5.377 | 1.00 | 31.90 | 6 |
| ATOM | 709 | OD1 | ASP | A | 88 | 25.301 | 0.444 | 5.714 | 1.00 | 34.25 | 8 |
| ATOM | 710 | OD2 | ASP | A | 88 | 26.819 | 1.060 | 4.237 | 1.00 | 30.16 | 8 |
| ATOM | 711 | N | LEU | A | 89 | 27.798 | 4.864 | 7.483 | 1.00 | 21.05 | 7 |
| ATOM | 712 | CA | LEU | A | 89 | 28.448 | 5.620 | 8.532 | 1.00 | 22.89 | 6 |
| ATOM | 713 | C | LEU | A | 89 | 29.085 | 6.879 | 7.997 | 1.00 | 25.24 | 6 |
| ATOM | 714 | O | LEU | A | 89 | 29.775 | 6.771 | 6.967 | 1.00 | 24.36 | 8 |
| ATOM | 715 | CB | LEU | A | 89 | 29.561 | 4.723 | 9.069 | 1.00 | 27.61 | 6 |
| ATOM | 716 | CG | LEU | A | 89 | 30.275 | 5.099 | 10.342 | 1.00 | 31.35 | 6 |
| ATOM | 717 | CD1 | LEU | A | 89 | 30.916 | 3.857 | 10.963 | 1.00 | 34.98 | 6 |
| ATOM | 718 | CD2 | LEU | A | 89 | 31.363 | 6.137 | 10.099 | 1.00 | 33.01 | 6 |
| ATOM | 719 | N | VAL | A | 90 | 28.910 | 7.987 | 8.677 | 1.00 | 22.49 | 7 |
| ATOM | 720 | CA | VAL | A | 90 | 29.577 | 9.200 | 8.296 | 1.00 | 23.34 | 6 |
| ATOM | 721 | C | VAL | A | 90 | 30.551 | 9.518 | 9.431 | 1.00 | 24.94 | 6 |
| ATOM | 722 | O | VAL | A | 90 | 30.041 | 9.581 | 10.575 | 1.00 | 25.44 | 8 |
| ATOM | 723 | CB | VAL | A | 90 | 28.602 | 10.366 | 8.153 | 1.00 | 21.61 | 6 |
| ATOM | 724 | CG1 | VAL | A | 90 | 29.294 | 11.692 | 7.966 | 1.00 | 23.24 | 6 |
| ATOM | 725 | CG2 | VAL | A | 90 | 27.695 | 10.065 | 6.945 | 1.00 | 24.01 | 6 |
| ATOM | 726 | N | PHE | A | 91 | 31.819 | 9.736 | 9.120 | 1.00 | 20.62 | 7 |
| ATOM | 727 | CA | PHE | A | 91 | 32.779 | 10.106 | 10.131 | 1.00 | 21.25 | 6 |
| ATOM | 728 | C | PHE | A | 91 | 33.008 | 11.589 | 9.966 | 1.00 | 22.65 | 6 |
| ATOM | 729 | O | PHE | A | 91 | 33.612 | 12.028 | 8.957 | 1.00 | 20.89 | 8 |
| ATOM | 730 | CB | PHE | A | 91 | 34.059 | 9.254 | 9.968 | 1.00 | 20.01 | 6 |
| ATOM | 731 | CG | PHE | A | 91 | 35.181 | 9.639 | 10.897 | 1.00 | 20.02 | 6 |
| ATOM | 732 | CD1 | PHE | A | 91 | 34.954 | 9.716 | 12.277 | 1.00 | 20.82 | 6 |
| ATOM | 733 | CD2 | PHE | A | 91 | 36.465 | 9.830 | 10.421 | 1.00 | 21.38 | 6 |
| ATOM | 734 | CE1 | PHE | A | 91 | 36.004 | 10.045 | 13.150 | 1.00 | 21.05 | 6 |
| ATOM | 735 | CE2 | PHE | A | 91 | 37.503 | 10.196 | 11.281 | 1.00 | 23.76 | 6 |
| ATOM | 736 | CZ | PHE | A | 91 | 37.261 | 10.233 | 12.631 | 1.00 | 21.99 | 6 |
| ATOM | 737 | N | ALA | A | 92 | 32.580 | 12.382 | 10.985 | 1.00 | 23.09 | 7 |
| ATOM | 738 | CA | ALA | A | 92 | 32.750 | 13.824 | 10.898 | 1.00 | 23.04 | 6 |
| ATOM | 739 | C | ALA | A | 92 | 33.406 | 14.387 | 12.142 | 1.00 | 24.15 | 6 |
| ATOM | 740 | O | ALA | A | 92 | 32.699 | 14.986 | 12.979 | 1.00 | 24.45 | 8 |
| ATOM | 741 | CB | ALA | A | 92 | 31.368 | 14.496 | 10.717 | 1.00 | 23.41 | 6 |
| ATOM | 742 | N | PRO | A | 93 | 34.701 | 14.252 | 12.284 | 1.00 | 23.10 | 7 |
| ATOM | 743 | CA | PRO | A | 93 | 35.387 | 14.638 | 13.507 | 1.00 | 21.87 | 6 |
| ATOM | 744 | C | PRO | A | 93 | 35.695 | 16.093 | 13.560 | 1.00 | 23.67 | 6 |
| ATOM | 745 | O | PRO | A | 93 | 35.740 | 16.790 | 12.510 | 1.00 | 24.71 | 8 |
| ATOM | 746 | CB | PRO | A | 93 | 36.687 | 13.798 | 13.426 | 1.00 | 21.94 | 6 |
| ATOM | 747 | CG | PRO | A | 93 | 37.002 | 13.904 | 11.930 | 1.00 | 23.58 | 6 |
| ATOM | 748 | CD | PRO | A | 93 | 35.643 | 13.553 | 11.336 | 1.00 | 21.29 | 6 |
| ATOM | 749 | N | SER | A | 94 | 35.940 | 16.664 | 14.752 | 1.00 | 23.63 | 7 |
| ATOM | 750 | CA | SER | A | 94 | 36.447 | 18.022 | 14.812 | 1.00 | 26.17 | 6 |
| ATOM | 751 | C | SER | A | 94 | 37.939 | 18.117 | 14.561 | 1.00 | 26.12 | 6 |
| ATOM | 752 | O | SER | A | 94 | 38.700 | 17.126 | 14.588 | 1.00 | 25.24 | 8 |
| ATOM | 753 | CB | SER | A | 94 | 36.151 | 18.617 | 16.207 | 1.00 | 26.90 | 6 |
| ATOM | 754 | OG | SER | A | 94 | 36.930 | 17.871 | 17.168 | 1.00 | 27.23 | 8 |
| ATOM | 755 | N | VAL | A | 95 | 38.487 | 19.308 | 14.308 | 1.00 | 25.69 | 7 |
| ATOM | 756 | CA | VAL | A | 95 | 39.900 | 19.519 | 14.115 | 1.00 | 25.50 | 6 |
| ATOM | 757 | C | VAL | A | 95 | 40.639 | 19.107 | 15.409 | 1.00 | 28.17 | 6 |
| ATOM | 758 | O | VAL | A | 95 | 41.692 | 18.475 | 15.307 | 1.00 | 27.54 | 8 |
| ATOM | 759 | CB | VAL | A | 95 | 40.319 | 20.963 | 13.788 | 1.00 | 27.40 | 6 |
| ATOM | 760 | CG1 | VAL | A | 95 | 41.808 | 21.236 | 13.929 | 1.00 | 27.91 | 6 |
| ATOM | 761 | CG2 | VAL | A | 95 | 39.873 | 21.263 | 12.346 | 1.00 | 26.36 | 6 |
| ATOM | 762 | N | LYS | A | 96 | 40.047 | 19.405 | 16.570 | 1.00 | 26.82 | 7 |
| ATOM | 763 | CA | LYS | A | 96 | 40.718 | 18.994 | 17.823 | 1.00 | 28.89 | 6 |
| ATOM | 764 | C | LYS | A | 96 | 40.773 | 17.474 | 17.962 | 1.00 | 28.61 | 6 |
| ATOM | 765 | O | LYS | A | 96 | 41.723 | 16.951 | 18.539 | 1.00 | 27.95 | 8 |
| ATOM | 766 | CB | LYS | A | 96 | 40.013 | 19.550 | 19.066 | 1.00 | 29.19 | 6 |
| ATOM | 767 | N | GLU | A | 97 | 39.756 | 16.765 | 17.486 | 1.00 | 28.36 | 7 |
| ATOM | 768 | CA | GLU | A | 97 | 39.748 | 15.295 | 17.583 | 1.00 | 29.80 | 6 |
| ATOM | 769 | C | GLU | A | 97 | 40.830 | 14.674 | 16.708 | 1.00 | 29.13 | 6 |
| ATOM | 770 | O | GLU | A | 97 | 41.565 | 13.752 | 17.126 | 1.00 | 29.24 | 8 |
| ATOM | 771 | CB | GLU | A | 97 | 38.365 | 14.782 | 17.214 | 1.00 | 29.05 | 6 |
| ATOM | 772 | CG | GLU | A | 97 | 38.194 | 13.265 | 17.303 | 1.00 | 28.83 | 6 |
| ATOM | 773 | CD | GLU | A | 97 | 38.133 | 12.796 | 18.762 | 1.00 | 30.81 | 6 |
| ATOM | 774 | OE1 | GLU | A | 97 | 38.046 | 13.687 | 19.649 | 1.00 | 32.00 | 8 |
| ATOM | 775 | OE2 | GLU | A | 97 | 38.132 | 11.592 | 19.080 | 1.00 | 28.32 | 8 |
| ATOM | 776 | N | ILE | A | 98 | 41.066 | 15.194 | 15.516 | 1.00 | 26.74 | 7 |

TABLE 1-continued

| | | | | | | | | | | |
|---|---|---|---|---|---|---|---|---|---|---|
| ATOM | 777 | CA | ILE | A | 98 | 42.110 | 14.673 | 14.641 | 1.00 | 24.88 | 6 |
| ATOM | 778 | C | ILE | A | 98 | 43.483 | 15.219 | 14.955 | 1.00 | 26.67 | 6 |
| ATOM | 779 | O | ILE | A | 98 | 44.485 | 14.459 | 14.852 | 1.00 | 24.09 | 8 |
| ATOM | 780 | CB | ILE | A | 98 | 41.817 | 14.972 | 13.147 | 1.00 | 23.79 | 6 |
| ATOM | 781 | CG1 | ILE | A | 98 | 40.483 | 14.337 | 12.789 | 1.00 | 22.35 | 6 |
| ATOM | 782 | CG2 | ILE | A | 98 | 42.971 | 14.486 | 12.252 | 1.00 | 22.39 | 6 |
| ATOM | 783 | CD1 | ILE | A | 98 | 40.431 | 12.804 | 12.865 | 1.00 | 24.57 | 6 |
| ATOM | 784 | N | TYR | A | 99 | 43.603 | 16.493 | 15.375 | 1.00 | 24.39 | 7 |
| ATOM | 785 | CA | TYR | A | 99 | 44.886 | 17.127 | 15.585 | 1.00 | 26.57 | 6 |
| ATOM | 786 | C | TYR | A | 99 | 44.917 | 17.788 | 16.978 | 1.00 | 26.98 | 6 |
| ATOM | 787 | O | TYR | A | 99 | 44.959 | 18.984 | 17.080 | 1.00 | 29.92 | 8 |
| ATOM | 788 | CB | TYR | A | 99 | 45.244 | 18.185 | 14.514 | 1.00 | 24.58 | 6 |
| ATOM | 789 | CG | TYR | A | 99 | 45.318 | 17.673 | 13.080 | 1.00 | 24.59 | 6 |
| ATOM | 790 | CD1 | TYR | A | 99 | 44.461 | 18.086 | 12.085 | 1.00 | 23.63 | 6 |
| ATOM | 791 | CD2 | TYR | A | 99 | 46.371 | 16.838 | 12.709 | 1.00 | 23.01 | 6 |
| ATOM | 792 | CE1 | TYR | A | 99 | 44.573 | 17.677 | 10.760 | 1.00 | 23.55 | 6 |
| ATOM | 793 | CE2 | TYR | A | 99 | 46.491 | 16.358 | 11.405 | 1.00 | 25.75 | 6 |
| ATOM | 794 | CZ | TYR | A | 99 | 45.593 | 16.773 | 10.447 | 1.00 | 24.33 | 6 |
| ATOM | 795 | OH | TYR | A | 99 | 45.814 | 16.340 | 9.160 | 1.00 | 22.62 | 8 |
| ATOM | 796 | N | PRO | A | 100 | 44.891 | 17.004 | 18.020 | 1.00 | 29.54 | 7 |
| ATOM | 797 | CA | PRO | A | 100 | 44.819 | 17.563 | 19.401 | 1.00 | 30.81 | 6 |
| ATOM | 798 | C | PRO | A | 100 | 46.024 | 18.411 | 19.723 | 1.00 | 33.04 | 6 |
| ATOM | 799 | O | PRO | A | 100 | 45.855 | 19.351 | 20.545 | 1.00 | 34.95 | 8 |
| ATOM | 800 | CB | PRO | A | 100 | 44.652 | 16.358 | 20.291 | 1.00 | 32.03 | 6 |
| ATOM | 801 | CG | PRO | A | 100 | 45.376 | 15.277 | 19.517 | 1.00 | 31.65 | 6 |
| ATOM | 802 | CD | PRO | A | 100 | 44.894 | 15.532 | 18.081 | 1.00 | 29.86 | 6 |
| ATOM | 803 | N | ASN | A | 101 | 47.177 | 18.234 | 19.116 | 1.00 | 30.09 | 7 |
| ATOM | 804 | CA | ASN | A | 101 | 48.364 | 19.030 | 19.406 | 1.00 | 29.38 | 6 |
| ATOM | 805 | C | ASN | A | 101 | 48.732 | 19.925 | 18.258 | 1.00 | 28.34 | 6 |
| ATOM | 806 | O | ASN | A | 101 | 49.831 | 20.474 | 18.133 | 1.00 | 29.73 | 8 |
| ATOM | 807 | CB | ASN | A | 101 | 49.573 | 18.111 | 19.726 | 1.00 | 32.63 | 6 |
| ATOM | 808 | CG | ASN | A | 101 | 49.136 | 17.044 | 20.693 | 1.00 | 32.29 | 6 |
| ATOM | 809 | OD1 | ASN | A | 101 | 49.095 | 15.839 | 20.358 | 1.00 | 35.88 | 8 |
| ATOM | 810 | ND2 | ASN | A | 101 | 48.725 | 17.480 | 21.868 | 1.00 | 33.54 | 7 |
| ATOM | 811 | N | GLY | A | 102 | 47.764 | 20.158 | 17.344 | 1.00 | 28.24 | 7 |
| ATOM | 812 | CA | GLY | A | 102 | 48.018 | 20.969 | 16.192 | 1.00 | 28.54 | 6 |
| ATOM | 813 | C | GLY | A | 102 | 48.572 | 20.122 | 15.054 | 1.00 | 28.73 | 6 |
| ATOM | 814 | O | GLY | A | 102 | 48.848 | 18.918 | 15.212 | 1.00 | 28.80 | 8 |
| ATOM | 815 | N | THR | A | 103 | 48.797 | 20.786 | 13.929 | 1.00 | 28.45 | 7 |
| ATOM | 816 | CA | THR | A | 103 | 49.271 | 20.035 | 12.755 | 1.00 | 27.44 | 6 |
| ATOM | 817 | C | THR | A | 103 | 50.751 | 20.121 | 12.584 | 1.00 | 27.75 | 6 |
| ATOM | 818 | O | THR | A | 103 | 51.419 | 19.270 | 11.979 | 1.00 | 28.24 | 8 |
| ATOM | 819 | CB | THR | A | 103 | 48.585 | 20.545 | 11.461 | 1.00 | 28.39 | 6 |
| ATOM | 820 | OG1 | THR | A | 103 | 49.011 | 21.911 | 11.287 | 1.00 | 29.31 | 8 |
| ATOM | 821 | CG2 | THR | A | 103 | 47.081 | 20.410 | 11.575 | 1.00 | 25.68 | 6 |
| ATOM | 822 | N | GLU | A | 104 | 51.410 | 21.114 | 13.189 | 1.00 | 26.94 | 7 |
| ATOM | 823 | CA | GLU | A | 104 | 52.843 | 21.274 | 12.953 | 1.00 | 30.65 | 6 |
| ATOM | 824 | C | GLU | A | 104 | 53.682 | 20.149 | 13.572 | 1.00 | 27.87 | 6 |
| ATOM | 825 | O | GLU | A | 104 | 54.755 | 19.902 | 13.010 | 1.00 | 30.98 | 8 |
| ATOM | 826 | CB | GLU | A | 104 | 53.353 | 22.617 | 13.515 | 1.00 | 34.13 | 6 |
| ATOM | 827 | CG | GLU | A | 104 | 52.613 | 23.746 | 12.784 | 1.00 | 40.22 | 6 |
| ATOM | 828 | CD | GLU | A | 104 | 51.319 | 24.211 | 13.411 | 1.00 | 44.21 | 6 |
| ATOM | 829 | OE1 | GLU | A | 104 | 50.583 | 23.551 | 14.187 | 1.00 | 42.68 | 8 |
| ATOM | 830 | OE2 | GLU | A | 104 | 50.972 | 25.409 | 13.090 | 1.00 | 48.99 | 8 |
| ATOM | 831 | N | THR | A | 105 | 53.210 | 19.618 | 14.686 | 1.00 | 24.87 | 7 |
| ATOM | 832 | CA | THR | A | 105 | 54.112 | 18.554 | 15.230 | 1.00 | 25.37 | 6 |
| ATOM | 833 | C | THR | A | 105 | 53.586 | 17.170 | 14.962 | 1.00 | 24.14 | 6 |
| ATOM | 834 | O | THR | A | 105 | 54.100 | 16.162 | 15.504 | 1.00 | 23.64 | 8 |
| ATOM | 835 | CB | THR | A | 105 | 54.301 | 18.763 | 16.735 | 1.00 | 24.29 | 6 |
| ATOM | 836 | OG1 | THR | A | 105 | 53.037 | 18.773 | 17.363 | 1.00 | 27.37 | 8 |
| ATOM | 837 | CG2 | THR | A | 105 | 55.020 | 20.098 | 16.999 | 1.00 | 27.01 | 6 |
| ATOM | 838 | N | HIS | A | 106 | 52.456 | 17.094 | 14.251 | 1.00 | 22.37 | 7 |
| ATOM | 839 | CA | HIS | A | 106 | 51.897 | 15.760 | 13.955 | 1.00 | 22.53 | 6 |
| ATOM | 840 | C | HIS | A | 106 | 52.748 | 15.031 | 12.927 | 1.00 | 20.08 | 6 |
| ATOM | 841 | O | HIS | A | 106 | 53.289 | 15.552 | 11.960 | 1.00 | 22.95 | 8 |
| ATOM | 842 | CB | HIS | A | 106 | 50.457 | 15.962 | 13.432 | 1.00 | 20.21 | 6 |
| ATOM | 843 | CG | HIS | A | 106 | 49.534 | 14.791 | 13.386 | 1.00 | 19.83 | 6 |
| ATOM | 844 | ND1 | HIS | A | 106 | 49.650 | 13.883 | 12.350 | 1.00 | 19.73 | 7 |
| ATOM | 845 | CD2 | HIS | A | 106 | 48.484 | 14.387 | 14.112 | 1.00 | 18.64 | 6 |
| ATOM | 846 | CE1 | HIS | A | 106 | 48.695 | 13.003 | 12.509 | 1.00 | 17.48 | 6 |
| ATOM | 847 | NE2 | HIS | A | 106 | 47.914 | 13.255 | 13.533 | 1.00 | 19.68 | 7 |
| ATOM | 848 | N | THR | A | 107 | 52.772 | 13.689 | 13.062 | 1.00 | 21.05 | 7 |
| ATOM | 849 | CA | THR | A | 107 | 53.466 | 12.840 | 12.117 | 1.00 | 20.53 | 6 |
| ATOM | 850 | C | THR | A | 107 | 52.946 | 13.066 | 10.697 | 1.00 | 20.02 | 6 |
| ATOM | 851 | O | THR | A | 107 | 51.730 | 13.301 | 10.684 | 1.00 | 20.34 | 8 |
| ATOM | 852 | CB | THR | A | 107 | 53.232 | 11.366 | 12.525 | 1.00 | 21.22 | 6 |
| ATOM | 853 | OG1 | THR | A | 107 | 53.808 | 11.185 | 13.848 | 1.00 | 22.21 | 8 |
| ATOM | 854 | CG2 | THR | A | 107 | 53.856 | 10.364 | 11.540 | 1.00 | 21.83 | 6 |
| ATOM | 855 | N | TYR | A | 108 | 53.769 | 13.113 | 9.699 | 1.00 | 20.01 | 7 |

TABLE 1-continued

| | | | | | | | | | | |
|---|---|---|---|---|---|---|---|---|---|---|
| ATOM | 856 | CA | TYR | A | 108 | 53.224 | 13.286 | 8.347 | 1.00 | 22.77 | 6 |
| ATOM | 857 | C | TYR | A | 108 | 53.796 | 12.231 | 7.405 | 1.00 | 21.91 | 6 |
| ATOM | 858 | O | TYR | A | 108 | 54.794 | 11.532 | 7.605 | 1.00 | 19.88 | 8 |
| ATOM | 859 | CB | TYR | A | 108 | 53.505 | 14.695 | 7.860 | 1.00 | 23.51 | 6 |
| ATOM | 860 | CG | TYR | A | 108 | 54.978 | 15.076 | 7.762 | 1.00 | 24.54 | 6 |
| ATOM | 861 | CD1 | TYR | A | 108 | 55.707 | 14.832 | 6.624 | 1.00 | 25.82 | 6 |
| ATOM | 862 | CD2 | TYR | A | 108 | 55.623 | 15.677 | 8.857 | 1.00 | 26.49 | 6 |
| ATOM | 863 | CE1 | TYR | A | 108 | 57.051 | 15.146 | 6.526 | 1.00 | 29.12 | 6 |
| ATOM | 864 | CE2 | TYR | A | 108 | 56.970 | 16.024 | 8.781 | 1.00 | 29.06 | 6 |
| ATOM | 865 | CZ | TYR | A | 108 | 57.664 | 15.733 | 7.631 | 1.00 | 29.44 | 6 |
| ATOM | 866 | OH | TYR | A | 108 | 58.995 | 16.072 | 7.478 | 1.00 | 32.47 | 8 |
| ATOM | 867 | N | VAL | A | 109 | 53.052 | 12.125 | 6.280 | 1.00 | 19.53 | 7 |
| ATOM | 868 | CA | VAL | A | 109 | 53.431 | 11.213 | 5.194 | 1.00 | 20.38 | 6 |
| ATOM | 869 | C | VAL | A | 109 | 53.653 | 12.022 | 3.954 | 1.00 | 24.73 | 6 |
| ATOM | 870 | O | VAL | A | 109 | 52.756 | 12.811 | 3.553 | 1.00 | 23.81 | 8 |
| ATOM | 871 | CB | VAL | A | 109 | 52.263 | 10.230 | 4.964 | 1.00 | 20.04 | 6 |
| ATOM | 872 | CG1 | VAL | A | 109 | 52.619 | 9.362 | 3.731 | 1.00 | 23.57 | 6 |
| ATOM | 873 | CG2 | VAL | A | 109 | 51.946 | 9.420 | 6.209 | 1.00 | 17.72 | 6 |
| ATOM | 874 | N | ASP | A | 110 | 54.753 | 11.885 | 3.237 | 1.00 | 25.18 | 7 |
| ATOM | 875 | CA | ASP | A | 110 | 55.054 | 12.663 | 2.047 | 1.00 | 28.26 | 6 |
| ATOM | 876 | C | ASP | A | 110 | 55.453 | 11.784 | 0.881 | 1.00 | 25.00 | 6 |
| ATOM | 877 | O | ASP | A | 110 | 56.220 | 10.815 | 1.006 | 1.00 | 23.50 | 8 |
| ATOM | 878 | CB | ASP | A | 110 | 56.199 | 13.596 | 2.383 | 1.00 | 34.46 | 6 |
| ATOM | 879 | CG | ASP | A | 110 | 56.031 | 15.027 | 1.970 | 1.00 | 42.11 | 6 |
| ATOM | 880 | OD1 | ASP | A | 110 | 56.945 | 15.774 | 2.403 | 1.00 | 48.30 | 8 |
| ATOM | 881 | OD2 | ASP | A | 110 | 55.098 | 15.496 | 1.290 | 1.00 | 46.79 | 8 |
| ATOM | 882 | N | VAL | A | 111 | 54.851 | 11.964 | −0.272 | 1.00 | 24.14 | 7 |
| ATOM | 883 | CA | VAL | A | 111 | 55.111 | 11.236 | −1.493 | 1.00 | 23.80 | 6 |
| ATOM | 884 | C | VAL | A | 111 | 56.023 | 12.085 | −2.363 | 1.00 | 24.56 | 6 |
| ATOM | 885 | O | VAL | A | 111 | 55.572 | 13.037 | −3.027 | 1.00 | 25.12 | 8 |
| ATOM | 886 | CB | VAL | A | 111 | 53.771 | 10.929 | −2.218 | 1.00 | 23.25 | 6 |
| ATOM | 887 | CG1 | VAL | A | 111 | 54.020 | 10.068 | −3.456 | 1.00 | 22.00 | 6 |
| ATOM | 888 | CG2 | VAL | A | 111 | 52.810 | 10.285 | −1.246 | 1.00 | 22.35 | 6 |
| ATOM | 889 | N | PRO | A | 112 | 57.278 | 11.687 | −2.453 | 1.00 | 26.28 | 7 |
| ATOM | 890 | CA | PRO | A | 112 | 58.274 | 12.438 | −3.222 | 1.00 | 27.97 | 6 |
| ATOM | 891 | C | PRO | A | 112 | 57.906 | 12.619 | −4.650 | 1.00 | 30.72 | 6 |
| ATOM | 892 | O | PRO | A | 112 | 57.272 | 11.711 | −5.253 | 1.00 | 30.37 | 8 |
| ATOM | 893 | CB | PRO | A | 112 | 59.532 | 11.573 | −3.106 | 1.00 | 27.29 | 6 |
| ATOM | 894 | CG | PRO | A | 112 | 59.413 | 10.926 | −1.769 | 1.00 | 27.60 | 6 |
| ATOM | 895 | CD | PRO | A | 112 | 57.905 | 10.536 | −1.762 | 1.00 | 24.64 | 6 |
| ATOM | 896 | N | GLY | A | 113 | 58.211 | 13.800 | −5.209 | 1.00 | 30.66 | 7 |
| ATOM | 897 | CA | GLY | A | 113 | 57.940 | 14.000 | −6.614 | 1.00 | 32.72 | 6 |
| ATOM | 898 | C | GLY | A | 113 | 56.543 | 14.464 | −6.926 | 1.00 | 31.39 | 6 |
| ATOM | 899 | O | GLY | A | 113 | 56.346 | 15.614 | −7.280 | 1.00 | 30.61 | 8 |
| ATOM | 900 | N | LEU | A | 114 | 55.558 | 13.575 | −6.772 | 1.00 | 27.67 | 7 |
| ATOM | 901 | CA | LEU | A | 114 | 54.192 | 13.922 | −7.023 | 1.00 | 28.50 | 6 |
| ATOM | 902 | C | LEU | A | 114 | 53.677 | 15.086 | −6.186 | 1.00 | 29.37 | 6 |
| ATOM | 903 | O | LEU | A | 114 | 52.810 | 15.829 | −6.657 | 1.00 | 33.05 | 8 |
| ATOM | 904 | CB | LEU | A | 114 | 53.283 | 12.710 | −6.702 | 1.00 | 29.66 | 6 |
| ATOM | 905 | CG | LEU | A | 114 | 53.515 | 11.551 | −7.669 | 1.00 | 31.75 | 6 |
| ATOM | 906 | CD1 | LEU | A | 114 | 52.703 | 10.351 | −7.233 | 1.00 | 31.73 | 6 |
| ATOM | 907 | CD2 | LEU | A | 114 | 53.134 | 11.977 | −9.059 | 1.00 | 35.50 | 6 |
| ATOM | 908 | N | SER | A | 115 | 54.161 | 15.180 | −4.965 | 1.00 | 26.50 | 7 |
| ATOM | 909 | CA | SER | A | 115 | 53.664 | 16.206 | −4.063 | 1.00 | 27.52 | 6 |
| ATOM | 910 | C | SER | A | 115 | 54.245 | 17.582 | −4.400 | 1.00 | 30.00 | 6 |
| ATOM | 911 | O | SER | A | 115 | 53.590 | 18.536 | −3.932 | 1.00 | 28.18 | 8 |
| ATOM | 912 | CB | SER | A | 115 | 53.978 | 15.885 | −2.599 | 1.00 | 25.46 | 6 |
| ATOM | 913 | OG | SER | A | 115 | 55.407 | 15.846 | −2.464 | 1.00 | 30.73 | 8 |
| ATOM | 914 | N | THR | A | 116 | 55.312 | 17.617 | −5.177 | 1.00 | 30.25 | 7 |
| ATOM | 915 | CA | THR | A | 116 | 55.884 | 18.969 | −5.426 | 1.00 | 32.64 | 6 |
| ATOM | 916 | C | THR | A | 116 | 55.854 | 19.345 | −6.870 | 1.00 | 33.28 | 6 |
| ATOM | 917 | O | THR | A | 116 | 56.516 | 20.337 | −7.260 | 1.00 | 37.48 | 8 |
| ATOM | 918 | CB | THR | A | 116 | 57.318 | 19.018 | −4.839 | 1.00 | 31.68 | 6 |
| ATOM | 919 | OG1 | THR | A | 116 | 58.066 | 17.923 | −5.419 | 1.00 | 33.81 | 8 |
| ATOM | 920 | CG2 | THR | A | 116 | 57.348 | 18.863 | −3.344 | 1.00 | 30.91 | 6 |
| ATOM | 921 | N | MET | A | 117 | 55.075 | 18.691 | −7.725 | 1.00 | 34.70 | 7 |
| ATOM | 922 | CA | MET | A | 117 | 54.978 | 19.104 | −9.116 | 1.00 | 36.76 | 6 |
| ATOM | 923 | C | MET | A | 117 | 53.599 | 19.679 | −9.408 | 1.00 | 35.12 | 6 |
| ATOM | 924 | O | MET | A | 117 | 52.722 | 19.561 | −8.569 | 1.00 | 34.04 | 8 |
| ATOM | 925 | CB | MET | A | 117 | 55.258 | 17.952 | −10.067 | 1.00 | 38.70 | 6 |
| ATOM | 926 | CG | MET | A | 117 | 54.494 | 16.690 | −9.707 | 1.00 | 41.51 | 6 |
| ATOM | 927 | SD | MET | A | 117 | 55.327 | 15.244 | −10.403 | 1.00 | 45.13 | 16 |
| ATOM | 928 | CE | MET | A | 117 | 55.643 | 15.848 | −12.065 | 1.00 | 43.90 | 6 |
| ATOM | 929 | N | LEU | A | 118 | 53.449 | 20.272 | −10.578 | 1.00 | 35.18 | 7 |
| ATOM | 930 | CA | LEU | A | 118 | 52.173 | 20.846 | −10.995 | 1.00 | 36.73 | 6 |
| ATOM | 931 | C | LEU | A | 118 | 51.570 | 21.660 | −9.877 | 1.00 | 36.48 | 6 |
| ATOM | 932 | O | LEU | A | 118 | 52.236 | 22.552 | −9.330 | 1.00 | 36.60 | 8 |
| ATOM | 933 | CB | LEU | A | 118 | 51.252 | 19.706 | −11.478 | 1.00 | 38.22 | 6 |
| ATOM | 934 | CG | LEU | A | 118 | 51.872 | 18.829 | −12.571 | 1.00 | 39.36 | 6 |

TABLE 1-continued

| | | | | | | | | | | |
|---|---|---|---|---|---|---|---|---|---|---|
| ATOM | 935 | CD1 | LEU | A | 118 | 51.001 | 17.679 | −13.051 | 1.00 | 41.36 | 6 |
| ATOM | 936 | CD2 | LEU | A | 118 | 52.194 | 19.710 | −13.783 | 1.00 | 41.80 | 6 |
| ATOM | 937 | N | GLU | A | 119 | 50.329 | 21.339 | −9.481 | 1.00 | 38.80 | 7 |
| ATOM | 938 | CA | GLU | A | 119 | 49.645 | 22.049 | −8.411 | 1.00 | 37.83 | 6 |
| ATOM | 939 | C | GLU | A | 119 | 50.401 | 22.088 | −7.102 | 1.00 | 38.27 | 6 |
| ATOM | 940 | O | GLU | A | 119 | 50.416 | 23.101 | −6.393 | 1.00 | 38.36 | 8 |
| ATOM | 941 | CB | GLU | A | 119 | 48.255 | 21.394 | −8.141 | 1.00 | 41.10 | 6 |
| ATOM | 942 | CG | GLU | A | 119 | 47.470 | 22.109 | −7.049 | 1.00 | 41.69 | 6 |
| ATOM | 943 | CD | GLU | A | 119 | 46.082 | 21.559 | −6.784 | 1.00 | 44.93 | 6 |
| ATOM | 944 | OE1 | GLU | A | 119 | 45.654 | 20.593 | −7.453 | 1.00 | 40.85 | 8 |
| ATOM | 945 | OE2 | GLU | A | 119 | 45.379 | 22.098 | −5.892 | 1.00 | 45.21 | 8 |
| ATOM | 946 | N | GLY | A | 120 | 51.165 | 21.031 | −6.805 | 1.00 | 35.61 | 7 |
| ATOM | 947 | CA | GLY | A | 120 | 51.945 | 20.951 | −5.595 | 1.00 | 33.60 | 6 |
| ATOM | 948 | C | GLY | A | 120 | 53.033 | 22.013 | −5.540 | 1.00 | 34.42 | 6 |
| ATOM | 949 | O | GLY | A | 120 | 53.390 | 22.405 | −4.437 | 1.00 | 36.33 | 8 |
| ATOM | 950 | N | ALA | A | 121 | 53.588 | 22.394 | −6.677 | 1.00 | 35.01 | 7 |
| ATOM | 951 | CA | ALA | A | 121 | 54.622 | 23.437 | −6.741 | 1.00 | 35.93 | 6 |
| ATOM | 952 | C | ALA | A | 121 | 54.069 | 24.789 | −6.295 | 1.00 | 39.30 | 6 |
| ATOM | 953 | O | ALA | A | 121 | 54.752 | 25.536 | −5.588 | 1.00 | 40.98 | 8 |
| ATOM | 954 | CB | ALA | A | 121 | 55.189 | 23.547 | −8.150 | 1.00 | 32.29 | 6 |
| ATOM | 955 | N | SER | A | 122 | 52.818 | 25.124 | −6.644 | 1.00 | 41.40 | 7 |
| ATOM | 956 | CA | SER | A | 122 | 52.261 | 26.415 | −6.226 | 1.00 | 44.40 | 6 |
| ATOM | 957 | C | SER | A | 122 | 51.626 | 26.354 | −4.849 | 1.00 | 45.24 | 6 |
| ATOM | 958 | O | SER | A | 122 | 51.056 | 27.328 | −4.339 | 1.00 | 44.99 | 8 |
| ATOM | 959 | CB | SER | A | 122 | 51.226 | 26.909 | −7.241 | 1.00 | 45.02 | 6 |
| ATOM | 960 | OG | SER | A | 122 | 50.178 | 25.972 | −7.432 | 1.00 | 46.98 | 8 |
| ATOM | 961 | N | ARG | A | 123 | 51.634 | 25.169 | −4.197 | 1.00 | 45.65 | 7 |
| ATOM | 962 | CA | ARG | A | 123 | 51.045 | 24.991 | −2.876 | 1.00 | 44.81 | 6 |
| ATOM | 963 | C | ARG | A | 123 | 51.908 | 24.083 | −2.006 | 1.00 | 44.93 | 6 |
| ATOM | 964 | O | ARG | A | 123 | 51.557 | 22.916 | −1.788 | 1.00 | 44.88 | 8 |
| ATOM | 965 | CB | ARG | A | 123 | 49.631 | 24.419 | −2.992 | 1.00 | 45.81 | 6 |
| ATOM | 966 | CG | ARG | A | 123 | 48.629 | 25.367 | −3.630 | 1.00 | 46.85 | 6 |
| ATOM | 967 | CD | ARG | A | 123 | 47.248 | 24.736 | −3.714 | 1.00 | 50.24 | 6 |
| ATOM | 968 | NE | ARG | A | 123 | 46.466 | 24.971 | −2.504 | 1.00 | 52.21 | 7 |
| ATOM | 969 | CZ | ARG | A | 123 | 45.271 | 24.437 | −2.271 | 1.00 | 52.64 | 6 |
| ATOM | 970 | NH1 | ARG | A | 123 | 44.718 | 23.633 | −3.169 | 1.00 | 52.96 | 7 |
| ATOM | 971 | NH2 | ARG | A | 123 | 44.633 | 24.708 | −1.141 | 1.00 | 53.34 | 7 |
| ATOM | 972 | N | PRO | A | 124 | 52.717 | 24.827 | −1.604 | 1.00 | 44.27 | 7 |
| ATOM | 973 | CA | PRO | A | 124 | 53.669 | 24.219 | −0.725 | 1.00 | 43.54 | 6 |
| ATOM | 974 | C | PRO | A | 124 | 53.075 | 23.501 | 0.473 | 1.00 | 43.43 | 6 |
| ATOM | 975 | O | PRO | A | 124 | 52.427 | 24.264 | 1.223 | 1.00 | 44.21 | 8 |
| ATOM | 976 | CB | PRO | A | 124 | 54.534 | 25.391 | −0.224 | 1.00 | 43.61 | 6 |
| ATOM | 977 | CG | PRO | A | 124 | 54.396 | 26.439 | −1.257 | 1.00 | 44.17 | 6 |
| ATOM | 978 | CD | PRO | A | 124 | 52.971 | 26.302 | −1.746 | 1.00 | 44.92 | 6 |
| ATOM | 979 | N | GLY | A | 125 | 53.248 | 21.897 | 0.840 | 1.00 | 39.19 | 7 |
| ATOM | 980 | CA | GLY | A | 125 | 52.585 | 21.453 | 2.061 | 1.00 | 34.50 | 6 |
| ATOM | 981 | C | GLY | A | 125 | 51.230 | 20.789 | 1.809 | 1.00 | 32.64 | 6 |
| ATOM | 982 | O | GLY | A | 125 | 50.689 | 20.112 | 2.669 | 1.00 | 32.97 | 8 |
| ATOM | 983 | N | HIS | A | 126 | 50.594 | 21.246 | 0.725 | 1.00 | 29.92 | 7 |
| ATOM | 984 | CA | HIS | A | 126 | 49.259 | 20.776 | 0.381 | 1.00 | 29.41 | 6 |
| ATOM | 985 | C | HIS | A | 126 | 49.186 | 19.276 | 0.256 | 1.00 | 29.27 | 6 |
| ATOM | 986 | O | HIS | A | 126 | 48.500 | 18.637 | 1.071 | 1.00 | 29.29 | 8 |
| ATOM | 987 | CB | HIS | A | 126 | 48.782 | 21.451 | −0.934 | 1.00 | 29.82 | 6 |
| ATOM | 988 | CG | HIS | A | 126 | 47.453 | 20.951 | −1.417 | 1.00 | 30.87 | 6 |
| ATOM | 989 | ND1 | HIS | A | 126 | 46.254 | 21.263 | −0.790 | 1.00 | 32.42 | 7 |
| ATOM | 990 | CD2 | HIS | A | 126 | 47.135 | 20.149 | −2.435 | 1.00 | 30.12 | 6 |
| ATOM | 991 | CE1 | HIS | A | 126 | 45.274 | 20.643 | −1.373 | 1.00 | 30.81 | 6 |
| ATOM | 992 | NE2 | HIS | A | 126 | 45.765 | 19.970 | −2.384 | 1.00 | 33.87 | 7 |
| ATOM | 993 | N | PHE | A | 127 | 49.882 | 18.662 | −0.698 | 1.00 | 25.60 | 7 |
| ATOM | 994 | CA | PHE | A | 127 | 49.770 | 17.232 | −0.922 | 1.00 | 25.14 | 6 |
| ATOM | 995 | C | PHE | A | 127 | 50.320 | 16.367 | 0.221 | 1.00 | 24.25 | 6 |
| ATOM | 996 | O | PHE | A | 127 | 49.733 | 15.332 | 0.490 | 1.00 | 23.64 | 8 |
| ATOM | 997 | CB | PHE | A | 127 | 50.454 | 16.851 | −2.264 | 1.00 | 25.66 | 6 |
| ATOM | 998 | CG | PHE | A | 127 | 49.518 | 17.250 | −3.398 | 1.00 | 24.51 | 6 |
| ATOM | 999 | CD1 | PHE | A | 127 | 49.899 | 18.239 | −4.302 | 1.00 | 25.76 | 6 |
| ATOM | 1000 | CD2 | PHE | A | 127 | 48.239 | 16.734 | −3.509 | 1.00 | 26.77 | 6 |
| ATOM | 1001 | CE1 | PHE | A | 127 | 49.026 | 18.618 | −5.301 | 1.00 | 27.57 | 6 |
| ATOM | 1002 | CE2 | PHE | A | 127 | 47.381 | 17.086 | −4.518 | 1.00 | 27.77 | 6 |
| ATOM | 1003 | CZ | PHE | A | 127 | 47.749 | 18.072 | −5.444 | 1.00 | 28.09 | 6 |
| ATOM | 1004 | N | ARG | A | 128 | 51.218 | 16.966 | 1.006 | 1.00 | 24.68 | 7 |
| ATOM | 1005 | CA | ARG | A | 128 | 51.645 | 16.377 | 2.261 | 1.00 | 23.44 | 6 |
| ATOM | 1006 | C | ARG | A | 128 | 50.408 | 16.283 | 3.155 | 1.00 | 21.06 | 6 |
| ATOM | 1007 | O | ARG | A | 128 | 50.190 | 15.299 | 3.852 | 1.00 | 22.12 | 8 |
| ATOM | 1008 | CB | ARG | A | 128 | 52.743 | 17.172 | 2.975 | 1.00 | 26.43 | 6 |
| ATOM | 1009 | CG | ARG | A | 128 | 53.051 | 16.644 | 4.371 | 1.00 | 28.47 | 6 |
| ATOM | 1010 | CD | ARG | A | 128 | 54.116 | 17.508 | 5.117 | 1.00 | 27.86 | 6 |
| ATOM | 1011 | NE | ARG | A | 128 | 55.345 | 17.336 | 4.336 | 1.00 | 31.98 | 7 |
| ATOM | 1012 | CZ | ARG | A | 128 | 56.526 | 17.872 | 4.699 | 1.00 | 36.93 | 6 |
| ATOM | 1013 | NH1 | ARG | A | 128 | 56.631 | 18.561 | 5.825 | 1.00 | 34.28 | 7 |

TABLE 1-continued

| ATOM | 1014 | NH2 | ARG | A | 128 | 57.586 | 17.630 | 3.912 | 1.00 | 38.42 | 7 |
|------|------|-----|-----|---|-----|--------|--------|-------|------|-------|---|
| ATOM | 1015 | N | GLY | A | 129 | 49.588 | 17.337 | 3.161 | 1.00 | 21.21 | 7 |
| ATOM | 1016 | CA | GLY | A | 129 | 48.391 | 17.274 | 4.018 | 1.00 | 21.01 | 6 |
| ATOM | 1017 | C | GLY | A | 129 | 47.468 | 16.152 | 3.484 | 1.00 | 21.29 | 6 |
| ATOM | 1018 | O | GLY | A | 129 | 46.782 | 15.601 | 4.321 | 1.00 | 21.30 | 8 |
| ATOM | 1019 | N | VAL | A | 130 | 47.317 | 16.084 | 2.166 | 1.00 | 21.70 | 7 |
| ATOM | 1020 | CA | VAL | A | 130 | 46.441 | 15.028 | 1.634 | 1.00 | 21.40 | 6 |
| ATOM | 1021 | C | VAL | A | 130 | 46.908 | 13.587 | 1.970 | 1.00 | 20.52 | 6 |
| ATOM | 1022 | O | VAL | A | 130 | 46.140 | 12.807 | 2.542 | 1.00 | 19.78 | 8 |
| ATOM | 1023 | CB | VAL | A | 130 | 46.256 | 15.179 | 0.107 | 1.00 | 22.23 | 6 |
| ATOM | 1024 | CG1 | VAL | A | 130 | 45.496 | 13.992 | −0.479 | 1.00 | 22.29 | 6 |
| ATOM | 1025 | CG2 | VAL | A | 130 | 45.587 | 16.550 | −0.161 | 1.00 | 22.53 | 6 |
| ATOM | 1026 | N | SER | A | 131 | 48.184 | 13.286 | 1.709 | 1.00 | 22.62 | 7 |
| ATOM | 1027 | CA | SER | A | 131 | 48.669 | 11.951 | 2.032 | 1.00 | 22.39 | 6 |
| ATOM | 1028 | C | SER | A | 131 | 48.617 | 11.685 | 3.541 | 1.00 | 20.26 | 6 |
| ATOM | 1029 | O | SER | A | 131 | 48.328 | 10.545 | 3.924 | 1.00 | 22.14 | 8 |
| ATOM | 1030 | CB | SER | A | 131 | 50.095 | 11.641 | 1.549 | 1.00 | 22.52 | 6 |
| ATOM | 1031 | OG | SER | A | 131 | 50.924 | 12.773 | 1.784 | 1.00 | 24.21 | 8 |
| ATOM | 1032 | N | THR | A | 132 | 48.883 | 12.678 | 4.393 | 1.00 | 17.99 | 7 |
| ATOM | 1033 | CA | THR | A | 132 | 48.785 | 12.419 | 5.812 | 1.00 | 17.46 | 6 |
| ATOM | 1034 | C | THR | A | 132 | 47.375 | 12.119 | 6.296 | 1.00 | 17.48 | 6 |
| ATOM | 1035 | O | THR | A | 132 | 47.180 | 11.104 | 7.013 | 1.00 | 17.25 | 8 |
| ATOM | 1036 | CB | THR | A | 132 | 49.386 | 13.645 | 6.619 | 1.00 | 17.40 | 6 |
| ATOM | 1037 | OG1 | THR | A | 132 | 50.726 | 13.812 | 6.145 | 1.00 | 20.91 | 8 |
| ATOM | 1038 | CG2 | THR | A | 132 | 49.302 | 13.374 | 8.096 | 1.00 | 18.97 | 6 |
| ATOM | 1039 | N | ILE | A | 133 | 46.378 | 12.918 | 5.840 | 1.00 | 17.51 | 7 |
| ATOM | 1040 | CA | ILE | A | 133 | 45.048 | 12.635 | 6.366 | 1.00 | 17.42 | 6 |
| ATOM | 1041 | C | ILE | A | 133 | 44.514 | 11.317 | 5.727 | 1.00 | 17.76 | 6 |
| ATOM | 1042 | O | ILE | A | 133 | 43.831 | 10.598 | 6.432 | 1.00 | 16.73 | 8 |
| ATOM | 1043 | CB | ILE | A | 133 | 44.056 | 13.814 | 6.199 | 1.00 | 19.04 | 6 |
| ATOM | 1044 | CG1 | ILE | A | 133 | 42.772 | 13.574 | 6.991 | 1.00 | 18.12 | 6 |
| ATOM | 1045 | CG2 | ILE | A | 133 | 43.692 | 14.007 | 4.713 | 1.00 | 19.62 | 6 |
| ATOM | 1046 | CD1 | ILE | A | 133 | 43.077 | 13.562 | 8.543 | 1.00 | 19.23 | 6 |
| ATOM | 1047 | N | VAL | A | 134 | 44.834 | 11.013 | 4.468 | 1.00 | 20.06 | 7 |
| ATOM | 1048 | CA | VAL | A | 134 | 44.318 | 9.805 | 3.843 | 1.00 | 20.66 | 6 |
| ATOM | 1049 | C | VAL | A | 134 | 44.943 | 8.567 | 4.523 | 1.00 | 16.68 | 6 |
| ATOM | 1050 | O | VAL | A | 134 | 44.181 | 7.608 | 4.840 | 1.00 | 16.16 | 8 |
| ATOM | 1051 | CB | VAL | A | 134 | 44.556 | 9.769 | 2.329 | 1.00 | 20.12 | 6 |
| ATOM | 1052 | CG1 | VAL | A | 134 | 43.968 | 8.529 | 1.685 | 1.00 | 20.31 | 6 |
| ATOM | 1053 | CG2 | VAL | A | 134 | 43.953 | 11.019 | 1.680 | 1.00 | 21.96 | 6 |
| ATOM | 1054 | N | SER | A | 135 | 46.232 | 8.622 | 4.793 | 1.00 | 17.42 | 7 |
| ATOM | 1055 | CA | SER | A | 135 | 46.862 | 7.515 | 5.554 | 1.00 | 18.57 | 6 |
| ATOM | 1056 | C | SER | A | 135 | 46.167 | 7.337 | 6.870 | 1.00 | 18.10 | 6 |
| ATOM | 1057 | O | SER | A | 135 | 45.906 | 6.226 | 7.307 | 1.00 | 17.58 | 8 |
| ATOM | 1058 | CB | SER | A | 135 | 48.367 | 7.725 | 5.776 | 1.00 | 21.85 | 6 |
| ATOM | 1059 | OG | SER | A | 135 | 49.165 | 7.574 | 4.629 | 1.00 | 26.07 | 8 |
| ATOM | 1060 | N | LYS | A | 136 | 45.960 | 8.454 | 7.642 | 1.00 | 17.06 | 7 |
| ATOM | 1061 | CA | LYS | A | 136 | 45.344 | 8.319 | 8.939 | 1.00 | 16.75 | 6 |
| ATOM | 1062 | C | LYS | A | 136 | 43.943 | 7.726 | 8.855 | 1.00 | 16.59 | 6 |
| ATOM | 1063 | O | LYS | A | 136 | 43.549 | 6.804 | 9.565 | 1.00 | 17.77 | 8 |
| ATOM | 1064 | CB | LYS | A | 136 | 45.347 | 9.698 | 9.654 | 1.00 | 17.50 | 6 |
| ATOM | 1065 | CG | LYS | A | 136 | 44.778 | 9.658 | 11.055 | 1.00 | 17.92 | 6 |
| ATOM | 1066 | CD | LYS | A | 136 | 45.193 | 10.949 | 11.821 | 1.00 | 18.19 | 6 |
| ATOM | 1067 | CE | LYS | A | 136 | 44.719 | 10.824 | 13.255 | 1.00 | 20.47 | 6 |
| ATOM | 1068 | NZ | LYS | A | 136 | 45.341 | 11.921 | 14.099 | 1.00 | 21.74 | 7 |
| ATOM | 1069 | N | LEU | A | 137 | 43.114 | 8.215 | 7.905 | 1.00 | 16.58 | 7 |
| ATOM | 1070 | CA | LEU | A | 137 | 41.820 | 7.610 | 7.620 | 1.00 | 16.97 | 6 |
| ATOM | 1071 | C | LEU | A | 137 | 41.917 | 6.145 | 7.208 | 1.00 | 16.87 | 6 |
| ATOM | 1072 | O | LEU | A | 137 | 41.086 | 5.366 | 7.671 | 1.00 | 18.31 | 8 |
| ATOM | 1073 | CB | LEU | A | 137 | 41.186 | 8.426 | 6.450 | 1.00 | 16.26 | 6 |
| ATOM | 1074 | CG | LEU | A | 137 | 40.680 | 9.774 | 6.970 | 1.00 | 19.05 | 6 |
| ATOM | 1075 | CD1 | LEU | A | 137 | 40.287 | 10.582 | 5.686 | 1.00 | 19.51 | 6 |
| ATOM | 1076 | CD2 | LEU | A | 137 | 39.540 | 9.723 | 7.939 | 1.00 | 20.72 | 6 |
| ATOM | 1077 | N | PHE | A | 138 | 42.967 | 5.788 | 6.451 | 1.00 | 16.58 | 7 |
| ATOM | 1078 | CA | PHE | A | 138 | 43.010 | 4.341 | 6.127 | 1.00 | 18.39 | 6 |
| ATOM | 1079 | C | PHE | A | 138 | 43.255 | 3.486 | 7.348 | 1.00 | 18.60 | 6 |
| ATOM | 1080 | O | PHE | A | 138 | 42.757 | 2.384 | 7.504 | 1.00 | 17.30 | 8 |
| ATOM | 1081 | CB | PHE | A | 138 | 44.122 | 4.115 | 5.093 | 1.00 | 17.12 | 6 |
| ATOM | 1082 | CG | PHE | A | 138 | 43.764 | 4.570 | 3.689 | 1.00 | 18.73 | 6 |
| ATOM | 1083 | CD1 | PHE | A | 138 | 44.806 | 4.543 | 2.766 | 1.00 | 17.88 | 6 |
| ATOM | 1084 | CD2 | PHE | A | 138 | 42.473 | 4.892 | 3.307 | 1.00 | 18.91 | 6 |
| ATOM | 1085 | CE1 | PHE | A | 138 | 44.536 | 4.879 | 1.448 | 1.00 | 20.01 | 6 |
| ATOM | 1886 | CE2 | PHE | A | 138 | 42.230 | 5.257 | 1.997 | 1.00 | 19.56 | 6 |
| ATOM | 1087 | CZ | PHE | A | 138 | 43.254 | 5.215 | 1.074 | 1.00 | 19.96 | 6 |
| ATOM | 1088 | N | ASN | A | 139 | 44.082 | 4.007 | 8.264 | 1.00 | 18.42 | 7 |
| ATOM | 1089 | CA | ASN | A | 139 | 44.379 | 3.252 | 9.498 | 1.00 | 18.84 | 6 |
| ATOM | 1090 | C | ASN | A | 139 | 43.214 | 3.179 | 10.420 | 1.00 | 18.89 | 6 |
| ATOM | 1091 | O | ASN | A | 139 | 43.006 | 2.188 | 11.154 | 1.00 | 20.77 | 8 |
| ATOM | 1092 | CB | ASN | A | 139 | 45.584 | 3.896 | 10.226 | 1.00 | 18.65 | 6 |

TABLE 1-continued

| ATOM | 1093 | CG  | ASN | A | 139 | 46.893 | 3.695  | 9.486   | 1.00 | 21.58 | 6  |
|------|------|-----|-----|---|-----|--------|--------|---------|------|-------|----|
| ATOM | 1094 | OD1 | ASN | A | 139 | 47.077 | 2.678  | 8.835   | 1.00 | 23.27 | 8  |
| ATOM | 1095 | ND2 | ASN | A | 139 | 47.838 | 4.616  | 9.605   | 1.00 | 23.11 | 7  |
| ATOM | 1096 | N   | LEU | A | 140 | 42.380 | 4.245  | 10.477  | 1.00 | 18.73 | 7  |
| ATOM | 1097 | CA  | LEU | A | 140 | 41.227 | 4.287  | 11.337  | 1.00 | 19.89 | 6  |
| ATOM | 1098 | C   | LEU | A | 140 | 40.035 | 3.500  | 10.798  | 1.00 | 22.66 | 6  |
| ATOM | 1099 | O   | LEU | A | 140 | 39.348 | 2.886  | 11.581  | 1.00 | 23.40 | 8  |
| ATOM | 1100 | CB  | LEU | A | 140 | 40.725 | 5.736  | 11.530  | 1.00 | 19.74 | 6  |
| ATOM | 1101 | CG  | LEU | A | 140 | 41.667 | 6.734  | 12.211  | 1.00 | 20.69 | 6  |
| ATOM | 1102 | CD1 | LEU | A | 140 | 41.159 | 8.189  | 12.222  | 1.00 | 20.47 | 6  |
| ATOM | 1103 | CD2 | LEU | A | 140 | 41.923 | 6.357  | 13.687  | 1.00 | 21.82 | 6  |
| ATOM | 1104 | N   | VAL | A | 141 | 39.777 | 3.644  | 9.493   | 1.00 | 21.89 | 7  |
| ATOM | 1105 | CA  | VAL | A | 141 | 38.625 | 2.951  | 8.912   | 1.00 | 18.58 | 6  |
| ATOM | 1106 | C   | VAL | A | 141 | 38.930 | 1.566  | 8.477   | 1.00 | 18.27 | 6  |
| ATOM | 1107 | O   | VAL | A | 141 | 37.992 | 0.726  | 8.348   | 1.00 | 21.83 | 8  |
| ATOM | 1108 | CB  | VAL | A | 141 | 38.121 | 3.897  | 7.749   | 1.00 | 17.89 | 6  |
| ATOM | 1109 | CG1 | VAL | A | 141 | 37.004 | 3.204  | 6.948   | 1.00 | 19.45 | 6  |
| ATOM | 1110 | CG2 | VAL | A | 141 | 37.684 | 5.229  | 8.360   | 1.00 | 19.31 | 6  |
| ATOM | 1111 | N   | GLN | A | 142 | 40.157 | 1.207  | 8.147   | 1.00 | 19.32 | 7  |
| ATOM | 1112 | CA  | GLN | A | 142 | 40.614 | -0.046 | 7.611   | 1.00 | 22.31 | 6  |
| ATOM | 1113 | C   | GLN | A | 142 | 39.731 | -0.535 | 6.460   | 1.00 | 19.60 | 6  |
| ATOM | 1114 | O   | GLN | A | 142 | 39.182 | -1.647 | 6.518   | 1.00 | 20.68 | 8  |
| ATOM | 1115 | CB  | GLN | A | 142 | 40.661 | -1.162 | 8.674   | 1.00 | 23.95 | 6  |
| ATOM | 1116 | CG  | GLN | A | 142 | 41.594 | -0.685 | 9.829   | 1.00 | 28.73 | 6  |
| ATOM | 1117 | CD  | GLN | A | 142 | 41.536 | -1.705 | 10.951  | 1.00 | 34.39 | 6  |
| ATOM | 1118 | OE1 | GLN | A | 142 | 42.491 | -2.469 | 11.021  | 1.00 | 39.24 | 8  |
| ATOM | 1119 | NE2 | GLN | A | 142 | 40.502 | -1.784 | 11.754  | 1.00 | 35.26 | 7  |
| ATOM | 1120 | N   | PRO | A | 143 | 39.558 | 0.297  | 5.442   | 1.00 | 18.88 | 7  |
| ATOM | 1121 | CA  | PRO | A | 143 | 38.717 | -0.119 | 4.346   | 1.00 | 18.57 | 6  |
| ATOM | 1122 | C   | PRO | A | 143 | 39.398 | -1.140 | 3.497   | 1.00 | 19.27 | 6  |
| ATOM | 1123 | O   | PRO | A | 143 | 40.627 | -1.225 | 3.382   | 1.00 | 21.22 | 8  |
| ATOM | 1124 | CB  | PRO | A | 143 | 38.538 | 1.179  | 3.558   | 1.00 | 17.81 | 6  |
| ATOM | 1125 | CG  | PRO | A | 143 | 39.829 | 1.905  | 3.755   | 1.00 | 17.73 | 6  |
| ATOM | 1126 | CD  | PRO | A | 143 | 40.201 | 1.627  | 5.230   | 1.00 | 17.54 | 6  |
| ATOM | 1127 | N   | ASP | A | 144 | 38.648 | -1.982 | 2.768   | 1.00 | 17.55 | 7  |
| ATOM | 1128 | CA  | ASP | A | 144 | 39.097 | -2.852 | 1.720   | 1.00 | 20.28 | 6  |
| ATOM | 1129 | C   | ASP | A | 144 | 39.283 | -2.125 | 0.399   | 1.00 | 19.25 | 6  |
| ATOM | 1130 | O   | ASP | A | 144 | 40.083 | -2.459 | -0.481  | 1.00 | 20.98 | 8  |
| ATOM | 1131 | CB  | ASP | A | 144 | 38.033 | -3.936 | 1.546   | 1.00 | 20.76 | 6  |
| ATOM | 1132 | CG  | ASP | A | 144 | 37.957 | -4.815 | 2.798   | 1.00 | 26.72 | 6  |
| ATOM | 1133 | OD1 | ASP | A | 144 | 36.961 | -4.629 | 3.528   | 1.00 | 28.28 | 8  |
| ATOM | 1134 | OD2 | ASP | A | 144 | 38.895 | -5.587 | 3.031   | 1.00 | 31.50 | 8  |
| ATOM | 1135 | N   | ILE | A | 145 | 38.477 | -1.081 | 0.131   | 1.00 | 17.25 | 7  |
| ATOM | 1136 | CA  | ILE | A | 145 | 38.375 | -0.260 | -1.035  | 1.00 | 18.60 | 6  |
| ATOM | 1137 | C   | ILE | A | 145 | 38.239 | 1.190  | -0.687  | 1.00 | 18.09 | 6  |
| ATOM | 1138 | O   | ILE | A | 145 | 37.607 | 1.491  | 0.327   | 1.00 | 18.47 | 8  |
| ATOM | 1139 | CB  | ILE | A | 145 | 37.081 | -0.719 | -1.802  | 1.00 | 22.13 | 6  |
| ATOM | 1140 | CG1 | ILE | A | 145 | 37.350 | -2.164 | -2.291  | 1.00 | 26.63 | 6  |
| ATOM | 1141 | CG2 | ILE | A | 145 | 36.613 | 0.193  | -2.934  | 1.00 | 28.58 | 6  |
| ATOM | 1142 | CD1 | ILE | A | 145 | 35.987 | -2.820 | -2.537  | 1.00 | 33.01 | 6  |
| ATOM | 1143 | N   | ALA | A | 146 | 38.745 | 2.119  | -1.471  | 1.00 | 18.54 | 7  |
| ATOM | 1144 | CA  | ALA | A | 146 | 38.555 | 3.525  | -1.287  | 1.00 | 17.65 | 6  |
| ATOM | 1145 | C   | ALA | A | 146 | 38.386 | 4.174  | -2.669  | 1.00 | 18.82 | 6  |
| ATOM | 1146 | O   | ALA | A | 146 | 39.158 | 3.831  | -3.590  | 1.00 | 20.86 | 8  |
| ATOM | 1147 | CB  | ALA | A | 146 | 39.754 | 4.169  | -0.561  | 1.00 | 17.02 | 6  |
| ATOM | 1148 | N   | CYS | A | 147 | 37.421 | 5.032  | -2.758  | 1.00 | 17.39 | 7  |
| ATOM | 1149 | CA  | CYS | A | 147 | 37.059 | 5.669  | -4.042  | 1.00 | 19.79 | 6  |
| ATOM | 1150 | C   | CYS | A | 147 | 37.462 | 7.132  | -4.108  | 1.00 | 20.20 | 6  |
| ATOM | 1151 | O   | CYS | A | 147 | 37.292 | 7.934  | -3.181  | 1.00 | 20.69 | 8  |
| ATOM | 1152 | CB  | CYS | A | 147 | 35.534 | 5.576  | -4.235  | 1.00 | 21.84 | 6  |
| ATOM | 1153 | SG  | CYS | A | 147 | 34.881 | 3.895  | -4.275  | 1.00 | 25.91 | 16 |
| ATOM | 1154 | N   | PHE | A | 148 | 38.073 | 7.481  | -5.256  | 1.00 | 20.78 | 7  |
| ATOM | 1155 | CA  | PHE | A | 148 | 38.521 | 8.824  | -5.534  | 1.00 | 20.56 | 6  |
| ATOM | 1156 | C   | PHE | A | 148 | 38.105 | 9.201  | -6.955  | 1.00 | 20.31 | 6  |
| ATOM | 1157 | O   | PHE | A | 148 | 38.047 | 8.291  | -7.790  | 1.00 | 21.33 | 8  |
| ATOM | 1158 | CB  | PHE | A | 148 | 40.044 | 8.856  | -5.392  | 1.00 | 19.98 | 6  |
| ATOM | 1159 | CG  | PHE | A | 148 | 40.527 | 8.697  | -3.964  | 1.00 | 21.76 | 6  |
| ATOM | 1160 | CD1 | PHE | A | 148 | 40.803 | 7.418  | -3.472  | 1.00 | 21.62 | 6  |
| ATOM | 1161 | CD2 | PHE | A | 148 | 40.682 | 9.781  | -3.137  | 1.00 | 24.08 | 6  |
| ATOM | 1162 | CE1 | PHE | A | 148 | 41.217 | 7.237  | -2.164  | 1.00 | 21.64 | 6  |
| ATOM | 1163 | CE2 | PHE | A | 148 | 41.150 | 9.580  | -1.833  | 1.00 | 22.23 | 6  |
| ATOM | 1164 | CZ  | PHE | A | 148 | 41.384 | 8.321  | -1.337  | 1.00 | 21.48 | 6  |
| ATOM | 1165 | N   | GLY | A | 149 | 37.874 | 10.485 | -7.215  | 1.00 | 19.66 | 7  |
| ATOM | 1166 | CA  | GLY | A | 149 | 37.457 | 10.782 | -8.630  | 1.00 | 19.28 | 6  |
| ATOM | 1167 | C   | GLY | A | 149 | 38.663 | 10.981 | -9.537  | 1.00 | 21.16 | 6  |
| ATOM | 1168 | O   | GLY | A | 149 | 39.696 | 11.548 | -9.117  | 1.00 | 25.03 | 8  |
| ATOM | 1169 | N   | GLU | A | 150 | 38.524 | 10.707 | -10.848 | 1.00 | 21.70 | 7  |
| ATOM | 1170 | CA  | GLU | A | 150 | 39.588 | 10.939 | -11.809 | 1.00 | 25.98 | 6  |
| ATOM | 1171 | C   | GLU | A | 150 | 39.777 | 12.386 | -12.160 | 1.00 | 25.10 | 6  |

TABLE 1-continued

| ATOM | 1172 | O | GLU | A | 150 | 40.841 | 12.764 | −12.668 | 1.00 | 26.55 | 8 |
|---|---|---|---|---|---|---|---|---|---|---|---|
| ATOM | 1173 | CB | GLU | A | 150 | 39.316 | 10.178 | −13.146 | 1.00 | 28.34 | 6 |
| ATOM | 1174 | CG | GLU | A | 150 | 39.447 | 8.683 | −12.924 | 1.00 | 30.38 | 6 |
| ATOM | 1175 | CD | GLU | A | 150 | 39.464 | 7.923 | −14.241 | 1.00 | 36.75 | 6 |
| ATOM | 1176 | OE1 | GLU | A | 150 | 39.222 | 8.536 | −15.309 | 1.00 | 39.43 | 8 |
| ATOM | 1177 | OE2 | GLU | A | 150 | 39.770 | 6.715 | −14.171 | 1.00 | 39.37 | 8 |
| ATOM | 1178 | N | LYS | A | 151 | 38.795 | 13.240 | −11.874 | 1.00 | 25.17 | 7 |
| ATOM | 1179 | CA | LYS | A | 151 | 38.970 | 14.660 | −12.162 | 1.00 | 28.17 | 6 |
| ATOM | 1180 | C | LYS | A | 151 | 40.159 | 15.229 | −11.400 | 1.00 | 29.47 | 6 |
| ATOM | 1181 | O | LYS | A | 151 | 40.955 | 16.017 | −11.930 | 1.00 | 29.69 | 8 |
| ATOM | 1182 | CB | LYS | A | 151 | 37.710 | 15.423 | −11.787 | 1.00 | 30.49 | 6 |
| ATOM | 1183 | CG | LYS | A | 151 | 37.865 | 16.877 | −12.255 | 1.00 | 34.63 | 6 |
| ATOM | 1184 | CD | LYS | A | 151 | 37.021 | 17.827 | −11.434 | 1.00 | 40.81 | 6 |
| ATOM | 1185 | CE | LYS | A | 151 | 37.161 | 19.249 | −12.007 | 1.00 | 42.71 | 6 |
| ATOM | 1186 | NZ | LYS | A | 151 | 35.905 | 20.032 | −11.825 | 1.00 | 46.87 | 7 |
| ATOM | 1187 | N | ASP | A | 152 | 40.274 | 14.877 | −10.114 | 1.00 | 26.84 | 7 |
| ATOM | 1188 | CA | ASP | A | 152 | 41.456 | 15.268 | −9.322 | 1.00 | 26.83 | 6 |
| ATOM | 1189 | C | ASP | A | 152 | 42.545 | 14.241 | −9.529 | 1.00 | 26.30 | 6 |
| ATOM | 1190 | O | ASP | A | 152 | 42.933 | 13.366 | −8.715 | 1.00 | 24.08 | 8 |
| ATOM | 1191 | CB | ASP | A | 152 | 41.078 | 15.419 | −7.846 | 1.00 | 29.39 | 6 |
| ATOM | 1192 | N | PHE | A | 153 | 43.137 | 14.340 | −10.746 | 1.00 | 24.76 | 7 |
| ATOM | 1193 | CA | PHE | A | 153 | 44.063 | 13.342 | −11.241 | 1.00 | 24.28 | 6 |
| ATOM | 1194 | C | PHE | A | 153 | 45.350 | 13.353 | −10.435 | 1.00 | 24.40 | 6 |
| ATOM | 1195 | O | PHE | A | 153 | 45.891 | 12.270 | −10.274 | 1.00 | 24.91 | 8 |
| ATOM | 1196 | CB | PHE | A | 153 | 44.385 | 13.509 | −12.748 | 1.00 | 26.30 | 6 |
| ATOM | 1197 | CG | PHE | A | 153 | 45.137 | 14.809 | −12.939 | 1.00 | 29.67 | 6 |
| ATOM | 1198 | CD1 | PHE | A | 153 | 46.517 | 14.828 | −13.025 | 1.00 | 30.48 | 6 |
| ATOM | 1199 | CD2 | PHE | A | 153 | 44.443 | 16.015 | −13.033 | 1.00 | 32.69 | 6 |
| ATOM | 1200 | CE1 | PHE | A | 153 | 47.203 | 16.017 | −13.147 | 1.00 | 31.59 | 6 |
| ATOM | 1201 | CE2 | PHE | A | 153 | 45.124 | 17.212 | −13.186 | 1.00 | 33.09 | 6 |
| ATOM | 1202 | CZ | PHE | A | 153 | 46.511 | 17.215 | −13.241 | 1.00 | 34.20 | 6 |
| ATOM | 1203 | N | GLN | A | 154 | 45.781 | 14.510 | −9.931 | 1.00 | 25.98 | 7 |
| ATOM | 1204 | CA | GLN | A | 154 | 47.028 | 14.521 | −9.174 | 1.00 | 22.85 | 6 |
| ATOM | 1205 | C | GLN | A | 154 | 46.851 | 13.825 | −7.837 | 1.00 | 22.38 | 6 |
| ATOM | 1206 | O | GLN | A | 154 | 47.695 | 13.032 | −7.413 | 1.00 | 22.53 | 8 |
| ATOM | 1207 | CB | GLN | A | 154 | 47.542 | 15.952 | −8.933 | 1.00 | 24.08 | 6 |
| ATOM | 1208 | CG | GLN | A | 154 | 48.929 | 15.967 | −8.287 | 1.00 | 26.39 | 6 |
| ATOM | 1209 | CD | GLN | A | 154 | 49.688 | 17.287 | −8.508 | 1.00 | 28.37 | 6 |
| ATOM | 1210 | OE1 | GLN | A | 154 | 49.098 | 18.244 | −8.993 | 1.00 | 28.49 | 8 |
| ATOM | 1211 | NE2 | GLN | A | 154 | 50.978 | 17.318 | −8.158 | 1.00 | 26.87 | 7 |
| ATOM | 1212 | N | GLN | A | 155 | 45.747 | 14.096 | −7.174 | 1.00 | 21.22 | 7 |
| ATOM | 1213 | CA | GLN | A | 155 | 45.470 | 13.411 | −5.896 | 1.00 | 21.76 | 6 |
| ATOM | 1214 | C | GLN | A | 155 | 45.362 | 11.902 | −6.092 | 1.00 | 21.39 | 6 |
| ATOM | 1215 | O | GLN | A | 155 | 45.852 | 11.100 | −5.289 | 1.00 | 20.96 | 8 |
| ATOM | 1216 | CB | GLN | A | 155 | 44.157 | 13.885 | −5.251 | 1.00 | 23.33 | 6 |
| ATOM | 1217 | CG | GLN | A | 155 | 44.285 | 15.020 | −4.241 | 0.50 | 22.16 | 6 |
| ATOM | 1218 | CD | GLN | A | 155 | 43.185 | 14.991 | −3.184 | 0.50 | 22.84 | 6 |
| ATOM | 1219 | OE1 | GLN | A | 155 | 42.574 | 13.952 | −2.872 | 0.50 | 25.23 | 8 |
| ATOM | 1220 | NE2 | GLN | A | 155 | 42.921 | 16.140 | −2.600 | 0.50 | 20.85 | 7 |
| ATOM | 1221 | N | LEU | A | 156 | 44.752 | 11.455 | −7.214 | 1.00 | 20.25 | 7 |
| ATOM | 1222 | CA | LEU | A | 156 | 44.592 | 10.045 | −7.465 | 1.00 | 18.93 | 6 |
| ATOM | 1223 | C | LEU | A | 156 | 45.938 | 9.367 | −7.681 | 1.00 | 20.91 | 6 |
| ATOM | 1224 | O | LEU | A | 156 | 46.240 | 8.334 | −7.081 | 1.00 | 20.99 | 8 |
| ATOM | 1225 | CB | LEU | A | 156 | 43.684 | 9.840 | −8.695 | 1.00 | 20.06 | 6 |
| ATOM | 1226 | CG | LEU | A | 156 | 43.409 | 8.396 | −9.060 | 1.00 | 21.79 | 6 |
| ATOM | 1227 | CD1 | LEU | A | 156 | 42.773 | 7.624 | −7.893 | 1.00 | 20.19 | 6 |
| ATOM | 1228 | CD2 | LEU | A | 156 | 42.493 | 8.367 | −10.300 | 1.00 | 23.41 | 6 |
| ATOM | 1229 | N | ALA | A | 157 | 46.790 | 9.991 | −8.498 | 1.00 | 21.27 | 7 |
| ATOM | 1230 | CA | ALA | A | 157 | 48.139 | 9.424 | −8.654 | 1.00 | 20.85 | 6 |
| ATOM | 1231 | C | ALA | A | 157 | 48.896 | 9.402 | −7.339 | 1.00 | 22.15 | 6 |
| ATOM | 1232 | O | ALA | A | 157 | 49.617 | 8.451 | −7.039 | 1.00 | 23.09 | 8 |
| ATOM | 1233 | CB | ALA | A | 157 | 48.919 | 10.292 | −9.658 | 1.00 | 21.65 | 6 |
| ATOM | 1234 | N | LEU | A | 158 | 48.771 | 10.447 | −6.537 | 1.00 | 21.63 | 7 |
| ATOM | 1235 | CA | LEU | A | 158 | 49.507 | 10.508 | −5.235 | 1.00 | 20.79 | 6 |
| ATOM | 1236 | C | LEU | A | 158 | 49.117 | 9.373 | −4.311 | 1.00 | 22.51 | 6 |
| ATOM | 1237 | O | LEU | A | 158 | 49.950 | 8.663 | −3.702 | 1.00 | 22.35 | 8 |
| ATOM | 1238 | CB | LEU | A | 158 | 49.227 | 11.847 | −4.583 | 1.00 | 23.18 | 6 |
| ATOM | 1239 | CG | LEU | A | 158 | 49.828 | 12.175 | −3.211 | 1.00 | 25.19 | 6 |
| ATOM | 1240 | CD1 | LEU | A | 158 | 51.099 | 12.952 | −3.381 | 1.00 | 28.19 | 6 |
| ATOM | 1241 | CD2 | LEU | A | 158 | 48.782 | 12.989 | −2.433 | 1.00 | 26.28 | 6 |
| ATOM | 1242 | N | ILE | A | 159 | 47.765 | 9.231 | −4.212 | 1.00 | 18.01 | 7 |
| ATOM | 1243 | CA | ILE | A | 159 | 47.322 | 8.127 | −3.317 | 1.00 | 19.99 | 6 |
| ATOM | 1244 | C | ILE | A | 159 | 47.680 | 6.760 | −3.864 | 1.00 | 18.66 | 6 |
| ATOM | 1245 | O | ILE | A | 159 | 48.038 | 5.871 | −3.083 | 1.00 | 19.24 | 8 |
| ATOM | 1246 | CB | ILE | A | 159 | 45.805 | 8.275 | −3.083 | 1.00 | 23.08 | 6 |
| ATOM | 1247 | CG1 | ILE | A | 159 | 45.455 | 9.626 | −2.443 | 1.00 | 21.73 | 6 |
| ATOM | 1248 | CG2 | ILE | A | 159 | 45.232 | 7.181 | −2.187 | 1.00 | 23.20 | 6 |
| ATOM | 1249 | CD1 | ILE | A | 159 | 46.056 | 9.774 | −1.063 | 1.00 | 27.28 | 6 |
| ATOM | 1250 | N | ARG | A | 160 | 47.514 | 6.493 | −5.148 | 1.00 | 20.78 | 7 |

TABLE 1-continued

| ATOM | 1251 | CA | ARG | A | 160 | 47.956 | 5.202 | −5.694 | 1.00 | 20.24 | 6 |
|---|---|---|---|---|---|---|---|---|---|---|---|
| ATOM | 1252 | C | ARG | A | 160 | 49.422 | 4.914 | −5.397 | 1.00 | 21.57 | 6 |
| ATOM | 1253 | O | ARG | A | 160 | 49.738 | 3.802 | −4.971 | 1.00 | 19.80 | 8 |
| ATOM | 1254 | CB | ARG | A | 160 | 47.708 | 5.074 | −7.218 | 1.00 | 21.86 | 6 |
| ATOM | 1255 | CG | ARG | A | 160 | 46.192 | 5.007 | −7.567 | 1.00 | 21.60 | 6 |
| ATOM | 1256 | CD | ARG | A | 160 | 46.195 | 4.575 | −9.066 | 1.00 | 25.76 | 6 |
| ATOM | 1257 | NE | ARG | A | 160 | 44.867 | 4.625 | −9.678 | 1.00 | 29.84 | 7 |
| ATOM | 1258 | CZ | ARG | A | 160 | 43.905 | 3.713 | −9.455 | 1.00 | 32.53 | 6 |
| ATOM | 1259 | NH1 | ARG | A | 160 | 44.040 | 2.653 | −8.651 | 1.00 | 32.58 | 7 |
| ATOM | 1260 | NH2 | ARG | A | 160 | 42.788 | 3.911 | −10.168 | 1.00 | 34.80 | 7 |
| ATOM | 1261 | N | LYS | A | 161 | 50.322 | 5.905 | −5.460 | 1.00 | 20.74 | 7 |
| ATOM | 1262 | CA | LYS | A | 161 | 51.733 | 5.714 | −5.164 | 1.00 | 19.39 | 6 |
| ATOM | 1263 | C | LYS | A | 161 | 51.925 | 5.506 | −3.674 | 1.00 | 19.31 | 6 |
| ATOM | 1264 | O | LYS | A | 161 | 52.628 | 4.596 | −3.191 | 1.00 | 22.15 | 8 |
| ATOM | 1265 | CB | LYS | A | 161 | 52.523 | 6.929 | −5.649 | 1.00 | 21.10 | 6 |
| ATOM | 1266 | CG | LYS | A | 161 | 54.009 | 6.900 | −5.202 | 1.00 | 24.79 | 6 |
| ATOM | 1267 | CD | LYS | A | 161 | 54.612 | 5.615 | −5.820 | 1.00 | 28.31 | 6 |
| ATOM | 1268 | CE | LYS | A | 161 | 56.100 | 5.758 | −6.162 | 1.00 | 31.56 | 6 |
| ATOM | 1269 | NZ | LYS | A | 161 | 56.913 | 6.424 | −5.128 | 1.00 | 26.44 | 7 |
| ATOM | 1270 | N | MET | A | 162 | 51.191 | 6.312 | −2.834 | 1.00 | 20.30 | 7 |
| ATOM | 1271 | CA | MET | A | 162 | 51.287 | 6.115 | −1.383 | 1.00 | 18.85 | 6 |
| ATOM | 1272 | C | MET | A | 162 | 50.851 | 4.750 | −0.908 | 1.00 | 21.35 | 6 |
| ATOM | 1273 | O | MET | A | 162 | 51.504 | 4.085 | −0.089 | 1.00 | 20.93 | 8 |
| ATOM | 1274 | CB | MET | A | 162 | 50.412 | 7.231 | −0.702 | 1.00 | 21.14 | 6 |
| ATOM | 1275 | CG | MET | A | 162 | 50.512 | 7.132 | 0.818 | 1.00 | 21.47 | 6 |
| ATOM | 1276 | SD | MET | A | 162 | 49.291 | 8.186 | 1.642 | 1.00 | 23.59 | 16 |
| ATOM | 1277 | CE | MET | A | 162 | 47.948 | 6.994 | 1.780 | 1.00 | 27.52 | 6 |
| ATOM | 1278 | N | VAL | A | 163 | 49.808 | 4.217 | −1.577 | 1.00 | 19.66 | 7 |
| ATOM | 1279 | CA | VAL | A | 163 | 49.304 | 2.897 | −1.214 | 1.00 | 20.50 | 6 |
| ATOM | 1280 | C | VAL | A | 163 | 50.289 | 1.806 | −1.612 | 1.00 | 19.37 | 6 |
| ATOM | 1281 | O | VAL | A | 163 | 50.554 | 0.867 | −0.837 | 1.00 | 20.07 | 8 |
| ATOM | 1282 | CB | VAL | A | 163 | 47.914 | 2.672 | −1.873 | 1.00 | 21.79 | 6 |
| ATOM | 1283 | CG1 | VAL | A | 163 | 47.540 | 1.204 | −1.894 | 1.00 | 22.15 | 6 |
| ATOM | 1284 | CG2 | VAL | A | 163 | 46.897 | 3.536 | −1.100 | 1.00 | 22.77 | 6 |
| ATOM | 1285 | N | ALA | A | 164 | 50.784 | 1.931 | −2.837 | 1.00 | 21.03 | 7 |
| ATOM | 1286 | CA | ALA | A | 164 | 51.773 | 0.937 | −3.276 | 1.00 | 22.98 | 6 |
| ATOM | 1287 | C | ALA | A | 164 | 53.006 | 0.925 | −2.380 | 1.00 | 23.44 | 6 |
| ATOM | 1288 | O | ALA | A | 164 | 53.478 | −0.126 | −1.927 | 1.00 | 23.96 | 8 |
| ATOM | 1289 | CB | ALA | A | 164 | 52.136 | 1.263 | −4.719 | 1.00 | 23.95 | 6 |
| ATOM | 1290 | N | ASP | A | 165 | 53.552 | 2.121 | −2.154 | 1.00 | 21.54 | 7 |
| ATOM | 1291 | CA | ASP | A | 165 | 54.788 | 2.231 | −1.387 | 1.00 | 23.74 | 6 |
| ATOM | 1292 | C | ASP | A | 165 | 54.639 | 1.784 | 0.052 | 1.00 | 24.26 | 6 |
| ATOM | 1293 | O | ASP | A | 165 | 55.440 | 1.000 | 0.544 | 1.00 | 24.84 | 8 |
| ATOM | 1294 | CB | ASP | A | 165 | 55.321 | 3.664 | −1.384 | 1.00 | 22.61 | 6 |
| ATOM | 1295 | CG | ASP | A | 165 | 55.980 | 4.130 | −2.662 | 1.00 | 24.69 | 6 |
| ATOM | 1296 | OD1 | ASP | A | 165 | 56.269 | 3.286 | −3.531 | 1.00 | 24.19 | 8 |
| ATOM | 1297 | OD2 | ASP | A | 165 | 56.220 | 5.356 | −2.781 | 1.00 | 24.88 | 8 |
| ATOM | 1298 | N | MET | A | 166 | 53.590 | 2.288 | 0.725 | 1.00 | 21.43 | 7 |
| ATOM | 1299 | CA | MET | A | 166 | 53.378 | 2.007 | 2.157 | 1.00 | 20.10 | 6 |
| ATOM | 1300 | C | MET | A | 166 | 52.785 | 0.652 | 2.486 | 1.00 | 21.04 | 6 |
| ATOM | 1301 | O | MET | A | 166 | 52.605 | 0.347 | 3.671 | 1.00 | 21.28 | 8 |
| ATOM | 1302 | CB | MET | A | 166 | 52.540 | 3.142 | 2.751 | 1.00 | 20.75 | 6 |
| ATOM | 1303 | CG | MET | A | 166 | 53.288 | 4.458 | 2.868 | 1.00 | 22.14 | 6 |
| ATOM | 1304 | SD | MET | A | 166 | 55.034 | 4.259 | 3.242 | 1.00 | 26.84 | 16 |
| ATOM | 1305 | CE | MET | A | 166 | 54.959 | 3.835 | 4.983 | 1.00 | 27.47 | 6 |
| ATOM | 1306 | N | GLY | A | 167 | 52.458 | −0.170 | 1.510 | 1.00 | 20.03 | 7 |
| ATOM | 1307 | CA | GLY | A | 167 | 51.975 | −1.522 | 1.790 | 1.00 | 22.00 | 6 |
| ATOM | 1308 | C | GLY | A | 167 | 50.526 | −1.606 | 2.218 | 1.00 | 20.49 | 6 |
| ATOM | 1309 | O | GLY | A | 167 | 50.190 | −2.660 | 2.782 | 1.00 | 24.46 | 8 |
| ATOM | 1310 | N | PHE | A | 168 | 49.685 | −0.585 | 2.002 | 1.00 | 21.54 | 7 |
| ATOM | 1311 | CA | PHE | A | 168 | 48.287 | −0.824 | 2.403 | 1.00 | 20.47 | 6 |
| ATOM | 1312 | C | PHE | A | 168 | 47.645 | −1.917 | 1.546 | 1.00 | 19.05 | 6 |
| ATOM | 1313 | O | PHE | A | 168 | 47.704 | −1.739 | 0.320 | 1.00 | 20.71 | 8 |
| ATOM | 1314 | CB | PHE | A | 168 | 47.563 | 0.509 | 2.296 | 1.00 | 21.24 | 6 |
| ATOM | 1315 | CG | PHE | A | 168 | 47.788 | 1.632 | 3.277 | 1.00 | 20.78 | 6 |
| ATOM | 1316 | CD1 | PHE | A | 168 | 48.548 | 2.751 | 2.932 | 1.00 | 22.23 | 6 |
| ATOM | 1317 | CD2 | PHE | A | 168 | 47.186 | 1.509 | 4.509 | 1.00 | 21.78 | 6 |
| ATOM | 1318 | CE1 | PHE | A | 168 | 48.736 | 3.747 | 3.913 | 1.00 | 20.66 | 6 |
| ATOM | 1319 | CE2 | PHE | A | 168 | 47.353 | 2.544 | 5.432 | 1.00 | 19.66 | 6 |
| ATOM | 1320 | CZ | PHE | A | 168 | 48.085 | 3.665 | 5.136 | 1.00 | 20.15 | 6 |
| ATOM | 1321 | N | ASP | A | 169 | 46.769 | −2.693 | 2.126 | 1.00 | 22.42 | 7 |
| ATOM | 1322 | CA | ASP | A | 169 | 46.084 | −3.767 | 1.356 | 1.00 | 22.89 | 6 |
| ATOM | 1323 | C | ASP | A | 169 | 44.743 | −3.167 | 0.938 | 1.00 | 23.53 | 6 |
| ATOM | 1324 | O | ASP | A | 169 | 43.705 | −3.617 | 1.427 | 1.00 | 23.13 | 8 |
| ATOM | 1325 | CB | ASP | A | 169 | 45.975 | −5.057 | 2.147 | 1.00 | 28.05 | 6 |
| ATOM | 1326 | CG | ASP | A | 169 | 45.399 | −6.229 | 1.376 | 1.00 | 32.61 | 6 |
| ATOM | 1327 | OD1 | ASP | A | 169 | 45.492 | −6.192 | 0.129 | 1.00 | 35.09 | 8 |
| ATOM | 1328 | OD2 | ASP | A | 169 | 44.838 | −7.159 | 1.975 | 1.00 | 37.69 | 8 |
| ATOM | 1329 | N | ILE | A | 170 | 44.751 | −2.104 | 0.146 | 1.00 | 21.02 | 7 |

TABLE 1-continued

| ATOM | 1330 | CA | ILE | A | 170 | 43.499 | -1.409 | -0.181 | 1.00 | 21.69 | 6 |
| --- | --- | --- | --- | --- | --- | --- | --- | --- | --- | --- | --- |
| ATOM | 1331 | C | ILE | A | 170 | 43.372 | -1.265 | -1.677 | 1.00 | 21.49 | 6 |
| ATOM | 1332 | O | ILE | A | 170 | 44.334 | -0.773 | -2.304 | 1.00 | 22.63 | 8 |
| ATOM | 1333 | CB | ILE | A | 170 | 43.443 | -0.013 | 0.493 | 1.00 | 21.71 | 6 |
| ATOM | 1334 | CG1 | ILE | A | 170 | 43.459 | -0.124 | 2.030 | 1.00 | 21.39 | 6 |
| ATOM | 1335 | CG2 | ILE | A | 170 | 42.221 | 0.770 | 0.037 | 1.00 | 22.28 | 6 |
| ATOM | 1336 | CD1 | ILE | A | 170 | 43.745 | 1.240 | 2.694 | 1.00 | 23.40 | 6 |
| ATOM | 1337 | N | GLU | A | 171 | 42.206 | -1.583 | -2.244 | 1.00 | 22.35 | 7 |
| ATOM | 1338 | CA | GLU | A | 171 | 41.960 | -1.346 | -3.656 | 1.00 | 22.51 | 6 |
| ATOM | 1339 | C | GLU | A | 171 | 41.609 | 0.133 | -3.871 | 1.00 | 22.05 | 6 |
| ATOM | 1340 | O | GLU | A | 171 | 40.625 | 0.577 | -3.278 | 1.00 | 20.97 | 8 |
| ATOM | 1341 | CB | GLU | A | 171 | 40.841 | -2.288 | -4.152 | 1.00 | 21.82 | 6 |
| ATOM | 1342 | CG | GLU | A | 171 | 40.514 | -1.978 | -5.601 | 1.00 | 28.71 | 6 |
| ATOM | 1343 | CD | GLU | A | 171 | 39.364 | -2.857 | -6.098 | 1.00 | 34.21 | 6 |
| ATOM | 1344 | OE1 | GLU | A | 171 | 38.911 | -3.740 | -5.361 | 1.00 | 36.00 | 8 |
| ATOM | 1345 | OE2 | GLU | A | 171 | 38.953 | -2.650 | -7.272 | 1.00 | 38.31 | 8 |
| ATOM | 1346 | N | ILE | A | 172 | 42.352 | 0.886 | -4.680 | 1.00 | 20.37 | 7 |
| ATOM | 1347 | CA | ILE | A | 172 | 42.017 | 2.294 | -4.940 | 1.00 | 19.10 | 6 |
| ATOM | 1348 | C | ILE | A | 172 | 41.196 | 2.347 | -6.217 | 1.00 | 23.26 | 6 |
| ATOM | 1349 | O | ILE | A | 172 | 41.716 | 1.875 | -7.239 | 1.00 | 26.08 | 8 |
| ATOM | 1350 | CB | ILE | A | 172 | 43.306 | 3.159 | -5.019 | 1.00 | 22.26 | 6 |
| ATOM | 1351 | CG1 | ILE | A | 172 | 44.060 | 2.969 | -3.686 | 1.00 | 21.42 | 6 |
| ATOM | 1352 | CG2 | ILE | A | 172 | 42.975 | 4.587 | -5.345 | 1.00 | 23.49 | 6 |
| ATOM | 1353 | CD1 | ILE | A | 172 | 43.283 | 3.498 | -2.483 | 1.00 | 22.09 | 6 |
| ATOM | 1354 | N | VAL | A | 173 | 39.937 | 2.751 | -6.114 | 1.00 | 20.87 | 7 |
| ATOM | 1355 | CA | VAL | A | 173 | 39.045 | 2.789 | -7.278 | 1.00 | 23.09 | 6 |
| ATOM | 1356 | C | VAL | A | 173 | 39.073 | 4.218 | -7.811 | 1.00 | 23.54 | 6 |
| ATOM | 1357 | O | VAL | A | 173 | 38.637 | 5.125 | -7.058 | 1.00 | 23.05 | 8 |
| ATOM | 1358 | CB | VAL | A | 173 | 37.637 | 2.318 | -6.861 | 1.00 | 22.84 | 6 |
| ATOM | 1359 | CG1 | VAL | A | 173 | 36.675 | 2.449 | -8.040 | 1.00 | 24.23 | 6 |
| ATOM | 1360 | CG2 | VAL | A | 173 | 37.756 | 0.893 | -6.307 | 1.00 | 23.19 | 6 |
| ATOM | 1361 | N | GLY | A | 174 | 39.480 | 4.451 | -9.055 | 1.00 | 22.79 | 7 |
| ATOM | 1362 | CA | GLY | A | 174 | 39.509 | 5.765 | -9.652 | 1.00 | 22.28 | 6 |
| ATOM | 1363 | C | GLY | A | 174 | 38.217 | 5.872 | -10.462 | 1.00 | 25.76 | 6 |
| ATOM | 1364 | O | GLY | A | 174 | 37.972 | 4.984 | -11.306 | 1.00 | 25.34 | 8 |
| ATOM | 1365 | N | VAL | A | 175 | 37.340 | 6.803 | -10.087 | 1.00 | 22.69 | 7 |
| ATOM | 1366 | CA | VAL | A | 175 | 35.996 | 6.810 | -10.712 | 1.00 | 21.96 | 6 |
| ATOM | 1367 | C | VAL | A | 175 | 36.025 | 7.779 | -11.858 | 1.00 | 22.74 | 6 |
| ATOM | 1368 | O | VAL | A | 175 | 36.298 | 8.938 | -11.632 | 1.00 | 19.20 | 8 |
| ATOM | 1369 | CB | VAL | A | 175 | 34.977 | 7.161 | -9.632 | 1.00 | 21.95 | 6 |
| ATOM | 1370 | CG1 | VAL | A | 175 | 33.557 | 7.328 | -10.233 | 1.00 | 23.84 | 6 |
| ATOM | 1371 | CG2 | VAL | A | 175 | 34.914 | 6.111 | -8.501 | 1.00 | 20.67 | 6 |
| ATOM | 1372 | N | PRO | A | 176 | 35.590 | 7.430 | -13.068 | 1.00 | 23.97 | 7 |
| ATOM | 1373 | CA | PRO | A | 176 | 35.714 | 8.344 | -14.172 | 1.00 | 26.00 | 6 |
| ATOM | 1374 | C | PRO | A | 176 | 34.750 | 9.485 | -14.090 | 1.00 | 23.25 | 6 |
| ATOM | 1375 | O | PRO | A | 176 | 33.689 | 9.357 | -13.462 | 1.00 | 23.13 | 8 |
| ATOM | 1376 | CB | PRO | A | 176 | 35.429 | 7.464 | -15.401 | 1.00 | 26.90 | 6 |
| ATOM | 1377 | CG | PRO | A | 176 | 35.554 | 6.062 | -14.946 | 1.00 | 30.42 | 6 |
| ATOM | 1378 | CD | PRO | A | 176 | 35.214 | 6.053 | -13.467 | 1.00 | 26.21 | 6 |
| ATOM | 1379 | N | ILE | A | 177 | 35.026 | 10.601 | -14.706 | 1.00 | 25.15 | 7 |
| ATOM | 1380 | CA | ILE | A | 177 | 34.220 | 11.792 | -14.882 | 1.00 | 25.60 | 6 |
| ATOM | 1381 | C | ILE | A | 177 | 32.858 | 11.452 | -15.470 | 1.00 | 26.15 | 6 |
| ATOM | 1382 | O | ILE | A | 177 | 32.823 | 10.610 | -16.392 | 1.00 | 25.13 | 8 |
| ATOM | 1383 | CB | ILE | A | 177 | 35.002 | 12.755 | -15.816 | 1.00 | 27.16 | 6 |
| ATOM | 1384 | CG1 | ILE | A | 177 | 36.095 | 13.432 | -14.910 | 1.00 | 32.12 | 6 |
| ATOM | 1385 | CG2 | ILE | A | 177 | 34.203 | 13.794 | -16.565 | 1.00 | 27.48 | 6 |
| ATOM | 1386 | CD1 | ILE | A | 177 | 37.253 | 13.907 | -15.774 | 1.00 | 33.86 | 6 |
| ATOM | 1387 | N | MET | A | 178 | 31.789 | 11.892 | -14.839 | 1.00 | 23.56 | 7 |
| ATOM | 1388 | CA | MET | A | 178 | 30.439 | 11.695 | -15.338 | 1.00 | 22.41 | 6 |
| ATOM | 1389 | C | MET | A | 178 | 30.253 | 12.624 | -16.564 | 1.00 | 19.13 | 6 |
| ATOM | 1390 | O | MET | A | 178 | 30.623 | 13.780 | -16.493 | 1.00 | 19.54 | 8 |
| ATOM | 1391 | CB | MET | A | 178 | 29.352 | 12.079 | -14.359 | 1.00 | 28.06 | 6 |
| ATOM | 1392 | CG | MET | A | 178 | 29.443 | 11.331 | -13.018 | 1.00 | 34.50 | 6 |
| ATOM | 1393 | SD | MET | A | 178 | 28.135 | 11.774 | -11.868 | 1.00 | 41.82 | 16 |
| ATOM | 1394 | CE | MET | A | 178 | 28.027 | 13.573 | -11.994 | 1.00 | 44.07 | 6 |
| ATOM | 1395 | N | ARG | A | 179 | 29.559 | 12.130 | -17.573 | 1.00 | 19.57 | 7 |
| ATOM | 1396 | CA | ARG | A | 179 | 29.384 | 12.934 | -18.776 | 1.00 | 18.81 | 6 |
| ATOM | 1397 | C | ARG | A | 179 | 27.950 | 12.914 | -19.257 | 1.00 | 19.43 | 6 |
| ATOM | 1398 | O | ARG | A | 179 | 27.182 | 12.014 | -18.938 | 1.00 | 19.78 | 8 |
| ATOM | 1399 | CB | ARG | A | 179 | 30.252 | 12.380 | -19.936 | 1.00 | 20.44 | 6 |
| ATOM | 1400 | CG | ARG | A | 179 | 31.757 | 12.403 | -19.680 | 1.00 | 21.94 | 6 |
| ATOM | 1401 | CD | ARG | A | 179 | 32.547 | 11.665 | -20.791 | 1.00 | 22.96 | 6 |
| ATOM | 1402 | NE | ARG | A | 179 | 33.928 | 11.849 | -20.377 | 1.00 | 24.17 | 7 |
| ATOM | 1403 | CZ | ARG | A | 179 | 34.636 | 12.995 | -20.379 | 1.00 | 23.08 | 6 |
| ATOM | 1404 | NH1 | ARG | A | 179 | 34.146 | 14.147 | -20.883 | 1.00 | 22.58 | 7 |
| ATOM | 1405 | NH2 | ARG | A | 179 | 35.872 | 12.925 | -19.895 | 1.00 | 25.87 | 7 |
| ATOM | 1406 | N | ALA | A | 180 | 27.526 | 13.954 | -19.931 | 1.00 | 19.29 | 7 |
| ATOM | 1407 | CA | ALA | A | 180 | 26.247 | 14.023 | -20.609 | 1.00 | 20.57 | 6 |
| ATOM | 1408 | C | ALA | A | 180 | 26.269 | 13.017 | -21.785 | 1.00 | 20.46 | 6 |

TABLE 1-continued

| ATOM | 1409 | O | ALA | A | 180 | 27.305 | 12.438 | −22.089 | 1.00 | 20.53 | 8 |
|---|---|---|---|---|---|---|---|---|---|---|---|
| ATOM | 1410 | CB | ALA | A | 180 | 26.009 | 15.430 | −21.100 | 1.00 | 20.95 | 6 |
| ATOM | 1411 | N | LYS | A | 181 | 25.065 | 12.823 | −22.355 | 1.00 | 23.00 | 7 |
| ATOM | 1412 | CA | LYS | A | 181 | 24.978 | 11.807 | −23.436 | 1.00 | 25.24 | 6 |
| ATOM | 1413 | C | LYS | A | 181 | 25.745 | 12.150 | −24.672 | 1.00 | 23.73 | 6 |
| ATOM | 1414 | O | LYS | A | 181 | 26.108 | 11.238 | −25.439 | 1.00 | 25.08 | 8 |
| ATOM | 1415 | CB | LYS | A | 181 | 23.496 | 11.637 | −23.802 | 1.00 | 25.36 | 6 |
| ATOM | 1416 | CG | LYS | A | 181 | 22.670 | 10.939 | −22.755 | 1.00 | 29.60 | 6 |
| ATOM | 1417 | CD | LYS | A | 181 | 23.217 | 9.642 | −22.291 | 1.00 | 31.75 | 6 |
| ATOM | 1418 | N | ASP | A | 182 | 26.027 | 13.427 | −24.854 | 1.00 | 22.41 | 7 |
| ATOM | 1419 | CA | ASP | A | 182 | 26.844 | 13.896 | −25.958 | 1.00 | 23.30 | 6 |
| ATOM | 1420 | C | ASP | A | 182 | 28.319 | 13.944 | −25.618 | 1.00 | 24.01 | 6 |
| ATOM | 1421 | O | ASP | A | 182 | 29.102 | 14.328 | −26.481 | 1.00 | 23.06 | 8 |
| ATOM | 1422 | CB | ASP | A | 182 | 26.269 | 15.241 | −26.435 | 1.00 | 23.96 | 6 |
| ATOM | 1423 | CG | ASP | A | 182 | 26.307 | 16.365 | −25.427 | 1.00 | 25.62 | 6 |
| ATOM | 1424 | OD1 | ASP | A | 182 | 26.954 | 16.241 | −24.359 | 1.00 | 24.83 | 8 |
| ATOM | 1425 | OD2 | ASP | A | 182 | 25.690 | 17.397 | −25.755 | 1.00 | 27.42 | 8 |
| ATOM | 1426 | N | GLY | A | 183 | 28.808 | 13.557 | −24.413 | 1.00 | 19.95 | 7 |
| ATOM | 1427 | CA | GLY | A | 183 | 30.201 | 13.464 | −24.071 | 1.00 | 23.13 | 6 |
| ATOM | 1428 | C | GLY | A | 1B3 | 30.666 | 14.607 | −23.127 | 1.00 | 19.95 | 6 |
| ATOM | 1429 | O | GLY | A | 183 | 31.799 | 14.532 | −22.661 | 1.00 | 21.39 | 8 |
| ATOM | 1430 | N | LEU | A | 184 | 29.882 | 15.681 | −23.119 | 1.00 | 19.14 | 7 |
| ATOM | 1431 | CA | LEU | A | 184 | 30.339 | 16.847 | −22.301 | 1.00 | 18.16 | 6 |
| ATOM | 1432 | C | LEU | A | 184 | 30.494 | 16.470 | −20.832 | 1.00 | 18.40 | 6 |
| ATOM | 1433 | O | LEU | A | 184 | 29.587 | 15.913 | −20.225 | 1.00 | 19.97 | 8 |
| ATOM | 1434 | CB | LEU | A | 184 | 29.377 | 18.028 | −22.486 | 1.00 | 18.63 | 6 |
| ATOM | 1435 | CG | LEU | A | 184 | 29.738 | 19.280 | −21.652 | 1.00 | 17.34 | 6 |
| ATOM | 1436 | CD1 | LEU | A | 184 | 31.065 | 19.909 | −22.111 | 1.00 | 19.12 | 6 |
| ATOM | 1437 | CD2 | LEU | A | 184 | 28.615 | 20.311 | −21.740 | 1.00 | 19.88 | 6 |
| ATOM | 1438 | N | ALA | A | 185 | 31.607 | 16.870 | −20.184 | 1.00 | 16.12 | 7 |
| ATOM | 1439 | CA | ALA | A | 185 | 31.782 | 16.555 | −18.761 | 1.00 | 18.63 | 6 |
| ATOM | 1440 | C | ALA | A | 185 | 30.744 | 17.337 | −17.942 | 1.00 | 17.79 | 6 |
| ATOM | 1441 | O | ALA | A | 185 | 30.537 | 18.511 | −18.196 | 1.00 | 18.57 | 8 |
| ATOM | 1442 | CB | ALA | A | 185 | 33.237 | 16.872 | −18.396 | 1.00 | 20.34 | 6 |
| ATOM | 1443 | N | LEU | A | 186 | 30.024 | 16.634 | −17.065 | 1.00 | 16.87 | 7 |
| ATOM | 1444 | CA | LEU | A | 186 | 29.020 | 17.352 | −16.271 | 1.00 | 16.99 | 6 |
| ATOM | 1445 | C | LEU | A | 186 | 29.790 | 18.284 | −15.327 | 1.00 | 17.67 | 6 |
| ATOM | 1446 | O | LEU | A | 186 | 30.768 | 17.866 | −14.658 | 1.00 | 20.34 | 8 |
| ATOM | 1447 | CB | LEU | A | 186 | 28.117 | 16.384 | −15.513 | 1.00 | 16.87 | 6 |
| ATOM | 1448 | CG | LEU | A | 186 | 27.300 | 15.408 | −16.358 | 1.00 | 18.67 | 6 |
| ATOM | 1449 | CD1 | LEU | A | 186 | 26.353 | 14.626 | −15.456 | 1.00 | 20.67 | 6 |
| ATOM | 1450 | CD2 | LEU | A | 186 | 26.520 | 16.166 | −17.415 | 1.00 | 17.31 | 6 |
| ATOM | 1451 | N | SER | A | 187 | 29.252 | 19.481 | −15.220 | 1.00 | 18.83 | 7 |
| ATOM | 1452 | CA | SER | A | 187 | 29.915 | 20.486 | −14.382 | 1.00 | 17.18 | 6 |
| ATOM | 1453 | C | SER | A | 187 | 29.000 | 21.631 | −14.105 | 1.00 | 17.64 | 6 |
| ATOM | 1454 | O | SER | A | 187 | 28.216 | 22.057 | −14.964 | 1.00 | 18.63 | 8 |
| ATOM | 1455 | CB | SER | A | 187 | 31.153 | 21.021 | −15.151 | 1.00 | 20.23 | 6 |
| ATOM | 1456 | OG | SER | A | 187 | 31.730 | 22.134 | −14.430 | 1.00 | 20.91 | 8 |
| ATOM | 1457 | N | SER | A | 188 | 29.176 | 22.275 | −12.905 | 1.00 | 17.55 | 7 |
| ATOM | 1458 | CA | SER | A | 188 | 28.463 | 23.548 | −12.722 | 1.00 | 17.70 | 6 |
| ATOM | 1459 | C | SER | A | 188 | 28.806 | 24.605 | −13.755 | 1.00 | 17.74 | 6 |
| ATOM | 1460 | O | SER | A | 188 | 28.014 | 25.522 | −14.095 | 1.00 | 18.92 | 8 |
| ATOM | 1461 | CB | SER | A | 188 | 28.799 | 24.124 | −11.327 | 1.00 | 19.73 | 6 |
| ATOM | 1462 | OG | SER | A | 188 | 30.220 | 24.296 | −11.200 | 1.00 | 20.84 | 8 |
| ATOM | 1463 | N | ARG | A | 189 | 29.969 | 24.554 | −14.393 | 1.00 | 18.16 | 7 |
| ATOM | 1464 | CA | ARG | A | 189 | 30.424 | 25.497 | −15.393 | 1.00 | 19.85 | 6 |
| ATOM | 1465 | C | ARG | A | 189 | 29.538 | 25.498 | −16.634 | 1.00 | 20.33 | 6 |
| ATOM | 1466 | O | ARG | A | 189 | 29.484 | 26.473 | −17.348 | 1.00 | 21.91 | 8 |
| ATOM | 1467 | CB | ARG | A | 189 | 31.879 | 25.201 | −15.823 | 1.00 | 20.55 | 6 |
| ATOM | 1468 | CG | ARG | A | 189 | 32.801 | 25.314 | −14.605 | 1.00 | 22.89 | 6 |
| ATOM | 1469 | CD | ARG | A | 189 | 34.254 | 25.061 | −15.042 | 1.00 | 23.21 | 6 |
| ATOM | 1470 | NE | ARG | A | 189 | 35.037 | 25.170 | −13.785 | 1.00 | 25.97 | 7 |
| ATOM | 1471 | CZ | ARG | A | 189 | 36.121 | 25.924 | −13.683 | 1.00 | 28.29 | 6 |
| ATOM | 1472 | NH1 | ARG | A | 189 | 36.608 | 26.564 | −14.711 | 1.00 | 26.60 | 7 |
| ATOM | 1473 | NH2 | ARG | A | 189 | 36.744 | 25.966 | −12.487 | 1.00 | 28.41 | 7 |
| ATOM | 1474 | N | ASN | A | 190 | 28.914 | 24.324 | −16.956 | 1.00 | 19.42 | 7 |
| ATOM | 1475 | CA | ASN | A | 190 | 28.105 | 24.261 | −18.156 | 1.00 | 19.64 | 6 |
| ATOM | 1476 | C | ASN | A | 190 | 26.963 | 25.235 | −18.114 | 1.00 | 22.61 | 6 |
| ATOM | 1477 | O | ASN | A | 190 | 26.271 | 25.606 | −19.109 | 1.00 | 23.27 | 8 |
| ATOM | 1478 | CB | ASN | A | 190 | 27.544 | 22.841 | −18.332 | 1.00 | 19.54 | 6 |
| ATOM | 1479 | CG | ASN | A | 190 | 28.675 | 21.842 | −18.530 | 1.00 | 21.41 | 6 |
| ATOM | 1480 | OD1 | ASN | A | 190 | 28.471 | 20.621 | −18.265 | 1.00 | 21.40 | 8 |
| ATOM | 1481 | ND2 | ASN | A | 190 | 29.819 | 22.309 | −18.997 | 1.00 | 19.16 | 7 |
| ATOM | 1497 | N | GLY | A | 191 | 26.554 | 25.616 | −16.760 | 1.00 | 27.44 | 7 |
| ATOM | 1498 | CA | GLY | A | 191 | 25.459 | 26.574 | −16.600 | 1.00 | 28.04 | 6 |
| ATOM | 1499 | C | GLY | A | 191 | 25.750 | 27.966 | −17.117 | 1.00 | 29.70 | 6 |
| ATOM | 1500 | O | GLY | A | 191 | 24.790 | 28.715 | −17.294 | 1.00 | 31.47 | 8 |
| ATOM | 1482 | N | TYR | A | 192 | 26.966 | 28.311 | −17.457 | 1.00 | 26.92 | 7 |
| ATOM | 1483 | CA | TYR | A | 192 | 27.272 | 29.642 | −17.970 | 1.00 | 29.88 | 6 |

TABLE 1-continued

| ATOM | 1484 | C | TYR | A | 192 | 27.308 | 29.633 | −19.479 | 1.00 | 29.91 | 6 |
|---|---|---|---|---|---|---|---|---|---|---|---|
| ATOM | 1485 | O | TYR | A | 192 | 27.538 | 30.724 | −20.046 | 1.00 | 34.28 | 8 |
| ATOM | 1486 | CB | TYR | A | 192 | 28.611 | 30.173 | −17.427 | 1.00 | 30.32 | 6 |
| ATOM | 1487 | CG | TYR | A | 192 | 28.459 | 30.366 | −15.928 | 1.00 | 32.17 | 6 |
| ATOM | 1488 | CD1 | TYR | A | 192 | 28.608 | 29.256 | −15.102 | 1.00 | 32.38 | 6 |
| ATOM | 1489 | CD2 | TYR | A | 192 | 28.097 | 31.585 | −15.362 | 1.00 | 34.00 | 6 |
| ATOM | 1490 | CE1 | TYR | A | 192 | 28.438 | 29.352 | −13.751 | 1.00 | 35.21 | 6 |
| ATOM | 1491 | CE2 | TYR | A | 192 | 27.927 | 31.687 | −13.985 | 1.00 | 34.55 | 6 |
| ATOM | 1492 | CZ | TYR | A | 192 | 28.106 | 30.589 | −13.195 | 1.00 | 36.66 | 6 |
| ATOM | 1493 | OH | TYR | A | 192 | 27.942 | 30.636 | −11.819 | 1.00 | 38.33 | 8 |
| ATOM | 1494 | N | LEU | A | 193 | 27.090 | 28.487 | −20.135 | 1.00 | 28.20 | 7 |
| ATOM | 1495 | CA | LEU | A | 193 | 27.054 | 28.479 | −21.575 | 1.00 | 26.63 | 6 |
| ATOM | 1496 | C | LEU | A | 193 | 25.718 | 28.903 | −22.154 | 1.00 | 27.15 | 6 |
| ATOM | 1497 | O | LEU | A | 193 | 24.697 | 28.434 | −21.647 | 1.00 | 28.28 | 8 |
| ATOM | 1498 | CB | LEU | A | 193 | 27.315 | 27.057 | −22.112 | 1.00 | 26.20 | 6 |
| ATOM | 1499 | CG | LEU | A | 193 | 28.613 | 26.402 | −21.654 | 1.00 | 25.58 | 6 |
| ATOM | 1500 | CD1 | LEU | A | 193 | 28.593 | 24.905 | −21.877 | 1.00 | 24.08 | 6 |
| ATOM | 1501 | CD2 | LEU | A | 193 | 29.827 | 27.005 | −22.390 | 1.00 | 27.77 | 6 |
| ATOM | 1502 | N | THR | A | 194 | 25.679 | 29.616 | −23.303 | 1.00 | 28.42 | 7 |
| ATOM | 1503 | CA | THR | A | 194 | 24.376 | 29.825 | −23.934 | 1.00 | 27.62 | 6 |
| ATOM | 1504 | C | THR | A | 194 | 23.892 | 28.531 | −24.561 | 1.00 | 25.74 | 6 |
| ATOM | 1505 | O | THR | A | 194 | 24.735 | 27.621 | −24.723 | 1.00 | 26.48 | 8 |
| ATOM | 1506 | CB | THR | A | 194 | 24.463 | 30.922 | −25.011 | 1.00 | 29.34 | 6 |
| ATOM | 1507 | OG1 | THR | A | 194 | 25.465 | 30.535 | −25.956 | 1.00 | 30.55 | 8 |
| ATOM | 1508 | CG2 | THR | A | 194 | 24.862 | 32.238 | −24.353 | 1.00 | 32.65 | 6 |
| ATOM | 1509 | N | ALA | A | 195 | 22.663 | 28.446 | −25.043 | 1.00 | 25.15 | 7 |
| ATOM | 1510 | CA | ALA | A | 195 | 22.211 | 27.253 | −25.755 | 1.00 | 25.73 | 6 |
| ATOM | 1511 | C | ALA | A | 195 | 23.105 | 26.994 | −26.972 | 1.00 | 28.33 | 6 |
| ATOM | 1512 | O | ALA | A | 195 | 23.460 | 25.834 | −27.241 | 1.00 | 28.09 | 8 |
| ATOM | 1513 | CB | ALA | A | 195 | 20.768 | 27.315 | −26.209 | 1.00 | 25.63 | 6 |
| ATOM | 1514 | N | GLU | A | 196 | 23.486 | 28.068 | −27.703 | 1.00 | 27.21 | 7 |
| ATOM | 1515 | CA | GLU | A | 196 | 24.366 | 27.886 | −28.843 | 1.00 | 28.84 | 6 |
| ATOM | 1516 | C | GLU | A | 196 | 25.718 | 27.351 | −28.424 | 1.00 | 25.77 | 6 |
| ATOM | 1517 | O | GLU | A | 196 | 26.282 | 26.445 | −29.054 | 1.00 | 30.10 | 8 |
| ATOM | 1518 | CB | GLU | A | 196 | 24.534 | 29.239 | −29.570 | 1.00 | 31.35 | 6 |
| ATOM | 1519 | N | GLN | A | 197 | 26.278 | 27.889 | −27.328 | 1.00 | 26.45 | 7 |
| ATOM | 1520 | CA | GLN | A | 197 | 27.567 | 27.412 | −26.855 | 1.00 | 25.85 | 6 |
| ATOM | 1521 | C | GLN | A | 197 | 27.489 | 25.961 | −26.330 | 1.00 | 25.97 | 6 |
| ATOM | 1522 | O | GLN | A | 197 | 28.406 | 25.210 | −26.618 | 1.00 | 25.79 | 8 |
| ATOM | 1523 | CB | GLN | A | 197 | 28.157 | 28.273 | −25.717 | 1.00 | 27.14 | 6 |
| ATOM | 1524 | CG | GLN | A | 197 | 28.452 | 29.662 | −26.408 | 1.00 | 29.94 | 6 |
| ATOM | 1525 | CD | GLN | A | 197 | 28.544 | 30.739 | −25.358 | 1.00 | 31.03 | 6 |
| ATOM | 1526 | OE1 | GLN | A | 197 | 28.249 | 30.597 | −24.174 | 1.00 | 31.48 | 8 |
| ATOM | 1527 | NE2 | GLN | A | 197 | 28.949 | 31.963 | −25.739 | 1.00 | 30.58 | 7 |
| ATOM | 1528 | N | ARG | A | 198 | 26.335 | 25.639 | −25.736 | 1.00 | 23.62 | 7 |
| ATOM | 1529 | CA | ARG | A | 198 | 26.151 | 24.282 | −25.209 | 1.00 | 23.58 | 6 |
| ATOM | 1530 | C | ARG | A | 198 | 26.204 | 23.282 | −26.345 | 1.00 | 24.98 | 6 |
| ATOM | 1531 | O | ARG | A | 198 | 26.761 | 22.214 | −26.214 | 1.00 | 25.17 | 8 |
| ATOM | 1532 | CB | ARG | A | 198 | 24.831 | 24.133 | −24.454 | 1.00 | 22.16 | 6 |
| ATOM | 1533 | CG | ARG | A | 198 | 24.576 | 22.689 | −23.946 | 1.00 | 21.81 | 6 |
| ATOM | 1534 | CD | ARG | A | 198 | 25.656 | 22.194 | −23.010 | 1.00 | 22.56 | 6 |
| ATOM | 1535 | NE | ARG | A | 198 | 25.386 | 20.830 | −22.532 | 1.00 | 21.88 | 7 |
| ATOM | 1536 | CZ | ARG | A | 198 | 25.614 | 19.724 | −23.247 | 1.00 | 24.32 | 6 |
| ATOM | 1537 | NH1 | ARG | A | 198 | 25.384 | 18.481 | −22.824 | 1.00 | 23.45 | 7 |
| ATOM | 1538 | NH2 | ARG | A | 198 | 26.118 | 19.830 | −24.477 | 1.00 | 25.14 | 7 |
| ATOM | 1539 | N | LYS | A | 199 | 25.707 | 23.649 | −27.549 | 1.00 | 23.80 | 7 |
| ATOM | 1540 | CA | LYS | A | 199 | 25.820 | 22.710 | −28.684 | 1.00 | 22.66 | 6 |
| ATOM | 1541 | C | LYS | A | 199 | 27.221 | 22.558 | −29.202 | 1.00 | 22.59 | 6 |
| ATOM | 1542 | O | LYS | A | 199 | 27.608 | 21.508 | −29.753 | 1.00 | 24.00 | 8 |
| ATOM | 1543 | CB | LYS | A | 199 | 24.855 | 23.272 | −29.743 | 1.00 | 25.23 | 6 |
| ATOM | 1544 | CG | LYS | A | 199 | 24.661 | 22.284 | −30.903 | 1.00 | 27.40 | 6 |
| ATOM | 1545 | CD | LYS | A | 199 | 23.602 | 22.991 | −31.802 | 1.00 | 32.35 | 6 |
| ATOM | 1546 | CE | LYS | A | 199 | 23.336 | 22.059 | −32.983 | 1.00 | 36.02 | 6 |
| ATOM | 1547 | NZ | LYS | A | 199 | 22.311 | 22.674 | −33.894 | 1.00 | 38.59 | 7 |
| ATOM | 1548 | N | ILE | A | 200 | 28.111 | 23.556 | −29.074 | 1.00 | 22.04 | 7 |
| ATOM | 1549 | CA | ILE | A | 200 | 29.513 | 23.458 | −29.440 | 1.00 | 25.05 | 6 |
| ATOM | 1550 | C | ILE | A | 200 | 30.415 | 22.725 | −28.438 | 1.00 | 23.70 | 6 |
| ATOM | 1551 | O | ILE | A | 200 | 31.347 | 21.980 | −28.775 | 1.00 | 22.15 | 8 |
| ATOM | 1552 | CB | ILE | A | 200 | 30.128 | 24.863 | −29.575 | 1.00 | 25.43 | 6 |
| ATOM | 1553 | CG1 | ILE | A | 200 | 29.457 | 25.528 | −30.809 | 1.00 | 26.99 | 6 |
| ATOM | 1554 | CG2 | ILE | A | 200 | 31.644 | 24.911 | −29.704 | 1.00 | 26.61 | 6 |
| ATOM | 1555 | CD1 | ILE | A | 200 | 29.746 | 27.029 | −30.827 | 1.00 | 28.65 | 6 |
| ATOM | 1556 | N | ALA | A | 201 | 29.987 | 22.836 | −27.170 | 1.00 | 22.88 | 7 |
| ATOM | 1557 | CA | ALA | A | 201 | 30.773 | 22.278 | −26.053 | 1.00 | 24.80 | 6 |
| ATOM | 1558 | C | ALA | A | 201 | 31.217 | 20.829 | −26.110 | 1.00 | 23.52 | 6 |
| ATOM | 1559 | O | ALA | A | 201 | 32.363 | 20.607 | −25.709 | 1.00 | 21.96 | 8 |
| ATOM | 1560 | CB | ALA | A | 201 | 29.913 | 22.499 | −24.781 | 1.00 | 24.70 | 6 |
| ATOM | 1561 | N | PRO | A | 202 | 30.498 | 19.846 | −26.659 | 1.00 | 24.18 | 7 |
| ATOM | 1562 | CA | PRO | A | 202 | 30.946 | 18.473 | −26.796 | 1.00 | 24.19 | 6 |

TABLE 1-continued

| | | | | | | | | | |
|---|---|---|---|---|---|---|---|---|---|
| ATOM | 1563 | C | PRO | A | 202 | 32.191 | 18.288 | −27.649 | 1.00 | 26.04 | 6 |
| ATOM | 1564 | O | PRO | A | 202 | 32.900 | 17.282 | −27.556 | 1.00 | 25.77 | 8 |
| ATOM | 1565 | CB | PRO | A | 202 | 29.759 | 17.693 | −27.382 | 1.00 | 24.31 | 6 |
| ATOM | 1566 | CG | PRO | A | 202 | 28.579 | 18.572 | −27.068 | 1.00 | 23.02 | 6 |
| ATOM | 1567 | CD | PRO | A | 202 | 29.073 | 19.991 | −27.051 | 1.00 | 22.33 | 6 |
| ATOM | 1568 | N | GLY | A | 203 | 32.559 | 19.351 | −28.406 | 1.00 | 25.61 | 7 |
| ATOM | 1569 | CA | GLY | A | 203 | 33.779 | 19.327 | −29.179 | 1.00 | 26.22 | 6 |
| ATOM | 1570 | C | GLY | A | 203 | 35.012 | 19.196 | −28.324 | 1.00 | 24.81 | 6 |
| ATOM | 1571 | O | GLY | A | 203 | 36.061 | 18.750 | −28.817 | 1.00 | 24.88 | 8 |
| ATOM | 1572 | N | LEU | A | 204 | 34.999 | 19.724 | −27.082 | 1.00 | 23.90 | 7 |
| ATOM | 1573 | CA | LEU | A | 204 | 36.199 | 19.561 | −26.254 | 1.00 | 23.72 | 6 |
| ATOM | 1574 | C | LEU | A | 204 | 36.550 | 18.119 | −26.035 | 1.00 | 23.32 | 6 |
| ATOM | 1575 | O | LEU | A | 204 | 37.689 | 17.689 | −26.239 | 1.00 | 24.33 | 8 |
| ATOM | 1576 | CB | LEU | A | 204 | 35.957 | 20.361 | −24.936 | 1.00 | 24.53 | 6 |
| ATOM | 1577 | CG | LEU | A | 204 | 37.111 | 20.290 | −23.972 | 1.00 | 25.84 | 6 |
| ATOM | 1578 | CD1 | LEU | A | 204 | 38.425 | 20.791 | −24.586 | 1.00 | 26.75 | 6 |
| ATOM | 1579 | CD2 | LEU | A | 204 | 36.806 | 21.156 | −22.742 | 1.00 | 26.68 | 6 |
| ATOM | 1580 | N | TYR | A | 205 | 35.580 | 17.243 | −25.663 | 1.00 | 21.57 | 7 |
| ATOM | 1581 | CA | TYR | A | 205 | 35.804 | 15.836 | −25.435 | 1.00 | 22.36 | 6 |
| ATOM | 1582 | C | TYR | A | 205 | 36.200 | 15.116 | −26.748 | 1.00 | 21.69 | 6 |
| ATOM | 1583 | O | TYR | A | 205 | 37.041 | 14.212 | −26.762 | 1.00 | 23.95 | 8 |
| ATOM | 1584 | CB | TYR | A | 205 | 34.533 | 15.211 | −24.809 | 1.00 | 21.96 | 6 |
| ATOM | 1585 | CG | TYR | A | 205 | 34.766 | 13.758 | −24.505 | 1.00 | 25.55 | 6 |
| ATOM | 1586 | CD1 | TYR | A | 205 | 35.727 | 13.322 | −23.619 | 1.00 | 27.86 | 6 |
| ATOM | 1587 | CD2 | TYR | A | 205 | 34.059 | 12.802 | −25.253 | 1.00 | 29.16 | 6 |
| ATOM | 1588 | CE1 | TYR | A | 205 | 35.901 | 11.979 | −23.364 | 1.00 | 30.07 | 6 |
| ATOM | 1589 | CE2 | TYR | A | 205 | 34.261 | 11.448 | −25.003 | 1.00 | 30.89 | 6 |
| ATOM | 1590 | CZ | TYR | A | 205 | 35.158 | 11.053 | −24.064 | 1.00 | 32.67 | 6 |
| ATOM | 1591 | OH | TYR | A | 205 | 35.373 | 9.702 | −23.839 | 1.00 | 36.20 | 8 |
| ATOM | 1592 | N | LYS | A | 206 | 35.652 | 15.679 | −27.833 | 1.00 | 23.35 | 7 |
| ATOM | 1593 | CA | LYS | A | 206 | 36.040 | 15.114 | −29.149 | 1.00 | 24.75 | 6 |
| ATOM | 1594 | C | LYS | A | 206 | 37.530 | 15.306 | −29.401 | 1.00 | 24.74 | 6 |
| ATOM | 1595 | O | LYS | A | 206 | 38.252 | 14.359 | −29.757 | 1.00 | 26.16 | 8 |
| ATOM | 1596 | CB | LYS | A | 206 | 35.223 | 15.740 | −30.293 | 1.00 | 25.21 | 6 |
| ATOM | 1597 | CG | LYS | A | 206 | 33.784 | 15.236 | −30.295 | 1.00 | 30.61 | 6 |
| ATOM | 1598 | CD | LYS | A | 206 | 33.118 | 15.648 | −31.621 | 1.00 | 34.58 | 6 |
| ATOM | 1599 | CE | LYS | A | 206 | 31.600 | 15.547 | −31.489 | 1.00 | 37.70 | 6 |
| ATOM | 1600 | NZ | LYS | A | 206 | 30.951 | 15.934 | −32.794 | 1.00 | 40.74 | 7 |
| ATOM | 1601 | N | VAL | A | 207 | 37.995 | 16.518 | −29.128 | 1.00 | 25.56 | 7 |
| ATOM | 1602 | CA | VAL | A | 207 | 39.432 | 16.818 | −29.324 | 1.00 | 26.41 | 6 |
| ATOM | 1603 | C | VAL | A | 207 | 40.240 | 16.016 | −28.333 | 1.00 | 26.75 | 6 |
| ATOM | 1604 | O | VAL | A | 207 | 41.246 | 15.351 | −28.662 | 1.00 | 26.06 | 8 |
| ATOM | 1605 | CB | VAL | A | 207 | 39.714 | 18.318 | −29.266 | 1.00 | 26.88 | 6 |
| ATOM | 1606 | CG1 | VAL | A | 207 | 41.212 | 18.590 | −29.172 | 1.00 | 27.69 | 6 |
| ATOM | 1607 | CG2 | VAL | A | 207 | 39.062 | 18.967 | −30.489 | 1.00 | 27.15 | 6 |
| ATOM | 1608 | N | LEU | A | 208 | 39.793 | 15.917 | −27.065 | 1.00 | 26.81 | 7 |
| ATOM | 1609 | CA | LEU | A | 208 | 40.472 | 15.110 | −26.079 | 1.00 | 26.80 | 6 |
| ATOM | 1610 | C | LEU | A | 208 | 40.555 | 13.645 | −26.462 | 1.00 | 27.53 | 6 |
| ATOM | 1611 | O | LEU | A | 208 | 41.616 | 13.017 | −26.276 | 1.00 | 27.79 | 8 |
| ATOM | 1612 | CB | LEU | A | 208 | 39.736 | 15.325 | −24.732 | 1.00 | 28.31 | 6 |
| ATOM | 1613 | CG | LEU | A | 208 | 40.248 | 14.531 | −23.535 | 1.00 | 31.14 | 6 |
| ATOM | 1614 | CD1 | LEU | A | 208 | 41.649 | 14.906 | −23.142 | 1.00 | 31.37 | 6 |
| ATOM | 1615 | CD2 | LEU | A | 208 | 39.288 | 14.741 | −22.347 | 1.00 | 33.29 | 6 |
| ATOM | 1616 | N | SER | A | 209 | 39.539 | 13.042 | −27.028 | 1.00 | 26.96 | 7 |
| ATOM | 1617 | CA | SER | A | 209 | 39.536 | 11.655 | −27.442 | 1.00 | 28.65 | 6 |
| ATOM | 1618 | C | SER | A | 209 | 40.427 | 11.463 | −28.696 | 1.00 | 30.30 | 6 |
| ATOM | 1619 | O | SER | A | 209 | 41.021 | 10.401 | −28.829 | 1.00 | 29.86 | 8 |
| ATOM | 1620 | CB | SER | A | 209 | 38.141 | 11.126 | −27.751 | 1.00 | 32.08 | 6 |
| ATOM | 1621 | OG | SER | A | 209 | 37.320 | 11.455 | −26.630 | 1.00 | 36.96 | 8 |
| ATOM | 1622 | N | SER | A | 210 | 40.502 | 12.521 | −29.507 | 1.00 | 31.09 | 7 |
| ATOM | 1623 | CA | SEP | A | 210 | 41.372 | 12.426 | −30.703 | 1.00 | 33.89 | 6 |
| ATOM | 1624 | C | SER | A | 210 | 42.826 | 12.447 | −30.297 | 1.00 | 33.77 | 6 |
| ATOM | 1625 | O | SER | A | 210 | 43.687 | 11.734 | −30.842 | 1.00 | 34.87 | 8 |
| ATOM | 1626 | CB | SER | A | 210 | 41.024 | 13.563 | −31.655 | 1.00 | 36.51 | 6 |
| ATOM | 1627 | OG | SER | A | 210 | 42.171 | 13.743 | −32.490 | 1.00 | 42.40 | 8 |
| ATOM | 1628 | N | ILE | A | 211 | 43.172 | 13.190 | −29.230 | 1.00 | 31.25 | 7 |
| ATOM | 1629 | CA | ILE | A | 211 | 44.530 | 13.129 | −28.705 | 1.00 | 30.79 | 6 |
| ATOM | 1630 | C | ILE | A | 211 | 44.815 | 11.731 | −28.188 | 1.00 | 31.65 | 6 |
| ATOM | 1631 | O | ILE | A | 211 | 45.878 | 11.124 | −28.405 | 1.00 | 31.20 | 8 |
| ATOM | 1632 | CB | ILE | A | 211 | 44.710 | 14.154 | −27.580 | 1.00 | 30.45 | 6 |
| ATOM | 1633 | CG1 | ILE | A | 211 | 44.646 | 15.580 | −28.137 | 1.00 | 29.16 | 6 |
| ATOM | 1634 | CG2 | ILE | A | 211 | 46.009 | 13.912 | −26.797 | 1.00 | 28.20 | 6 |
| ATOM | 1635 | CD1 | ILE | A | 211 | 44.501 | 16.613 | −27.014 | 1.00 | 28.78 | 6 |
| ATOM | 1636 | N | ALA | A | 212 | 43.882 | 11.162 | −27.426 | 1.00 | 31.19 | 7 |
| ATOM | 1637 | CA | ALA | A | 212 | 44.069 | 9.828 | −26.852 | 1.00 | 31.19 | 6 |
| ATOM | 1638 | C | ALA | A | 212 | 44.251 | 8.789 | −27.955 | 1.00 | 33.70 | 6 |
| ATOM | 1639 | O | ALA | A | 212 | 45.100 | 7.892 | −27.832 | 1.00 | 34.72 | 8 |
| ATOM | 1640 | CB | ALA | A | 212 | 42.879 | 9.427 | −25.995 | 1.00 | 31.27 | 6 |
| ATOM | 1641 | N | ASP | A | 213 | 43.478 | 8.916 | −29.045 | 1.00 | 32.83 | 7 |

TABLE 1-continued

| | | | | | | | | | |
|---|---|---|---|---|---|---|---|---|---|
| ATOM | 1642 | CA | ASP | A | 213 | 43.576 | 7.982 | −30.167 | 1.00 | 34.55 | 6 |
| ATOM | 1643 | C | ASP | A | 213 | 45.008 | 7.998 | −30.723 | 1.00 | 34.80 | 6 |
| ATOM | 1644 | O | ASP | A | 213 | 45.616 | 6.938 | −30.847 | 1.00 | 36.87 | 8 |
| ATOM | 1645 | CB | ASP | A | 213 | 42.567 | 8.322 | −31.256 | 1.00 | 33.87 | 6 |
| ATOM | 1646 | CG | ASP | A | 213 | 41.145 | 7.900 | −30.886 | 1.00 | 36.07 | 6 |
| ATOM | 1647 | OD1 | ASP | A | 213 | 40.932 | 7.091 | −29.951 | 1.00 | 36.03 | 8 |
| ATOM | 1648 | OD2 | ASP | A | 213 | 40.224 | 8.400 | −31.585 | 1.00 | 36.99 | 8 |
| ATOM | 1649 | N | LYS | A | 214 | 45.527 | 9.193 | −30.994 | 1.00 | 34.39 | 7 |
| ATOM | 1650 | CA | LYS | A | 214 | 46.892 | 9.357 | −31.506 | 1.00 | 35.31 | 6 |
| ATOM | 1651 | C | LYS | A | 214 | 47.904 | 8.782 | −30.536 | 1.00 | 37.91 | 6 |
| ATOM | 1652 | O | LYS | A | 214 | 48.900 | 8.106 | −30.920 | 1.00 | 39.73 | 8 |
| ATOM | 1653 | CB | LYS | A | 214 | 47.196 | 10.833 | −31.789 | 1.00 | 33.06 | 6 |
| ATOM | 1654 | CG | LYS | A | 214 | 46.295 | 11.525 | −32.774 | 1.00 | 33.68 | 6 |
| ATOM | 1655 | CD | LYS | A | 214 | 46.733 | 12.968 | −33.079 | 1.00 | 32.27 | 6 |
| ATOM | 1656 | CE | LYS | A | 214 | 45.891 | 13.544 | −34.215 | 1.00 | 33.88 | 6 |
| ATOM | 1657 | NZ | LYS | A | 214 | 46.243 | 14.978 | −34.497 | 1.00 | 35.57 | 7 |
| ATOM | 1658 | N | LEU | A | 215 | 47.726 | 9.056 | −29.227 | 1.00 | 38.37 | 7 |
| ATOM | 1659 | CA | LEU | A | 215 | 48.742 | 8.507 | −28.299 | 1.00 | 41.26 | 6 |
| ATOM | 1660 | C | LEU | A | 215 | 48.676 | 6.988 | −28.267 | 1.00 | 42.76 | 6 |
| ATOM | 1661 | O | LEU | A | 215 | 49.717 | 6.311 | −28.250 | 1.00 | 43.43 | 8 |
| ATOM | 1662 | CB | LEU | A | 215 | 48.615 | 9.016 | −26.871 | 1.00 | 38.15 | 6 |
| ATOM | 1663 | CG | LEU | A | 215 | 48.941 | 10.483 | −26.658 | 1.00 | 39.14 | 6 |
| ATOM | 1664 | CD1 | LEU | A | 215 | 48.406 | 10.973 | −25.306 | 1.00 | 39.20 | 6 |
| ATOM | 1665 | CD2 | LEU | A | 215 | 50.441 | 10.749 | −26.718 | 1.00 | 39.00 | 6 |
| ATOM | 1666 | N | GLN | A | 216 | 47.493 | 6.407 | −28.253 | 1.00 | 44.37 | 7 |
| ATOM | 1667 | CA | GLN | A | 216 | 47.328 | 4.952 | −28.225 | 1.00 | 47.10 | 6 |
| ATOM | 1668 | C | GLN | A | 216 | 47.833 | 4.272 | −29.499 | 1.00 | 47.76 | 6 |
| ATOM | 1669 | O | GLN | A | 216 | 48.153 | 3.081 | −29.469 | 1.00 | 48.80 | 6 |
| ATOM | 1670 | CD | GLN | A | 216 | 45.859 | 4.643 | −27.991 | 1.00 | 48.55 | 6 |
| ATOM | 1671 | CG | GLN | A | 216 | 45.452 | 3.303 | −27.435 | 1.00 | 50.81 | 6 |
| ATOM | 1672 | CD | GLN | A | 216 | 44.259 | 3.444 | −26.493 | 1.00 | 53.17 | 6 |
| ATOM | 1673 | OE1 | GLN | A | 216 | 43.252 | 4.063 | −26.856 | 1.00 | 54.69 | 8 |
| ATOM | 1674 | NE2 | GLN | A | 216 | 44.354 | 2.898 | −25.279 | 1.00 | 53.81 | 7 |
| ATOM | 1675 | N | ALA | A | 217 | 47.944 | 4.977 | −30.617 | 1.00 | 47.64 | 7 |
| ATOM | 1676 | CA | ALA | A | 217 | 48.431 | 4.433 | −31.869 | 1.00 | 48.49 | 6 |
| ATOM | 1677 | C | ALA | A | 217 | 49.948 | 4.569 | −31.997 | 1.00 | 48.68 | 6 |
| ATOM | 1678 | O | ALA | A | 217 | 50.517 | 4.182 | −33.024 | 1.00 | 51.00 | 8 |
| ATOM | 1679 | CB | ALA | A | 217 | 47.789 | 5.138 | −33.060 | 1.00 | 47.71 | 6 |
| ATOM | 1680 | N | GLY | A | 218 | 50.612 | 5.211 | −31.056 | 1.00 | 47.70 | 7 |
| ATOM | 1681 | CA | GLY | A | 218 | 52.037 | 5.390 | −31.027 | 1.00 | 46.44 | 6 |
| ATOM | 1682 | C | GLY | A | 218 | 52.539 | 6.780 | −31.316 | 1.00 | 47.59 | 6 |
| ATOM | 1683 | O | GLY | A | 218 | 53.771 | 6.979 | −31.285 | 1.00 | 47.50 | 8 |
| ATOM | 1684 | N | GLU | A | 219 | 51.677 | 7.755 | −31.607 | 1.00 | 45.89 | 7 |
| ATOM | 1685 | CA | GLU | A | 219 | 52.216 | 9.086 | −31.891 | 1.00 | 46.96 | 6 |
| ATOM | 1686 | C | GLU | A | 219 | 52.912 | 9.624 | −30.651 | 1.00 | 48.26 | 6 |
| ATOM | 1687 | O | GLU | A | 219 | 52.403 | 9.484 | −29.530 | 1.00 | 48.86 | 8 |
| ATOM | 1688 | CB | GLU | A | 219 | 51.146 | 10.071 | −32.380 | 1.00 | 47.88 | 6 |
| ATOM | 1689 | CG | GLU | A | 219 | 50.460 | 9.695 | −33.672 | 1.00 | 48.05 | 6 |
| ATOM | 1690 | CD | GLU | A | 219 | 49.744 | 10.817 | −34.384 | 1.00 | 50.68 | 6 |
| ATOM | 1691 | OE1 | GLU | A | 219 | 50.134 | 12.015 | −34.408 | 1.00 | 51.01 | 8 |
| ATOM | 1692 | OE2 | GLU | A | 219 | 48.702 | 10.497 | −35.025 | 1.00 | 52.09 | 8 |
| ATOM | 1693 | N | ARG | A | 220 | 54.135 | 10.154 | −30.831 | 1.00 | 47.68 | 7 |
| ATOM | 1694 | CA | ARG | A | 220 | 54.868 | 10.698 | −29.694 | 1.00 | 47.37 | 6 |
| ATOM | 1695 | C | ARG | A | 220 | 55.402 | 12.091 | −29.989 | 1.00 | 47.62 | 6 |
| ATOM | 1696 | O | ARG | A | 220 | 56.106 | 12.622 | −29.125 | 1.00 | 49.49 | 8 |
| ATOM | 1697 | CB | ARG | A | 220 | 56.014 | 9.790 | −29.239 | 1.00 | 46.78 | 6 |
| ATOM | 1698 | CG | ARG | A | 220 | 55.570 | 8.463 | −28.643 | 1.00 | 46.54 | 6 |
| ATOM | 1699 | CD | ARG | A | 220 | 54.878 | 8.628 | −27.293 | 1.00 | 45.80 | 6 |
| ATOM | 1700 | NE | ARG | A | 220 | 54.371 | 7.359 | −26.801 | 1.00 | 45.04 | 7 |
| ATOM | 1701 | CZ | ARG | A | 220 | 53.281 | 6.683 | −27.074 | 1.00 | 44.93 | 6 |
| ATOM | 1702 | NH1 | ARG | A | 220 | 52.341 | 7.093 | −27.930 | 1.00 | 45.42 | 7 |
| ATOM | 1703 | NH2 | ARG | A | 220 | 53.080 | 5.516 | −26.476 | 1.00 | 44.28 | 7 |
| ATOM | 1704 | N | ASP | A | 221 | 54.976 | 12.756 | −31.052 | 1.00 | 48.60 | 7 |
| ATOM | 1705 | CA | ASP | A | 221 | 55.381 | 14.161 | −31.242 | 1.00 | 48.15 | 6 |
| ATOM | 1706 | C | ASP | A | 221 | 54.296 | 15.005 | −30.557 | 1.00 | 46.06 | 6 |
| ATOM | 1707 | O | ASP | A | 221 | 53.379 | 15.515 | −31.197 | 1.00 | 44.76 | 8 |
| ATOM | 1708 | CB | ASP | A | 221 | 55.576 | 14.527 | −32.691 | 1.00 | 50.20 | 6 |
| ATOM | 1709 | CG | ASP | A | 221 | 56.053 | 15.928 | −32.988 | 1.00 | 53.21 | 6 |
| ATOM | 1710 | OD1 | ASP | A | 221 | 56.188 | 16.801 | −32.101 | 1.00 | 53.81 | 8 |
| ATOM | 1711 | OD2 | ASP | A | 221 | 56.309 | 16.204 | −34.191 | 1.00 | 55.09 | 8 |
| ATOM | 1712 | N | LEU | A | 222 | 54.465 | 15.167 | −29.249 | 1.00 | 43.92 | 7 |
| ATOM | 1713 | CA | LEU | A | 222 | 53.451 | 15.829 | −28.427 | 1.00 | 42.81 | 6 |
| ATOM | 1714 | C | LEU | A | 222 | 53.215 | 17.271 | −28.774 | 1.00 | 43.64 | 6 |
| ATOM | 1715 | O | LEU | A | 222 | 52.066 | 17.762 | −28.789 | 1.00 | 41.82 | 8 |
| ATOM | 1716 | CB | LEU | A | 222 | 53.894 | 15.652 | −26.952 | 1.00 | 43.09 | 6 |
| ATOM | 1717 | CG | LEU | A | 222 | 54.196 | 14.191 | −26.578 | 1.00 | 41.83 | 6 |
| ATOM | 1718 | CD1 | LEU | A | 222 | 54.442 | 14.033 | −25.081 | 1.00 | 42.53 | 6 |
| ATOM | 1719 | CD2 | LEU | A | 222 | 53.086 | 13.237 | −26.991 | 1.00 | 41.15 | 6 |
| ATOM | 1720 | N | ASP | A | 223 | 54.285 | 18.012 | −29.105 | 1.00 | 43.23 | 7 |

TABLE 1-continued

| ATOM | 1721 | CA | ASP | A | 223 | 54.124 | 19.416 | −29.472 | 1.00 | 44.33 | 6 |
|---|---|---|---|---|---|---|---|---|---|---|---|
| ATOM | 1722 | C | ASP | A | 223 | 53.223 | 19.562 | −30.688 | 1.00 | 44.26 | 6 |
| ATOM | 1723 | O | ASP | A | 223 | 52.401 | 20.490 | −30.770 | 1.00 | 45.10 | 8 |
| ATOM | 1724 | CB | ASP | A | 223 | 55.508 | 20.042 | −29.717 | 1.00 | 45.77 | 6 |
| ATOM | 1725 | N | GLU | A | 224 | 53.398 | 18.654 | −31.651 | 1.00 | 44.43 | 7 |
| ATOM | 1726 | CA | GLU | A | 224 | 52.583 | 18.676 | −32.863 | 1.00 | 45.57 | 6 |
| ATOM | 1727 | C | GLU | A | 224 | 51.126 | 18.332 | −32.533 | 1.00 | 41.13 | 6 |
| ATOM | 1728 | O | GLU | A | 224 | 50.187 | 18.995 | −32.967 | 1.00 | 40.57 | 8 |
| ATOM | 1729 | CB | GLU | A | 224 | 53.146 | 17.723 | −33.915 | 1.00 | 49.14 | 6 |
| ATOM | 1730 | CG | GLU | A | 224 | 52.327 | 17.645 | −35.186 | 1.00 | 53.71 | 6 |
| ATOM | 1731 | CD | GLU | A | 224 | 52.241 | 18.926 | −35.991 | 1.00 | 57.27 | 6 |
| ATOM | 1732 | OE1 | GLU | A | 224 | 52.627 | 20.028 | −35.530 | 1.00 | 58.34 | 8 |
| ATOM | 1733 | OE2 | GLU | A | 224 | 51.738 | 18.792 | −37.141 | 1.00 | 59.44 | 8 |
| ATOM | 1734 | N | ILE | A | 225 | 50.928 | 17.234 | −31.837 | 1.00 | 38.07 | 7 |
| ATOM | 1735 | CA | ILE | A | 225 | 49.602 | 16.821 | −31.360 | 1.00 | 36.44 | 6 |
| ATOM | 1736 | C | ILE | A | 225 | 48.838 | 17.929 | −30.641 | 1.00 | 35.31 | 6 |
| ATOM | 1737 | O | ILE | A | 225 | 47.630 | 18.075 | −30.873 | 1.00 | 34.79 | 8 |
| ATOM | 1738 | CB | ILE | A | 225 | 49.745 | 15.630 | −30.401 | 1.00 | 36.23 | 6 |
| ATOM | 1739 | CG1 | ILE | A | 225 | 50.310 | 14.449 | −31.200 | 1.00 | 36.60 | 6 |
| ATOM | 1740 | CG2 | ILE | A | 225 | 48.432 | 15.233 | −29.722 | 1.00 | 36.18 | 6 |
| ATOM | 1741 | CD1 | ILE | A | 225 | 50.515 | 13.174 | −30.428 | 1.00 | 37.76 | 6 |
| ATOM | 1742 | N | ILE | A | 226 | 49.522 | 18.680 | −29.780 | 1.00 | 33.53 | 7 |
| ATOM | 1743 | CA | ILE | A | 226 | 48.922 | 19.759 | −29.025 | 1.00 | 33.52 | 6 |
| ATOM | 1744 | C | ILE | A | 226 | 48.614 | 20.969 | −29.881 | 1.00 | 33.80 | 6 |
| ATOM | 1745 | O | ILE | A | 226 | 47.581 | 21.655 | −29.737 | 1.00 | 32.30 | 8 |
| ATOM | 1746 | CB | ILE | A | 226 | 49.877 | 20.107 | −27.843 | 1.00 | 34.98 | 6 |
| ATOM | 1747 | CG1 | ILE | A | 226 | 49.847 | 18.937 | −26.874 | 1.00 | 34.99 | 6 |
| ATOM | 1748 | CG2 | ILE | A | 226 | 49.490 | 21.417 | −27.159 | 1.00 | 34.94 | 6 |
| ATOM | 1749 | CD1 | ILE | A | 226 | 50.657 | 19.117 | −25.611 | 1.00 | 36.97 | 6 |
| ATOM | 1750 | N | THR | A | 227 | 49.527 | 21.261 | −30.830 | 1.00 | 33.69 | 7 |
| ATOM | 1751 | CA | THR | A | 227 | 49.287 | 22.418 | −31.697 | 1.00 | 34.02 | 6 |
| ATOM | 1752 | C | THR | A | 227 | 48.040 | 22.160 | −32.526 | 1.00 | 32.93 | 6 |
| ATOM | 1753 | O | THR | A | 227 | 47.183 | 23.034 | −32.604 | 1.00 | 33.21 | 8 |
| ATOM | 1754 | CB | THR | A | 227 | 50.469 | 22.754 | −32.630 | 1.00 | 36.23 | 6 |
| ATOM | 1755 | OG1 | THR | A | 227 | 51.656 | 22.905 | −31.839 | 1.00 | 38.63 | 8 |
| ATOM | 1756 | CG2 | THR | A | 227 | 50.229 | 24.059 | −33.378 | 1.00 | 37.54 | 6 |
| ATOM | 1757 | N | ILE | A | 228 | 47.887 | 20.967 | −33.060 | 1.00 | 33.57 | 7 |
| ATOM | 1758 | CA | ILE | A | 228 | 46.742 | 20.647 | −33.899 | 1.00 | 33.85 | 6 |
| ATOM | 1759 | C | ILE | A | 228 | 45.453 | 20.703 | −33.074 | 1.00 | 33.32 | 6 |
| ATOM | 1760 | O | ILE | A | 228 | 44.417 | 21.205 | −33.482 | 1.00 | 31.47 | 8 |
| ATOM | 1761 | CB | ILE | A | 228 | 46.908 | 19.275 | −34.533 | 1.00 | 36.08 | 6 |
| ATOM | 1762 | CG1 | ILE | A | 228 | 48.002 | 19.323 | −35.634 | 1.00 | 39.34 | 6 |
| ATOM | 1763 | CG2 | ILE | A | 228 | 45.610 | 18.758 | −35.136 | 1.00 | 35.68 | 6 |
| ATOM | 1764 | CD1 | ILE | A | 228 | 48.385 | 17.919 | −36.092 | 1.00 | 39.59 | 6 |
| ATOM | 1765 | N | ALA | A | 229 | 45.597 | 20.146 | −31.859 | 1.00 | 33.09 | 7 |
| ATOM | 1766 | CA | ALA | A | 229 | 44.441 | 20.114 | −30.930 | 1.00 | 31.53 | 6 |
| ATOM | 1767 | C | ALA | A | 229 | 43.948 | 21.497 | −30.607 | 1.00 | 28.89 | 6 |
| ATOM | 1768 | O | ALA | A | 229 | 42.733 | 21.771 | −30.644 | 1.00 | 28.46 | 8 |
| ATOM | 1769 | CB | ALA | A | 229 | 44.898 | 19.315 | −29.707 | 1.00 | 31.42 | 6 |
| ATOM | 1770 | N | GLY | A | 230 | 44.836 | 22.471 | −30.407 | 1.00 | 29.20 | 7 |
| ATOM | 1771 | CA | GLY | A | 230 | 44.485 | 23.857 | −30.166 | 1.00 | 30.51 | 6 |
| ATOM | 1772 | C | GLY | A | 230 | 43.797 | 24.472 | −31.372 | 1.00 | 31.48 | 6 |
| ATOM | 1773 | O | GLY | A | 230 | 42.759 | 25.155 | −31.288 | 1.00 | 33.24 | 8 |
| ATOM | 1774 | N | GLN | A | 231 | 44.374 | 24.217 | −32.569 | 1.00 | 33.19 | 7 |
| ATOM | 1775 | CA | GLN | A | 231 | 43.812 | 24.700 | −33.823 | 1.00 | 33.48 | 6 |
| ATOM | 1776 | C | GLN | A | 231 | 42.396 | 24.206 | −34.027 | 1.00 | 32.96 | 6 |
| ATOM | 1777 | O | GLN | A | 231 | 41.476 | 24.995 | −34.324 | 1.00 | 34.21 | 8 |
| ATOM | 1778 | CB | GLN | A | 231 | 44.704 | 24.245 | −35.003 | 1.00 | 34.34 | 6 |
| ATOM | 1779 | CG | GLN | A | 231 | 46.007 | 25.041 | −35.007 | 1.00 | 36.14 | 6 |
| ATOM | 1780 | CD | GLN | A | 231 | 47.002 | 24.556 | −36.052 | 1.00 | 38.53 | 6 |
| ATOM | 1781 | OE1 | GLN | A | 231 | 46.812 | 23.541 | −36.732 | 1.00 | 39.14 | 8 |
| ATOM | 1782 | NE2 | GLN | A | 231 | 48.085 | 25.312 | −36.189 | 1.00 | 39.12 | 7 |
| ATOM | 1783 | N | GLU | A | 232 | 42.214 | 22.900 | −33.801 | 1.00 | 31.08 | 7 |
| ATOM | 1784 | CA | GLU | A | 232 | 40.897 | 22.280 | −33.907 | 1.00 | 33.90 | 6 |
| ATOM | 1785 | C | GLU | A | 232 | 39.897 | 22.898 | −32.923 | 1.00 | 32.97 | 6 |
| ATOM | 1786 | O | GLU | A | 232 | 38.785 | 23.235 | −33.345 | 1.00 | 30.71 | 8 |
| ATOM | 1787 | CB | GLU | A | 232 | 40.956 | 20.772 | −33.659 | 1.00 | 36.16 | 6 |
| ATOM | 1788 | CG | GLU | A | 232 | 41.681 | 19.963 | −34.705 | 1.00 | 40.99 | 6 |
| ATOM | 1789 | CD | GLU | A | 232 | 41.956 | 18.526 | −34.336 | 1.00 | 43.88 | 6 |
| ATOM | 1790 | OE1 | GLU | A | 232 | 42.231 | 18.222 | −33.162 | 1.00 | 46.75 | 8 |
| ATOM | 1791 | OE2 | GLU | A | 232 | 41.978 | 17.624 | −35.213 | 1.00 | 46.96 | 8 |
| ATOM | 1792 | N | LEU | A | 233 | 40.279 | 23.075 | −31.654 | 1.00 | 31.79 | 7 |
| ATOM | 1793 | CA | LEU | A | 233 | 39.390 | 23.738 | −30.717 | 1.00 | 31.75 | 6 |
| ATOM | 1794 | C | LEU | A | 233 | 39.053 | 25.159 | −31.151 | 1.00 | 30.93 | 6 |
| ATOM | 1795 | O | LEU | A | 233 | 37.914 | 25.617 | −31.117 | 1.00 | 29.58 | 8 |
| ATOM | 1796 | CB | LEU | A | 233 | 40.002 | 23.804 | −29.306 | 1.00 | 28.67 | 6 |
| ATOM | 1797 | CG | LEU | A | 233 | 40.122 | 22.439 | −28.598 | 1.00 | 29.48 | 6 |
| ATOM | 1798 | CD1 | LEU | A | 233 | 41.084 | 22.505 | −27.425 | 1.00 | 29.09 | 6 |
| ATOM | 1799 | CD2 | LEU | A | 233 | 38.712 | 21.976 | −28.189 | 1.00 | 30.10 | 6 |

TABLE 1-continued

| ATOM | 1800 | N | ASN | A | 234 | 40.083 | 25.889 | −31.615 | 1.00 | 32.79 | 7 |
| ATOM | 1801 | CA | ASN | A | 234 | 39.861 | 27.288 | −32.011 | 1.00 | 33.77 | 6 |
| ATOM | 1802 | C | ASN | A | 234 | 38.946 | 27.388 | −33.220 | 1.00 | 31.44 | 6 |
| ATOM | 1803 | O | ASN | A | 234 | 38.071 | 28.254 | −33.258 | 1.00 | 32.82 | 8 |
| ATOM | 1804 | CB | ASN | A | 234 | 41.220 | 27.972 | −32.243 | 1.00 | 36.16 | 6 |
| ATOM | 1805 | CG | ASN | A | 234 | 41.890 | 28.295 | −30.919 | 1.00 | 39.98 | 6 |
| ATOM | 1806 | OD1 | ASN | A | 234 | 41.296 | 28.257 | −29.838 | 1.00 | 40.76 | 8 |
| ATOM | 1807 | ND2 | ASN | A | 234 | 43.185 | 28.592 | −30.922 | 1.00 | 39.55 | 7 |
| ATOM | 1808 | N | GLU | A | 235 | 39.068 | 26.440 | −34.127 | 1.00 | 31.44 | 7 |
| ATOM | 1809 | CA | GLU | A | 235 | 38.223 | 26.392 | −35.306 | 1.00 | 34.68 | 6 |
| ATOM | 1810 | C | GLU | A | 235 | 36.779 | 26.082 | −34.971 | 1.00 | 34.35 | 6 |
| ATOM | 1811 | O | GLU | A | 235 | 35.878 | 26.565 | −35.629 | 1.00 | 35.56 | 8 |
| ATOM | 1812 | CB | GLU | A | 235 | 38.763 | 25.314 | −36.244 | 1.00 | 36.35 | 6 |
| ATOM | 1813 | N | LYS | A | 236 | 36.532 | 25.307 | −33.908 | 1.00 | 36.15 | 7 |
| ATOM | 1814 | CA | LYS | A | 236 | 35.169 | 24.977 | −33.488 | 1.00 | 35.47 | 6 |
| ATOM | 1815 | C | LYS | A | 236 | 34.483 | 26.106 | −32.738 | 1.00 | 34.87 | 6 |
| ATOM | 1816 | O | LYS | A | 236 | 33.253 | 26.085 | −32.561 | 1.00 | 36.38 | 8 |
| ATOM | 1817 | CB | LYS | A | 236 | 35.213 | 23.748 | −32.577 | 1.00 | 37.47 | 6 |
| ATOM | 1818 | CG | LYS | A | 236 | 35.609 | 22.450 | −33.245 | 1.00 | 38.51 | 6 |
| ATOM | 1819 | CD | LYS | A | 236 | 35.643 | 21.345 | −32.192 | 1.00 | 40.94 | 6 |
| ATOM | 1820 | CE | LYS | A | 236 | 36.184 | 20.083 | −32.827 | 1.00 | 42.93 | 6 |
| ATOM | 1821 | NZ | LYS | A | 236 | 36.231 | 18.973 | −31.850 | 1.00 | 45.15 | 7 |
| ATOM | 1822 | N | GLY | A | 237 | 35.225 | 27.094 | −32.274 | 1.00 | 33.61 | 7 |
| ATOM | 1823 | CA | GLY | A | 237 | 34.660 | 28.241 | −31.576 | 1.00 | 33.28 | 6 |
| ATOM | 1824 | C | GLY | A | 237 | 35.127 | 28.401 | −30.157 | 1.00 | 32.89 | 6 |
| ATOM | 1825 | O | GLY | A | 237 | 34.644 | 29.291 | −29.429 | 1.00 | 36.87 | 8 |
| ATOM | 1826 | N | PHE | A | 238 | 36.017 | 27.546 | −29.668 | 1.00 | 30.90 | 7 |
| ATOM | 1827 | CA | PHE | A | 238 | 36.629 | 27.664 | −28.380 | 1.00 | 31.61 | 6 |
| ATOM | 1828 | C | PHE | A | 238 | 37.817 | 28.641 | −28.417 | 1.00 | 35.03 | 6 |
| ATOM | 1829 | O | PHE | A | 238 | 38.191 | 29.022 | −29.528 | 1.00 | 37.95 | 8 |
| ATOM | 1830 | CB | PHE | A | 238 | 37.201 | 26.338 | −27.875 | 1.00 | 29.76 | 6 |
| ATOM | 1831 | CG | PHE | A | 238 | 36.165 | 25.258 | −27.686 | 1.00 | 30.50 | 6 |
| ATOM | 1832 | CD1 | PHE | A | 238 | 35.712 | 24.500 | −28.727 | 1.00 | 29.47 | 6 |
| ATOM | 1833 | CD2 | PHE | A | 238 | 35.679 | 24.979 | −26.414 | 1.00 | 31.42 | 6 |
| ATOM | 1834 | CE1 | PHE | A | 238 | 34.752 | 23.501 | −28.555 | 1.00 | 31.11 | 6 |
| ATOM | 1835 | CE2 | PHE | A | 238 | 34.731 | 23.986 | −26.233 | 1.00 | 29.77 | 6 |
| ATOM | 1836 | CZ | PHE | A | 238 | 34.284 | 23.235 | −27.279 | 1.00 | 29.29 | 6 |
| ATOM | 1837 | N | ARG | A | 239 | 38.388 | 28.963 | −27.268 | 1.00 | 34.76 | 7 |
| ATOM | 1838 | CA | ARG | A | 239 | 39.674 | 29.645 | −27.216 | 1.00 | 35.49 | 6 |
| ATOM | 1839 | C | ARG | A | 239 | 40.472 | 28.742 | −26.270 | 1.00 | 35.32 | 6 |
| ATOM | 1840 | O | ARG | A | 239 | 40.308 | 28.724 | −25.057 | 1.00 | 32.89 | 8 |
| ATOM | 1841 | CB | ARG | A | 239 | 39.721 | 31.088 | −26.754 | 1.00 | 37.36 | 6 |
| ATOM | 1842 | CG | ARG | A | 239 | 39.226 | 32.068 | −27.822 | 1.00 | 39.64 | 6 |
| ATOM | 1843 | N | ALA | A | 240 | 41.233 | 27.877 | −26.931 | 1.00 | 36.31 | 7 |
| ATOM | 1844 | CA | ALA | A | 240 | 42.124 | 26.921 | −26.293 | 1.00 | 36.79 | 6 |
| ATOM | 1845 | C | ALA | A | 240 | 42.906 | 27.617 | −25.203 | 1.00 | 38.54 | 6 |
| ATOM | 1846 | O | ALA | A | 240 | 43.360 | 28.735 | −25.495 | 1.00 | 39.25 | 8 |
| ATOM | 1847 | CB | ALA | A | 240 | 43.087 | 26.347 | −27.333 | 1.00 | 36.86 | 6 |
| ATOM | 1848 | N | ASP | A | 241 | 43.035 | 27.053 | −24.024 | 1.00 | 39.01 | 7 |
| ATOM | 1849 | CA | ASP | A | 241 | 43.689 | 27.789 | −22.947 | 1.00 | 42.42 | 6 |
| ATOM | 1850 | C | ASP | A | 241 | 44.867 | 27.010 | −22.396 | 1.00 | 43.73 | 6 |
| ATOM | 1851 | O | ASP | A | 241 | 45.894 | 27.608 | −22.061 | 1.00 | 46.19 | 8 |
| ATOM | 1852 | CB | ASP | A | 241 | 42.686 | 28.105 | −21.828 | 1.00 | 43.72 | 6 |
| ATOM | 1853 | CG | ASP | A | 241 | 43.319 | 28.991 | −20.771 | 1.00 | 46.29 | 6 |
| ATOM | 1854 | OD1 | ASP | A | 241 | 43.712 | 30.124 | −21.130 | 1.00 | 47.38 | 8 |
| ATOM | 1855 | OD2 | ASP | A | 241 | 43.433 | 28.560 | −19.610 | 1.00 | 46.21 | 8 |
| ATOM | 1856 | N | ASP | A | 242 | 44.733 | 25.690 | −22.292 | 1.00 | 41.53 | 7 |
| ATOM | 1857 | CA | ASP | A | 242 | 45.828 | 24.876 | −21.764 | 1.00 | 39.46 | 6 |
| ATOM | 1858 | C | ASP | A | 242 | 45.607 | 23.442 | −22.177 | 1.00 | 37.10 | 6 |
| ATOM | 1859 | O | ASP | A | 242 | 44.496 | 22.895 | −22.059 | 1.00 | 34.02 | 8 |
| ATOM | 1860 | CB | ASP | A | 242 | 45.908 | 25.001 | −20.242 | 1.00 | 43.32 | 6 |
| ATOM | 1861 | CG | ASP | A | 242 | 47.103 | 24.275 | −19.661 | 1.00 | 47.37 | 6 |
| ATOM | 1862 | OD1 | ASP | A | 242 | 46.980 | 23.437 | −18.736 | 1.00 | 49.59 | 8 |
| ATOM | 1863 | OD2 | ASP | A | 242 | 48.231 | 24.530 | −20.158 | 1.00 | 50.50 | 8 |
| ATOM | 1864 | N | ILE | A | 243 | 46.597 | 22.785 | −22.750 | 1.00 | 33.48 | 7 |
| ATOM | 1865 | CA | ILE | A | 243 | 46.550 | 21.419 | −23.193 | 1.00 | 32.08 | 6 |
| ATOM | 1866 | C | ILE | A | 243 | 47.853 | 20.812 | −22.718 | 1.00 | 33.41 | 6 |
| ATOM | 1867 | O | ILE | A | 243 | 48.895 | 21.390 | −23.062 | 1.00 | 32.28 | 8 |
| ATOM | 1868 | CB | ILE | A | 243 | 46.424 | 21.205 | −24.719 | 1.00 | 33.19 | 6 |
| ATOM | 1869 | CG1 | ILE | A | 243 | 45.141 | 21.847 | −25.222 | 1.00 | 33.31 | 6 |
| ATOM | 1870 | CG2 | ILE | A | 243 | 46.504 | 19.703 | −24.995 | 1.00 | 32.88 | 6 |
| ATOM | 1871 | CD1 | ILE | A | 243 | 44.892 | 21.792 | −26.713 | 1.00 | 33.52 | 6 |
| ATOM | 1872 | N | GLN | A | 244 | 47.829 | 19.735 | −21.975 | 1.00 | 33.31 | 7 |
| ATOM | 1873 | CA | GLN | A | 244 | 49.003 | 19.097 | −21.436 | 1.00 | 35.24 | 6 |
| ATOM | 1874 | C | GLN | A | 244 | 48.849 | 17.592 | −21.483 | 1.00 | 34.74 | 6 |
| ATOM | 1875 | O | GLN | A | 244 | 47.741 | 17.056 | −21.422 | 1.00 | 33.25 | 8 |
| ATOM | 1876 | CB | GLN | A | 244 | 49.300 | 19.528 | −19.967 | 1.00 | 39.02 | 6 |
| ATOM | 1877 | CG | GLN | A | 244 | 49.773 | 20.962 | −19.905 | 1.00 | 43.89 | 6 |
| ATOM | 1878 | CD | GLN | A | 244 | 50.076 | 21.564 | −18.569 | 1.00 | 47.28 | 6 |

TABLE 1-continued

| ATOM | 1879 | OE1 | GLN | A | 244 | 50.148 | 20.870 | −17.548 | 1.00 | 48.52 | 8 |
|---|---|---|---|---|---|---|---|---|---|---|---|
| ATOM | 1880 | NE2 | GLN | A | 244 | 50.259 | 22.895 | −18.597 | 1.00 | 49.46 | 7 |
| ATOM | 1881 | N | ILE | A | 245 | 49.943 | 16.870 | −21.716 | 1.00 | 31.86 | 7 |
| ATOM | 1882 | CA | ILE | A | 245 | 50.000 | 15.439 | −21.801 | 1.00 | 31.75 | 6 |
| ATOM | 1883 | C | ILE | A | 245 | 51.110 | 14.967 | −20.852 | 1.00 | 33.59 | 6 |
| ATOM | 1884 | O | ILE | A | 245 | 52.183 | 15.586 | −20.888 | 1.00 | 36.14 | 8 |
| ATOM | 1885 | CB | ILE | A | 245 | 50.299 | 14.888 | −23.213 | 1.00 | 33.28 | 6 |
| ATOM | 1886 | CG1 | ILE | A | 245 | 49.188 | 15.324 | −24.177 | 1.00 | 32.78 | 6 |
| ATOM | 1887 | CG2 | ILE | A | 245 | 50.470 | 13.387 | −23.164 | 1.00 | 33.13 | 6 |
| ATOM | 1888 | CD1 | ILE | A | 245 | 49.424 | 15.049 | −25.648 | 1.00 | 33.13 | 6 |
| ATOM | 1889 | N | ARG | A | 246 | 50.827 | 14.054 | −19.946 | 1.00 | 34.84 | 7 |
| ATOM | 1890 | CA | ARG | A | 246 | 51.816 | 13.609 | −18.982 | 1.00 | 35.92 | 6 |
| ATOM | 1891 | C | ARG | A | 246 | 51.687 | 12.122 | −18.690 | 1.00 | 35.36 | 6 |
| ATOM | 1892 | O | ARG | A | 246 | 50.697 | 11.461 | −18.911 | 1.00 | 35.88 | 8 |
| ATOM | 1893 | CB | ARG | A | 246 | 51.713 | 14.251 | −17.589 | 1.00 | 36.79 | 6 |
| ATOM | 1894 | CG | ARG | A | 246 | 51.674 | 15.747 | −17.458 | 1.00 | 41.24 | 6 |
| ATOM | 1895 | CD | ARG | A | 246 | 53.032 | 16.284 | −17.914 | 1.00 | 46.18 | 6 |
| ATOM | 1896 | NE | ARG | A | 246 | 53.251 | 17.654 | −17.502 | 1.00 | 49.48 | 7 |
| ATOM | 1897 | CZ | ARG | A | 246 | 53.913 | 18.040 | −16.420 | 1.00 | 51.58 | 6 |
| ATOM | 1898 | NH1 | ARG | A | 246 | 54.466 | 17.155 | −15.603 | 1.00 | 51.91 | 7 |
| ATOM | 1899 | NH2 | ARG | A | 246 | 54.006 | 19.352 | −16.229 | 1.00 | 53.89 | 7 |
| ATOM | 1900 | N | ASP | A | 247 | 52.730 | 11.616 | −18.003 | 1.00 | 35.81 | 7 |
| ATOM | 1901 | CA | ASP | A | 247 | 52.753 | 10.248 | −17.537 | 1.00 | 34.88 | 6 |
| ATOM | 1902 | C | ASP | A | 247 | 51.652 | 10.087 | −16.495 | 1.00 | 31.75 | 6 |
| ATOM | 1903 | O | ASP | A | 247 | 51.690 | 10.908 | −15.584 | 1.00 | 32.95 | 8 |
| ATOM | 1904 | CB | ASP | A | 247 | 54.146 | 9.952 | −16.954 | 1.00 | 37.68 | 6 |
| ATOM | 1905 | CG | ASP | A | 247 | 54.195 | 8.479 | −16.611 | 1.00 | 39.66 | 6 |
| ATOM | 1906 | OD1 | ASP | A | 247 | 53.482 | 8.015 | −15.710 | 1.00 | 41.79 | 8 |
| ATOM | 1907 | OD2 | ASP | A | 247 | 54.924 | 7.748 | −17.284 | 1.00 | 42.94 | 8 |
| ATOM | 1908 | N | ALA | A | 248 | 50.712 | 9.185 | −16.600 | 1.00 | 33.81 | 7 |
| ATOM | 1909 | CA | ALA | A | 248 | 49.616 | 9.156 | −15.609 | 1.00 | 32.51 | 6 |
| ATOM | 1910 | C | ALA | A | 248 | 50.041 | 8.675 | −14.232 | 1.00 | 34.35 | 6 |
| ATOM | 1911 | O | ALA | A | 248 | 49.399 | 9.063 | −13.249 | 1.00 | 33.85 | 8 |
| ATOM | 1912 | CB | ALA | A | 248 | 48.499 | 8.253 | −16.070 | 1.00 | 33.01 | 6 |
| ATOM | 1913 | N | ASP | A | 249 | 51.057 | 7.825 | −14.103 | 1.00 | 36.10 | 7 |
| ATOM | 1914 | CA | ASP | A | 249 | 51.462 | 7.281 | −12.822 | 1.00 | 35.70 | 6 |
| ATOM | 1915 | C | ASP | A | 249 | 52.421 | 8.185 | −12.073 | 1.00 | 33.40 | 6 |
| ATOM | 1916 | O | ASP | A | 249 | 52.399 | 8.230 | −10.818 | 1.00 | 31.30 | 8 |
| ATOM | 1917 | CB | ASP | A | 249 | 52.152 | 5.916 | −13.031 | 1.00 | 39.11 | 6 |
| ATOM | 1918 | CG | ASP | A | 249 | 51.137 | 5.007 | −13.715 | 1.00 | 43.20 | 6 |
| ATOM | 1919 | OD1 | ASP | A | 249 | 50.028 | 4.826 | −13.134 | 1.00 | 45.31 | 8 |
| ATOM | 1920 | OD2 | ASP | A | 249 | 51.423 | 4.514 | −14.817 | 1.00 | 43.99 | 8 |
| ATOM | 1921 | N | THR | A | 250 | 53.275 | 8.844 | −12.857 | 1.00 | 31.16 | 7 |
| ATOM | 1922 | CA | THR | A | 250 | 54.301 | 9.667 | −12.240 | 1.00 | 32.87 | 6 |
| ATOM | 1923 | C | THR | A | 250 | 54.087 | 11.144 | −12.416 | 1.00 | 32.81 | 6 |
| ATOM | 1924 | O | THR | A | 250 | 54.760 | 11.935 | −11.789 | 1.00 | 30.56 | 8 |
| ATOM | 1925 | CB | THR | A | 250 | 55.740 | 9.378 | −12.792 | 1.00 | 34.12 | 6 |
| ATOM | 1926 | OG1 | THR | A | 250 | 55.779 | 9.795 | −14.158 | 1.00 | 34.42 | 8 |
| ATOM | 1927 | CG2 | THR | A | 250 | 56.080 | 7.911 | −12.637 | 1.00 | 34.28 | 6 |
| ATOM | 1928 | N | LEU | A | 251 | 53.281 | 11.587 | −13.365 | 1.00 | 32.56 | 7 |
| ATOM | 1929 | CA | LEU | A | 251 | 52.972 | 12.978 | −13.672 | 1.00 | 34.35 | 6 |
| ATOM | 1930 | C | LEU | A | 251 | 54.124 | 13.689 | −14.360 | 1.00 | 35.41 | 6 |
| ATOM | 1931 | O | LEU | A | 251 | 54.093 | 14.893 | −14.592 | 1.00 | 35.99 | 8 |
| ATOM | 1932 | CB | LEU | A | 251 | 52.494 | 13.758 | −12.418 | 1.00 | 33.68 | 6 |
| ATOM | 1933 | CG | LEU | A | 251 | 51.220 | 13.147 | −11.792 | 1.00 | 34.55 | 6 |
| ATOM | 1934 | CD1 | LEU | A | 251 | 50.797 | 13.969 | −10.573 | 1.00 | 35.91 | 6 |
| ATOM | 1935 | CD2 | LEU | A | 251 | 50.101 | 13.012 | −12.821 | 1.00 | 35.43 | 6 |
| ATOM | 1936 | N | LEU | A | 252 | 55.194 | 12.962 | −14.695 | 1.00 | 39.58 | 7 |
| ATOM | 1937 | CA | LEU | A | 252 | 56.323 | 13.587 | −15.418 | 1.00 | 40.96 | 6 |
| ATOM | 1938 | C | LEU | A | 252 | 55.945 | 13.614 | −16.874 | 1.00 | 43.27 | 6 |
| ATOM | 1939 | O | LEU | A | 252 | 54.906 | 13.129 | −17.318 | 1.00 | 40.97 | 8 |
| ATOM | 1940 | CB | LEU | A | 252 | 57.550 | 12.584 | −15.264 | 1.00 | 42.55 | 6 |
| ATOM | 1941 | CG | LEU | A | 252 | 58.072 | 12.496 | −13.823 | 1.00 | 43.46 | 6 |
| ATOM | 1942 | CD1 | LEU | A | 252 | 59.196 | 11.476 | −13.685 | 1.00 | 44.26 | 6 |
| ATOM | 1943 | CD2 | LEU | A | 252 | 58.546 | 13.868 | −13.341 | 1.00 | 43.34 | 6 |
| ATOM | 1944 | N | GLU | A | 253 | 56.855 | 14.189 | −17.659 | 1.00 | 46.27 | 7 |
| ATOM | 1945 | CA | GLU | A | 253 | 56.716 | 14.144 | −19.109 | 1.00 | 48.94 | 6 |
| ATOM | 1946 | C | GLU | A | 253 | 56.642 | 12.706 | −19.612 | 1.00 | 48.01 | 6 |
| ATOM | 1947 | O | GLU | A | 253 | 57.291 | 11.928 | −18.871 | 1.00 | 48.08 | 8 |
| ATOM | 1948 | CB | GLU | A | 253 | 57.877 | 14.878 | −19.783 | 1.00 | 52.86 | 6 |
| ATOM | 1949 | CG | GLU | A | 253 | 57.914 | 16.371 | −19.500 | 1.00 | 57.25 | 6 |
| ATOM | 1950 | CD | GLU | A | 253 | 56.720 | 17.104 | −20.077 | 1.00 | 60.45 | 6 |
| ATOM | 1951 | OE1 | GLU | A | 253 | 56.308 | 16.771 | −21.207 | 1.00 | 61.73 | 8 |
| ATOM | 1952 | OE2 | GLU | A | 253 | 56.194 | 18.011 | −19.397 | 1.00 | 61.77 | 8 |
| ATOM | 1953 | N | VAL | A | 254 | 55.835 | 12.324 | −20.596 | 1.00 | 48.66 | 7 |
| ATOM | 1954 | CA | VAL | A | 254 | 55.849 | 10.887 | −20.872 | 1.00 | 49.85 | 6 |
| ATOM | 1955 | C | VAL | A | 254 | 57.149 | 10.638 | −21.614 | 1.00 | 51.30 | 6 |
| ATOM | 1956 | O | VAL | A | 254 | 57.658 | 11.494 | −22.340 | 1.00 | 49.27 | 8 |
| ATOM | 1957 | CB | VAL | A | 254 | 54.576 | 10.399 | −21.614 | 1.00 | 51.06 | 6 |

TABLE 1-continued

| ATOM | 1958 | CG1 | VAL | A | 254 | 53.600 | 11.541 | −21.825 | 1.00 | 50.21 | 6 |
| --- | --- | --- | --- | --- | --- | --- | --- | --- | --- | --- | --- |
| ATOM | 1959 | CG2 | VAL | A | 254 | 54.935 | 9.757 | −22.940 | 1.00 | 51.39 | 6 |
| ATOM | 1960 | N | SER | A | 255 | 57.636 | 9.432 | −21.398 | 1.00 | 50.78 | 7 |
| ATOM | 1961 | CA | SER | A | 255 | 58.878 | 8.951 | −21.946 | 1.00 | 52.29 | 6 |
| ATOM | 1962 | C | SER | A | 255 | 58.718 | 7.516 | −22.423 | 1.00 | 53.07 | 6 |
| ATOM | 1963 | O | SER | A | 255 | 57.625 | 6.965 | −22.444 | 1.00 | 53.08 | 8 |
| ATOM | 1964 | CB | SER | A | 255 | 59.978 | 8.985 | −20.878 | 1.00 | 51.99 | 6 |
| ATOM | 1965 | OG | SER | A | 255 | 59.761 | 7.859 | −20.013 | 1.00 | 51.83 | 8 |
| ATOM | 1966 | N | GLU | A | 256 | 59.844 | 6.858 | −22.692 | 1.00 | 55.01 | 7 |
| ATOM | 1967 | CA | GLU | A | 256 | 59.903 | 5.485 | −23.155 | 1.00 | 55.63 | 6 |
| ATOM | 1968 | C | GLU | A | 256 | 59.251 | 4.493 | −22.207 | 1.00 | 55.82 | 6 |
| ATOM | 1969 | O | GLU | A | 256 | 58.566 | 3.543 | −22.591 | 1.00 | 55.91 | 8 |
| ATOM | 1970 | CB | GLU | A | 256 | 61.380 | 5.091 | −23.350 | 1.00 | 56.43 | 6 |
| ATOM | 1971 | N | THR | A | 257 | 59.458 | 4.732 | −20.919 | 1.00 | 55.14 | 7 |
| ATOM | 1972 | CA | THR | A | 257 | 58.921 | 3.928 | −19.846 | 1.00 | 54.05 | 6 |
| ATOM | 1973 | C | THR | A | 257 | 57.443 | 4.151 | −19.554 | 1.00 | 51.69 | 6 |
| ATOM | 1974 | O | THR | A | 257 | 56.836 | 3.301 | −18.887 | 1.00 | 51.58 | 8 |
| ATOM | 1975 | CB | THR | A | 257 | 59.723 | 4.223 | −18.554 | 1.00 | 55.07 | 6 |
| ATOM | 1976 | OG1 | THR | A | 257 | 59.404 | 5.533 | −18.065 | 1.00 | 56.77 | 8 |
| ATOM | 1977 | CG2 | THR | A | 257 | 61.215 | 4.150 | −18.828 | 1.00 | 55.65 | 6 |
| ATOM | 1978 | N | SER | A | 258 | 56.834 | 5.252 | −20.000 | 1.00 | 49.85 | 7 |
| ATOM | 1979 | CA | SER | A | 258 | 55.426 | 5.481 | −19.663 | 1.00 | 46.23 | 6 |
| ATOM | 1980 | C | SER | A | 258 | 54.484 | 4.382 | −20.104 | 1.00 | 46.46 | 6 |
| ATOM | 1981 | O | SER | A | 258 | 54.511 | 3.984 | −21.269 | 1.00 | 47.83 | 8 |
| ATOM | 1982 | CB | SER | A | 258 | 54.950 | 6.783 | −20.306 | 1.00 | 44.06 | 6 |
| ATOM | 1983 | OG | SER | A | 258 | 55.742 | 7.841 | −19.839 | 1.00 | 40.94 | 8 |
| ATOM | 1984 | N | LYS | A | 259 | 53.626 | 3.905 | −19.221 | 1.00 | 46.05 | 7 |
| ATOM | 1985 | CA | LYS | A | 259 | 52.624 | 2.902 | −19.512 | 1.00 | 46.69 | 6 |
| ATOM | 1986 | C | LYS | A | 259 | 51.252 | 3.551 | −19.739 | 1.00 | 45.85 | 6 |
| ATOM | 1987 | O | LYS | A | 259 | 50.329 | 3.046 | −20.369 | 1.00 | 45.29 | 8 |
| ATOM | 1988 | CB | LYS | A | 259 | 52.455 | 1.886 | −18.382 | 1.00 | 46.44 | 6 |
| ATOM | 1989 | CG | LYS | A | 259 | 53.726 | 1.200 | −17.920 | 1.00 | 47.93 | 6 |
| ATOM | 1990 | N | ARG | A | 260 | 51.088 | 4.696 | −19.069 | 1.00 | 46.77 | 7 |
| ATOM | 1991 | CA | ARG | A | 260 | 49.800 | 5.397 | −19.104 | 1.00 | 45.39 | 6 |
| ATOM | 1992 | C | ARG | A | 260 | 49.991 | 6.882 | −19.278 | 1.00 | 41.75 | 6 |
| ATOM | 1993 | O | ARG | A | 260 | 50.970 | 7.421 | −18.763 | 1.00 | 41.96 | 8 |
| ATOM | 1994 | CB | ARG | A | 260 | 49.004 | 5.146 | −17.814 | 1.00 | 48.72 | 6 |
| ATOM | 1995 | CG | ARG | A | 260 | 48.340 | 3.797 | −17.715 | 1.00 | 52.78 | 6 |
| ATOM | 1996 | CD | ARG | A | 260 | 47.783 | 3.490 | −16.342 | 1.00 | 56.11 | 6 |
| ATOM | 1997 | NE | ARG | A | 260 | 48.800 | 3.016 | −15.423 | 1.00 | 60.02 | 7 |
| ATOM | 1998 | CZ | ARG | A | 260 | 49.366 | 1.817 | −15.362 | 1.00 | 61.86 | 6 |
| ATOM | 1999 | NH1 | ARG | A | 260 | 49.066 | 0.806 | −16.179 | 1.00 | 62.97 | 7 |
| ATOM | 2000 | NH2 | ARG | A | 260 | 50.275 | 1.615 | −14.410 | 1.00 | 62.19 | 7 |
| ATOM | 2001 | N | ALA | A | 261 | 49.079 | 7.547 | −20.024 | 1.00 | 39.42 | 7 |
| ATOM | 2002 | CA | ALA | A | 261 | 49.232 | 8.993 | −20.107 | 1.00 | 35.31 | 6 |
| ATOM | 2003 | C | ALA | A | 261 | 47.928 | 9.630 | −19.612 | 1.00 | 32.26 | 6 |
| ATOM | 2004 | O | ALA | A | 261 | 46.872 | 9.005 | −19.790 | 1.00 | 34.66 | 8 |
| ATOM | 2005 | CB | ALA | A | 261 | 49.538 | 9.504 | −21.504 | 1.00 | 34.95 | 6 |
| ATOM | 2006 | N | VAL | A | 262 | 48.060 | 10.831 | −19.087 | 1.00 | 29.67 | 7 |
| ATOM | 2007 | CA | VAL | A | 262 | 46.852 | 11.578 | −18.705 | 1.00 | 27.51 | 6 |
| ATOM | 2008 | C | VAL | A | 262 | 46.916 | 12.796 | −19.608 | 1.00 | 27.97 | 6 |
| ATOM | 2009 | O | VAL | A | 262 | 47.977 | 13.414 | −19.791 | 1.00 | 26.28 | 8 |
| ATOM | 2010 | CB | VAL | A | 262 | 46.750 | 11.979 | −17.233 | 1.00 | 29.25 | 6 |
| ATOM | 2011 | CG1 | VAL | A | 262 | 47.995 | 12.725 | −16.785 | 1.00 | 30.58 | 6 |
| ATOM | 2012 | CG2 | VAL | A | 262 | 45.527 | 12.884 | −16.976 | 1.00 | 30.36 | 6 |
| ATOM | 2013 | N | ILE | A | 263 | 45.801 | 13.185 | −20.185 | 1.00 | 26.21 | 7 |
| ATOM | 2014 | CA | ILE | A | 263 | 45.639 | 14.343 | −21.031 | 1.00 | 26.33 | 6 |
| ATOM | 2015 | C | ILE | A | 263 | 44.738 | 15.341 | −20.300 | 1.00 | 28.09 | 6 |
| ATOM | 2016 | O | ILE | A | 263 | 43.635 | 14.903 | −19.935 | 1.00 | 26.14 | 8 |
| ATOM | 2017 | CB | ILE | A | 263 | 44.977 | 13.970 | −22.357 | 1.00 | 27.18 | 6 |
| ATOM | 2018 | CG1 | ILE | A | 263 | 45.701 | 12.767 | −22.999 | 1.00 | 30.42 | 6 |
| ATOM | 2019 | CG2 | ILE | A | 263 | 44.931 | 15.184 | −23.302 | 1.00 | 26.41 | 6 |
| ATOM | 2020 | CD1 | ILE | A | 263 | 44.751 | 11.943 | −23.867 | 1.00 | 32.55 | 6 |
| ATOM | 2021 | N | LEU | A | 264 | 45.198 | 16.564 | −20.149 | 1.00 | 28.73 | 7 |
| ATOM | 2022 | CA | LEU | A | 264 | 44.453 | 17.626 | −19.514 | 1.00 | 30.58 | 6 |
| ATOM | 2023 | C | LEU | A | 264 | 44.108 | 18.698 | −20.530 | 1.00 | 29.44 | 6 |
| ATOM | 2024 | O | LEU | A | 264 | 45.005 | 19.177 | −21.235 | 1.00 | 30.50 | 8 |
| ATOM | 2025 | CB | LEU | A | 264 | 45.273 | 18.264 | −18.392 | 1.00 | 33.45 | 6 |
| ATOM | 2026 | CG | LEU | A | 264 | 46.310 | 17.397 | −17.677 | 1.00 | 35.36 | 6 |
| ATOM | 2027 | CD1 | LEU | A | 264 | 47.287 | 18.261 | −16.855 | 1.00 | 38.43 | 6 |
| ATOM | 2028 | CD2 | LEU | A | 264 | 45.634 | 16.357 | −16.800 | 1.00 | 36.22 | 6 |
| ATOM | 2029 | N | VAL | A | 265 | 42.875 | 19.166 | −20.643 | 1.00 | 28.12 | 7 |
| ATOM | 2030 | CA | VAL | A | 265 | 42.516 | 20.228 | −21.586 | 1.00 | 30.77 | 6 |
| ATOM | 2031 | C | VAL | A | 265 | 41.662 | 21.288 | −20.868 | 1.00 | 30.38 | 6 |
| ATOM | 2032 | O | VAL | A | 265 | 40.888 | 20.946 | −19.964 | 1.00 | 33.23 | 8 |
| ATOM | 2033 | CB | VAL | A | 265 | 41.740 | 19.716 | −22.798 | 1.00 | 30.45 | 6 |
| ATOM | 2034 | CG1 | VAL | A | 265 | 42.546 | 18.732 | −23.649 | 1.00 | 31.64 | 6 |
| ATOM | 2035 | CG2 | VAL | A | 265 | 40.456 | 18.962 | −22.415 | 1.00 | 30.65 | 6 |
| ATOM | 2036 | N | ALA | A | 266 | 41.822 | 22.538 | −21.233 | 1.00 | 30.29 | 7 |

TABLE 1-continued

| | | | | | | | | | | |
|---|---|---|---|---|---|---|---|---|---|---|
| ATOM | 2037 | CA | ALA | A | 266 | 40.992 | 23.628 | −20.697 | 1.00 | 27.93 | 6 |
| ATOM | 2038 | C | ALA | A | 266 | 40.722 | 24.514 | −21.890 | 1.00 | 28.75 | 6 |
| ATOM | 2039 | O | ALA | A | 266 | 41.687 | 24.771 | −22.653 | 1.00 | 31.65 | 8 |
| ATOM | 2040 | CB | ALA | A | 266 | 41.637 | 24.388 | −19.574 | 1.00 | 28.93 | 6 |
| ATOM | 2041 | N | ALA | A | 267 | 39.535 | 25.012 | −22.069 | 1.00 | 27.14 | 7 |
| ATOM | 2042 | CA | ALA | A | 267 | 39.237 | 25.880 | −23.189 | 1.00 | 28.13 | 6 |
| ATOM | 2043 | C | ALA | A | 267 | 38.051 | 26.744 | −22.796 | 1.00 | 29.67 | 6 |
| ATOM | 2044 | O | ALA | A | 267 | 37.054 | 26.257 | −22.261 | 1.00 | 27.60 | 8 |
| ATOM | 2045 | CB | ALA | A | 267 | 38.861 | 25.167 | −24.478 | 1.00 | 26.05 | 6 |
| ATOM | 2046 | N | TRP | A | 268 | 38.151 | 28.007 | −23.166 | 1.00 | 29.63 | 7 |
| ATOM | 2047 | CA | TRP | A | 268 | 37.074 | 28.951 | −22.969 | 1.00 | 28.26 | 6 |
| ATOM | 2048 | C | TRP | A | 268 | 36.049 | 28.766 | −24.072 | 1.00 | 29.88 | 6 |
| ATOM | 2049 | O | TRP | A | 268 | 36.407 | 28.609 | −25.245 | 1.00 | 30.20 | 8 |
| ATOM | 2050 | CB | TRP | A | 268 | 37.599 | 30.394 | −22.996 | 1.00 | 30.40 | 6 |
| ATOM | 2051 | CG | TRP | A | 268 | 38.406 | 30.735 | −21.778 | 1.00 | 31.50 | 6 |
| ATOM | 2052 | CD1 | TRP | A | 268 | 39.756 | 30.638 | −21.572 | 1.00 | 32.04 | 6 |
| ATOM | 2053 | CD2 | TRP | A | 268 | 37.850 | 31.336 | −20.602 | 1.00 | 29.94 | 6 |
| ATOM | 2054 | NE1 | TRP | A | 268 | 40.071 | 31.097 | −20.307 | 1.00 | 32.09 | 7 |
| ATOM | 2055 | CE2 | TRP | A | 268 | 38.905 | 31.521 | −19.699 | 1.00 | 32.20 | 6 |
| ATOM | 2056 | CE3 | TRP | A | 268 | 36.543 | 31.660 | −20.214 | 1.00 | 29.41 | 6 |
| ATOM | 2057 | CZ2 | TRP | A | 268 | 38.729 | 32.062 | −18.420 | 1.00 | 30.97 | 6 |
| ATOM | 2058 | CZ3 | TRP | A | 268 | 36.362 | 32.188 | −18.965 | 1.00 | 30.37 | 6 |
| ATOM | 2059 | CH2 | TRP | A | 268 | 37.448 | 32.390 | −18.097 | 1.00 | 29.74 | 6 |
| ATOM | 2060 | N | LEU | A | 269 | 34.789 | 28.947 | −23.715 | 1.00 | 28.17 | 7 |
| ATOM | 2061 | CA | LEU | A | 269 | 33.648 | 28.954 | −24.579 | 1.00 | 29.03 | 6 |
| ATOM | 2062 | C | LEU | A | 269 | 32.680 | 29.913 | −23.885 | 1.00 | 29.91 | 6 |
| ATOM | 2063 | O | LEU | A | 269 | 32.201 | 29.674 | −22.758 | 1.00 | 25.57 | 8 |
| ATOM | 2064 | CB | LEU | A | 269 | 33.139 | 27.528 | −24.786 | 1.00 | 30.48 | 6 |
| ATOM | 2065 | CG | LEU | A | 269 | 31.952 | 27.443 | −25.719 | 1.00 | 31.96 | 6 |
| ATOM | 2066 | CD1 | LEU | A | 269 | 32.337 | 27.993 | −27.103 | 1.00 | 30.89 | 6 |
| ATOM | 2067 | CD2 | LEU | A | 269 | 31.423 | 26.003 | −25.790 | 1.00 | 31.19 | 6 |
| ATOM | 2068 | N | GLY | A | 270 | 32.559 | 31.132 | −24.446 | 1.00 | 29.19 | 7 |
| ATOM | 2069 | CA | GLY | A | 270 | 31.738 | 32.156 | −23.798 | 1.00 | 29.83 | 6 |
| ATOM | 2070 | C | GLY | A | 270 | 32.341 | 32.563 | −22.463 | 1.00 | 32.39 | 6 |
| ATOM | 2071 | O | GLY | A | 270 | 33.549 | 32.829 | −22.369 | 1.00 | 32.69 | 8 |
| ATOM | 2072 | N | ASP | A | 271 | 31.552 | 32.562 | −21.390 | 1.00 | 30.56 | 7 |
| ATOM | 2073 | CA | ASP | A | 271 | 32.088 | 32.888 | −20.075 | 1.00 | 31.93 | 6 |
| ATOM | 2074 | C | ASP | A | 271 | 32.450 | 31.649 | −19.271 | 1.00 | 31.25 | 6 |
| ATOM | 2075 | O | ASP | A | 271 | 32.749 | 31.710 | −18.079 | 1.00 | 30.60 | 8 |
| ATOM | 2076 | CB | ASP | A | 271 | 31.087 | 33.758 | −19.289 | 1.00 | 33.98 | 6 |
| ATOM | 2077 | CG | ASP | A | 271 | 31.073 | 35.165 | −19.921 | 1.00 | 37.85 | 6 |
| ATOM | 2078 | OD1 | ASP | A | 271 | 32.103 | 35.682 | −20.401 | 1.00 | 38.52 | 8 |
| ATOM | 2079 | OD2 | ASP | A | 271 | 29.996 | 35.770 | −19.944 | 1.00 | 39.53 | 8 |
| ATOM | 2080 | N | ALA | A | 272 | 32.462 | 30.482 | −19.903 | 1.00 | 29.77 | 7 |
| ATOM | 2081 | CA | ALA | A | 272 | 32.828 | 29.254 | −19.228 | 1.00 | 27.77 | 6 |
| ATOM | 2082 | C | ALA | A | 272 | 34.256 | 28.826 | −19.557 | 1.00 | 26.45 | 6 |
| ATOM | 2083 | O | ALA | A | 272 | 34.545 | 28.837 | −20.745 | 1.00 | 26.44 | 8 |
| ATOM | 2084 | CB | ALA | A | 272 | 31.977 | 28.068 | −19.666 | 1.00 | 27.56 | 6 |
| ATOM | 2085 | N | ARG | A | 273 | 35.053 | 28.448 | −18.602 | 1.00 | 25.11 | 7 |
| ATOM | 2086 | CA | ARG | A | 273 | 36.354 | 27.839 | −18.859 | 1.00 | 25.96 | 6 |
| ATOM | 2087 | C | ARG | A | 273 | 36.194 | 26.346 | −18.606 | 1.00 | 23.79 | 6 |
| ATOM | 2088 | O | ARG | A | 273 | 36.292 | 25.868 | −17.465 | 1.00 | 25.36 | 8 |
| ATOM | 2089 | CB | ARG | A | 273 | 37.467 | 28.400 | −17.962 | 1.00 | 27.51 | 6 |
| ATOM | 2090 | CG | ARG | A | 273 | 38.864 | 27.853 | −18.355 | 1.00 | 27.52 | 6 |
| ATOM | 2091 | CD | ARG | A | 273 | 39.848 | 28.605 | −17.421 | 1.00 | 28.40 | 6 |
| ATOM | 2092 | NE | ARG | A | 273 | 41.215 | 28.212 | −17.720 | 0.50 | 26.25 | 7 |
| ATOM | 2093 | CZ | ARG | A | 273 | 41.850 | 27.144 | −17.306 | 0.50 | 26.10 | 6 |
| ATOM | 2094 | NH1 | ARG | A | 273 | 41.229 | 26.281 | −16.517 | 0.50 | 28.04 | 7 |
| ATOM | 2095 | NH2 | ARG | A | 273 | 43.107 | 26.909 | −17.691 | 0.50 | 25.33 | 7 |
| ATOM | 2096 | N | LEU | A | 274 | 35.918 | 25.587 | −19.693 | 1.00 | 25.09 | 7 |
| ATOM | 2097 | CA | LEU | A | 274 | 35.608 | 24.173 | −19.545 | 1.00 | 23.10 | 6 |
| ATOM | 2098 | C | LEU | A | 274 | 36.845 | 23.385 | −19.359 | 1.00 | 23.02 | 6 |
| ATOM | 2099 | O | LEU | A | 274 | 37.846 | 23.706 | −20.001 | 1.00 | 24.38 | 8 |
| ATOM | 2100 | CB | LEU | A | 274 | 34.863 | 23.714 | −20.847 | 1.00 | 22.40 | 6 |
| ATOM | 2101 | CG | LEU | A | 274 | 33.548 | 24.488 | −21.045 | 1.00 | 22.92 | 6 |
| ATOM | 2102 | CD1 | LEU | A | 274 | 32.953 | 24.119 | −22.368 | 1.00 | 25.59 | 6 |
| ATOM | 2103 | CD2 | LEU | A | 274 | 32.619 | 24.185 | −19.846 | 1.00 | 24.66 | 6 |
| ATOM | 2104 | N | ILE | A | 275 | 36.844 | 22.342 | −18.576 | 1.00 | 22.01 | 7 |
| ATOM | 2105 | CA | ILE | A | 275 | 37.965 | 21.529 | −18.235 | 1.00 | 24.38 | 6 |
| ATOM | 2106 | C | ILE | A | 275 | 37.640 | 20.072 | −18.439 | 1.00 | 24.31 | 6 |
| ATOM | 2107 | O | ILE | A | 275 | 36.504 | 19.675 | −18.126 | 1.00 | 23.32 | 8 |
| ATOM | 2108 | CB | ILE | A | 275 | 38.290 | 21.785 | −16.743 | 1.00 | 27.33 | 6 |
| ATOM | 2109 | CG1 | ILE | A | 275 | 38.853 | 23.233 | −16.577 | 1.00 | 30.12 | 6 |
| ATOM | 2110 | CG2 | ILE | A | 275 | 39.295 | 20.826 | −16.161 | 1.00 | 32.15 | 6 |
| ATOM | 2111 | CD1 | ILE | A | 275 | 38.634 | 23.632 | −15.112 | 1.00 | 33.95 | 6 |
| ATOM | 2112 | N | ASP | A | 276 | 38.611 | 19.282 | −18.865 | 1.00 | 23.56 | 7 |
| ATOM | 2113 | CA | ASP | A | 276 | 38.347 | 17.845 | −19.005 | 1.00 | 24.73 | 6 |
| ATOM | 2114 | C | ASP | A | 276 | 39.702 | 17.125 | −18.966 | 1.00 | 24.26 | 6 |
| ATOM | 2115 | O | ASP | A | 276 | 40.768 | 17.741 | −19.153 | 1.00 | 24.98 | 8 |

TABLE 1-continued

| | | | | | | | | | | |
|---|---|---|---|---|---|---|---|---|---|---|
| ATOM | 2116 | CB | ASP | A | 276 | 37.551 | 17.545 | −20.271 | 1.00 | 24.30 | 6 |
| ATOM | 2117 | CG | ASP | A | 276 | 36.730 | 16.276 | −20.290 | 1.00 | 26.28 | 6 |
| ATOM | 2118 | OD1 | ASP | A | 276 | 36.927 | 15.468 | −19.324 | 1.00 | 27.91 | 8 |
| ATOM | 2119 | OD2 | ASP | A | 276 | 35.946 | 16.119 | −21.251 | 1.00 | 25.73 | 8 |
| ATOM | 2120 | N | ASN | A | 277 | 39.671 | 15.855 | −18.697 | 1.00 | 22.14 | 7 |
| ATOM | 2121 | CA | ASN | A | 277 | 40.857 | 15.020 | −18.682 | 1.00 | 25.69 | 6 |
| ATOM | 2122 | C | ASN | A | 277 | 40.473 | 13.587 | −19.027 | 1.00 | 24.93 | 6 |
| ATOM | 2123 | O | ASN | A | 277 | 39.335 | 13.139 | −18.920 | 1.00 | 25.86 | 8 |
| ATOM | 2124 | CB | ASN | A | 277 | 41.608 | 15.073 | −17.350 | 1.00 | 28.42 | 6 |
| ATOM | 2125 | CG | ASN | A | 277 | 41.077 | 14.298 | −16.164 | 1.00 | 32.43 | 6 |
| ATOM | 2126 | OD1 | ASN | A | 277 | 40.715 | 13.140 | −16.247 | 1.00 | 37.45 | 8 |
| ATOM | 2127 | ND2 | ASN | A | 277 | 41.023 | 14.889 | −14.994 | 1.00 | 35.65 | 7 |
| ATOM | 2128 | N | LYS | A | 278 | 41.517 | 12.825 | −19.428 | 1.00 | 28.31 | 7 |
| ATOM | 2129 | CA | LYS | A | 278 | 41.338 | 11.429 | −19.765 | 1.00 | 31.78 | 6 |
| ATOM | 2130 | C | LYS | A | 278 | 42.655 | 10.677 | −19.634 | 1.00 | 33.11 | 6 |
| ATOM | 2131 | O | LYS | A | 278 | 43.692 | 11.227 | −19.991 | 1.00 | 33.12 | 8 |
| ATOM | 2132 | CB | LYS | A | 278 | 40.814 | 11.323 | −21.189 | 1.00 | 32.53 | 6 |
| ATOM | 2133 | CG | LYS | A | 278 | 40.748 | 10.008 | −21.905 | 1.00 | 35.09 | 6 |
| ATOM | 2134 | CD | LYS | A | 278 | 39.814 | 10.144 | −23.124 | 1.00 | 38.06 | 6 |
| ATOM | 2135 | CE | LYS | A | 278 | 39.115 | 8.808 | −23.384 | 1.00 | 39.45 | 6 |
| ATOM | 2136 | NZ | LYS | A | 278 | 37.984 | 9.018 | −24.354 | 1.00 | 40.81 | 7 |
| ATOM | 2137 | N | MET | A | 279 | 42.594 | 9.455 | −19.139 | 1.00 | 35.39 | 7 |
| ATOM | 2138 | CA | MET | A | 279 | 43.799 | 8.636 | −19.046 | 1.00 | 39.07 | 6 |
| ATOM | 2139 | C | MET | A | 279 | 43.777 | 7.645 | −20.201 | 1.00 | 40.75 | 6 |
| ATOM | 2140 | O | MET | A | 279 | 42.688 | 7.224 | −20.590 | 1.00 | 39.38 | 8 |
| ATOM | 2141 | CB | MET | A | 279 | 43.895 | 7.997 | −17.641 | 1.00 | 42.09 | 6 |
| ATOM | 2142 | CG | MET | A | 279 | 44.366 | 9.076 | −16.657 | 1.00 | 45.36 | 6 |
| ATOM | 2143 | SD | MET | A | 279 | 44.591 | 8.656 | −14.926 | 1.00 | 51.28 | 16 |
| ATOM | 2144 | CE | MET | A | 279 | 42.948 | 8.136 | −14.428 | 1.00 | 49.74 | 6 |
| ATOM | 2145 | N | VAL | A | 280 | 44.953 | 7.391 | −20.786 | 1.00 | 41.33 | 7 |
| ATOM | 2146 | CA | VAL | A | 280 | 44.994 | 6.466 | −21.917 | 1.00 | 44.04 | 6 |
| ATOM | 2147 | C | VAL | A | 280 | 46.138 | 5.483 | −21.692 | 1.00 | 45.91 | 6 |
| ATOM | 2148 | O | VAL | A | 280 | 47.232 | 5.881 | −21.274 | 1.00 | 44.69 | 8 |
| ATOM | 2149 | CB | VAL | A | 280 | 45.126 | 7.195 | −23.265 | 1.00 | 43.07 | 6 |
| ATOM | 2150 | CG1 | VAL | A | 280 | 46.430 | 7.978 | −23.326 | 1.00 | 43.41 | 6 |
| ATOM | 2151 | CG2 | VAL | A | 280 | 45.060 | 6.239 | −24.439 | 1.00 | 43.94 | 6 |
| ATOM | 2152 | N | GLU | A | 281 | 45.787 | 4.211 | −21.867 | 1.00 | 51.13 | 7 |
| ATOM | 2153 | CA | GLU | A | 281 | 46.797 | 3.151 | −21.712 | 1.00 | 54.78 | 6 |
| ATOM | 2154 | C | GLU | A | 281 | 47.658 | 3.176 | −22.971 | 1.00 | 55.75 | 6 |
| ATOM | 2155 | O | GLU | A | 281 | 47.155 | 3.235 | −24.094 | 1.00 | 55.40 | 8 |
| ATOM | 2156 | CB | GLU | A | 281 | 46.186 | 1.784 | −21.469 | 1.00 | 56.82 | 6 |
| ATOM | 2157 | CG | GLU | A | 281 | 45.244 | 1.658 | −20.296 | 1.00 | 59.30 | 6 |
| ATOM | 2158 | CD | GLU | A | 281 | 45.898 | 1.424 | −18.957 | 1.00 | 61.75 | 6 |
| ATOM | 2159 | OE1 | GLU | A | 281 | 47.135 | 1.218 | −18.919 | 1.00 | 62.80 | S |
| ATOM | 2160 | OE2 | GLU | A | 281 | 45.187 | 1.411 | −17.923 | 1.00 | 62.74 | 8 |
| ATOM | 2161 | N | LEU | A | 282 | 48.958 | 3.235 | −22.781 | 1.00 | 57.94 | 7 |
| ATOM | 2162 | CA | LEU | A | 282 | 49.944 | 3.334 | −23.844 | 1.00 | 60.20 | 6 |
| ATOM | 2163 | C | LEU | A | 282 | 50.394 | 1.966 | −24.343 | 1.00 | 62.75 | 6 |
| ATOM | 2164 | O | LEU | A | 282 | 50.792 | 1.813 | −25.501 | 1.00 | 63.61 | 8 |
| ATOM | 2165 | CB | LEU | A | 282 | 51.132 | 4.160 | −23.353 | 1.00 | 60.14 | 6 |
| ATOM | 2166 | CG | LEU | A | 282 | 51.250 | 5.643 | −23.655 | 1.00 | 59.64 | 6 |
| ATOM | 2167 | CD1 | LEU | A | 282 | 49.954 | 6.281 | −24.103 | 1.00 | 59.72 | 6 |
| ATOM | 2168 | CD2 | LEU | A | 282 | 51.880 | 6.386 | −22.494 | 1.00 | 58.92 | 6 |
| ATOM | 2169 | N | ALA | A | 283 | 50.285 | 0.961 | −23.484 | 1.00 | 64.72 | 7 |
| ATOM | 2170 | CA | ALA | A | 283 | 50.637 | −0.410 | −23.818 | 1.00 | 66.41 | 6 |
| ATOM | 2171 | C | ALA | A | 283 | 49.397 | −1.291 | −23.933 | 1.00 | 67.10 | 6 |
| ATOM | 2172 | O | ALA | A | 283 | 48.394 | −0.879 | −24.563 | 1.00 | 68.25 | 8 |
| ATOM | 2173 | CB | ALA | A | 283 | 51.563 | −1.007 | −22.764 | 1.00 | 66.62 | 6 |
| Monomer B | | | | | | | | | | | |
| ATOM | 2174 | N | MET | B | 1 | 58.003 | −23.593 | 11.263 | 1.00 | 36.48 | 7 |
| ATOM | 2175 | CA | MET | B | 1 | 58.132 | −22.126 | 11.083 | 1.00 | 33.40 | 6 |
| ATOM | 2176 | C | MET | B | 1 | 58.194 | −21.749 | 9.627 | 1.00 | 33.88 | 6 |
| ATOM | 2177 | O | MET | B | 1 | 59.003 | −22.271 | 8.843 | 1.00 | 34.96 | 8 |
| ATOM | 2178 | CB | MET | B | 1 | 59.383 | −21.686 | 11.860 | 1.00 | 32.85 | 6 |
| ATOM | 2179 | CG | MET | B | 1 | 59.602 | −20.178 | 11.711 | 1.00 | 32.05 | 6 |
| ATOM | 2180 | SD | MET | B | 1 | 61.001 | −19.706 | 12.738 | 1.00 | 32.48 | 16 |
| ATOM | 2181 | CE | MET | B | 1 | 62.316 | −19.795 | 11.507 | 1.00 | 33.02 | 6 |
| ATOM | 2182 | N | LEU | B | 2 | 57.366 | −20.850 | 9.145 | 1.00 | 30.67 | 7 |
| ATOM | 2183 | CA | LEU | B | 2 | 57.332 | −20.400 | 7.790 | 1.00 | 31.35 | 6 |
| ATOM | 2184 | C | LEU | B | 2 | 58.315 | −19.246 | 7.576 | 1.00 | 32.39 | 6 |
| ATOM | 2185 | O | LEU | B | 2 | 58.367 | −18.394 | 8.491 | 1.00 | 31.76 | 8 |
| ATOM | 2186 | CB | LEU | B | 2 | 55.926 | −19.896 | 7.473 | 1.00 | 35.48 | 6 |
| ATOM | 2187 | CG | LEU | B | 2 | 54.773 | −20.875 | 7.670 | 1.00 | 38.24 | 6 |
| ATOM | 2188 | CD1 | LEU | B | 2 | 53.410 | −20.187 | 7.668 | 1.00 | 37.95 | 6 |
| ATOM | 2189 | CD2 | LEU | B | 2 | 54.803 | −21.930 | 6.560 | 1.00 | 38.99 | 6 |
| ATOM | 2190 | N | ILE | B | 3 | 58.980 | −19.217 | 6.439 | 1.00 | 28.48 | 7 |
| ATOM | 2191 | CA | ILE | B | 3 | 59.916 | −18.162 | 6.099 | 1.00 | 29.00 | 6 |
| ATOM | 2192 | C | ILE | B | 3 | 59.442 | −17.553 | 4.806 | 1.00 | 30.65 | 6 |

TABLE 1-continued

| ATOM | 2193 | O | ILE | B | 3 | 59.350 | −18.257 | 3.778 | 1.00 | 31.80 | 8 |
|---|---|---|---|---|---|---|---|---|---|---|---|
| ATOM | 2194 | CB | ILE | B | 3 | 61.380 | −18.634 | 5.938 | 1.00 | 31.56 | 6 |
| ATOM | 2195 | CG1 | ILE | B | 3 | 61.859 | −19.222 | 7.261 | 1.00 | 31.29 | 6 |
| ATOM | 2196 | CG2 | ILE | B | 3 | 62.257 | −17.481 | 5.477 | 1.00 | 32.77 | 6 |
| ATOM | 2197 | CD1 | ILE | B | 3 | 63.283 | −19.769 | 7.266 | 1.00 | 37.37 | 6 |
| ATOM | 2198 | N | ILE | B | 4 | 58.918 | −16.333 | 4.826 | 1.00 | 24.55 | 7 |
| ATOM | 2199 | CA | ILE | B | 4 | 58.284 | −15.663 | 3.748 | 1.00 | 26.13 | 6 |
| ATOM | 2200 | C | ILE | B | 4 | 59.159 | −14.534 | 3.279 | 1.00 | 28.00 | 6 |
| ATOM | 2201 | O | ILE | B | 4 | 59.649 | −13.738 | 4.079 | 1.00 | 28.39 | 8 |
| ATOM | 2202 | CB | ILE | B | 4 | 56.926 | −15.034 | 4.179 | 1.00 | 26.38 | 6 |
| ATOM | 2203 | CG1 | ILE | B | 4 | 56.042 | −16.103 | 4.827 | 1.00 | 30.33 | 6 |
| ATOM | 2204 | CG2 | ILE | B | 4 | 56.248 | −14.318 | 3.013 | 1.00 | 28.07 | 6 |
| ATOM | 2205 | CD1 | ILE | B | 4 | 55.611 | −17.272 | 3.955 | 1.00 | 30.56 | 6 |
| ATOM | 2206 | N | GLU | B | 5 | 59.374 | −14.485 | 1.987 | 1.00 | 29.37 | 7 |
| ATOM | 2207 | CA | GLU | B | 5 | 60.209 | −13.449 | 1.380 | 1.00 | 31.10 | 6 |
| ATOM | 2208 | C | GLU | B | 5 | 59.387 | −12.614 | 0.487 | 1.00 | 30.29 | 6 |
| ATOM | 2209 | O | GLU | B | 5 | 59.982 | −11.574 | 0.059 | 1.00 | 32.17 | 8 |
| ATOM | 2210 | CB | GLU | B | 5 | 61.292 | −14.267 | 0.655 | 1.00 | 35.81 | 6 |
| ATOM | 2211 | CG | GLU | B | 5 | 62.267 | −15.017 | 1.547 | 1.00 | 40.51 | 6 |
| ATOM | 2212 | CD | GLU | B | 5 | 63.167 | −15.907 | 0.709 | 1.00 | 45.93 | 6 |
| ATOM | 2213 | OE1 | GLU | B | 5 | 63.562 | −16.994 | 1.195 | 1.00 | 48.88 | 8 |
| ATOM | 2214 | OE2 | GLU | B | 5 | 63.451 | −15.521 | −0.447 | 1.00 | 46.38 | 8 |
| ATOM | 2215 | N | THR | B | 6 | 58.142 | −12.721 | 0.076 | 1.00 | 26.13 | 7 |
| ATOM | 2216 | CA | THR | B | 6 | 57.578 | −11.758 | −0.836 | 1.00 | 27.91 | 6 |
| ATOM | 2217 | C | THR | B | 6 | 56.298 | −11.128 | −0.207 | 1.00 | 24.93 | 6 |
| ATOM | 2218 | O | THR | B | 6 | 55.656 | −11.788 | 0.619 | 1.00 | 27.98 | 8 |
| ATOM | 2219 | CB | THR | B | 6 | 57.229 | −12.351 | −2.205 | 1.00 | 31.04 | 6 |
| ATOM | 2220 | OG1 | THR | B | 6 | 56.159 | −13.300 | −2.052 | 1.00 | 30.86 | 8 |
| ATOM | 2221 | CG2 | THR | B | 6 | 58.425 | −13.076 | −2.851 | 1.00 | 31.94 | 6 |
| ATOM | 2222 | N | LEU | B | 7 | 55.927 | −10.037 | −0.790 | 1.00 | 27.39 | 7 |
| ATOM | 2223 | CA | LEU | B | 7 | 54.715 | −9.308 | −0.367 | 1.00 | 28.55 | 6 |
| ATOM | 2224 | C | LEU | B | 7 | 53.455 | −10.153 | −0.636 | 1.00 | 27.46 | 6 |
| ATOM | 2225 | O | LEU | B | 7 | 52.669 | −10.343 | 0.308 | 1.00 | 26.58 | 8 |
| ATOM | 2226 | CB | LEU | B | 7 | 54.583 | −7.921 | −0.986 | 1.00 | 29.88 | 6 |
| ATOM | 2227 | CG | LEU | B | 7 | 55.750 | −6.939 | −0.729 | 1.00 | 31.25 | 6 |
| ATOM | 2228 | CD1 | LEU | B | 7 | 55.361 | −5.499 | −1.043 | 1.00 | 31.80 | 6 |
| ATOM | 2229 | CD2 | LEU | B | 7 | 56.271 | −7.052 | 0.703 | 1.00 | 30.25 | 6 |
| ATOM | 2230 | N | PRO | B | 8 | 53.288 | −10.697 | −1.811 | 1.00 | 28.20 | 7 |
| ATOM | 2231 | CA | PRO | B | 8 | 52.092 | −11.501 | −2.092 | 1.00 | 28.01 | 6 |
| ATOM | 2232 | C | PRO | B | 8 | 51.973 | −12.671 | −1.172 | 1.00 | 27.27 | 6 |
| ATOM | 2233 | O | PRO | B | 8 | 50.869 | −12.943 | −0.641 | 1.00 | 26.76 | 8 |
| ATOM | 2234 | CB | PRO | B | 8 | 52.264 | −11.941 | −3.550 | 1.00 | 30.16 | 6 |
| ATOM | 2235 | CG | PRO | B | 8 | 53.126 | −10.877 | −4.147 | 1.00 | 30.87 | 6 |
| ATOM | 2236 | CD | PRO | B | 8 | 54.088 | −10.500 | −3.047 | 1.00 | 28.88 | 6 |
| ATOM | 2237 | N | LEU | B | 9 | 53.045 | −13.427 | −0.954 | 1.00 | 25.43 | 7 |
| ATOM | 2238 | CA | LEU | B | 9 | 53.054 | −14.599 | −0.088 | 1.00 | 25.93 | 6 |
| ATOM | 2239 | C | LEU | B | 9 | 52.839 | −14.206 | 1.363 | 1.00 | 27.59 | 6 |
| ATOM | 2240 | O | LEU | B | 9 | 52.069 | −14.843 | 2.081 | 1.00 | 25.94 | 8 |
| ATOM | 2241 | CB | LEU | B | 9 | 54.355 | −15.416 | −0.317 | 1.00 | 27.71 | 6 |
| ATOM | 2242 | CG | LEU | B | 9 | 54.311 | −16.200 | −1.656 | 1.00 | 31.97 | 6 |
| ATOM | 2243 | CD1 | LEU | B | 9 | 55.671 | −16.790 | −1.961 | 1.00 | 30.14 | 6 |
| ATOM | 2244 | CD2 | LEU | B | 9 | 53.236 | −17.279 | −1.607 | 1.00 | 32.64 | 6 |
| ATOM | 2245 | N | LEU | B | 10 | 53.323 | −13.028 | 1.819 | 1.00 | 25.26 | 7 |
| ATOM | 2246 | CA | LEU | B | 10 | 53.068 | −12.583 | 3.182 | 1.00 | 23.45 | 6 |
| ATOM | 2247 | C | LEU | B | 10 | 51.581 | −12.234 | 3.362 | 1.00 | 22.04 | 6 |
| ATOM | 2248 | O | LEU | B | 10 | 50.941 | −12.683 | 4.336 | 1.00 | 22.46 | 8 |
| ATOM | 2249 | CB | LEU | B | 10 | 53.963 | −11.368 | 3.535 | 1.00 | 25.32 | 6 |
| ATOM | 2250 | CG | LEU | B | 10 | 53.618 | −10.738 | 4.917 | 1.00 | 23.24 | 6 |
| ATOM | 2251 | CD1 | LEU | B | 10 | 53.904 | −11.665 | 6.068 | 1.00 | 21.41 | 6 |
| ATOM | 2252 | CD2 | LEU | B | 10 | 54.376 | −9.417 | 5.105 | 1.00 | 22.97 | 6 |
| ATOM | 2253 | N | ARG | B | 11 | 50.992 | −11.537 | 2.407 | 1.00 | 23.80 | 7 |
| ATOM | 2254 | CA | ARG | B | 11 | 49.591 | −11.130 | 2.459 | 1.00 | 26.88 | 6 |
| ATOM | 2255 | C | ARG | B | 11 | 48.681 | −12.350 | 2.583 | 1.00 | 26.18 | 6 |
| ATOM | 2256 | O | ARG | B | 11 | 47.707 | −12.322 | 3.328 | 1.00 | 23.87 | 8 |
| ATOM | 2257 | CB | ARG | B | 11 | 49.208 | −10.303 | 1.232 | 1.00 | 26.73 | 6 |
| ATOM | 2258 | CG | ARG | B | 11 | 49.968 | −8.984 | 1.209 | 1.00 | 29.98 | 6 |
| ATOM | 2259 | CD | ARG | B | 11 | 49.306 | −7.986 | 0.278 | 1.00 | 35.78 | 6 |
| ATOM | 2260 | NE | ARG | B | 11 | 49.673 | −6.602 | 0.492 | 1.00 | 38.73 | 7 |
| ATOM | 2261 | CZ | ARG | B | 11 | 50.447 | −5.830 | −0.254 | 1.00 | 39.79 | 6 |
| ATOM | 2262 | NH1 | ARG | B | 11 | 51.031 | −6.255 | −1.376 | 1.00 | 41.64 | 7 |
| ATOM | 2263 | NH2 | ARG | B | 11 | 50.651 | −4.546 | 0.070 | 1.00 | 40.26 | 7 |
| ATOM | 2264 | N | GLN | B | 12 | 48.992 | −13.409 | 1.864 | 1.00 | 24.75 | 7 |
| ATOM | 2265 | CA | GLN | B | 12 | 48.289 | −14.712 | 1.885 | 1.00 | 23.93 | 6 |
| ATOM | 2266 | C | GLN | B | 12 | 48.282 | −15.281 | 3.285 | 1.00 | 23.24 | 6 |
| ATOM | 2267 | O | GLN | B | 12 | 47.231 | −15.711 | 3.804 | 1.00 | 23.11 | 8 |
| ATOM | 2268 | CB | GLN | B | 12 | 48.919 | −15.669 | 0.879 | 1.00 | 25.20 | 6 |
| ATOM | 2269 | CG | GLN | B | 12 | 48.494 | −17.114 | 0.983 | 1.00 | 31.10 | 6 |
| ATOM | 2270 | CD | GLN | B | 12 | 48.983 | −18.004 | −0.160 | 1.00 | 33.85 | 6 |
| ATOM | 2271 | OE1 | GLN | B | 12 | 50.160 | −18.359 | −0.226 | 1.00 | 34.46 | 8 |

TABLE 1-continued

| | | | | | | | | | | |
|---|---|---|---|---|---|---|---|---|---|---|
| ATOM | 2272 | NE2 | GLN | B | 12 | 48.024 | −18.373 | −1.035 | 1.00 | 37.05 | 7 |
| ATOM | 2273 | N | GLN | B | 13 | 49.406 | −15.241 | 4.018 | 1.00 | 20.76 | 7 |
| ATOM | 2274 | CA | GLN | B | 13 | 49.531 | −15.725 | 5.367 | 1.00 | 21.58 | 6 |
| ATOM | 2275 | C | GLN | B | 13 | 48.755 | −14.802 | 6.342 | 1.00 | 19.88 | 6 |
| ATOM | 2276 | O | GLN | B | 13 | 48.070 | −15.312 | 7.250 | 1.00 | 20.12 | 8 |
| ATOM | 2277 | CB | GLN | B | 13 | 51.005 | −15.852 | 5.844 | 1.00 | 22.55 | 6 |
| ATOM | 2278 | CG | GLN | B | 13 | 51.779 | −16.951 | 5.087 | 1.00 | 25.94 | 6 |
| ATOM | 2279 | CD | GLN | B | 13 | 51.107 | −18.297 | 5.150 | 1.00 | 27.86 | 6 |
| ATOM | 2280 | OE1 | GLN | B | 13 | 50.677 | −18.693 | 6.225 | 1.00 | 28.91 | 8 |
| ATOM | 2281 | NE2 | GLN | B | 13 | 50.985 | −18.937 | 3.993 | 1.00 | 32.63 | 7 |
| ATOM | 2282 | N | ILE | B | 14 | 48.738 | −13.510 | 6.042 | 1.00 | 21.05 | 7 |
| ATOM | 2283 | CA | ILE | B | 14 | 48.035 | −12.575 | 6.947 | 1.00 | 20.18 | 6 |
| ATOM | 2284 | C | ILE | B | 14 | 46.501 | −12.822 | 6.819 | 1.00 | 21.51 | 6 |
| ATOM | 2285 | O | ILE | B | 14 | 45.800 | −12.838 | 7.850 | 1.00 | 21.76 | 8 |
| ATOM | 2286 | CB | ILE | B | 14 | 48.438 | −11.133 | 6.718 | 1.00 | 21.52 | 6 |
| ATOM | 2287 | CG1 | ILE | B | 14 | 49.931 | −10.873 | 7.014 | 1.00 | 21.53 | 6 |
| ATOM | 2288 | CG2 | ILE | B | 14 | 47.609 | −10.137 | 7.572 | 1.00 | 20.30 | 6 |
| ATOM | 2289 | CD1 | ILE | B | 14 | 50.448 | −11.493 | 8.287 | 1.00 | 20.36 | 6 |
| ATOM | 2290 | N | ARG | B | 15 | 46.060 | −13.042 | 5.580 | 1.00 | 21.97 | 7 |
| ATOM | 2291 | CA | ARG | B | 15 | 44.640 | −13.407 | 5.403 | 1.00 | 21.03 | 6 |
| ATOM | 2292 | C | ARG | B | 15 | 44.328 | −14.704 | 6.120 | 1.00 | 20.84 | 6 |
| ATOM | 2293 | O | ARG | B | 15 | 43.231 | −14.819 | 6.693 | 1.00 | 21.21 | 8 |
| ATOM | 2294 | CB | ARG | B | 15 | 44.362 | −13.468 | 3.903 | 1.00 | 23.95 | 6 |
| ATOM | 2295 | CG | ARG | B | 15 | 44.439 | −12.110 | 3.182 | 1.00 | 28.33 | 6 |
| ATOM | 2296 | CD | ARG | B | 15 | 43.633 | −12.304 | 1.885 | 1.00 | 35.29 | 6 |
| ATOM | 2297 | NE | ARG | B | 15 | 44.463 | −13.095 | 0.938 | 1.00 | 39.61 | 7 |
| ATOM | 2298 | CZ | ARG | B | 15 | 45.378 | −12.352 | 0.272 | 1.00 | 43.48 | 6 |
| ATOM | 2299 | NH1 | ARG | B | 15 | 45.533 | −11.036 | 0.426 | 1.00 | 44.40 | 7 |
| ATOM | 2300 | NH2 | ARG | B | 15 | 46.158 | −12.973 | −0.594 | 1.00 | 43.72 | 7 |
| ATOM | 2301 | N | ARG | B | 16 | 45.189 | −15.724 | 6.069 | 1.00 | 18.66 | 7 |
| ATOM | 2302 | CA | ARG | B | 16 | 44.923 | −16.986 | 6.717 | 1.00 | 19.99 | 6 |
| ATOM | 2303 | C | ARG | B | 16 | 44.816 | −16.743 | 8.234 | 1.00 | 20.42 | 6 |
| ATOM | 2304 | O | ARG | B | 16 | 43.855 | −17.229 | 8.824 | 1.00 | 19.70 | 8 |
| ATOM | 2305 | CB | ARG | B | 16 | 45.959 | −18.073 | 6.435 | 1.00 | 22.24 | 6 |
| ATOM | 2306 | CG | ARG | B | 16 | 45.869 | −19.264 | 7.352 | 1.00 | 23.29 | 6 |
| ATOM | 2307 | CD | ARG | B | 16 | 46.986 | −20.277 | 7.132 | 1.00 | 25.24 | 6 |
| ATOM | 2308 | NE | ARG | B | 16 | 48.309 | −19.702 | 7.470 | 1.00 | 27.88 | 7 |
| ATOM | 2309 | CZ | ARG | B | 16 | 48.797 | −19.716 | 8.706 | 1.00 | 28.92 | 6 |
| ATOM | 2310 | NH1 | ARG | B | 16 | 50.016 | −19.215 | 8.961 | 1.00 | 28.52 | 7 |
| ATOM | 2311 | NH2 | ARG | B | 16 | 48.126 | −20.327 | 9.679 | 1.00 | 24.92 | 7 |
| ATOM | 2312 | N | LEU | B | 17 | 45.716 | −15.933 | 8.815 | 1.00 | 19.27 | 7 |
| ATOM | 2313 | CA | LEU | B | 17 | 45.626 | −15.699 | 10.270 | 1.00 | 20.77 | 6 |
| ATOM | 2314 | C | LEU | B | 17 | 44.352 | −14.990 | 10.702 | 1.00 | 20.30 | 6 |
| ATOM | 2315 | O | LEU | B | 17 | 43.778 | −15.286 | 11.759 | 1.00 | 19.03 | 8 |
| ATOM | 2316 | CB | LEU | B | 17 | 46.900 | −14.923 | 10.697 | 1.00 | 22.28 | 6 |
| ATOM | 2317 | CG | LEU | B | 17 | 48.154 | −15.834 | 10.589 | 1.00 | 20.91 | 6 |
| ATOM | 2318 | CD1 | LEU | B | 17 | 49.346 | −14.854 | 10.747 | 1.00 | 23.26 | 6 |
| ATOM | 2319 | CD2 | LEU | B | 17 | 48.210 | −16.976 | 11.546 | 1.00 | 23.26 | 6 |
| ATOM | 2320 | N | ARG | B | 18 | 43.880 | −14.084 | 9.852 | 1.00 | 20.08 | 7 |
| ATOM | 2321 | CA | ARG | B | 18 | 42.616 | −13.394 | 10.085 | 1.00 | 20.19 | 6 |
| ATOM | 2322 | C | ARG | B | 18 | 41.443 | −14.367 | 10.053 | 1.00 | 20.24 | 6 |
| ATOM | 2323 | O | ARG | B | 18 | 40.595 | −14.419 | 10.938 | 1.00 | 19.77 | 8 |
| ATOM | 2324 | CB | ARG | B | 18 | 42.410 | −12.287 | 9.049 | 1.00 | 19.52 | 6 |
| ATOM | 2325 | CG | ARG | B | 18 | 41.388 | −11.239 | 9.456 | 1.00 | 25.28 | 6 |
| ATOM | 2326 | CD | ARG | B | 18 | 40.953 | −10.402 | 8.264 | 1.00 | 30.78 | 6 |
| ATOM | 2327 | NE | ARG | B | 18 | 42.033 | −9.556 | 7.766 | 1.00 | 37.79 | 7 |
| ATOM | 2328 | CZ | ARG | B | 18 | 42.285 | −9.348 | 6.478 | 1.00 | 41.34 | 6 |
| ATOM | 2329 | NH1 | ARG | B | 18 | 41.532 | −9.927 | 5.553 | 1.00 | 41.84 | 7 |
| ATOM | 2330 | NH2 | ARG | B | 18 | 43.290 | −8.562 | 6.119 | 1.00 | 42.14 | 7 |
| ATOM | 2331 | N | MET | B | 19 | 41.447 | −15.266 | 9.053 | 1.00 | 19.56 | 7 |
| ATOM | 2332 | CA | MET | B | 19 | 40.384 | −16.272 | 8.983 | 1.00 | 21.07 | 6 |
| ATOM | 2333 | C | MET | B | 19 | 40.376 | −17.192 | 10.199 | 1.00 | 19.93 | 6 |
| ATOM | 2334 | O | MET | B | 19 | 39.291 | −17.611 | 10.629 | 1.00 | 18.95 | 8 |
| ATOM | 2335 | CB | MET | B | 19 | 40.507 | −17.047 | 7.683 | 1.00 | 21.11 | 6 |
| ATOM | 2336 | CG | MET | B | 19 | 39.650 | −18.307 | 7.449 | 1.00 | 22.70 | 6 |
| ATOM | 2337 | SD | MET | B | 19 | 40.253 | −19.824 | 8.206 | 1.00 | 21.29 | 16 |
| ATOM | 2338 | CE | MET | B | 19 | 41.816 | −20.143 | 7.368 | 1.00 | 22.90 | 6 |
| ATOM | 2339 | N | GLU | B | 20 | 41.516 | −17.512 | 10.731 | 1.00 | 18.16 | 7 |
| ATOM | 2340 | CA | GLU | B | 20 | 41.687 | −18.429 | 11.858 | 1.00 | 20.12 | 6 |
| ATOM | 2341 | C | GLU | B | 20 | 41.280 | −17.732 | 13.182 | 1.00 | 20.85 | 6 |
| ATOM | 2342 | O | GLU | B | 20 | 41.156 | −18.387 | 14.243 | 1.00 | 24.28 | 8 |
| ATOM | 2343 | CB | GLU | B | 20 | 43.113 | −18.960 | 11.945 | 1.00 | 18.82 | 6 |
| ATOM | 2344 | CG | GLU | B | 20 | 43.467 | −19.977 | 10.846 | 1.00 | 21.83 | 6 |
| ATOM | 2345 | CD | GLU | B | 20 | 44.911 | −20.433 | 10.890 | 1.00 | 26.79 | 6 |
| ATOM | 2346 | OE1 | GLU | B | 20 | 45.611 | −20.063 | 11.869 | 1.00 | 28.93 | 8 |
| ATOM | 2347 | OE2 | GLU | B | 20 | 45.312 | −21.210 | 9.985 | 1.00 | 26.44 | 8 |
| ATOM | 2348 | N | GLY | B | 21 | 41.236 | −16.424 | 13.172 | 1.00 | 21.16 | 7 |
| ATOM | 2349 | CA | GLY | B | 21 | 40.877 | −15.568 | 14.299 | 1.00 | 20.08 | 6 |
| ATOM | 2350 | C | GLY | B | 21 | 42.055 | −15.540 | 15.311 | 1.00 | 21.45 | 6 |

TABLE 1-continued

| | | | | | | | | | |
|---|---|---|---|---|---|---|---|---|---|
| ATOM | 2351 | O | GLY | B | 21 | 41.856 | −15.580 | 16.546 | 1.00 | 20.95 | 8 |
| ATOM | 2352 | N | LYS | B | 22 | 43.279 | −15.515 | 14.815 | 1.00 | 17.96 | 7 |
| ATOM | 2353 | CA | LYS | B | 22 | 44.458 | −15.503 | 15.668 | 1.00 | 21.37 | 6 |
| ATOM | 2354 | C | LYS | B | 22 | 44.924 | −14.091 | 15.953 | 1.00 | 23.78 | 6 |
| ATOM | 2355 | O | LYS | B | 22 | 44.942 | −13.267 | 15.041 | 1.00 | 24.76 | 8 |
| ATOM | 2356 | CB | LYS | B | 22 | 45.638 | −16.191 | 14.984 | 1.00 | 22.71 | 6 |
| ATOM | 2357 | CG | LYS | B | 22 | 45.420 | −17.662 | 14.646 | 1.00 | 25.81 | 6 |
| ATOM | 2358 | CD | LYS | B | 22 | 45.337 | −18.553 | 15.836 | 1.00 | 28.29 | 6 |
| ATOM | 2359 | CE | LYS | B | 22 | 44.963 | −19.997 | 15.550 | 1.00 | 33.33 | 6 |
| ATOM | 2360 | NZ | LYS | B | 22 | 45.832 | −20.715 | 14.575 | 1.00 | 29.69 | 7 |
| ATOM | 2361 | N | ARG | B | 23 | 45.285 | −13.775 | 17.175 | 1.00 | 19.63 | 7 |
| ATOM | 2362 | CA | ARG | B | 23 | 45.917 | −12.467 | 17.446 | 1.00 | 22.19 | 6 |
| ATOM | 2363 | C | ARG | B | 23 | 47.415 | −12.521 | 17.203 | 1.00 | 20.99 | 6 |
| ATOM | 2364 | O | ARG | B | 23 | 48.014 | −13.529 | 17.533 | 1.00 | 22.27 | 8 |
| ATOM | 2365 | CB | ARG | B | 23 | 45.620 | −12.042 | 18.877 | 1.00 | 23.98 | 6 |
| ATOM | 2366 | CG | ARG | B | 23 | 44.149 | −11.748 | 19.161 | 1.00 | 33.05 | 6 |
| ATOM | 2367 | CD | ARG | B | 23 | 43.965 | −11.207 | 20.600 | 1.00 | 35.95 | 6 |
| ATOM | 2368 | NE | ARG | B | 23 | 44.774 | −11.865 | 21.560 | 1.00 | 39.00 | 7 |
| ATOM | 2369 | CZ | ARG | B | 23 | 45.045 | −12.903 | 22.319 | 1.00 | 38.30 | 6 |
| ATOM | 2370 | NH1 | ARG | B | 23 | 44.343 | −14.060 | 22.457 | 1.00 | 34.37 | 7 |
| ATOM | 2371 | NH2 | ARG | B | 23 | 46.204 | −12.653 | 22.881 | 1.00 | 33.10 | 7 |
| ATOM | 2372 | N | VAL | B | 24 | 47.873 | −11.534 | 16.444 | 1.00 | 19.44 | 7 |
| ATOM | 2373 | CA | VAL | B | 24 | 49.260 | −11.534 | 15.984 | 1.00 | 19.87 | 6 |
| ATOM | 2374 | C | VAL | B | 24 | 50.133 | −10.493 | 16.615 | 1.00 | 20.77 | 6 |
| ATOM | 2375 | O | VAL | B | 24 | 49.724 | −9.356 | 16.770 | 1.00 | 20.17 | 8 |
| ATOM | 2376 | CB | VAL | B | 24 | 49.220 | −11.301 | 14.473 | 1.00 | 20.82 | 6 |
| ATOM | 2377 | CG1 | VAL | B | 24 | 50.587 | −11.071 | 13.856 | 1.00 | 21.58 | 6 |
| ATOM | 2378 | CG2 | VAL | B | 24 | 48.493 | −12.516 | 13.838 | 1.00 | 22.44 | 6 |
| ATOM | 2379 | N | ALA | B | 25 | 51.327 | −10.950 | 17.072 | 1.00 | 18.32 | 7 |
| ATOM | 2380 | CA | ALA | B | 25 | 52.294 | −9.989 | 17.591 | 1.00 | 18.65 | 6 |
| ATOM | 2381 | C | ALA | B | 25 | 53.431 | −9.885 | 16.600 | 1.00 | 22.09 | 6 |
| ATOM | 2382 | O | ALA | B | 25 | 53.908 | −10.915 | 16.053 | 1.00 | 26.60 | 8 |
| ATOM | 2383 | CB | ALA | B | 25 | 52.871 | −10.371 | 18.953 | 1.00 | 20.06 | 6 |
| ATOM | 2384 | N | LEU | B | 26 | 53.922 | −8.705 | 16.329 | 1.00 | 18.28 | 7 |
| ATOM | 2385 | CA | LEU | B | 26 | 54.997 | −8.468 | 15.410 | 1.00 | 16.76 | 6 |
| ATOM | 2386 | C | LEU | B | 26 | 56.273 | −8.010 | 16.156 | 1.00 | 20.96 | 6 |
| ATOM | 2387 | O | LEU | B | 26 | 56.139 | −7.157 | 17.020 | 1.00 | 21.27 | 8 |
| ATOM | 2388 | CB | LEU | B | 26 | 54.673 | −7.425 | 14.340 | 1.00 | 19.09 | 6 |
| ATOM | 2389 | CG | LEU | B | 26 | 55.816 | −6.890 | 13.487 | 1.00 | 19.40 | 6 |
| ATOM | 2390 | CD1 | LEU | B | 26 | 56.464 | −7.969 | 12.603 | 1.00 | 21.45 | 6 |
| ATOM | 2391 | CD2 | LEU | B | 26 | 55.320 | −5.738 | 12.604 | 1.00 | 22.40 | 6 |
| ATOM | 2392 | N | VAL | B | 27 | 57.396 | −8.642 | 15.874 | 1.00 | 20.49 | 7 |
| ATOM | 2393 | CA | VAL | B | 27 | 58.684 | −8.136 | 16.430 | 1.00 | 19.53 | 6 |
| ATOM | 2394 | C | VAL | B | 27 | 59.576 | −7.694 | 15.308 | 1.00 | 21.55 | 6 |
| ATOM | 2395 | O | VAL | B | 27 | 60.170 | −8.516 | 14.520 | 1.00 | 22.20 | 8 |
| ATOM | 2396 | CB | VAL | B | 27 | 59.378 | −9.239 | 17.253 | 1.00 | 21.88 | 6 |
| ATOM | 2397 | CG1 | VAL | B | 27 | 60.658 | −8.617 | 17.884 | 1.00 | 21.20 | 6 |
| ATOM | 2398 | CG2 | VAL | B | 27 | 58.513 | −9.837 | 18.318 | 1.00 | 20.54 | 6 |
| ATOM | 2399 | N | PRO | B | 28 | 59.761 | −6.435 | 14.910 | 1.00 | 20.58 | 7 |
| ATOM | 2400 | CA | PRO | B | 28 | 60.557 | −5.881 | 13.878 | 1.00 | 21.31 | 6 |
| ATOM | 2401 | C | PRO | B | 28 | 62.068 | −5.886 | 14.202 | 1.00 | 24.78 | 6 |
| ATOM | 2402 | O | PRO | B | 28 | 62.428 | −5.538 | 15.336 | 1.00 | 26.50 | 8 |
| ATOM | 2403 | CB | PRO | B | 28 | 60.112 | −4.424 | 13.720 | 1.00 | 22.66 | 6 |
| ATOM | 2404 | CG | PRO | B | 28 | 58.741 | −4.426 | 14.395 | 1.00 | 20.85 | 6 |
| ATOM | 2405 | CD | PRO | B | 28 | 58.946 | −5.327 | 15.578 | 1.00 | 20.40 | 6 |
| ATOM | 2406 | N | THR | B | 29 | 62.875 | −6.483 | 13.317 | 1.00 | 26.26 | 7 |
| ATOM | 2407 | CA | THR | B | 29 | 64.329 | −6.556 | 13.614 | 1.00 | 25.08 | 6 |
| ATOM | 2408 | C | THR | B | 29 | 65.126 | −6.328 | 12.359 | 1.00 | 25.98 | 6 |
| ATOM | 2409 | O | THR | B | 29 | 64.643 | −6.415 | 11.228 | 1.00 | 23.47 | 8 |
| ATOM | 2410 | CB | THR | B | 29 | 64.820 | −7.900 | 14.201 | 1.00 | 26.97 | 6 |
| ATOM | 2411 | OG1 | THR | B | 29 | 65.022 | −8.817 | 13.088 | 1.00 | 26.74 | 8 |
| ATOM | 2412 | CG2 | THR | B | 29 | 63.914 | −8.579 | 15.219 | 1.00 | 25.95 | 6 |
| ATOM | 2413 | N | MET | B | 30 | 66.471 | −6.078 | 12.560 | 1.00 | 25.32 | 7 |
| ATOM | 2414 | CA | MET | B | 30 | 67.357 | −5.995 | 11.415 | 1.00 | 26.82 | 6 |
| ATOM | 2415 | C | MET | B | 30 | 68.261 | −7.249 | 11.384 | 1.00 | 28.96 | 6 |
| ATOM | 2416 | O | MET | B | 30 | 69.347 | −7.183 | 10.815 | 1.00 | 30.56 | 8 |
| ATOM | 2417 | CB | MET | B | 30 | 68.229 | −4.738 | 11.416 | 1.00 | 26.43 | 6 |
| ATOM | 2418 | CG | MET | B | 30 | 67.252 | −3.504 | 11.203 | 1.00 | 27.24 | 6 |
| ATOM | 2419 | SD | MET | B | 30 | 67.969 | −2.187 | 10.263 | 1.00 | 28.19 | 16 |
| ATOM | 2420 | CE | MET | B | 30 | 69.323 | −1.713 | 11.388 | 1.00 | 33.08 | 6 |
| ATOM | 2421 | N | GLY | B | 31 | 67.793 | −8.340 | 11.934 | 1.00 | 27.82 | 7 |
| ATOM | 2422 | CA | GLY | B | 31 | 68.599 | −9.593 | 11.926 | 1.00 | 29.40 | 6 |
| ATOM | 2423 | C | GLY | B | 31 | 69.833 | −9.495 | 12.829 | 1.00 | 31.29 | 6 |
| ATOM | 2424 | O | GLY | B | 31 | 69.934 | −8.645 | 13.713 | 1.00 | 28.83 | 8 |
| ATOM | 2425 | N | ASN | B | 32 | 70.728 | −10.486 | 12.690 | 1.00 | 31.40 | 7 |
| ATOM | 2426 | CA | ASN | B | 32 | 71.923 | −10.565 | 13.552 | 1.00 | 33.60 | 6 |
| ATOM | 2427 | C | ASN | B | 32 | 71.454 | −10.664 | 14.982 | 1.00 | 30.00 | 6 |
| ATOM | 2428 | O | ASN | B | 32 | 71.870 | −9.961 | 15.906 | 1.00 | 32.23 | 8 |
| ATOM | 2429 | CB | ASN | B | 32 | 72.857 | −9.379 | 13.347 | 1.00 | 35.71 | 6 |

TABLE 1-continued

| | | | | | | | | | | |
|---|---|---|---|---|---|---|---|---|---|---|
| ATOM | 2430 | CG | ASN | B | 32 | 74.231 | −9.610 | 13.979 | 1.00 | 39.99 | 6 |
| ATOM | 2431 | OD1 | ASN | B | 32 | 74.920 | −8.633 | 14.294 | 1.00 | 42.85 | 8 |
| ATOM | 2432 | ND2 | ASN | B | 32 | 74.607 | −10.864 | 14.228 | 1.00 | 40.08 | 7 |
| ATOM | 2433 | N | LEU | B | 33 | 70.506 | −11.572 | 15.191 | 1.00 | 30.19 | 7 |
| ATOM | 2434 | CA | LEU | B | 33 | 69.833 | −11.774 | 16.449 | 1.00 | 29.02 | 6 |
| ATOM | 2435 | C | LEU | B | 33 | 70.684 | −12.343 | 17.566 | 1.00 | 35.03 | 6 |
| ATOM | 2436 | O | LEU | B | 33 | 71.521 | −13.207 | 17.312 | 1.00 | 36.34 | 8 |
| ATOM | 2437 | CB | LEU | B | 33 | 68.616 | −12.717 | 16.279 | 1.00 | 30.07 | 6 |
| ATOM | 2438 | CG | LEU | B | 33 | 67.670 | −12.217 | 15.191 | 1.00 | 29.98 | 6 |
| ATOM | 2439 | CD1 | LEU | B | 33 | 66.434 | −13.121 | 15.083 | 1.00 | 31.08 | 6 |
| ATOM | 2440 | CD2 | LEU | B | 33 | 67.221 | −10.777 | 15.431 | 1.00 | 28.84 | 6 |
| ATOM | 2441 | N | HIS | B | 34 | 70.295 | −11.945 | 18.774 | 1.00 | 35.85 | 7 |
| ATOM | 2442 | CA | HIS | B | 34 | 71.004 | −12.381 | 19.965 | 1.00 | 39.05 | 6 |
| ATOM | 2443 | C | HIS | B | 34 | 69.976 | −12.567 | 21.067 | 1.00 | 37.94 | 6 |
| ATOM | 2444 | O | HIS | B | 34 | 68.762 | −12.451 | 20.791 | 1.00 | 37.26 | 8 |
| ATOM | 2445 | CB | HIS | B | 34 | 72.097 | −11.404 | 20.404 | 1.00 | 40.15 | 6 |
| ATOM | 2446 | CG | HIS | B | 34 | 71.668 | −10.006 | 20.714 | 1.00 | 42.43 | 6 |
| ATOM | 2447 | ND1 | HIS | B | 34 | 70.876 | −9.671 | 21.799 | 1.00 | 44.12 | 7 |
| ATOM | 2448 | CD2 | HIS | B | 34 | 71.953 | −8.848 | 20.062 | 1.00 | 43.13 | 6 |
| ATOM | 2449 | CE1 | HIS | B | 34 | 70.689 | −8.360 | 21.808 | 1.00 | 44.28 | 6 |
| ATOM | 2450 | NE2 | HIS | B | 34 | 71.323 | −7.840 | 20.763 | 1.00 | 44.67 | 7 |
| ATOM | 2451 | N | ASP | B | 35 | 70.439 | −12.874 | 22.263 | 1.00 | 36.30 | 7 |
| ATOM | 2452 | CA | ASP | B | 35 | 69.531 | −13.176 | 23.352 | 1.00 | 38.71 | 6 |
| ATOM | 2453 | C | ASP | B | 35 | 68.539 | −12.055 | 23.649 | 1.00 | 38.11 | 6 |
| ATOM | 2454 | O | ASP | B | 35 | 67.448 | −12.373 | 24.116 | 1.00 | 38.15 | 8 |
| ATOM | 2455 | CB | ASP | B | 35 | 70.309 | −13.480 | 24.637 | 1.00 | 43.89 | 6 |
| ATOM | 2456 | CG | ASP | B | 35 | 71.071 | −14.776 | 24.631 | 1.00 | 48.19 | 6 |
| ATOM | 2457 | OD1 | ASP | B | 35 | 71.046 | −15.496 | 23.603 | 1.00 | 50.75 | 8 |
| ATOM | 2458 | OD2 | ASP | B | 35 | 71.701 | −15.074 | 25.689 | 1.00 | 51.91 | 8 |
| ATOM | 2459 | N | GLY | B | 36 | 68.919 | −10.788 | 23.499 | 1.00 | 35.59 | 7 |
| ATOM | 2460 | CA | GLY | B | 36 | 68.007 | −9.688 | 23.778 | 1.00 | 33.96 | 6 |
| ATOM | 2461 | C | GLY | B | 36 | 66.844 | −9.774 | 22.751 | 1.00 | 32.11 | 6 |
| ATOM | 2462 | O | GLY | B | 36 | 65.738 | −9.524 | 23.235 | 1.00 | 30.98 | 8 |
| ATOM | 2463 | N | HIS | B | 37 | 67.149 | −10.177 | 21.521 | 1.00 | 31.48 | 7 |
| ATOM | 2464 | CA | HIS | B | 37 | 66.086 | −10.322 | 20.581 | 1.00 | 31.68 | 6 |
| ATOM | 2465 | C | HIS | B | 37 | 65.118 | −11.479 | 20.969 | 1.00 | 33.06 | 6 |
| ATOM | 2466 | O | HIS | B | 37 | 63.861 | −11.440 | 20.850 | 1.00 | 30.99 | 8 |
| ATOM | 2467 | CB | HIS | B | 37 | 66.507 | −10.514 | 19.175 | 1.00 | 31.96 | 6 |
| ATOM | 2468 | CG | HIS | B | 37 | 67.366 | −9.425 | 18.643 | 1.00 | 34.37 | 6 |
| ATOM | 2469 | ND1 | HIS | B | 37 | 66.888 | −8.299 | 18.005 | 1.00 | 37.43 | 7 |
| ATOM | 2470 | CD2 | HIS | B | 37 | 68.714 | −9.330 | 18.624 | 1.00 | 34.96 | 6 |
| ATOM | 2471 | CE1 | HIS | B | 37 | 67.890 | −7.535 | 17.580 | 1.00 | 35.54 | 6 |
| ATOM | 2472 | NE2 | HIS | B | 37 | 69.003 | −8.153 | 17.962 | 1.00 | 39.23 | 7 |
| ATOM | 2473 | N | MET | B | 38 | 65.704 | −12.577 | 21.486 | 1.00 | 31.32 | 7 |
| ATOM | 2474 | CA | MET | B | 38 | 64.880 | −13.668 | 22.001 | 1.00 | 31.44 | 6 |
| ATOM | 2475 | C | MET | B | 38 | 63.959 | −13.252 | 23.115 | 1.00 | 29.66 | 6 |
| ATOM | 2476 | O | MET | B | 38 | 62.851 | −13.809 | 23.253 | 1.00 | 28.40 | 8 |
| ATOM | 2477 | CB | MET | B | 38 | 65.799 | −14.827 | 22.487 | 1.00 | 34.21 | 6 |
| ATOM | 2478 | CG | MET | B | 38 | 66.423 | −15.620 | 21.375 | 1.00 | 35.15 | 6 |
| ATOM | 2479 | SD | MET | B | 38 | 65.631 | −15.970 | 19.832 | 1.00 | 35.12 | 16 |
| ATOM | 2480 | CE | MET | B | 38 | 66.123 | −14.628 | 18.770 | 1.00 | 36.33 | 6 |
| ATOM | 2481 | N | LYS | B | 39 | 64.228 | −12.308 | 23.996 | 1.00 | 29.09 | 7 |
| ATOM | 2482 | CA | LYS | B | 39 | 63.368 | −11.857 | 25.065 | 1.00 | 26.18 | 6 |
| ATOM | 2483 | C | LYS | B | 39 | 62.142 | −11.078 | 24.470 | 1.00 | 25.41 | 6 |
| ATOM | 2484 | O | LYS | B | 39 | 61.042 | −11.228 | 24.964 | 1.00 | 26.08 | 8 |
| ATOM | 2485 | CB | LYS | B | 39 | 64.048 | −10.935 | 26.076 | 1.00 | 27.75 | 6 |
| ATOM | 2486 | CG | LYS | B | 39 | 63.195 | −10.551 | 27.262 | 1.00 | 27.45 | 6 |
| ATOM | 2487 | CD | LYS | B | 39 | 64.031 | −9.643 | 28.216 | 1.00 | 30.13 | 6 |
| ATOM | 2488 | CE | LYS | B | 39 | 63.142 | −9.261 | 29.377 | 1.00 | 29.21 | 6 |
| ATOM | 2489 | NZ | LYS | B | 39 | 63.883 | −8.413 | 30.361 | 1.00 | 32.36 | 7 |
| ATOM | 2490 | N | LEU | B | 40 | 62.394 | −10.379 | 23.402 | 1.00 | 26.07 | 7 |
| ATOM | 2491 | CA | LEU | B | 40 | 61.256 | −9.741 | 22.709 | 1.00 | 25.52 | 6 |
| ATOM | 2492 | C | LEU | B | 40 | 60.254 | −10.805 | 22.220 | 1.00 | 25.72 | 6 |
| ATOM | 2493 | O | LEU | B | 40 | 59.855 | −10.609 | 22.293 | 1.00 | 23.50 | 8 |
| ATOM | 2494 | CB | LEU | B | 40 | 61.702 | −8.954 | 21.497 | 1.00 | 26.47 | 6 |
| ATOM | 2495 | CG | LEU | B | 40 | 62.739 | −7.859 | 21.758 | 1.00 | 30.07 | 6 |
| ATOM | 2496 | CD1 | LEU | B | 40 | 63.073 | −7.128 | 20.474 | 1.00 | 31.00 | 6 |
| ATOM | 2497 | CD2 | LEU | B | 40 | 62.237 | −6.905 | 22.832 | 1.00 | 30.41 | 6 |
| ATOM | 2498 | N | VAL | B | 41 | 60.844 | −11.842 | 21.611 | 1.00 | 25.04 | 7 |
| ATOM | 2499 | CA | VAL | B | 41 | 59.995 | −12.936 | 21.065 | 1.00 | 24.43 | 6 |
| ATOM | 2500 | C | VAL | B | 41 | 59.235 | −13.579 | 22.162 | 1.00 | 23.84 | 6 |
| ATOM | 2501 | O | VAL | B | 41 | 58.037 | −13.868 | 22.103 | 1.00 | 23.75 | 8 |
| ATOM | 2502 | CB | VAL | B | 41 | 60.893 | −13.922 | 20.289 | 1.00 | 24.40 | 6 |
| ATOM | 2503 | CG1 | VAL | B | 41 | 60.057 | −15.140 | 19.914 | 1.00 | 24.57 | 6 |
| ATOM | 2504 | CG2 | VAL | B | 41 | 61.496 | −13.337 | 19.819 | 1.00 | 25.66 | 6 |
| ATOM | 2505 | N | ASP | B | 42 | 59.826 | −13.850 | 23.376 | 1.00 | 25.85 | 7 |
| ATOM | 2506 | CA | ASP | B | 42 | 59.130 | −14.426 | 24.480 | 1.00 | 26.19 | 6 |
| ATOM | 2507 | C | ASP | B | 42 | 57.994 | −13.543 | 24.981 | 1.00 | 28.20 | 6 |
| ATOM | 2508 | O | ASP | B | 42 | 56.910 | −14.030 | 25.341 | 1.00 | 27.55 | 8 |

TABLE 1-continued

| ATOM | 2509 | CB | ASP | 8 | 42 | 60.131 | −14.709 | 25.659 | 1.00 | 29.50 | 6 |
|---|---|---|---|---|---|---|---|---|---|---|---|
| ATOM | 2510 | CG | ASP | B | 42 | 61.118 | −15.822 | 25.377 | 1.00 | 32.71 | 6 |
| ATOM | 2511 | OD1 | ASP | B | 42 | 61.051 | −16.616 | 24.419 | 1.00 | 33.03 | 8 |
| ATOM | 2512 | OD2 | ASP | B | 42 | 62.135 | −15.893 | 26.160 | 1.00 | 33.67 | 8 |
| ATOM | 2513 | N | GLU | B | 43 | 58.205 | −12.216 | 24.957 | 1.00 | 26.23 | 7 |
| ATOM | 2514 | CA | GLU | B | 43 | 57.130 | −11.321 | 25.355 | 1.00 | 27.21 | 6 |
| ATOM | 2515 | C | GLU | B | 43 | 55.973 | −11.339 | 24.327 | 1.00 | 24.30 | 6 |
| ATOM | 2516 | O | GLU | B | 43 | 54.809 | −11.340 | 24.709 | 1.00 | 24.66 | 8 |
| ATOM | 2517 | CB | GLU | B | 43 | 57.676 | −9.912 | 25.475 | 1.00 | 30.67 | 6 |
| ATOM | 2518 | CG | GLU | B | 43 | 56.740 | −8.904 | 26.130 | 1.00 | 36.81 | 6 |
| ATOM | 2519 | CD | GLU | B | 43 | 56.445 | −9.257 | 27.585 | 1.00 | 40.25 | 6 |
| ATOM | 2520 | OE1 | GLU | B | 43 | 57.347 | −9.847 | 28.236 | 1.00 | 44.07 | 8 |
| ATOM | 2521 | OE2 | GLU | B | 43 | 55.348 | −8.999 | 28.121 | 1.00 | 40.92 | 8 |
| ATOM | 2522 | N | ALA | B | 44 | 56.324 | −11.466 | 23.083 | 1.00 | 26.35 | 7 |
| ATOM | 2523 | CA | ALA | B | 44 | 55.321 | −11.474 | 21.969 | 1.00 | 23.41 | 6 |
| ATOM | 2524 | C | ALA | B | 44 | 54.526 | −12.754 | 22.879 | 1.00 | 26.63 | 6 |
| ATOM | 2525 | O | ALA | B | 44 | 53.287 | −12.728 | 22.074 | 1.00 | 26.61 | 8 |
| ATOM | 2526 | CB | ALA | B | 44 | 56.007 | −11.299 | 20.651 | 1.00 | 25.41 | 6 |
| ATOM | 2527 | N | LYS | B | 45 | 55.209 | −13.882 | 22.329 | 1.00 | 27.34 | 7 |
| ATOM | 2528 | CA | LYS | B | 45 | 54.542 | −15.169 | 22.501 | 1.00 | 29.71 | 6 |
| ATOM | 2529 | C | LYS | B | 45 | 53.589 | −15.160 | 23.659 | 1.00 | 28.45 | 6 |
| ATOM | 2530 | O | LYS | B | 45 | 52.559 | −15.805 | 23.717 | 1.00 | 28.18 | 8 |
| ATOM | 2531 | CB | LYS | B | 45 | 55.537 | −16.322 | 22.783 | 1.00 | 32.90 | 6 |
| ATOM | 2532 | CG | LYS | B | 45 | 56.368 | −16.726 | 21.588 | 1.00 | 38.80 | 6 |
| ATOM | 2533 | CD | LYS | B | 45 | 57.724 | −17.301 | 21.961 | 1.00 | 43.49 | 6 |
| ATOM | 2534 | CE | LYS | B | 45 | 57.757 | −18.398 | 23.004 | 1.00 | 46.00 | 6 |
| ATOM | 2535 | NZ | LYS | B | 45 | 59.077 | −18.396 | 23.727 | 1.00 | 47.62 | 7 |
| ATOM | 2536 | N | ALA | B | 46 | 53.935 | −14.446 | 24.748 | 1.00 | 27.58 | 7 |
| ATOM | 2537 | CA | ALA | B | 46 | 53.076 | −14.389 | 25.900 | 1.00 | 27.60 | 6 |
| ATOM | 2538 | C | ALA | B | 46 | 51.831 | −13.527 | 25.751 | 1.00 | 28.91 | 6 |
| ATOM | 2539 | O | ALA | B | 46 | 50.905 | −13.633 | 26.549 | 1.00 | 30.19 | 8 |
| ATOM | 2540 | CB | ALA | B | 46 | 53.882 | −13.818 | 27.097 | 1.00 | 28.29 | 6 |
| ATOM | 2541 | N | ARG | B | 47 | 51.754 | −12.657 | 24.741 | 1.00 | 26.88 | 7 |
| ATOM | 2542 | CA | ARG | B | 47 | 50.691 | −11.719 | 24.586 | 1.00 | 25.76 | 6 |
| ATOM | 2543 | C | ARG | B | 47 | 49.781 | −11.972 | 23.373 | 1.00 | 23.01 | 6 |
| ATOM | 2544 | O | ARG | B | 47 | 48.813 | −11.243 | 23.291 | 1.00 | 23.89 | 8 |
| ATOM | 2545 | CB | ARG | B | 47 | 51.345 | −10.312 | 24.433 | 1.00 | 24.92 | 6 |
| ATOM | 2546 | CG | ARG | B | 47 | 51.975 | −9.858 | 25.800 | 1.00 | 27.22 | 6 |
| ATOM | 2547 | CD | ARG | B | 47 | 52.755 | −8.575 | 25.491 | 1.00 | 29.69 | 6 |
| ATOM | 2548 | NE | ARG | B | 47 | 53.415 | −7.966 | 26.670 | 1.00 | 34.33 | 7 |
| ATOM | 2549 | CZ | ARG | B | 47 | 52.861 | −6.966 | 27.358 | 1.00 | 35.85 | 6 |
| ATOM | 2550 | NH1 | ARG | B | 47 | 51.688 | −6.442 | 27.073 | 1.00 | 35.22 | 7 |
| ATOM | 2551 | NH2 | ARG | B | 47 | 53.555 | −6.467 | 28.392 | 1.00 | 37.54 | 7 |
| ATOM | 2552 | N | ALA | B | 48 | 50.203 | −12.899 | 22.529 | 1.00 | 23.33 | 7 |
| ATOM | 2553 | CA | ALA | B | 48 | 49.413 | −13.114 | 21.284 | 1.00 | 23.32 | 6 |
| ATOM | 2554 | C | ALA | B | 48 | 49.405 | −14.574 | 20.933 | 1.00 | 26.45 | 6 |
| ATOM | 2555 | O | ALA | B | 48 | 50.224 | −15.356 | 21.466 | 1.00 | 24.59 | 8 |
| ATOM | 2556 | CB | ALA | B | 48 | 50.059 | −12.332 | 20.168 | 1.00 | 23.24 | 6 |
| ATOM | 2557 | N | ASP | B | 49 | 48.547 | −15.010 | 20.004 | 1.00 | 24.54 | 7 |
| ATOM | 2558 | CA | ASP | B | 49 | 48.537 | −16.394 | 19.594 | 1.00 | 24.90 | 6 |
| ATOM | 2559 | C | ASP | B | 49 | 49.677 | −16.770 | 18.689 | 1.00 | 24.42 | 6 |
| ATOM | 2560 | O | ASP | B | 49 | 50.254 | −17.869 | 18.668 | 1.00 | 26.07 | 8 |
| ATOM | 2561 | CB | ASP | B | 49 | 47.237 | −16.656 | 18.803 | 1.00 | 26.28 | 6 |
| ATOM | 2562 | CG | ASP | B | 49 | 45.979 | −16.417 | 19.627 | 1.00 | 30.04 | 6 |
| ATOM | 2563 | OD1 | ASP | B | 49 | 45.977 | −16.990 | 20.754 | 1.00 | 32.57 | 8 |
| ATOM | 2564 | OD2 | ASP | B | 49 | 45.038 | −15.712 | 19.183 | 1.00 | 30.75 | 8 |
| ATOM | 2565 | N | VAL | B | 50 | 50.004 | −15.842 | 17.792 | 1.00 | 20.95 | 7 |
| ATOM | 2566 | CA | VAL | B | 50 | 50.980 | −15.998 | 16.747 | 1.00 | 20.87 | 6 |
| ATOM | 2567 | C | VAL | B | 50 | 52.014 | −14.905 | 16.734 | 1.00 | 20.83 | 6 |
| ATOM | 2568 | O | VAL | B | 50 | 51.742 | −13.704 | 16.973 | 1.00 | 20.70 | 8 |
| ATOM | 2569 | CB | VAL | B | 50 | 50.241 | −16.031 | 15.369 | 1.00 | 22.53 | 6 |
| ATOM | 2570 | CG1 | VAL | B | 50 | 51.112 | −15.780 | 14.170 | 1.00 | 26.09 | 6 |
| ATOM | 2571 | CG2 | VAL | B | 50 | 49.536 | −17.393 | 15.199 | 1.00 | 25.40 | 6 |
| ATOM | 2572 | N | VAL | B | 51 | 53.286 | −15.325 | 16.567 | 1.00 | 19.42 | 7 |
| ATOM | 2573 | CA | VAL | B | 51 | 54.373 | −14.336 | 16.498 | 1.80 | 22.20 | 6 |
| ATOM | 2574 | C | VAL | B | 51 | 54.975 | −14.279 | 15.113 | 1.00 | 22.35 | 6 |
| ATOM | 2575 | O | VAL | B | 51 | 55.400 | −15.274 | 14.488 | 1.00 | 23.37 | 8 |
| ATOM | 2576 | CB | VAL | B | 51 | 55.498 | −14.618 | 17.516 | 1.00 | 23.80 | 6 |
| ATOM | 2577 | CG1 | VAL | B | 51 | 56.616 | −13.574 | 17.449 | 1.00 | 24.48 | 6 |
| ATOM | 2578 | CG2 | VAL | B | 51 | 54.855 | −14.682 | 18.910 | 1.00 | 28.00 | 6 |
| ATOM | 2579 | N | VAL | B | 52 | 55.108 | −13.080 | 14.590 | 1.00 | 18.68 | 7 |
| ATOM | 2580 | CA | VAL | B | 52 | 55.734 | −12.772 | 13.322 | 1.00 | 17.55 | 6 |
| ATOM | 2581 | C | VAL | B | 52 | 57.014 | −11.980 | 13.623 | 1.00 | 21.15 | 6 |
| ATOM | 2582 | O | VAL | B | 52 | 56.930 | −10.957 | 14.319 | 1.00 | 19.41 | 8 |
| ATOM | 2583 | CB | VAL | B | 52 | 54.885 | −11.936 | 12.341 | 1.00 | 19.87 | 6 |
| ATOM | 2584 | CG1 | VAL | B | 52 | 55.613 | −11.467 | 11.107 | 1.00 | 19.90 | 6 |
| ATOM | 2585 | CG2 | VAL | B | 52 | 53.651 | −12.759 | 11.943 | 1.00 | 20.31 | 6 |
| ATOM | 2586 | N | VAL | B | 53 | 58.150 | −12.469 | 13.104 | 1.00 | 20.72 | 7 |
| ATOM | 2587 | CA | VAL | B | 53 | 59.396 | −11.698 | 13.267 | 1.00 | 20.35 | 6 |

TABLE 1-continued

| | | | | | | | | | | |
|---|---|---|---|---|---|---|---|---|---|---|
| ATOM | 2588 | C | VAL | B | 53 | 59.854 | −11.261 | 11.925 | 1.00 | 22.26 | 6 |
| ATOM | 2589 | O | VAL | B | 53 | 59.933 | −12.026 | 10.948 | 1.00 | 23.47 | 8 |
| ATOM | 2590 | CB | VAL | B | 53 | 60.505 | −12.545 | 13.977 | 1.00 | 20.44 | 6 |
| ATOM | 2591 | CG1 | VAL | B | 53 | 61.791 | −11.700 | 14.053 | 1.00 | 22.35 | 6 |
| ATOM | 2592 | CG2 | VAL | B | 53 | 60.059 | −13.004 | 15.346 | 1.00 | 22.26 | 6 |
| ATOM | 2593 | N | SER | B | 54 | 60.144 | −9.957 | 11.694 | 1.00 | 20.14 | 7 |
| ATOM | 2594 | CA | SER | B | 54 | 60.629 | −9.453 | 10.425 | 1.00 | 20.53 | 6 |
| ATOM | 2595 | C | SER | B | 54 | 62.157 | −9.208 | 10.601 | 1.00 | 23.03 | 6 |
| ATOM | 2596 | O | SER | B | 54 | 62.594 | −8.867 | 11.697 | 1.00 | 23.22 | 8 |
| ATOM | 2597 | CB | SER | B | 54 | 59.973 | −8.182 | 9.883 | 1.00 | 24.56 | 6 |
| ATOM | 2598 | OG | SER | B | 54 | 60.079 | −7.161 | 10.861 | 1.00 | 24.52 | 8 |
| ATOM | 2599 | N | ILE | B | 55 | 62.804 | −9.615 | 9.537 | 1.00 | 25.11 | 7 |
| ATOM | 2600 | CA | ILE | B | 55 | 64.289 | −9.443 | 9.508 | 1.00 | 23.93 | 6 |
| ATOM | 2601 | C | ILE | B | 55 | 64.589 | −8.756 | 8.220 | 1.00 | 22.42 | 6 |
| ATOM | 2602 | O | ILE | B | 55 | 64.333 | −9.214 | 7.082 | 1.00 | 23.75 | 8 |
| ATOM | 2603 | CB | ILE | B | 55 | 65.017 | −10.788 | 9.599 | 1.00 | 25.95 | 6 |
| ATOM | 2604 | CG1 | ILE | B | 55 | 64.888 | −11.494 | 10.920 | 1.00 | 25.74 | 6 |
| ATOM | 2605 | CG2 | ILE | B | 55 | 66.512 | −10.480 | 9.307 | 1.00 | 26.43 | 6 |
| ATOM | 2606 | CD1 | ILE | B | 55 | 65.315 | −12.955 | 10.805 | 1.00 | 29.38 | 6 |
| ATOM | 2607 | N | PHE | B | 56 | 65.039 | −7.469 | 8.273 | 1.00 | 23.82 | 7 |
| ATOM | 2608 | CA | PHE | B | 56 | 65.225 | −6.624 | 7.153 | 1.00 | 24.66 | 6 |
| ATOM | 2609 | C | PHE | B | 56 | 66.202 | −5.465 | 7.454 | 1.00 | 26.79 | 6 |
| ATOM | 2610 | O | PHE | B | 56 | 65.937 | −4.712 | 8.392 | 1.00 | 26.50 | 8 |
| ATOM | 2611 | CB | PHE | B | 56 | 63.878 | −6.011 | 6.668 | 1.00 | 22.93 | 6 |
| ATOM | 2612 | CG | PHE | B | 56 | 64.081 | −5.130 | 5.476 | 1.00 | 24.37 | 6 |
| ATOM | 2613 | CD1 | PHE | B | 56 | 64.570 | −5.602 | 4.262 | 1.00 | 25.67 | 6 |
| ATOM | 2614 | CD2 | PHE | B | 56 | 63.711 | −3.781 | 5.549 | 1.00 | 23.80 | 6 |
| ATOM | 2615 | CE1 | PHE | B | 56 | 64.765 | −4.758 | 3.193 | 1.00 | 25.30 | 6 |
| ATOM | 2616 | CE2 | PHE | B | 56 | 63.882 | −2.969 | 4.441 | 1.00 | 25.84 | 6 |
| ATOM | 2617 | CZ | PHE | B | 56 | 64.399 | −3.429 | 3.249 | 1.00 | 27.27 | 6 |
| ATOM | 2618 | N | VAL | B | 57 | 67.330 | −5.512 | 6.717 | 1.00 | 28.13 | 7 |
| ATOM | 2619 | CA | VAL | B | 57 | 68.347 | −4.471 | 7.001 | 1.00 | 27.59 | 6 |
| ATOM | 2620 | C | VAL | B | 57 | 67.968 | −3.357 | 6.089 | 1.00 | 26.50 | 6 |
| ATOM | 2621 | O | VAL | B | 57 | 68.047 | −3.404 | 4.871 | 1.00 | 28.47 | 8 |
| ATOM | 2622 | CB | VAL | B | 57 | 69.787 | −5.034 | 6.846 | 1.00 | 28.54 | 6 |
| ATOM | 2623 | CG1 | VAL | B | 57 | 70.795 | −3.915 | 7.235 | 1.00 | 30.14 | 6 |
| ATOM | 2624 | CG2 | VAL | B | 57 | 70.028 | −6.232 | 7.674 | 1.00 | 27.80 | 6 |
| ATOM | 2625 | N | ASN | B | 58 | 67.280 | −2.367 | 6.723 | 1.00 | 27.33 | 7 |
| ATOM | 2626 | CA | ASN | B | 58 | 66.643 | −1.277 | 5.989 | 1.00 | 28.47 | 6 |
| ATOM | 2627 | C | ASN | B | 58 | 67.589 | −0.208 | 5.529 | 1.00 | 28.30 | 6 |
| ATOM | 2628 | O | ASN | B | 58 | 68.068 | 0.587 | 6.350 | 1.00 | 29.87 | 8 |
| ATOM | 2629 | CB | ASN | B | 58 | 65.608 | −0.711 | 7.004 | 1.00 | 27.68 | 6 |
| ATOM | 2630 | CG | ASN | B | 58 | 64.919 | 0.542 | 6.507 | 1.00 | 24.26 | 6 |
| ATOM | 2631 | OD1 | ASN | B | 58 | 64.739 | 0.717 | 5.381 | 1.00 | 26.55 | 8 |
| ATOM | 2632 | ND2 | ASN | B | 58 | 64.487 | 1.392 | 7.445 | 1.00 | 24.78 | 7 |
| ATOM | 2633 | N | PRO | B | 59 | 67.828 | −0.063 | 4.251 | 1.00 | 32.20 | 7 |
| ATOM | 2634 | CA | PRO | B | 59 | 68.766 | 0.929 | 3.749 | 1.00 | 32.85 | 6 |
| ATOM | 2635 | C | PRO | B | 59 | 68.415 | 2.336 | 4.177 | 1.00 | 35.54 | 6 |
| ATOM | 2636 | C | PRO | B | 59 | 69.298 | 3.191 | 4.360 | 1.00 | 33.70 | 8 |
| ATOM | 2637 | CB | PRO | B | 59 | 68.703 | 0.729 | 2.239 | 1.00 | 36.08 | 6 |
| ATOM | 2638 | CG | PRO | B | 59 | 68.404 | −0.761 | 2.113 | 1.00 | 35.06 | 6 |
| ATOM | 2639 | CD | PRO | B | 59 | 67.336 | −0.957 | 3.170 | 1.00 | 34.20 | 6 |
| ATOM | 2640 | N | MET | B | 60 | 67.111 | 2.642 | 4.360 | 1.00 | 34.39 | 7 |
| ATOM | 2641 | CA | MET | B | 60 | 66.683 | 3.994 | 4.699 | 1.00 | 36.32 | 6 |
| ATOM | 2642 | C | MET | B | 60 | 67.197 | 4.523 | 6.022 | 1.00 | 37.35 | 6 |
| ATOM | 2643 | O | MET | B | 60 | 67.169 | 5.772 | 6.239 | 1.00 | 38.05 | 8 |
| ATOM | 2644 | CB | MET | B | 60 | 65.148 | 4.088 | 4.790 | 1.00 | 37.91 | 6 |
| ATOM | 2645 | CG | MET | B | 60 | 64.450 | 4.720 | 3.624 | 1.00 | 39.92 | 6 |
| ATOM | 2646 | SD | MET | B | 60 | 62.934 | 5.666 | 4.060 | 1.00 | 39.02 | 16 |
| ATOM | 2647 | CE | MET | B | 60 | 61.890 | 5.076 | 2.719 | 1.00 | 40.24 | 6 |
| ATOM | 2648 | N | GLN | B | 61 | 67.520 | 3.632 | 6.950 | 1.00 | 36.15 | 7 |
| ATOM | 2649 | CA | GLN | B | 61 | 67.973 | 4.079 | 8.262 | 1.00 | 37.72 | 6 |
| ATOM | 2650 | C | GLN | B | 61 | 69.493 | 3.884 | 8.375 | 1.00 | 39.87 | 6 |
| ATOM | 2651 | O | GLN | B | 61 | 70.042 | 3.727 | 9.476 | 1.00 | 42.79 | 8 |
| ATOM | 2652 | CB | GLN | B | 61 | 67.179 | 3.390 | 9.361 | 1.00 | 35.80 | 6 |
| ATOM | 2653 | CG | GLN | B | 61 | 67.540 | 1.949 | 9.681 | 1.00 | 32.41 | 6 |
| ATOM | 2654 | CD | GLN | B | 61 | 66.514 | 1.303 | 10.572 | 1.00 | 29.81 | 6 |
| ATOM | 2655 | OE1 | GLN | B | 61 | 65.349 | 0.972 | 10.194 | 1.00 | 28.50 | 8 |
| ATOM | 2656 | NE2 | GLN | B | 61 | 66.860 | 0.939 | 11.787 | 1.00 | 27.42 | 7 |
| ATOM | 2657 | N | PHE | B | 62 | 70.210 | 3.961 | 7.244 | 1.00 | 39.42 | 7 |
| ATOM | 2658 | CA | PHE | B | 62 | 71.665 | 3.901 | 7.241 | 1.00 | 40.52 | 6 |
| ATOM | 2659 | C | PHE | B | 62 | 72.216 | 5.205 | 6.643 | 1.00 | 43.48 | 6 |
| ATOM | 2660 | O | PHE | B | 62 | 71.742 | 5.679 | 5.613 | 1.00 | 41.80 | 8 |
| ATOM | 2661 | CB | PHE | B | 62 | 72.285 | 2.727 | 6.462 | 1.00 | 39.44 | 6 |
| ATOM | 2662 | CG | PHE | B | 62 | 72.261 | 1.476 | 7.310 | 1.00 | 38.25 | 6 |
| ATOM | 2663 | CD1 | PHE | B | 62 | 71.094 | 0.697 | 7.350 | 1.00 | 37.73 | 6 |
| ATOM | 2664 | CD2 | PHE | B | 62 | 73.329 | 1.085 | 8.076 | 1.00 | 37.32 | 6 |
| ATOM | 2665 | CE1 | PHE | B | 62 | 71.053 | −0.422 | 8.157 | 1.00 | 37.14 | 6 |
| ATOM | 2666 | CE2 | PHE | B | 62 | 73.294 | −0.044 | 8.870 | 1.00 | 36.89 | 6 |

TABLE 1-continued

| | | | | | | | | | | |
|---|---|---|---|---|---|---|---|---|---|---|
| ATOM | 2667 | CZ | PHE | B | 62 | 72.145 | −0.825 | B.902 | 1.00 | 37.49 | 6 |
| ATOM | 2668 | N | ASP | B | 63 | 73.267 | 5.723 | 7.257 | 1.00 | 48.37 | 7 |
| ATOM | 2669 | CA | ASP | B | 63 | 73.887 | 6.980 | 6.816 | 1.00 | 51.97 | 6 |
| ATOM | 2670 | C | ASP | B | 63 | 74.709 | 6.872 | 5.539 | 1.00 | 53.02 | 6 |
| ATOM | 2671 | O | ASP | B | 63 | 74.642 | 7.765 | 4.679 | 1.00 | 53.58 | 8 |
| ATOM | 2672 | CB | ASP | B | 63 | 74.800 | 7.511 | 7.922 | 1.00 | 53.54 | 6 |
| ATOM | 2673 | CG | ASP | B | 63 | 74.087 | 7.668 | 9.251 | 1.00 | 55.47 | 6 |
| ATOM | 2674 | OD1 | ASP | B | 63 | 72.832 | 7.712 | 9.265 | 1.00 | 57.99 | 8 |
| ATOM | 2675 | OD2 | ASP | B | 63 | 74.767 | 7.751 | 10.294 | 1.00 | 56.33 | 8 |
| ATOM | 2676 | N | ARG | B | 64 | 75.521 | 5.830 | 5.420 | 1.00 | 52.77 | 7 |
| ATOM | 2677 | CA | ARG | B | 64 | 76.344 | 5.697 | 4.211 | 1.00 | 54.08 | 6 |
| ATOM | 2678 | C | ARG | B | 64 | 76.323 | 4.250 | 3.759 | 1.00 | 54.41 | 6 |
| ATOM | 2679 | O | ARG | B | 64 | 76.037 | 3.392 | 4.582 | 1.00 | 53.32 | 8 |
| ATOM | 2680 | CB | ARG | B | 64 | 77.758 | 6.205 | 4.486 | 1.00 | 53.78 | 6 |
| ATOM | 2681 | N | PRO | B | 65 | 76.658 | 3.987 | 2.505 | 1.00 | 56.79 | 7 |
| ATOM | 2682 | CA | PRO | B | 65 | 76.654 | 2.637 | 1.974 | 1.00 | 57.90 | 6 |
| ATOM | 2683 | C | PRO | B | 65 | 77.533 | 1.632 | 2.682 | 1.00 | 59.54 | 6 |
| ATOM | 2684 | O | PRO | B | 65 | 77.159 | 0.456 | 2.659 | 1.00 | 59.29 | 8 |
| ATOM | 2685 | CB | PRO | B | 65 | 77.123 | 2.790 | 0.528 | 1.00 | 58.01 | 6 |
| ATOM | 2686 | CG | PRO | B | 65 | 77.017 | 4.235 | 0.201 | 1.00 | 58.02 | 6 |
| ATOM | 2687 | CD | PRO | B | 65 | 77.011 | 5.007 | 1.489 | 1.00 | 57.36 | 6 |
| ATOM | 2688 | N | GLU | B | 66 | 78.651 | 1.990 | 3.291 | 1.00 | 60.73 | 7 |
| ATOM | 2689 | CA | GLU | B | 66 | 79.545 | 1.029 | 3.926 | 1.00 | 60.74 | 6 |
| ATOM | 2690 | C | GLU | B | 66 | 78.996 | 0.590 | 5.268 | 1.00 | 58.41 | 6 |
| ATOM | 2691 | O | GLU | B | 66 | 79.184 | −0.554 | 5.672 | 1.00 | 59.32 | 8 |
| ATOM | 2692 | CB | GLU | B | 66 | 80.949 | 1.612 | 4.114 | 1.00 | 63.95 | 6 |
| ATOM | 2693 | CG | GLU | B | 66 | 81.554 | 2.085 | 2.807 | 1.00 | 67.09 | 6 |
| ATOM | 2694 | CD | GLU | B | 66 | 81.129 | 3.469 | 2.387 | 1.00 | 69.60 | 6 |
| ATOM | 2695 | OE1 | GLU | B | 66 | 80.077 | 4.027 | 2.774 | 1.00 | 71.11 | 8 |
| ATOM | 2696 | OE2 | GLU | B | 66 | 81.873 | 4.122 | 1.612 | 1.00 | 71.37 | 8 |
| ATOM | 2697 | N | ASP | B | 67 | 78.271 | 1.521 | 5.890 | 1.00 | 55.22 | 7 |
| ATOM | 2698 | CA | ASP | B | 67 | 77.618 | 1.142 | 7.151 | 1.00 | 53.44 | 6 |
| ATOM | 2699 | C | ASP | B | 67 | 76.586 | 0.068 | 6.773 | 1.00 | 49.67 | 6 |
| ATOM | 2700 | O | ASP | B | 67 | 76.505 | −0.978 | 7.418 | 1.00 | 47.57 | 8 |
| ATOM | 2701 | CB | ASP | B | 67 | 77.109 | 2.400 | 7.818 | 1.00 | 55.45 | 6 |
| ATOM | 2702 | CG | ASP | B | 67 | 78.226 | 3.389 | 8.134 | 1.00 | 58.05 | 6 |
| ATOM | 2703 | OD1 | ASP | B | 67 | 79.352 | 3.283 | 7.602 | 1.00 | 58.16 | 8 |
| ATOM | 2704 | OD2 | ASP | B | 67 | 77.993 | 4.307 | 8.954 | 1.00 | 58.74 | 8 |
| ATOM | 2705 | N | LEU | B | 68 | 75.906 | 0.243 | 5.640 | 1.00 | 47.47 | 7 |
| ATOM | 2706 | CA | LEU | B | 68 | 74.908 | −0.706 | 5.170 | 1.00 | 45.94 | 6 |
| ATOM | 2707 | C | LEU | B | 68 | 75.575 | −2.002 | 4.715 | 1.00 | 46.59 | 6 |
| ATOM | 2708 | O | LEU | B | 68 | 75.241 | −3.082 | 5.201 | 1.00 | 47.70 | 8 |
| ATOM | 2709 | CB | LEU | B | 68 | 74.066 | −0.198 | 4.001 | 1.00 | 44.25 | 6 |
| ATOM | 2710 | CG | LEU | B | 68 | 72.989 | −1.184 | 3.489 | 1.00 | 42.50 | 6 |
| ATOM | 2711 | CD1 | LEU | B | 68 | 72.064 | −1.563 | 4.634 | 1.00 | 40.69 | 6 |
| ATOM | 2712 | CD2 | LEU | B | 68 | 72.214 | −0.620 | 2.317 | 1.00 | 42.43 | 6 |
| ATOM | 2713 | N | ALA | B | 69 | 76.513 | −1.866 | 3.793 | 1.00 | 46.99 | 7 |
| ATOM | 2714 | CA | ALA | B | 69 | 77.238 | −3.024 | 3.259 | 1.00 | 47.49 | 6 |
| ATOM | 2715 | C | ALA | B | 69 | 77.930 | −3.829 | 4.337 | 1.00 | 46.64 | 6 |
| ATOM | 2716 | O | ALA | B | 69 | 77.913 | −5.072 | 4.256 | 1.00 | 48.02 | 8 |
| ATOM | 2717 | CB | ALA | B | 69 | 78.258 | −2.532 | 2.235 | 1.00 | 48.47 | 6 |
| ATOM | 2718 | N | ARG | B | 70 | 78.475 | −3.201 | 5.370 | 1.00 | 45.74 | 7 |
| ATOM | 2719 | CA | ARG | B | 70 | 79.158 | −3.961 | 6.411 | 1.00 | 44.24 | 6 |
| ATOM | 2720 | C | ARG | B | 70 | 78.246 | −4.487 | 7.495 | 1.00 | 44.00 | 6 |
| ATOM | 2721 | O | ARG | B | 70 | 78.700 | −5.308 | 8.281 | 1.00 | 41.15 | 8 |
| ATOM | 2722 | CB | ARG | B | 70 | 80.247 | −3.071 | 7.038 | 1.00 | 46.62 | 6 |
| ATOM | 2723 | N | TYR | B | 71 | 76.966 | −4.108 | 7.573 | 1.00 | 41.84 | 7 |
| ATOM | 2724 | CA | TYR | B | 71 | 76.076 | −4.624 | 8.609 | 1.00 | 39.35 | 6 |
| ATOM | 2725 | C | TYR | B | 71 | 75.935 | −6.141 | 8.508 | 1.00 | 37.54 | 6 |
| ATOM | 2726 | O | TYR | B | 71 | 75.788 | −6.673 | 7.410 | 1.00 | 37.39 | 8 |
| ATOM | 2727 | CB | TYR | B | 71 | 74.712 | −3.919 | 8.487 | 1.00 | 38.73 | 6 |
| ATOM | 2728 | CG | TYR | B | 71 | 73.927 | −4.054 | 9.778 | 1.00 | 36.95 | 6 |
| ATOM | 2729 | CD1 | TYR | B | 71 | 74.099 | −3.155 | 10.806 | 1.00 | 34.97 | 6 |
| ATOM | 2730 | CD2 | TYR | B | 71 | 72.993 | −5.079 | 9.946 | 1.00 | 35.71 | 6 |
| ATOM | 2731 | CE1 | TYR | B | 71 | 73.405 | −3.260 | 12.004 | 1.00 | 35.01 | 6 |
| ATOM | 2732 | CE2 | TYR | B | 71 | 72.287 | −5.192 | 11.109 | 1.00 | 33.37 | 6 |
| ATOM | 2733 | CZ | TYR | B | 71 | 72.462 | −4.292 | 12.119 | 1.00 | 34.69 | 6 |
| ATOM | 2734 | OH | TYR | B | 71 | 71.765 | −4.407 | 13.290 | 1.00 | 34.77 | 8 |
| ATOM | 2735 | N | PRO | B | 72 | 75.985 | −6.835 | 9.625 | 1.00 | 37.73 | 7 |
| ATOM | 2736 | CA | PRO | B | 72 | 76.030 | −8.293 | 9.644 | 1.00 | 40.09 | 6 |
| ATOM | 2737 | C | PRO | B | 72 | 74.756 | −8.966 | 9.194 | 1.00 | 42.74 | 6 |
| ATOM | 2738 | O | PRO | B | 72 | 73.697 | −8.753 | 9.783 | 1.00 | 42.94 | 8 |
| ATOM | 2739 | CB | PRO | B | 72 | 76.369 | −8.681 | 11.080 | 1.00 | 39.27 | 6 |
| ATOM | 2740 | CG | PRO | B | 72 | 76.366 | −7.442 | 11.876 | 1.00 | 39.73 | 6 |
| ATOM | 2741 | CD | PRO | B | 72 | 76.222 | −6.266 | 10.967 | 1.00 | 37.89 | 6 |
| ATOM | 2742 | N | ARG | B | 73 | 74.856 | −9.773 | 8.147 | 1.00 | 42.53 | 7 |
| ATOM | 2743 | CA | ARG | B | 73 | 73.687 | −10.492 | 7.639 | 1.00 | 43.36 | 6 |
| ATOM | 2744 | C | ARG | B | 73 | 73.881 | −11.945 | 7.992 | 1.00 | 43.07 | 6 |
| ATOM | 2745 | O | ARG | B | 73 | 74.875 | −12.526 | 7.534 | 1.00 | 42.68 | 8 |

TABLE 1-continued

| | | | | | | | | | |
|---|---|---|---|---|---|---|---|---|---|
| ATOM | 2746 | CB | ARG | B | 73 | 73.524 | −10.225 | 6.143 | 1.00 | 45.53 | 6 |
| ATOM | 2747 | CG | ARG | B | 73 | 73.306 | −8.700 | 5.962 | 1.00 | 48.13 | 6 |
| ATOM | 2748 | CD | ARG | B | 73 | 72.868 | −8.393 | 4.559 | 1.00 | 49.65 | 6 |
| ATOM | 2749 | NE | ARG | B | 73 | 72.537 | −7.021 | 4.268 | 1.00 | 51.16 | 7 |
| ATOM | 2750 | CZ | ARG | B | 73 | 73.255 | −5.930 | 4.486 | 1.00 | 51.88 | 6 |
| ATOM | 2751 | NH1 | ARG | B | 73 | 74.449 | −5.968 | 5.071 | 1.00 | 53.24 | 7 |
| ATOM | 2752 | NH2 | ARG | B | 73 | 72.779 | −4.755 | 4.085 | 1.00 | 51.96 | 7 |
| ATOM | 2753 | N | THR | B | 74 | 73.054 | −12.505 | 8.869 | 1.00 | 40.78 | 7 |
| ATOM | 2754 | CA | THR | B | 74 | 73.184 | −13.870 | 9.338 | 1.00 | 38.76 | 6 |
| ATOM | 2755 | C | THR | B | 74 | 71.806 | −14.564 | 9.373 | 1.00 | 36.02 | 6 |
| ATOM | 2756 | O | THR | B | 74 | 71.381 | −15.074 | 10.395 | 1.00 | 35.74 | 8 |
| ATOM | 2757 | CB | THR | B | 74 | 73.825 | −13.949 | 10.726 | 1.00 | 39.81 | 6 |
| ATOM | 2758 | OG1 | THR | B | 74 | 72.965 | −13.304 | 11.686 | 1.00 | 41.92 | 8 |
| ATOM | 2759 | CG2 | THR | B | 74 | 75.176 | −13.231 | 10.872 | 1.00 | 39.68 | 6 |
| ATOM | 2760 | N | LEU | B | 75 | 71.163 | −14.648 | 8.241 | 1.00 | 38.12 | 7 |
| ATOM | 2761 | CA | LEU | B | 75 | 69.795 | −15.148 | 8.140 | 1.00 | 38.95 | 6 |
| ATOM | 2762 | C | LEU | B | 75 | 69.657 | −16.574 | 8.644 | 1.00 | 39.45 | 6 |
| ATOM | 2763 | O | LEU | B | 75 | 68.791 | −16.843 | 9.478 | 1.00 | 37.24 | 8 |
| ATOM | 2764 | CB | LEU | B | 75 | 69.269 | −15.024 | 6.693 | 1.00 | 41.95 | 6 |
| ATOM | 2765 | CG | LEU | B | 75 | 67.785 | −15.355 | 6.505 | 1.00 | 42.42 | 6 |
| ATOM | 2766 | CD1 | LEU | B | 75 | 66.907 | −14.527 | 7.453 | 1.00 | 43.76 | 6 |
| ATOM | 2767 | CD2 | LEU | B | 75 | 67.332 | −15.146 | 5.070 | 1.00 | 42.41 | 6 |
| ATOM | 2768 | N | GLN | B | 76 | 70.525 | −17.509 | 8.187 | 1.00 | 39.28 | 7 |
| ATOM | 2769 | CA | GLN | B | 76 | 70.400 | −18.884 | 8.667 | 1.00 | 39.73 | 6 |
| ATOM | 2770 | C | GLN | B | 76 | 70.476 | −18.965 | 10.181 | 1.00 | 36.54 | 6 |
| ATOM | 2771 | O | GLN | B | 76 | 69.671 | −19.700 | 10.759 | 1.00 | 35.73 | 8 |
| ATOM | 2772 | CB | GLN | B | 76 | 71.477 | −19.872 | 8.150 | 1.00 | 42.75 | 6 |
| ATOM | 2773 | CG | GLN | B | 76 | 71.375 | −21.209 | 8.897 | 1.00 | 45.19 | 6 |
| ATOM | 2774 | CD | GLN | B | 76 | 72.464 | −22.227 | 8.683 | 1.00 | 48.00 | 6 |
| ATOM | 2775 | OE1 | GLN | B | 76 | 72.386 | −23.355 | 9.236 | 1.00 | 51.20 | 8 |
| ATOM | 2776 | NE2 | GLN | B | 76 | 73.482 | −21.896 | 7.921 | 1.00 | 46.67 | 7 |
| ATOM | 2777 | N | GLU | B | 77 | 71.442 | −18.317 | 10.808 | 1.00 | 33.90 | 7 |
| ATOM | 2778 | CA | GLU | B | 77 | 71.585 | −18.356 | 12.259 | 1.00 | 33.25 | 6 |
| ATOM | 2779 | C | GLU | B | 77 | 70.408 | −17.708 | 13.013 | 1.00 | 32.48 | 6 |
| ATOM | 2780 | O | GLU | B | 77 | 69.960 | −18.170 | 14.072 | 1.00 | 31.46 | 8 |
| ATOM | 2781 | CB | GLU | B | 77 | 72.885 | −17.636 | 12.627 | 1.00 | 33.79 | 6 |
| ATOM | 2782 | N | ASP | B | 78 | 69.915 | −16.625 | 12.388 | 1.00 | 32.55 | 7 |
| ATOM | 2783 | CA | ASP | B | 78 | 68.738 | −15.937 | 12.973 | 1.00 | 30.24 | 6 |
| ATOM | 2784 | C | ASP | B | 78 | 67.576 | −16.964 | 12.993 | 1.00 | 28.55 | 6 |
| ATOM | 2785 | O | ASP | B | 78 | 66.981 | −17.174 | 14.032 | 1.00 | 29.32 | 8 |
| ATOM | 2786 | CB | ASP | B | 78 | 68.337 | −14.697 | 12.209 | 1.00 | 31.00 | 6 |
| ATOM | 2787 | CG | ASP | B | 78 | 69.331 | −13.551 | 12.195 | 1.00 | 34.64 | 6 |
| ATOM | 2788 | OD1 | ASP | B | 78 | 70.144 | −13.494 | 13.151 | 1.00 | 37.80 | 8 |
| ATOM | 2789 | OD2 | ASP | B | 78 | 69.328 | −12.744 | 11.228 | 1.00 | 36.82 | 8 |
| ATOM | 2790 | N | CYS | B | 79 | 67.355 | −17.543 | 11.825 | 1.00 | 30.19 | 7 |
| ATOM | 2791 | CA | CYS | B | 79 | 66.231 | −18.500 | 11.625 | 1.00 | 33.57 | 6 |
| ATOM | 2792 | C | CYS | B | 79 | 66.327 | −19.720 | 12.495 | 1.00 | 35.51 | 6 |
| ATOM | 2793 | O | CYS | B | 79 | 65.350 | −20.136 | 13.149 | 1.00 | 34.66 | 8 |
| ATOM | 2794 | CB | CYS | B | 79 | 66.184 | −18.792 | 10.132 | 1.00 | 33.80 | 6 |
| ATOM | 2795 | SG | CYS | B | 79 | 65.381 | −17.456 | 9.190 | 1.00 | 37.92 | 16 |
| ATOM | 2796 | N | GLU | B | 80 | 67.543 | −20.281 | 12.707 | 1.00 | 36.68 | 7 |
| ATOM | 2797 | CA | GLU | B | 80 | 67.692 | −21.347 | 13.691 | 1.00 | 35.97 | 6 |
| ATOM | 2798 | C | GLU | B | 80 | 67.370 | −20.883 | 15.088 | 1.00 | 33.68 | 6 |
| ATOM | 2799 | O | GLU | B | 80 | 66.764 | −21.625 | 15.883 | 1.00 | 34.88 | 8 |
| ATOM | 2800 | CB | GLU | B | 80 | 69.130 | −21.906 | 13.660 | 1.00 | 36.66 | 6 |
| ATOM | 2801 | N | LYS | B | 81 | 67.668 | −19.638 | 15.520 | 1.00 | 34.02 | 7 |
| ATOM | 2802 | CA | LYS | B | 81 | 67.277 | −19.253 | 16.875 | 1.00 | 31.36 | 6 |
| ATOM | 2803 | C | LYS | B | 81 | 65.756 | −19.047 | 17.017 | 1.00 | 30.38 | 6 |
| ATOM | 2804 | O | LYS | B | 81 | 65.183 | −19.326 | 18.068 | 1.00 | 29.64 | 8 |
| ATOM | 2805 | CB | LYS | B | 81 | 67.967 | −17.965 | 17.314 | 1.00 | 35.26 | 6 |
| ATOM | 2806 | CG | LYS | B | 81 | 69.451 | −18.114 | 17.566 | 1.00 | 37.30 | 6 |
| ATOM | 2807 | CD | LYS | B | 81 | 70.118 | −16.744 | 17.730 | 1.00 | 39.14 | 6 |
| ATOM | 2808 | CE | LYS | B | 81 | 71.635 | −17.011 | 17.782 | 1.00 | 41.26 | 6 |
| ATOM | 2809 | NZ | LYS | B | 81 | 72.310 | −15.733 | 18.142 | 1.00 | 43.00 | 7 |
| ATOM | 2810 | N | LEU | B | 82 | 65.158 | −18.495 | 15.965 | 1.00 | 30.34 | 7 |
| ATOM | 2811 | CA | LEU | B | 82 | 63.700 | −18.248 | 16.019 | 1.00 | 30.06 | 6 |
| ATOM | 2812 | C | LEU | B | 82 | 62.914 | −19.540 | 16.028 | 1.00 | 32.53 | 6 |
| ATOM | 2813 | O | LEU | B | 82 | 61.880 | −19.695 | 16.694 | 1.00 | 32.69 | 8 |
| ATOM | 2814 | CB | LEU | B | 82 | 63.335 | −17.328 | 14.845 | 1.00 | 30.48 | 6 |
| ATOM | 2815 | CG | LEU | B | 82 | 63.981 | −15.924 | 14.936 | 1.00 | 28.69 | 6 |
| ATOM | 2816 | CD1 | LEU | B | 82 | 63.820 | −15.222 | 13.603 | 1.00 | 25.14 | 6 |
| ATOM | 2817 | CD2 | LEU | B | 82 | 63.412 | −15.105 | 16.103 | 1.00 | 28.77 | 6 |
| ATOM | 2818 | N | ASN | B | 83 | 63.438 | −20.549 | 15.323 | 1.00 | 33.22 | 7 |
| ATOM | 2819 | CA | ASN | B | 83 | 62.748 | −21.849 | 15.282 | 1.00 | 36.28 | 6 |
| ATOM | 2820 | C | ASN | B | 83 | 62.747 | −22.507 | 16.648 | 1.00 | 36.28 | 6 |
| ATOM | 2821 | O | ASN | B | 83 | 61.735 | −23.043 | 17.139 | 1.00 | 35.49 | 8 |
| ATOM | 2822 | CB | ASN | B | 83 | 63.419 | −22.656 | 14.181 | 1.00 | 39.05 | 6 |
| ATOM | 2823 | CG | ASN | B | 83 | 62.717 | −23.983 | 13.943 | 1.00 | 42.41 | 6 |
| ATOM | 2824 | OD1 | ASN | B | 83 | 63.382 | −25.000 | 14.194 | 1.00 | 45.42 | 8 |

TABLE 1-continued

| | | | | | | | | | | |
|---|---|---|---|---|---|---|---|---|---|---|
| ATOM | 2825 | ND2 | ASN | B | 83 | 61.474 | −23.962 | 13.533 | 1.00 | 41.68 | 7 |
| ATOM | 2826 | N | LYS | B | 84 | 63.820 | −22.351 | 17.437 | 1.00 | 37.37 | 7 |
| ATOM | 2827 | CA | LYS | B | 84 | 63.850 | −22.927 | 18.780 | 1.00 | 39.89 | 6 |
| ATOM | 2828 | C | LYS | B | 84 | 62.942 | −22.200 | 19.747 | 1.00 | 40.11 | 6 |
| ATOH | 2829 | O | LYS | B | 84 | 62.533 | −22.693 | 20.801 | 1.00 | 40.80 | 8 |
| ATOM | 2830 | CB | LYS | B | 84 | 65.305 | −22.932 | 19.291 | 1.00 | 39.81 | 6 |
| ATOM | 2831 | N | ARG | B | 85 | 62.590 | −20.942 | 19.425 | 1.00 | 40.09 | 7 |
| ATOM | 2832 | CA | ARG | B | 85 | 61.718 | −20.125 | 20.235 | 1.00 | 39.63 | 6 |
| ATOM | 2833 | C | ARG | B | 85 | 60.260 | −20.305 | 19.812 | 1.00 | 40.59 | 6 |
| ATOM | 2834 | O | ARG | B | 85 | 59.373 | −19.647 | 20.334 | 1.00 | 42.54 | 8 |
| ATOM | 2835 | CB | ARG | B | 85 | 62.093 | −18.647 | 20.134 | 1.00 | 40.48 | 6 |
| ATOM | 2836 | CG | ARG | B | 85 | 62.052 | −17.972 | 21.510 | 1.00 | 41.38 | 6 |
| ATOM | 2837 | CD | ARG | B | 85 | 63.336 | −18.317 | 22.253 | 1.00 | 42.99 | 6 |
| ATOM | 2838 | NE | ARG | B | 85 | 63.380 | −17.724 | 23.588 | 1.00 | 42.49 | 7 |
| ATOM | 2839 | CZ | ARG | B | 85 | 64.475 | −17.764 | 24.342 | 1.00 | 43.47 | 6 |
| ATOM | 2840 | NH1 | ARG | B | 85 | 64.483 | −17.233 | 25.553 | 1.00 | 42.44 | 7 |
| ATOM | 2841 | NH2 | ARG | B | 85 | 65.570 | −18.361 | 23.872 | 1.00 | 44.83 | 7 |
| ATOM | 2842 | N | LYS | B | 86 | 60.041 | −21.151 | 18.827 | 1.00 | 39.06 | 7 |
| ATOM | 2843 | CA | LYS | B | 86 | 58.702 | −21.492 | 18.348 | 1.00 | 38.48 | 6 |
| ATOM | 2844 | C | LYS | B | 86 | 57.996 | −20.296 | 17.712 | 1.00 | 36.35 | 6 |
| ATOM | 2845 | O | LYS | B | 86 | 56.785 | −20.127 | 17.808 | 1.00 | 34.81 | 8 |
| ATOM | 2846 | CB | LYS | B | 86 | 57.903 | −22.087 | 19.511 | 1.00 | 39.68 | 6 |
| ATOM | 2847 | N | VAL | B | 87 | 58.751 | −19.515 | 16.953 | 1.00 | 33.22 | 7 |
| ATOM | 2848 | CA | VAL | B | 87 | 58.133 | −18.416 | 16.204 | 1.00 | 29.42 | 6 |
| ATOM | 2849 | C | VAL | B | 87 | 57.340 | −18.986 | 15.051 | 1.00 | 30.11 | 6 |
| ATOM | 2850 | O | VAL | B | 87 | 57.704 | −19.959 | 14.359 | 1.00 | 29.33 | 8 |
| ATOM | 2851 | CB | VAL | B | 87 | 59.267 | −17.508 | 15.732 | 1.00 | 27.19 | 6 |
| ATOM | 2852 | CG1 | VAL | B | 87 | 58.859 | −16.637 | 14.581 | 1.00 | 28.11 | 6 |
| ATOM | 2853 | CG2 | VAL | B | 87 | 59.756 | −16.644 | 16.909 | 1.00 | 28.45 | 6 |
| ATOM | 2854 | N | ASP | B | 88 | 56.179 | −18.408 | 14.740 | 1.00 | 27.32 | 7 |
| ATOM | 2855 | CA | ASP | B | 88 | 55.356 | −18.963 | 13.667 | 1.00 | 26.78 | 6 |
| ATOM | 2856 | C | ASP | B | 88 | 55.778 | −18.589 | 12.285 | 1.00 | 26.80 | 6 |
| ATOM | 2857 | O | ASP | B | 88 | 55.687 | −19.415 | 11.342 | 1.00 | 26.44 | 8 |
| ATOM | 2858 | CB | ASP | B | 88 | 53.895 | −18.488 | 13.889 | 1.00 | 29.04 | 6 |
| ATOM | 2859 | CG | ASP | B | 88 | 53.482 | −18.856 | 15.298 | 1.00 | 30.71 | 6 |
| ATOM | 2860 | OD1 | ASP | B | 88 | 52.991 | −20.020 | 15.427 | 1.00 | 32.60 | 8 |
| ATOM | 2861 | OD2 | ASP | B | 88 | 53.717 | −18.147 | 16.323 | 1.00 | 30.59 | 8 |
| ATOM | 2862 | N | LEU | B | 89 | 56.204 | −17.356 | 12.062 | 1.00 | 23.49 | 7 |
| ATOM | 2863 | CA | LEU | B | 89 | 56.498 | −16.854 | 10.756 | 1.00 | 23.51 | 6 |
| ATOM | 2864 | C | LEU | B | 89 | 57.676 | −15.880 | 10.729 | 1.00 | 23.91 | 6 |
| ATOM | 2865 | O | LEU | B | 89 | 57.609 | −14.975 | 11.552 | 1.00 | 24.58 | 8 |
| ATOM | 2866 | CB | LEU | B | 89 | 55.236 | −16.101 | 10.292 | 1.00 | 26.12 | 6 |
| ATOM | 2867 | CG | LEU | B | 89 | 55.179 | −15.845 | 8.823 | 1.00 | 29.47 | 6 |
| ATOM | 2868 | CD1 | LEU | B | 89 | 53.725 | −15.783 | 8.333 | 1.00 | 31.30 | 6 |
| ATOM | 2869 | CD2 | LEU | B | 89 | 55.883 | −14.542 | 8.494 | 1.00 | 32.84 | 6 |
| ATOM | 2870 | N | VAL | B | 90 | 58.629 | −15.971 | 9.842 | 1.00 | 23.43 | 7 |
| ATOM | 2871 | CA | VAL | B | 90 | 59.716 | −15.006 | 9.714 | 1.00 | 23.35 | 6 |
| ATOM | 2872 | C | VAL | B | 90 | 59.553 | −14.315 | 8.413 | 1.00 | 24.66 | 6 |
| ATOM | 2873 | O | VAL | B | 90 | 59.386 | −14.905 | 7.324 | 1.00 | 24.98 | 8 |
| ATOM | 2874 | CB | VAL | B | 90 | 61.116 | −15.722 | 9.862 | 1.00 | 23.84 | 6 |
| ATOM | 2875 | CG1 | VAL | B | 90 | 62.212 | −14.701 | 9.640 | 1.00 | 26.41 | 6 |
| ATOM | 2876 | CG2 | VAL | B | 90 | 61.195 | −16.379 | 11.217 | 1.00 | 23.75 | 6 |
| ATOM | 2877 | N | PHE | B | 91 | 59.462 | −12.972 | 8.351 | 1.00 | 23.00 | 7 |
| ATOM | 2878 | CA | PHE | B | 91 | 59.363 | −12.240 | 7.147 | 1.00 | 21.82 | 6 |
| ATOM | 2879 | C | PHE | B | 91 | 60.754 | −11.693 | 6.787 | 1.00 | 24.30 | 6 |
| ATOM | 2880 | O | PHE | B | 91 | 61.258 | −10.892 | 7.578 | 1.00 | 25.55 | 8 |
| ATOM | 2881 | CB | PHE | B | 91 | 58.346 | −11.073 | 7.207 | 1.00 | 20.44 | 6 |
| ATOM | 2882 | CG | PHE | B | 91 | 58.180 | −10.275 | 5.969 | 1.00 | 22.85 | 6 |
| ATOM | 2883 | CD1 | PHE | B | 91 | 58.030 | −10.779 | 4.676 | 1.00 | 21.26 | 6 |
| ATOM | 2884 | CD2 | PHE | B | 91 | 58.164 | −8.848 | 6.101 | 1.00 | 22.68 | 6 |
| ATOM | 2885 | CE1 | PHE | B | 91 | 57.900 | −9.976 | 3.571 | 1.00 | 22.13 | 6 |
| ATOM | 2886 | CE2 | PHE | B | 91 | 58.006 | −8.055 | 4.990 | 1.00 | 21.70 | 6 |
| ATOM | 2887 | CZ | PHE | B | 91 | 57.852 | −8.587 | 3.703 | 1.00 | 23.17 | 6 |
| ATOM | 2888 | N | ALA | B | 92 | 61.345 | −12.164 | 5.695 | 1.00 | 24.62 | 7 |
| ATOM | 2889 | CA | ALA | B | 92 | 62.738 | −11.659 | 5.375 | 1.00 | 23.61 | 6 |
| ATOM | 2890 | C | ALA | B | 92 | 62.815 | −11.216 | 3.975 | 1.00 | 25.99 | 6 |
| ATOM | 2891 | O | ALA | B | 92 | 63.216 | −12.052 | 3.123 | 1.00 | 27.84 | 8 |
| ATOM | 2892 | CB | ALA | B | 92 | 63.656 | −12.811 | 5.743 | 1.00 | 25.77 | 6 |
| ATOM | 2893 | N | PRO | B | 93 | 62.300 | −10.088 | 3.518 | 1.00 | 25.21 | 7 |
| ATOM | 2894 | CA | PRO | B | 93 | 62.258 | −9.655 | 2.170 | 1.00 | 26.28 | 6 |
| ATOM | 2895 | C | PRO | B | 93 | 63.583 | −9.189 | 1.617 | 1.00 | 25.56 | 6 |
| ATOM | 2896 | O | PRO | B | 93 | 64.455 | −8.761 | 2.381 | 1.00 | 27.95 | 8 |
| ATOM | 2897 | CB | PRO | B | 93 | 61.283 | −8.471 | 2.238 | 1.00 | 26.93 | 6 |
| ATOM | 2898 | CG | PRO | B | 93 | 61.547 | −7.888 | 3.586 | 1.00 | 26.11 | 6 |
| ATOM | 2899 | CD | PRO | B | 93 | 61.769 | −9.060 | 4.516 | 1.00 | 24.38 | 6 |
| ATOM | 2900 | N | SER | B | 94 | 63.668 | −9.114 | 0.292 | 1.00 | 28.86 | 7 |
| ATOM | 2901 | CA | SER | B | 94 | 64.891 | −8.524 | −0.309 | 1.00 | 30.21 | 6 |
| ATOM | 2902 | C | SER | B | 94 | 64.735 | −7.010 | −0.305 | 1.00 | 31.63 | 6 |
| ATOM | 2903 | O | SER | B | 94 | 63.635 | −6.521 | −0.100 | 1.00 | 27.09 | 8 |

TABLE 1-continued

| | | | | | | | | | | |
|---|---|---|---|---|---|---|---|---|---|---|
| ATOM | 2904 | CB | SER | B | 94 | 65.138 | −8.951 | −1.719 | 1.00 | 28.52 | 6 |
| ATOM | 2905 | OG | SER | B | 94 | 64.254 | −8.353 | −2.673 | 1.00 | 29.83 | 8 |
| ATOM | 2906 | N | VAL | B | 95 | 65.802 | −6.264 | −0.628 | 1.00 | 32.49 | 7 |
| ATOM | 2907 | CA | VAL | B | 95 | 65.724 | −4.840 | −0.723 | 1.00 | 31.55 | 6 |
| ATOM | 2908 | C | VAL | B | 95 | 64.919 | −4.487 | −1.938 | 1.00 | 31.75 | 6 |
| ATOM | 2909 | O | VAL | B | 95 | 64.138 | −3.540 | −1.883 | 1.00 | 31.41 | 8 |
| ATOM | 2910 | CB | VAL | B | 95 | 67.144 | −4.172 | −0.780 | 1.00 | 32.74 | 6 |
| ATOM | 2911 | CG1 | VAL | B | 95 | 67.050 | −2.736 | −1.221 | 1.00 | 34.17 | 6 |
| ATOM | 2912 | CG2 | VAL | B | 95 | 67.813 | −4.258 | 0.570 | 1.00 | 33.43 | 6 |
| ATOM | 2913 | N | LYS | B | 96 | 65.004 | −5.262 | −3.023 | 1.00 | 31.26 | 7 |
| ATOM | 2914 | CA | LYS | B | 96 | 64.226 | −5.022 | −4.212 | 1.00 | 31.62 | 6 |
| ATOM | 2915 | C | LYS | B | 96 | 62.744 | −5.267 | −3.889 | 1.00 | 29.22 | 6 |
| ATOM | 2916 | O | LYS | B | 96 | 61.905 | −4.611 | −4.487 | 1.00 | 32.48 | 8 |
| ATOM | 2917 | CB | LYS | B | 96 | 64.685 | −5.913 | −5.380 | 1.00 | 32.35 | 6 |
| ATOM | 2918 | N | GLU | B | 97 | 62.464 | −6.172 | −2.988 | 1.00 | 30.27 | 7 |
| ATOM | 2919 | CA | GLU | B | 97 | 61.056 | −6.463 | −2.667 | 1.00 | 31.03 | 6 |
| ATOM | 2920 | C | GLU | B | 97 | 60.375 | −5.301 | −1.936 | 1.00 | 30.11 | 6 |
| ATOM | 2921 | O | GLU | B | 97 | 59.235 | −4.950 | −2.211 | 1.00 | 31.04 | 8 |
| ATOM | 2922 | CB | GLU | B | 97 | 61.000 | −7.749 | −1.850 | 1.00 | 32.49 | 6 |
| ATOM | 2923 | CG | GLU | B | 97 | 59.570 | −8.220 | −1.623 | 1.00 | 33.54 | 6 |
| ATOM | 2924 | CD | GLU | B | 97 | 58.875 | −8.792 | −2.844 | 1.00 | 35.26 | 6 |
| ATOM | 2925 | OE1 | GLU | B | 97 | 59.540 | −9.132 | −3.867 | 1.00 | 34.07 | 8 |
| ATOM | 2926 | OE2 | GLU | B | 97 | 57.632 | −8.980 | −2.841 | 1.00 | 32.87 | 8 |
| ATOM | 2927 | N | ILE | B | 98 | 61.084 | −4.723 | −0.999 | 1.00 | 28.92 | 7 |
| ATOM | 2928 | CA | ILE | B | 98 | 60.582 | −3.564 | −0.235 | 1.00 | 28.98 | 6 |
| ATOM | 2929 | C | ILE | B | 98 | 60.727 | −2.241 | −0.955 | 1.00 | 30.40 | 6 |
| ATOM | 2930 | O | ILE | B | 98 | 59.849 | −1.353 | −0.964 | 1.00 | 25.83 | 8 |
| ATOM | 2931 | CB | ILE | B | 98 | 61.320 | −3.544 | 1.123 | 1.00 | 26.40 | 6 |
| ATOM | 2932 | CG1 | ILE | B | 98 | 60.992 | −4.753 | 1.985 | 1.00 | 30.78 | 6 |
| ATOM | 2933 | CG2 | ILE | B | 98 | 60.988 | −2.241 | 1.865 | 1.00 | 26.02 | 6 |
| ATOM | 2934 | CD1 | ILE | B | 98 | 59.551 | −5.137 | 2.182 | 1.00 | 30.67 | 6 |
| ATOM | 2935 | N | TYR | B | 99 | 61.889 | −2.036 | −1.638 | 1.00 | 31.00 | 7 |
| ATOM | 2936 | CA | TYR | B | 99 | 62.170 | −0.808 | −2.356 | 1.00 | 32.52 | 6 |
| ATOM | 2937 | C | TYR | B | 99 | 62.505 | −1.034 | −3.812 | 1.00 | 34.54 | 6 |
| ATOM | 2938 | O | TYR | B | 99 | 63.655 | −0.817 | −4.255 | 1.00 | 35.45 | 8 |
| ATOM | 2939 | CB | TYR | B | 99 | 63.366 | −0.108 | −1.661 | 1.00 | 31.16 | 6 |
| ATOM | 2940 | CG | TYR | B | 99 | 63.179 | 0.250 | −0.213 | 1.00 | 28.25 | 6 |
| ATOM | 2941 | CD1 | TYR | B | 99 | 63.952 | −0.243 | 0.825 | 1.00 | 28.01 | 6 |
| ATOM | 2942 | CD2 | TYR | B | 99 | 62.202 | 1.193 | 0.117 | 1.00 | 28.98 | 6 |
| ATOM | 2943 | CE1 | TYR | B | 99 | 63.754 | 0.159 | 2.135 | 1.00 | 27.92 | 6 |
| ATOM | 2944 | CE2 | TYR | B | 99 | 62.006 | 1.609 | 1.427 | 1.00 | 28.86 | 6 |
| ATOM | 2945 | CZ | TYR | B | 99 | 62.774 | 1.073 | 2.446 | 1.00 | 27.90 | 6 |
| ATOM | 2946 | OH | TYR | B | 99 | 62.576 | 1.499 | 3.756 | 1.00 | 27.84 | 8 |
| ATOM | 2947 | N | PRO | B | 100 | 61.555 | −1.416 | −4.630 | 1.00 | 35.55 | 7 |
| ATOM | 2948 | CA | PRO | B | 100 | 61.774 | −1.742 | −6.033 | 1.00 | 37.21 | 6 |
| ATOM | 2949 | C | PRO | B | 100 | 62.327 | −0.598 | −6.843 | 1.00 | 38.72 | 6 |
| ATOM | 2950 | O | PRO | B | 100 | 63.107 | −0.784 | −7.787 | 1.00 | 39.39 | 8 |
| ATOM | 2951 | CB | PRO | B | 100 | 60.417 | −2.189 | −6.566 | 1.00 | 37.99 | 6 |
| ATOM | 2952 | CG | PRO | B | 100 | 59.412 | −1.828 | −5.543 | 1.00 | 35.50 | 6 |
| ATOM | 2953 | CD | PRO | B | 100 | 60.151 | −1.710 | −4.256 | 1.00 | 35.06 | 6 |
| ATOM | 2954 | N | ASN | B | 101 | 61.921 | 0.620 | −6.487 | 1.00 | 38.14 | 7 |
| ATOM | 2955 | CA | ASN | B | 101 | 62.391 | 1.803 | −7.192 | 1.00 | 38.05 | 6 |
| ATOM | 2956 | C | ASN | B | 101 | 63.459 | 2.537 | −6.385 | 1.00 | 36.99 | 6 |
| ATOM | 2957 | O | ASN | B | 101 | 63.676 | 3.726 | −6.653 | 1.00 | 39.29 | 8 |
| ATOM | 2958 | CB | ASN | B | 101 | 61.202 | 2.723 | −7.451 | 1.00 | 39.89 | 6 |
| ATOM | 2959 | CG | ASN | B | 101 | 60.007 | 1.987 | −8.013 | 1.00 | 41.77 | 6 |
| ATOM | 2960 | OD1 | ASN | B | 101 | 58.930 | 1.884 | −7.425 | 1.00 | 42.16 | 8 |
| ATOM | 2961 | ND2 | ASN | B | 101 | 60.229 | 1.436 | −9.197 | 1.00 | 42.54 | 7 |
| ATOM | 2962 | N | GLY | B | 102 | 64.028 | 1.920 | −5.376 | 1.00 | 34.24 | 7 |
| ATOM | 2963 | CA | GLY | B | 102 | 64.956 | 2.603 | −4.480 | 1.00 | 33.96 | 6 |
| ATOM | 2964 | C | GLY | B | 102 | 64.329 | 3.353 | −3.324 | 1.00 | 34.73 | 6 |
| ATOM | 2965 | O | GLY | B | 102 | 63.091 | 3.507 | −3.190 | 1.00 | 33.28 | 8 |
| ATOM | 2966 | N | THR | B | 103 | 65.153 | 3.914 | −2.430 | 1.00 | 32.52 | 7 |
| ATOM | 2967 | CA | THR | B | 103 | 64.591 | 4.613 | −1.279 | 1.00 | 32.04 | 6 |
| ATOM | 2968 | C | THR | B | 103 | 64.351 | 6.098 | −1.472 | 1.00 | 33.64 | 6 |
| ATOM | 2969 | O | THR | B | 103 | 63.426 | 6.615 | −0.800 | 1.00 | 32.63 | 8 |
| ATOM | 2970 | CB | THR | B | 103 | 65.544 | 4.405 | −0.100 | 1.00 | 34.27 | 6 |
| ATOM | 2971 | OG1 | THR | B | 103 | 66.808 | 4.981 | −0.489 | 1.00 | 34.81 | 8 |
| ATOM | 2972 | CG2 | THR | B | 103 | 65.762 | 2.948 | 0.225 | 1.00 | 34.11 | 6 |
| ATOM | 2973 | N | GLU | B | 104 | 65.063 | 6.775 | −2.375 | 1.00 | 31.00 | 7 |
| ATOM | 2974 | CA | GLU | B | 104 | 64.919 | 8.220 | −2.452 | 1.00 | 34.38 | 6 |
| ATOM | 2975 | C | GLU | B | 104 | 63.553 | 8.693 | −2.915 | 1.00 | 35.05 | 6 |
| ATOM | 2976 | O | GLU | B | 104 | 63.205 | 9.837 | −2.567 | 1.00 | 36.53 | 8 |
| ATOM | 2977 | CB | GLU | B | 104 | 66.012 | 8.810 | −3.394 | 1.00 | 37.66 | 6 |
| ATOM | 2978 | N | THR | B | 105 | 62.883 | 7.955 | −3.798 | 1.00 | 32.50 | 7 |
| ATOM | 2979 | CA | THR | B | 105 | 61.572 | 8.395 | −4.264 | 1.00 | 33.06 | 6 |
| ATOM | 2980 | C | THR | B | 105 | 60.409 | 7.607 | −3.633 | 1.00 | 30.67 | 6 |
| ATOM | 2981 | O | THR | B | 105 | 59.255 | 7.825 | −4.025 | 1.00 | 30.32 | 8 |
| ATOM | 2982 | CB | THR | B | 105 | 61.469 | 8.256 | −5.780 | 1.00 | 34.96 | 6 |

TABLE 1-continued

| ATOM | 2983 | OG1 | THR | B | 105 | 61.702 | 6.883 | -6.107 | 1.00 | 35.88 | 8 |
|---|---|---|---|---|---|---|---|---|---|---|---|
| ATOM | 2984 | CG2 | THR | B | 105 | 62.498 | 9.147 | -6.493 | 1.00 | 37.41 | 6 |
| ATOM | 2985 | N | HIS | B | 106 | 60.705 | 6.829 | -2.610 | 1.00 | 28.38 | 7 |
| ATOM | 2986 | CA | HIS | B | 106 | 59.686 | 6.055 | -1.897 | 1.00 | 26.95 | 6 |
| ATOM | 2987 | C | HIS | B | 106 | 58.943 | 6.945 | -0.916 | 1.00 | 27.21 | 6 |
| ATOM | 2988 | O | HIS | B | 106 | 59.558 | 7.820 | -0.286 | 1.00 | 25.40 | 8 |
| ATOM | 2989 | CB | HIS | B | 106 | 60.299 | 4.906 | -1.129 | 1.00 | 26.76 | 6 |
| ATOM | 2990 | CG | HIS | B | 106 | 59.397 | 3.804 | -0.619 | 1.00 | 26.50 | 6 |
| ATOM | 2991 | ND1 | HIS | B | 106 | 58.822 | 3.908 | 0.632 | 1.00 | 26.30 | 7 |
| ATOM | 2992 | CD2 | HIS | B | 106 | 59.017 | 2.642 | -1.214 | 1.00 | 26.99 | 6 |
| ATOM | 2993 | CE1 | HIS | B | 106 | 58.139 | 2.730 | 0.807 | 1.00 | 26.31 | 6 |
| ATOM | 2994 | NE2 | HIS | B | 106 | 58.209 | 1.992 | -0.276 | 1.00 | 27.12 | 7 |
| ATOM | 2995 | N | THR | B | 107 | 57.621 | 6.749 | -0.815 | 1.00 | 24.60 | 7 |
| ATOM | 2996 | CA | THR | B | 107 | 56.852 | 7.517 | 0.177 | 1.00 | 22.48 | 6 |
| ATOM | 2997 | C | THR | B | 107 | 57.510 | 7.428 | 1.528 | 1.00 | 23.26 | 6 |
| ATOM | 2998 | O | THR | B | 107 | 58.100 | 6.378 | 1.812 | 1.00 | 24.71 | 8 |
| ATOM | 2999 | CB | THR | B | 107 | 55.425 | 6.933 | 0.229 | 1.00 | 22.11 | 6 |
| ATOM | 3000 | OG1 | THR | B | 107 | 54.846 | 7.149 | -1.052 | 1.00 | 21.94 | 8 |
| ATOM | 3001 | CG2 | THR | B | 107 | 54.603 | 7.713 | 1.242 | 1.00 | 24.08 | 6 |
| ATOM | 3002 | N | TYR | B | 108 | 57.441 | 8.470 | 2.356 | 1.00 | 21.20 | 7 |
| ATOM | 3003 | CA | TYR | B | 108 | 58.037 | 8.298 | 3.677 | 1.00 | 22.80 | 6 |
| ATOM | 3004 | C | TYR | B | 108 | 57.170 | 8.870 | 4.799 | 1.00 | 23.19 | 6 |
| ATOM | 3005 | O | TYR | B | 108 | 56.257 | 9.711 | 4.564 | 1.00 | 20.67 | 8 |
| ATOM | 3006 | CB | TYR | B | 108 | 59.500 | 8.861 | 3.752 | 1.00 | 26.29 | 6 |
| ATOM | 3007 | CG | TYR | B | 108 | 59.581 | 10.367 | 3.586 | 1.00 | 27.43 | 6 |
| ATOM | 3008 | CD1 | TYR | B | 108 | 59.350 | 11.243 | 4.641 | 1.00 | 30.64 | 6 |
| ATOM | 3009 | CD2 | TYR | B | 108 | 59.795 | 10.914 | 2.331 | 1.00 | 31.95 | 6 |
| ATOM | 3010 | CE1 | TYR | B | 108 | 59.352 | 12.617 | 4.478 | 1.00 | 31.91 | 6 |
| ATOM | 3011 | CE2 | TYR | B | 108 | 59.821 | 12.272 | 2.159 | 1.00 | 34.14 | 6 |
| ATOM | 3012 | CZ | TYR | B | 108 | 59.609 | 13.130 | 3.235 | 1.00 | 34.42 | 6 |
| ATOM | 3013 | OH | TYR | B | 108 | 59.634 | 14.497 | 3.014 | 1.00 | 36.77 | 8 |
| ATOM | 3014 | N | VAL | B | 109 | 57.454 | 8.419 | 6.031 | 1.00 | 21.49 | 7 |
| ATOM | 3015 | CA | VAL | B | 109 | 56.734 | 8.809 | 7.224 | 1.00 | 21.55 | 6 |
| ATOM | 3016 | C | VAL | B | 109 | 57.707 | 9.552 | 8.149 | 1.00 | 23.45 | 6 |
| ATOM | 3017 | O | VAL | B | 109 | 58.712 | 8.918 | 8.447 | 1.00 | 22.21 | 8 |
| ATOM | 3018 | CB | VAL | B | 109 | 56.125 | 7.624 | 8.009 | 1.00 | 20.74 | 6 |
| ATOM | 3019 | CG1 | VAL | B | 109 | 55.351 | 8.074 | 9.216 | 1.00 | 22.40 | 6 |
| ATOM | 3020 | CG2 | VAL | B | 109 | 55.248 | 6.829 | 7.006 | 1.00 | 21.59 | 6 |
| ATOM | 3021 | N | ASP | B | 110 | 57.376 | 10.750 | 8.596 | 1.00 | 22.01 | 7 |
| ATOM | 3022 | CA | ASP | B | 110 | 58.343 | 11.465 | 9.478 | 1.00 | 24.43 | 6 |
| ATOM | 3023 | C | ASP | B | 110 | 57.632 | 11.952 | 10.711 | 1.00 | 23.59 | 6 |
| ATOM | 3024 | O | ASP | B | 110 | 56.504 | 12.458 | 10.672 | 1.00 | 21.44 | 8 |
| ATOM | 3025 | CB | ASP | B | 110 | 58.991 | 12.648 | 8.759 | 1.00 | 27.76 | 6 |
| ATOM | 3026 | CG | ASP | B | 110 | 60.461 | 12.751 | 9.239 | 1.00 | 36.19 | 6 |
| ATOM | 3027 | OD1 | ASP | B | 110 | 61.056 | 12.013 | 10.077 | 1.00 | 37.59 | 8 |
| ATOM | 3028 | OD2 | ASP | B | 110 | 61.173 | 13.585 | 8.645 | 1.00 | 39.38 | 8 |
| ATOM | 3029 | N | VAL | B | 111 | 58.257 | 11.795 | 11.892 | 1.00 | 23.56 | 7 |
| ATOM | 3030 | CA | VAL | B | 111 | 57.669 | 12.175 | 13.148 | 1.00 | 22.23 | 6 |
| ATOM | 3031 | C | VAL | B | 111 | 58.397 | 13.444 | 13.636 | 1.00 | 26.13 | 6 |
| ATOM | 3032 | O | VAL | B | 111 | 59.555 | 13.322 | 13.987 | 1.00 | 27.27 | 8 |
| ATOM | 3033 | CB | VAL | B | 111 | 57.822 | 11.100 | 14.216 | 1.00 | 23.73 | 6 |
| ATOM | 3034 | CG1 | VAL | B | 111 | 57.213 | 11.440 | 15.574 | 1.00 | 23.64 | 6 |
| ATOM | 3035 | CG2 | VAL | B | 111 | 57.143 | 9.759 | 13.858 | 1.00 | 24.27 | 6 |
| ATOM | 3036 | N | PRO | B | 112 | 57.801 | 14.619 | 13.564 | 1.00 | 24.70 | 7 |
| ATOM | 3037 | CA | PRO | B | 112 | 58.542 | 15.820 | 13.939 | 1.00 | 24.12 | 6 |
| ATOM | 3038 | C | PRO | B | 112 | 59.048 | 15.823 | 15.355 | 1.00 | 25.44 | 6 |
| ATOM | 3039 | O | PRO | B | 112 | 58.457 | 15.302 | 16.281 | 1.00 | 25.94 | 8 |
| ATOM | 3040 | CB | PRO | B | 112 | 57.517 | 16.950 | 13.719 | 1.00 | 26.49 | 6 |
| ATOM | 3041 | CG | PRO | B | 112 | 56.471 | 16.411 | 12.776 | 1.00 | 25.85 | 6 |
| ATOM | 3042 | CD | PRO | B | 112 | 56.449 | 14.912 | 13.005 | 1.00 | 25.31 | 6 |
| ATOM | 3043 | N | GLY | B | 113 | 60.180 | 16.517 | 15.580 | 1.00 | 27.49 | 7 |
| ATOM | 3044 | CA | GLY | B | 113 | 60.648 | 16.709 | 16.978 | 1.00 | 27.16 | 6 |
| ATOM | 3045 | C | GLY | B | 113 | 61.466 | 15.490 | 17.404 | 1.00 | 29.14 | 6 |
| ATOM | 3046 | O | GLY | B | 113 | 62.690 | 15.588 | 17.383 | 1.00 | 29.51 | 8 |
| ATOM | 3047 | N | LEU | B | 114 | 60.785 | 14.355 | 17.638 | 1.00 | 27.78 | 7 |
| ATOM | 3048 | CA | LEU | B | 114 | 61.512 | 13.141 | 18.019 | 1.00 | 28.34 | 6 |
| ATOM | 3049 | C | LEU | B | 114 | 62.545 | 12.685 | 17.019 | 1.00 | 29.38 | 6 |
| ATOM | 3050 | O | LEU | B | 114 | 63.611 | 12.122 | 17.362 | 1.00 | 28.08 | 8 |
| ATOM | 3051 | CB | LEU | B | 114 | 60.493 | 12.006 | 18.279 | 1.00 | 26.74 | 6 |
| ATOM | 3052 | CG | LEU | B | 114 | 59.539 | 12.250 | 19.424 | 1.00 | 28.28 | 6 |
| ATOM | 3053 | CD1 | LEU | B | 114 | 58.565 | 11.088 | 19.594 | 1.00 | 26.02 | 6 |
| ATOM | 3054 | CD2 | LEU | B | 114 | 60.295 | 12.476 | 20.742 | 1.00 | 28.90 | 6 |
| ATOM | 3055 | N | SER | B | 115 | 62.355 | 12.921 | 15.738 | 1.00 | 28.55 | 7 |
| ATOM | 3056 | CA | SER | B | 115 | 63.262 | 12.446 | 14.710 | 1.00 | 28.22 | 6 |
| ATOM | 3057 | C | SER | B | 115 | 64.540 | 13.284 | 14.611 | 1.00 | 30.73 | 6 |
| ATOM | 3058 | O | SER | B | 115 | 65.515 | 12.778 | 14.048 | 1.00 | 29.82 | 8 |
| ATOM | 3059 | CB | SER | B | 115 | 62.556 | 12.433 | 13.359 | 1.00 | 28.87 | 6 |
| ATOM | 3060 | OG | SER | B | 115 | 62.188 | 13.728 | 12.878 | 1.00 | 31.15 | 8 |
| ATOM | 3061 | N | THR | B | 116 | 64.480 | 14.501 | 15.168 | 1.00 | 30.45 | 7 |

TABLE 1-continued

| ATOM | 3062 | CA | THR | B | 116 | 65.625 | 15.383 | 14.934 | 1.00 | 32.38 | 6 |
|---|---|---|---|---|---|---|---|---|---|---|---|
| ATOM | 3063 | C | THR | B | 116 | 66.349 | 15.755 | 16.226 | 1.00 | 34.29 | 6 |
| ATOM | 3064 | O | THR | B | 116 | 67.346 | 16.447 | 16.085 | 1.00 | 38.91 | 8 |
| ATOM | 3065 | CB | THR | B | 116 | 65.213 | 16.700 | 14.232 | 1.00 | 32.70 | 6 |
| ATOM | 3066 | OG1 | THR | B | 116 | 64.062 | 17.200 | 14.921 | 1.00 | 32.18 | 8 |
| ATOM | 3067 | CG2 | THR | B | 116 | 64.868 | 16.509 | 12.776 | 1.00 | 33.85 | 6 |
| ATOM | 3068 | N | MET | B | 117 | 65.882 | 15.315 | 17.364 | 1.00 | 34.18 | 7 |
| ATOM | 3069 | CA | MET | B | 117 | 66.556 | 15.577 | 18.625 | 1.00 | 35.31 | 6 |
| ATOM | 3070 | C | MET | B | 117 | 67.520 | 14.454 | 18.990 | 1.00 | 37.27 | 6 |
| ATOM | 3071 | O | MET | B | 117 | 67.419 | 13.329 | 18.506 | 1.00 | 35.45 | 8 |
| ATOM | 3072 | CB | MET | B | 117 | 65.555 | 15.716 | 19.758 | 1.00 | 36.44 | 6 |
| ATOM | 3073 | CG | MET | B | 117 | 64.825 | 14.432 | 20.149 | 1.00 | 34.64 | 6 |
| ATOM | 3074 | SD | MET | B | 117 | 63.385 | 14.720 | 21.138 | 1.00 | 35.68 | 16 |
| ATOM | 3075 | CE | MET | B | 117 | 64.113 | 15.441 | 22.628 | 1.00 | 35.24 | 6 |
| ATOM | 3076 | N | LEU | B | 118 | 68.432 | 14.767 | 19.943 | 1.00 | 36.08 | 7 |
| ATOM | 3077 | CA | LEU | B | 118 | 69.384 | 13.776 | 20.444 | 1.00 | 35.32 | 6 |
| ATOM | 3078 | C | LEU | B | 118 | 70.141 | 13.060 | 19.370 | 1.00 | 36.49 | 6 |
| ATOM | 3079 | O | LEU | B | 118 | 70.769 | 13.672 | 18.490 | 1.00 | 38.03 | 8 |
| ATOM | 3080 | CB | LEU | B | 118 | 68.602 | 12.780 | 21.326 | 1.00 | 34.52 | 6 |
| ATOM | 3081 | CG | LEU | B | 118 | 67.955 | 13.401 | 22.550 | 1.00 | 34.53 | 6 |
| ATOM | 3082 | CD1 | LEU | B | 118 | 67.125 | 12.422 | 23.336 | 1.00 | 33.90 | 6 |
| ATOM | 3083 | CD2 | LEU | B | 118 | 69.054 | 13.987 | 23.492 | 1.00 | 36.09 | 6 |
| ATOM | 3084 | N | GLU | B | 119 | 70.061 | 11.719 | 19.302 | 1.00 | 39.19 | 7 |
| ATOM | 3085 | CA | GLU | B | 119 | 70.748 | 10.969 | 18.252 | 1.00 | 39.90 | 6 |
| ATOM | 3086 | C | GLU | B | 119 | 70.345 | 11.391 | 16.861 | 1.00 | 39.96 | 6 |
| ATOM | 3087 | O | GLU | B | 119 | 71.144 | 11.319 | 15.930 | 1.00 | 39.74 | 8 |
| ATOM | 3088 | CB | GLU | B | 119 | 70.439 | 9.477 | 18.447 | 1.00 | 42.37 | 6 |
| ATOM | 3089 | CG | GLU | B | 119 | 71.094 | 8.560 | 17.433 | 1.00 | 46.28 | 6 |
| ATOM | 3090 | CD | GLU | B | 119 | 70.981 | 7.080 | 17.777 | 1.00 | 47.62 | 6 |
| ATOM | 3091 | OE1 | GLU | B | 119 | 70.337 | 6.733 | 18.805 | 1.00 | 48.65 | 8 |
| ATOM | 3092 | OE2 | GLU | B | 119 | 71.561 | 6.302 | 16.970 | 1.00 | 49.17 | 8 |
| ATOM | 3093 | N | GLY | B | 120 | 69.102 | 11.892 | 16.668 | 1.00 | 38.75 | 7 |
| ATOM | 3094 | CA | GLY | B | 120 | 68.668 | 12.258 | 15.318 | 1.00 | 39.65 | 6 |
| ATOM | 3095 | C | GLY | B | 120 | 69.318 | 13.524 | 14.807 | 1.00 | 41.25 | 6 |
| ATOM | 3096 | O | GLY | B | 120 | 69.425 | 13.755 | 13.602 | 1.00 | 39.83 | 8 |
| ATOM | 3097 | N | ALA | B | 121 | 69.785 | 14.354 | 15.771 | 1.00 | 42.58 | 7 |
| ATOM | 3098 | CA | ALA | B | 121 | 70.410 | 15.623 | 15.404 | 1.00 | 44.15 | 6 |
| ATOM | 3099 | C | ALA | B | 121 | 71.647 | 15.421 | 14.552 | 1.00 | 44.51 | 6 |
| ATOM | 3100 | O | ALA | B | 121 | 71.836 | 16.162 | 13.587 | 1.00 | 46.30 | 8 |
| ATOM | 3101 | CB | ALA | B | 121 | 70.755 | 16.396 | 16.671 | 1.00 | 44.12 | 6 |
| ATOM | 3102 | N | SER | B | 122 | 72.464 | 14.428 | 14.839 | 1.00 | 46.51 | 7 |
| ATOM | 3103 | CA | SER | B | 122 | 73.663 | 14.179 | 14.040 | 1.00 | 48.95 | 6 |
| ATOM | 3104 | C | SER | B | 122 | 73.442 | 13.166 | 12.932 | 1.00 | 49.98 | 6 |
| ATOM | 3105 | O | SER | B | 122 | 74.351 | 12.912 | 12.125 | 1.00 | 49.74 | 8 |
| ATOM | 3106 | CB | SER | B | 122 | 74.790 | 13.675 | 14.943 | 1.00 | 49.52 | 6 |
| ATOM | 3107 | OG | SER | B | 122 | 74.248 | 12.758 | 15.879 | 1.00 | 51.88 | 8 |
| ATOM | 3108 | N | ARG | B | 123 | 72.222 | 12.591 | 12.854 | 1.00 | 48.32 | 7 |
| ATOM | 3109 | CA | ARG | B | 123 | 71.947 | 11.586 | 11.826 | 1.00 | 46.67 | 6 |
| ATOM | 3110 | C | ARG | B | 123 | 70.694 | 11.919 | 11.018 | 1.00 | 46.85 | 6 |
| ATOM | 3111 | O | ARG | B | 123 | 69.644 | 11.274 | 11.155 | 1.00 | 45.46 | 8 |
| ATOM | 3112 | CB | ARG | B | 123 | 71.789 | 10.202 | 12.467 | 1.00 | 46.37 | 6 |
| ATOM | 3113 | CG | ARG | B | 123 | 72.838 | 9.776 | 13.470 | 1.00 | 46.42 | 6 |
| ATOM | 3114 | CD | ARG | B | 123 | 72.773 | 8.316 | 13.871 | 1.00 | 46.50 | 6 |
| ATOM | 3115 | NE | ARG | B | 123 | 72.926 | 7.465 | 12.686 | 1.00 | 47.12 | 7 |
| ATOM | 3116 | CZ | ARG | B | 123 | 72.709 | 6.151 | 12.722 | 1.00 | 48.23 | 6 |
| ATOM | 3117 | NH1 | ARG | B | 123 | 72.343 | 5.594 | 13.870 | 1.00 | 48.08 | 7 |
| ATOM | 3118 | NH2 | ARG | B | 123 | 72.847 | 5.460 | 11.600 | 1.00 | 48.83 | 7 |
| ATOM | 3119 | N | PRO | B | 124 | 70.814 | 12.888 | 10.125 | 1.00 | 46.75 | 7 |
| ATOM | 3120 | CA | PRO | B | 124 | 69.724 | 13.307 | 9.272 | 1.00 | 45.09 | 6 |
| ATOM | 3121 | C | PRO | B | 124 | 69.159 | 12.130 | 8.501 | 1.00 | 43.72 | 6 |
| ATOM | 3122 | O | PRO | B | 124 | 69.907 | 11.332 | 7.919 | 1.00 | 42.42 | 8 |
| ATOM | 3123 | CB | PRO | B | 124 | 70.287 | 14.368 | 8.344 | 1.00 | 46.93 | 6 |
| ATOM | 3124 | CG | PRO | B | 124 | 71.771 | 14.278 | 8.490 | 1.00 | 47.37 | 6 |
| ATOM | 3125 | CD | PRO | B | 124 | 72.023 | 13.715 | 9.861 | 1.00 | 46.92 | 6 |
| ATOM | 3126 | N | GLY | B | 125 | 67.828 | 12.007 | 8.537 | 1.00 | 41.20 | 7 |
| ATOM | 3127 | CA | GLY | B | 125 | 67.230 | 10.900 | 7.774 | 1.00 | 39.29 | 6 |
| ATOM | 3128 | C | GLY | B | 125 | 67.135 | 9.577 | 8.510 | 1.00 | 37.20 | 6 |
| ATOM | 3129 | O | GLY | B | 125 | 66.420 | 8.699 | 7.989 | 1.00 | 36.11 | 8 |
| ATOM | 3130 | N | HIS | B | 126 | 67.837 | 9.368 | 9.601 | 1.00 | 34.73 | 7 |
| ATOM | 3131 | CA | HIS | B | 126 | 67.849 | 8.102 | 10.308 | 1.00 | 33.50 | 6 |
| ATOM | 3132 | C | HIS | B | 126 | 66.493 | 7.708 | 10.877 | 1.00 | 32.20 | 6 |
| ATOM | 3133 | O | HIS | B | 126 | 65.982 | 6.611 | 10.531 | 1.00 | 31.89 | 8 |
| ATOM | 3134 | CB | HIS | B | 126 | 68.894 | 8.136 | 11.442 | 1.00 | 32.39 | 6 |
| ATOM | 3135 | CG | HIS | B | 126 | 68.767 | 6.907 | 12.285 | 1.00 | 30.02 | 6 |
| ATOM | 3136 | ND1 | HIS | B | 126 | 69.142 | 5.669 | 11.764 | 1.00 | 32.16 | 7 |
| ATOM | 3137 | CD2 | HIS | B | 126 | 68.315 | 6.679 | 13.524 | 1.00 | 28.99 | 6 |
| ATOM | 3138 | CE1 | HIS | B | 126 | 68.928 | 4.739 | 12.670 | 1.00 | 30.29 | 6 |
| ATOM | 3139 | NE2 | HIS | B | 126 | 68.411 | 5.323 | 13.726 | 1.00 | 31.28 | 7 |
| ATOM | 3140 | N | PHE | B | 127 | 65.874 | 8.567 | 11.680 | 1.00 | 28.23 | 7 |

TABLE 1-continued

| | | | | | | | | | | |
|---|---|---|---|---|---|---|---|---|---|---|
| ATOM | 3141 | CA | PHE | B | 127 | 64.599 | 8.199 | 12.287 | 1.00 | 27.72 | 6 |
| ATOM | 3142 | C | PHE | B | 127 | 63.495 | 8.234 | 11.213 | 1.00 | 26.35 | 6 |
| ATOM | 3143 | O | PHE | B | 127 | 62.599 | 7.393 | 11.386 | 1.00 | 26.75 | 8 |
| ATOM | 3144 | CB | PHE | B | 127 | 64.268 | 9.034 | 13.528 | 1.00 | 27.25 | 6 |
| ATOM | 3145 | CG | PHE | B | 127 | 65.109 | 8.550 | 14.698 | 1.00 | 28.04 | 6 |
| ATOM | 3146 | CD1 | PHE | B | 127 | 66.034 | 9.472 | 15.239 | 1.00 | 27.72 | 6 |
| ATOM | 3147 | CD2 | PHE | B | 127 | 65.127 | 7.278 | 15.203 | 1.00 | 26.78 | 6 |
| ATOM | 3148 | CE1 | PHE | B | 127 | 66.838 | 9.035 | 16.291 | 1.00 | 26.75 | 6 |
| ATOM | 3149 | CE2 | PHE | B | 127 | 65.919 | 6.858 | 16.231 | 1.00 | 29.31 | 6 |
| ATOM | 3150 | CZ | PHE | B | 127 | 66.844 | 7.755 | 16.771 | 1.00 | 26.94 | 6 |
| ATOM | 3151 | N | ARG | B | 128 | 63.652 | 9.015 | 10.140 | 1.00 | 26.25 | 7 |
| ATOM | 3152 | CA | ARG | B | 128 | 62.665 | 8.940 | 9.054 | 1.00 | 26.31 | 6 |
| ATOM | 3153 | C | ARG | B | 128 | 62.641 | 7.529 | 8.474 | 1.00 | 27.01 | 6 |
| ATOM | 3154 | O | ARG | B | 128 | 61.607 | 6.896 | 8.176 | 1.00 | 27.70 | 8 |
| ATOM | 3155 | CB | ARG | B | 128 | 62.995 | 9.950 | 7.986 | 1.00 | 29.81 | 6 |
| ATOM | 3156 | CG | ARG | B | 128 | 62.174 | 9.865 | 6.694 | 1.00 | 28.97 | 6 |
| ATOM | 3157 | CD | ARG | B | 128 | 62.614 | 10.959 | 5.713 | 1.00 | 31.50 | 6 |
| ATOM | 3158 | NE | ARG | B | 128 | 62.199 | 12.249 | 6.307 | 1.00 | 36.12 | 7 |
| ATOM | 3159 | CZ | ARG | B | 128 | 62.359 | 13.422 | 5.685 | 1.00 | 36.94 | 6 |
| ATOM | 3160 | NH1 | ARG | B | 128 | 62.917 | 13.437 | 4.474 | 1.00 | 36.92 | 7 |
| ATOM | 3161 | NH2 | ARG | B | 128 | 61.956 | 14.553 | 6.237 | 1.00 | 36.80 | 7 |
| ATOM | 3162 | N | GLY | B | 129 | 63.823 | 6.942 | 8.316 | 1.00 | 25.53 | 7 |
| ATOM | 3163 | CA | GLY | B | 129 | 63.959 | 5.579 | 7.803 | 1.00 | 25.39 | 6 |
| ATOM | 3164 | C | GLY | B | 129 | 63.296 | 4.587 | 8.744 | 1.00 | 24.86 | 6 |
| ATOM | 3165 | O | GLY | B | 129 | 62.618 | 3.654 | 8.238 | 1.00 | 24.05 | 8 |
| ATOM | 3166 | N | VAL | B | 130 | 63.374 | 4.723 | 10.054 | 1.00 | 23.36 | 7 |
| ATOM | 3167 | CA | VAL | B | 130 | 62.752 | 3.848 | 11.024 | 1.00 | 22.23 | 6 |
| ATOM | 3168 | C | VAL | B | 130 | 61.208 | 3.977 | 10.944 | 1.00 | 23.73 | 6 |
| ATOM | 3169 | O | VAL | B | 130 | 60.528 | 2.931 | 10.910 | 1.00 | 21.98 | 8 |
| ATOM | 3170 | CB | VAL | B | 130 | 63.156 | 4.153 | 12.443 | 1.00 | 24.21 | 6 |
| ATOM | 3171 | CG1 | VAL | B | 130 | 62.503 | 3.325 | 13.534 | 1.00 | 24.51 | 6 |
| ATOM | 3172 | CG2 | VAL | B | 130 | 64.713 | 3.953 | 12.537 | 1.00 | 24.12 | 6 |
| ATOM | 3173 | N | SER | B | 131 | 60.667 | 5.199 | 11.057 | 1.00 | 21.64 | 7 |
| ATOM | 3174 | CA | SER | B | 131 | 59.218 | 5.336 | 11.014 | 1.00 | 21.18 | 6 |
| ATOM | 3175 | C | SER | B | 131 | 58.706 | 4.864 | 9.647 | 1.00 | 21.42 | 6 |
| ATOM | 3176 | O | SER | B | 131 | 57.688 | 4.304 | 9.684 | 1.00 | 22.71 | 8 |
| ATOM | 3177 | CB | SER | B | 131 | 58.790 | 6.781 | 11.406 | 1.00 | 20.10 | 6 |
| ATOM | 3178 | OG | SER | B | 131 | 59.534 | 7.744 | 10.678 | 1.00 | 22.33 | 8 |
| ATOM | 3179 | N | THR | B | 132 | 59.376 | 5.073 | 8.538 | 1.00 | 21.18 | 7 |
| ATOM | 3180 | CA | THR | B | 132 | 58.883 | 4.600 | 7.250 | 1.00 | 22.97 | 6 |
| ATOM | 3181 | C | THR | B | 132 | 58.795 | 3.079 | 7.224 | 1.00 | 25.11 | 6 |
| ATOM | 3182 | O | THR | B | 132 | 57.728 | 2.514 | 6.885 | 1.00 | 19.95 | 8 |
| ATOM | 3183 | CB | THR | B | 132 | 59.742 | 5.139 | 6.108 | 1.00 | 23.70 | 6 |
| ATOM | 3184 | OG1 | THR | B | 132 | 59.721 | 6.590 | 6.182 | 1.00 | 21.14 | 8 |
| ATOM | 3185 | CG2 | THR | B | 132 | 59.214 | 4.628 | 4.749 | 1.00 | 21.10 | 6 |
| ATOM | 3186 | N | ILE | B | 133 | 59.876 | 2.374 | 7.590 | 1.00 | 23.47 | 7 |
| ATOM | 3187 | CA | ILE | B | 133 | 59.792 | 0.897 | 7.444 | 1.00 | 22.30 | 6 |
| ATOM | 3188 | C | ILE | B | 133 | 58.868 | 0.339 | 8.499 | 1.00 | 20.08 | 6 |
| ATOM | 3189 | O | ILE | B | 133 | 58.186 | −0.702 | 8.247 | 1.00 | 20.82 | 8 |
| ATOM | 3190 | CB | ILE | B | 133 | 61.163 | 0.202 | 7.503 | 1.00 | 22.40 | 6 |
| ATOM | 3191 | CG1 | ILE | B | 133 | 61.076 | −1.270 | 7.056 | 1.00 | 22.66 | 6 |
| ATOM | 3192 | CG2 | ILE | B | 133 | 61.699 | 0.252 | 8.924 | 1.00 | 22.72 | 6 |
| ATOM | 3193 | CD1 | ILE | B | 133 | 60.726 | −1.465 | 5.594 | 1.00 | 24.76 | 6 |
| ATOM | 3194 | N | VAL | B | 134 | 58.775 | 0.887 | 9.716 | 1.00 | 19.44 | 7 |
| ATOM | 3195 | CA | VAL | B | 134 | 57.874 | 0.272 | 10.678 | 1.00 | 19.92 | 6 |
| ATOM | 3196 | C | VAL | B | 134 | 56.425 | 0.507 | 10.228 | 1.00 | 19.95 | 6 |
| ATOM | 3197 | O | VAL | B | 134 | 55.596 | −0.408 | 10.340 | 1.00 | 18.76 | 8 |
| ATOM | 3198 | CB | VAL | B | 134 | 58.087 | 0.785 | 12.093 | 1.00 | 20.66 | 6 |
| ATOM | 3199 | CG1 | VAL | B | 134 | 57.101 | 0.289 | 13.127 | 1.00 | 21.02 | 6 |
| ATOM | 3200 | CG2 | VAL | B | 134 | 59.472 | 0.315 | 12.628 | 1.00 | 23.22 | 6 |
| ATOM | 3201 | N | SER | B | 135 | 56.098 | 1.693 | 9.701 | 1.00 | 21.84 | 7 |
| ATOM | 3202 | CA | SER | B | 135 | 54.738 | 1.882 | 9.197 | 1.00 | 21.43 | 6 |
| ATOM | 3203 | C | SER | B | 135 | 54.448 | 0.852 | 8.088 | 1.00 | 20.41 | 6 |
| ATOM | 3204 | O | SER | B | 135 | 53.335 | 0.320 | 8.054 | 1.00 | 19.83 | 8 |
| ATOM | 3205 | CB | SER | B | 135 | 54.490 | 3.262 | 8.563 | 1.00 | 25.05 | 6 |
| ATOM | 3206 | OG | SER | B | 135 | 54.496 | 4.192 | 9.637 | 1.00 | 30.48 | 8 |
| ATOM | 3207 | N | LYS | B | 136 | 55.430 | 0.706 | 7.189 | 1.00 | 18.76 | 7 |
| ATOM | 3208 | CA | LYS | B | 136 | 55.189 | −0.267 | 6.067 | 1.00 | 20.34 | 6 |
| ATOM | 3209 | C | LYS | B | 136 | 54.944 | −1.659 | 6.626 | 1.00 | 19.06 | 6 |
| ATOM | 3210 | O | LYS | B | 136 | 54.010 | −2.371 | 6.185 | 1.00 | 18.19 | 8 |
| ATOM | 3211 | CB | LYS | B | 136 | 56.351 | −0.243 | 5.052 | 1.00 | 20.12 | 6 |
| ATOM | 3212 | CG | LYS | B | 136 | 56.143 | −1.143 | 3.805 | 1.00 | 20.78 | 6 |
| ATOM | 3213 | CD | LYS | B | 136 | 57.014 | −0.638 | 2.664 | 1.00 | 22.99 | 6 |
| ATOM | 3214 | CE | LYS | B | 136 | 56.995 | −1.594 | 1.478 | 1.00 | 25.34 | 6 |
| ATOM | 3215 | NZ | LYS | B | 136 | 57.435 | −0.897 | 0.229 | 1.00 | 25.62 | 7 |
| ATOM | 3216 | N | LEU | B | 137 | 55.713 | −2.120 | 7.604 | 1.00 | 17.80 | 7 |
| ATOM | 3217 | CA | LEU | B | 137 | 55.582 | −3.427 | 8.237 | 1.00 | 19.98 | 6 |
| ATOM | 3218 | C | LEU | B | 137 | 54.275 | −3.552 | 8.976 | 1.00 | 19.20 | 6 |
| ATOM | 3219 | O | LEU | B | 137 | 53.616 | −4.573 | 8.857 | 1.00 | 18.56 | 8 |

TABLE 1-continued

| ATOM | 3220 | CB | LEU | B | 137 | 56.745 | −3.696 | 9.220 | 1.00 | 19.53 | 6 |
|---|---|---|---|---|---|---|---|---|---|---|---|
| ATOM | 3221 | CG | LEU | B | 137 | 58.074 | −4.009 | 8.556 | 1.00 | 22.60 | 6 |
| ATOM | 3222 | CD1 | LEU | B | 137 | 59.179 | −3.990 | 9.627 | 1.00 | 18.94 | 6 |
| ATOM | 3223 | CD2 | LEU | B | 137 | 58.043 | −5.360 | 7.886 | 1.00 | 20.42 | 6 |
| ATOM | 3224 | N | PHE | B | 138 | 53.777 | −2.469 | 9.583 | 1.00 | 16.81 | 7 |
| ATOM | 3225 | CA | PHE | B | 138 | 52.487 | −2.532 | 10.200 | 1.00 | 17.03 | 6 |
| ATOM | 3226 | C | PHE | B | 138 | 51.342 | −2.677 | 9.163 | 1.00 | 15.57 | 6 |
| ATOM | 3227 | O | PHE | B | 138 | 50.365 | −3.369 | 9.434 | 1.00 | 17.73 | 8 |
| ATOM | 3228 | CB | PHE | B | 138 | 52.183 | −1.237 | 10.974 | 1.00 | 17.43 | 6 |
| ATOM | 3229 | CG | PHE | B | 138 | 52.989 | −1.110 | 12.277 | 1.00 | 18.89 | 6 |
| ATOM | 3230 | CD1 | PHE | B | 138 | 52.929 | 0.069 | 12.997 | 1.00 | 18.99 | 6 |
| ATOM | 3231 | CD2 | PHE | B | 138 | 53.729 | −2.164 | 12.784 | 1.00 | 19.88 | 6 |
| ATOM | 3232 | CE1 | PHE | B | 138 | 53.604 | 0.229 | 14.200 | 1.00 | 18.80 | 6 |
| ATOM | 3233 | CE2 | PHE | B | 138 | 54.411 | −2.031 | 14.006 | 1.00 | 21.38 | 6 |
| ATOM | 3234 | CZ | PHE | B | 138 | 54.324 | −0.829 | 14.750 | 1.00 | 19.09 | 6 |
| ATOM | 3235 | N | ASN | B | 139 | 51.457 | −2.015 | 8.033 | 1.00 | 18.34 | 7 |
| ATOM | 3236 | CA | ASN | B | 139 | 50.419 | −2.157 | 7.032 | 1.00 | 17.77 | 6 |
| ATOM | 3237 | C | ASN | B | 139 | 50.464 | −3.511 | 6.357 | 1.00 | 18.27 | 6 |
| ATOM | 3238 | O | ASN | B | 139 | 49.403 | −4.059 | 5.975 | 1.00 | 20.66 | 8 |
| ATOM | 3239 | CB | ASN | B | 139 | 50.565 | −1.044 | 5.974 | 1.00 | 19.21 | 6 |
| ATOM | 3240 | CG | ASN | B | 139 | 50.220 | 0.335 | 6.571 | 1.00 | 23.72 | 6 |
| ATOM | 3241 | OD1 | ASN | B | 139 | 49.304 | 0.418 | 7.359 | 1.00 | 24.33 | 8 |
| ATOM | 3242 | ND2 | ASN | B | 139 | 50.901 | 1.344 | 6.090 | 1.00 | 25.57 | 7 |
| ATOM | 3243 | N | LEU | B | 140 | 51.670 | −4.126 | 6.251 | 1.00 | 17.43 | 7 |
| ATOM | 3244 | CA | LEU | B | 140 | 51.816 | −5.435 | 5.643 | 1.00 | 19.77 | 6 |
| ATOM | 3245 | C | LEU | B | 140 | 51.392 | −6.531 | 6.585 | 1.00 | 21.88 | 6 |
| ATOM | 3246 | O | LEU | B | 140 | 50.667 | −7.465 | 6.154 | 1.00 | 22.03 | 8 |
| ATOM | 3247 | CB | LEU | B | 140 | 53.291 | −5.684 | 5.198 | 1.00 | 18.61 | 6 |
| ATOM | 3248 | CG | LEU | B | 140 | 53.850 | −4.849 | 4.059 | 1.00 | 20.20 | 6 |
| ATOM | 3249 | CD1 | LEU | B | 140 | 55.377 | −5.000 | 3.978 | 1.00 | 21.39 | 6 |
| ATOM | 3250 | CD2 | LEU | B | 140 | 53.219 | −5.272 | 2.744 | 1.00 | 21.81 | 6 |
| ATOM | 3251 | N | VAL | B | 141 | 51.714 | −6.509 | 7.876 | 1.00 | 19.81 | 7 |
| ATOM | 3252 | CA | VAL | B | 141 | 51.423 | −7.589 | 8.813 | 1.00 | 19.15 | 6 |
| ATOM | 3253 | C | VAL | B | 141 | 50.129 | −7.384 | 9.575 | 1.00 | 18.23 | 6 |
| ATOM | 3254 | O | VAL | B | 141 | 49.508 | −8.383 | 9.942 | 1.00 | 20.17 | 8 |
| ATOM | 3255 | CB | VAL | B | 141 | 52.613 | −7.729 | 9.811 | 1.00 | 18.50 | 6 |
| ATOM | 3256 | CG1 | VAL | B | 141 | 52.402 | −8.790 | 10.886 | 1.00 | 19.99 | 6 |
| ATOM | 3257 | CG2 | VAL | B | 141 | 53.895 | −8.020 | 9.003 | 1.00 | 21.20 | 6 |
| ATOM | 3258 | N | GLN | B | 142 | 49.697 | −6.125 | 9.766 | 1.00 | 19.03 | 7 |
| ATOM | 3259 | CA | GLN | B | 142 | 48.456 | −5.803 | 10.496 | 1.00 | 18.67 | 6 |
| ATOM | 3260 | C | GLN | B | 142 | 48.367 | −6.472 | 11.813 | 1.00 | 18.44 | 6 |
| ATOM | 3261 | O | GLN | B | 142 | 47.434 | −7.193 | 12.153 | 1.00 | 18.66 | 8 |
| ATOM | 3262 | CB | GLN | B | 142 | 47.254 | −6.242 | 9.585 | 1.00 | 23.65 | 6 |
| ATOM | 3263 | CG | GLN | B | 142 | 47.341 | −5.370 | 8.311 | 1.00 | 27.77 | 6 |
| ATOM | 3264 | CD | GLN | B | 142 | 46.179 | −5.714 | 7.395 | 1.00 | 31.00 | 6 |
| ATOM | 3265 | OE1 | GLN | B | 142 | 45.039 | −5.391 | 7.745 | 1.00 | 34.74 | 8 |
| ATOM | 3266 | NE2 | GLN | B | 142 | 46.447 | −6.335 | 6.281 | 1.00 | 33.99 | 7 |
| ATOM | 3267 | N | PRO | B | 143 | 49.444 | −6.363 | 12.645 | 1.00 | 19.66 | 7 |
| ATOM | 3268 | CA | PRO | B | 143 | 49.526 | −7.003 | 13.913 | 1.00 | 21.32 | 6 |
| ATOM | 3269 | C | PRO | B | 143 | 48.579 | −6.373 | 14.939 | 1.00 | 20.88 | 6 |
| ATOM | 3270 | O | PRO | B | 143 | 48.162 | −5.222 | 14.777 | 1.00 | 23.53 | 8 |
| ATOM | 3271 | CB | PRO | B | 143 | 50.974 | −6.829 | 14.398 | 1.00 | 19.63 | 6 |
| ATOM | 3272 | CG | PRO | B | 143 | 51.245 | −5.445 | 13.833 | 1.00 | 20.10 | 6 |
| ATOM | 3273 | CD | PRO | B | 143 | 50.576 | −5.419 | 12.433 | 1.00 | 20.21 | 6 |
| ATOM | 3274 | N | ASP | B | 144 | 48.242 | −7.127 | 15.964 | 1.00 | 19.65 | 7 |
| ATOM | 3275 | CA | ASP | B | 144 | 47.481 | −6.572 | 17.069 | 1.00 | 19.58 | 6 |
| ATOM | 3276 | C | ASP | B | 144 | 48.443 | −5.798 | 17.998 | 1.00 | 20.96 | 6 |
| ATOM | 3277 | O | ASP | B | 144 | 48.078 | −4.862 | 18.701 | 1.00 | 21.10 | 8 |
| ATOM | 3278 | CB | ASP | B | 144 | 46.769 | −7.645 | 17.857 | 1.00 | 21.71 | 6 |
| ATOM | 3279 | CG | ASP | B | 144 | 45.715 | −8.336 | 16.977 | 1.00 | 29.09 | 6 |
| ATOM | 3280 | OD1 | ASP | B | 144 | 46.026 | −9.413 | 16.419 | 1.00 | 28.54 | 8 |
| ATOM | 3281 | OD2 | ASP | B | 144 | 44.670 | −7.652 | 16.763 | 1.00 | 29.74 | 8 |
| ATOM | 3282 | N | ILE | B | 145 | 49.639 | −6.395 | 18.133 | 1.00 | 19.56 | 7 |
| ATOM | 3283 | CA | ILE | B | 145 | 50.662 | −5.948 | 19.117 | 1.00 | 20.94 | 6 |
| ATOM | 3284 | C | ILE | B | 145 | 52.010 | −5.887 | 18.446 | 1.00 | 19.85 | 6 |
| ATOM | 3285 | O | ILE | B | 145 | 52.279 | −6.676 | 17.481 | 1.00 | 19.52 | 8 |
| ATOM | 3286 | CB | ILE | B | 145 | 50.680 | −6.958 | 20.269 | 1.00 | 21.71 | 6 |
| ATOM | 3287 | CG1 | ILE | B | 145 | 49.386 | −6.954 | 21.122 | 1.00 | 24.70 | 6 |
| ATOM | 3288 | CG2 | ILE | B | 145 | 51.900 | −6.729 | 21.173 | 1.00 | 26.93 | 6 |
| ATOM | 3289 | CD1 | ILE | B | 145 | 49.072 | −8.328 | 21.695 | 1.00 | 28.80 | 6 |
| ATOM | 3290 | N | ALA | B | 146 | 52.910 | −4.978 | 18.807 | 1.00 | 20.13 | 7 |
| ATOM | 3291 | CA | ALA | B | 146 | 54.247 | −4.939 | 18.221 | 1.00 | 20.86 | 6 |
| ATOM | 3292 | C | ALA | B | 146 | 55.243 | −4.703 | 19.396 | 1.00 | 23.49 | 6 |
| ATOM | 3293 | O | ALA | B | 146 | 54.897 | −3.879 | 20.234 | 1.00 | 21.46 | 8 |
| ATOM | 3294 | CB | ALA | B | 146 | 54.442 | −3.869 | 17.206 | 1.00 | 21.57 | 6 |
| ATOM | 3295 | N | CYS | B | 147 | 56.282 | −5.520 | 19.470 | 1.00 | 21.24 | 7 |
| ATOM | 3296 | CA | CYS | B | 147 | 57.227 | −5.418 | 20.634 | 1.00 | 21.57 | 6 |
| ATOM | 3297 | C | CYS | B | 147 | 58.514 | −4.835 | 20.232 | 1.00 | 19.68 | 6 |
| ATOM | 3298 | O | CYS | B | 147 | 59.148 | −5.086 | 19.189 | 1.00 | 23.55 | 8 |

TABLE 1-continued

| | | | | | | | | | | |
|---|---|---|---|---|---|---|---|---|---|---|
| ATOM | 3299 | CB | CYS | B | 147 | 57.487 | −6.803 | 21.192 | 1.00 | 25.97 | 6 |
| ATOM | 3300 | SG | CYS | B | 147 | 56.049 | −7.649 | 21.811 | 1.00 | 30.41 | 16 |
| ATOM | 3301 | N | PHE | B | 148 | 59.070 | −3.904 | 21.116 | 1.00 | 21.36 | 7 |
| ATOM | 3302 | CA | PHE | B | 148 | 60.268 | −3.195 | 20.823 | 1.00 | 19.98 | 6 |
| ATOM | 3303 | C | PHE | B | 148 | 61.134 | −3.123 | 22.146 | 1.00 | 19.23 | 6 |
| ATOM | 3304 | O | PHE | B | 148 | 60.479 | −3.140 | 23.148 | 1.00 | 23.93 | 8 |
| ATOM | 3305 | CB | PHE | B | 148 | 60.072 | −1.760 | 20.374 | 1.00 | 22.31 | 6 |
| ATOM | 3306 | CG | PHE | B | 148 | 59.349 | −1.636 | 19.056 | 1.00 | 21.62 | 6 |
| ATOM | 3307 | CD1 | PHE | B | 148 | 57.968 | −1.677 | 19.110 | 1.00 | 22.35 | 6 |
| ATOM | 3308 | CD2 | PHE | B | 148 | 60.045 | −1.548 | 17.891 | 1.00 | 24.41 | 6 |
| ATOM | 3309 | CE1 | PHE | B | 148 | 57.226 | −1.664 | 17.918 | 1.00 | 21.17 | 6 |
| ATOM | 3310 | CE2 | PHE | B | 148 | 59.307 | −1.425 | 16.674 | 1.00 | 23.20 | 6 |
| ATOM | 3311 | CZ | PHE | B | 148 | 57.930 | −1.509 | 16.754 | 1.00 | 19.10 | 6 |
| ATOM | 3312 | N | GLY | B | 149 | 62.415 | −3.168 | 22.002 | 1.00 | 22.90 | 7 |
| ATOM | 3313 | CA | GLY | B | 149 | 63.243 | −3.177 | 23.235 | 1.00 | 24.26 | 6 |
| ATOM | 3314 | C | GLY | B | 149 | 63.315 | −1.783 | 23.884 | 1.00 | 26.58 | 6 |
| ATOM | 3315 | O | GLY | B | 149 | 63.397 | −0.779 | 23.199 | 1.00 | 27.16 | 8 |
| ATOM | 3316 | N | GLU | B | 150 | 63.380 | −1.759 | 25.212 | 1.00 | 27.01 | 7 |
| ATOM | 3317 | CA | GLU | B | 150 | 63.530 | −0.425 | 25.870 | 1.00 | 29.68 | 6 |
| ATOM | 3318 | C | GLU | B | 150 | 64.894 | 0.200 | 25.737 | 1.00 | 31.07 | 6 |
| ATOM | 3319 | O | GLU | B | 150 | 65.020 | 1.425 | 25.978 | 1.00 | 30.50 | 8 |
| ATOM | 3320 | CB | GLU | B | 150 | 63.214 | −0.532 | 27.368 | 1.00 | 31.68 | 6 |
| ATOM | 3321 | CG | GLU | B | 150 | 61.747 | −0.632 | 27.660 | 1.00 | 34.09 | 6 |
| ATOM | 3322 | CD | GLU | B | 150 | 61.359 | −0.743 | 29.111 | 1.00 | 37.99 | 6 |
| ATOM | 3323 | OE1 | GLU | B | 150 | 62.205 | −0.936 | 30.001 | 1.00 | 38.43 | 8 |
| ATOM | 3324 | OE2 | GLU | B | 150 | 60.143 | −0.643 | 29.350 | 1.00 | 40.17 | 8 |
| ATOM | 3325 | N | LYS | B | 151 | 65.951 | −0.544 | 25.401 | 1.00 | 29.23 | 7 |
| ATOM | 3326 | CA | LYS | B | 151 | 67.258 | 0.093 | 25.292 | 1.00 | 31.41 | 6 |
| ATOM | 3327 | C | LYS | B | 151 | 67.273 | 1.220 | 24.300 | 1.00 | 31.27 | 6 |
| ATOM | 3328 | O | LYS | B | 151 | 67.936 | 2.260 | 24.433 | 1.00 | 27.21 | 8 |
| ATOM | 3329 | CB | LYS | B | 151 | 68.320 | −0.926 | 24.878 | 1.00 | 34.10 | 6 |
| ATOM | 3330 | CG | LYS | B | 151 | 69.755 | −0.397 | 24.923 | 1.00 | 37.66 | 6 |
| ATOM | 3331 | CD | LYS | B | 151 | 70.640 | −1.476 | 24.317 | 1.00 | 41.05 | 6 |
| ATOM | 3332 | CE | LYS | B | 151 | 72.080 | −1.431 | 24.765 | 1.00 | 43.98 | 6 |
| ATOM | 3333 | NZ | LYS | B | 151 | 72.893 | −0.452 | 23.975 | 1.00 | 44.59 | 7 |
| ATOM | 3334 | N | ASP | B | 152 | 66.506 | 1.027 | 23.164 | 1.00 | 28.39 | 7 |
| ATOM | 3335 | CA | ASP | B | 152 | 66.518 | 2.032 | 22.110 | 1.00 | 28.38 | 6 |
| ATOM | 3336 | C | ASP | B | 152 | 65.332 | 2.937 | 22.374 | 1.00 | 28.23 | 6 |
| ATOM | 3337 | O | ASP | B | 152 | 64.210 | 2.803 | 21.783 | 1.00 | 26.26 | 8 |
| ATOM | 3338 | CB | ASP | B | 152 | 66.440 | 1.375 | 20.725 | 1.00 | 28.61 | 6 |
| ATOM | 3339 | N | PHE | B | 153 | 65.516 | 3.702 | 23.467 | 1.00 | 25.07 | 7 |
| ATOM | 3340 | CA | PHE | B | 153 | 64.373 | 4.471 | 23.974 | 1.00 | 26.53 | 6 |
| ATOM | 3341 | C | PHE | B | 153 | 63.892 | 5.520 | 22.974 | 1.00 | 21.61 | 6 |
| ATOM | 3342 | O | PHE | B | 153 | 62.708 | 5.839 | 23.024 | 1.00 | 24.77 | 8 |
| ATOM | 3343 | CB | PHE | B | 153 | 64.730 | s.118 | 25.330 | 1.00 | 26.51 | 6 |
| ATOM | 3344 | CG | PHE | B | 153 | 65.779 | 6.167 | 25.190 | 1.00 | 29.71 | 6 |
| ATOM | 3345 | CD1 | PHE | B | 153 | 65.443 | 7.493 | 24.943 | 1.00 | 29.96 | 6 |
| ATOM | 3346 | CD2 | PHE | B | 153 | 67.132 | 5.855 | 25.398 | 1.00 | 29.77 | 6 |
| ATOM | 3347 | CE1 | PHE | B | 153 | 66.423 | 8.454 | 24.846 | 1.00 | 31.18 | 6 |
| ATOM | 3348 | CE2 | PHE | B | 153 | 68.099 | 6.820 | 25.256 | 1.00 | 28.84 | 6 |
| ATOM | 3349 | CZ | PHE | B | 153 | 67.763 | 8.135 | 24.997 | 1.00 | 31.32 | 6 |
| ATOM | 3350 | N | GLN | B | 154 | 64.740 | 6.002 | 22.113 | 1.00 | 23.01 | 7 |
| ATOM | 3351 | CA | GLN | B | 154 | 64.352 | 7.012 | 21.149 | 1.00 | 24.58 | 6 |
| ATOM | 3352 | C | GLN | B | 154 | 63.443 | 6.353 | 20.075 | 1.00 | 24.87 | 6 |
| ATOM | 3353 | O | GLN | B | 154 | 62.466 | 6.997 | 19.7D7 | 1.00 | 23.87 | 8 |
| ATOM | 3354 | CB | GLN | B | 154 | 65.558 | 7.664 | 20.502 | 1.00 | 26.01 | 6 |
| ATOM | 3355 | CG | GLN | B | 154 | 65.117 | 8.877 | 19.710 | 1.00 | 28.34 | 6 |
| ATOM | 3356 | CD | GLN | B | 154 | 66.171 | 9.934 | 19.456 | 1.00 | 30.51 | 6 |
| ATOM | 3357 | OE1 | GLN | B | 154 | 67.342 | 9.742 | 19.766 | 1.00 | 32.27 | 8 |
| ATOM | 3358 | NE2 | GLN | B | 154 | 65.742 | 11.030 | 18.839 | 1.00 | 28.70 | 7 |
| ATOM | 3359 | N | GLN | B | 155 | 63.841 | 5.183 | 19.619 | 1.00 | 24.42 | 7 |
| ATOM | 3360 | CA | GLN | B | 155 | 62.944 | 4.439 | 18.714 | 1.00 | 24.63 | 6 |
| ATOM | 3361 | C | GLN | B | 155 | 61.612 | 4.204 | 19.382 | 1.00 | 22.70 | 6 |
| ATOM | 3362 | O | GLN | B | 155 | 60.577 | 4.285 | 18.652 | 1.00 | 24.30 | 8 |
| ATOM | 3363 | CB | GLN | B | 155 | 63.549 | 3.094 | 18.268 | 1.00 | 25.06 | 6 |
| ATOM | 3364 | CG | GLN | B | 155 | 64.450 | 3.209 | 17.029 | 1.00 | 29.61 | 6 |
| ATOM | 3365 | CD | GLN | B | 155 | 64.506 | 1.856 | 16.285 | 1.00 | 32.67 | 6 |
| ATOM | 3366 | OE1 | GLN | B | 155 | 65.360 | 1.610 | 15.440 | 1.00 | 37.92 | 8 |
| ATOM | 3367 | NE2 | GLN | B | 155 | 63.610 | 0.953 | 16.599 | 1.00 | 28.61 | 7 |
| ATOM | 3368 | N | LEU | B | 156 | 61.522 | 3.748 | 20.602 | 1.00 | 20.20 | 7 |
| ATOM | 3369 | CA | LEU | B | 156 | 60.288 | 3.409 | 21.273 | 1.00 | 22.81 | 6 |
| ATOM | 3370 | C | LEU | B | 156 | 59.381 | 4.671 | 21.280 | 1.00 | 25.01 | 6 |
| ATOM | 3371 | O | LEU | B | 156 | 58.192 | 4.596 | 20.961 | 1.00 | 22.03 | 8 |
| ATOM | 3372 | CB | LEU | B | 156 | 60.549 | 2.887 | 22.651 | 1.00 | 23.28 | 6 |
| ATOM | 3373 | CG | LEU | B | 156 | 59.393 | 2.429 | 23.497 | 1.00 | 22.55 | 6 |
| ATOM | 3374 | CD1 | LEU | B | 156 | 58.484 | 1.403 | 22.784 | 1.80 | 24.60 | 6 |
| ATOM | 3375 | CD2 | LEU | B | 156 | 59.895 | 1.814 | 24.812 | 1.00 | 24.72 | 6 |
| ATOM | 3376 | N | ALA | B | 157 | 59.971 | 5.799 | 21.745 | 1.00 | 21.98 | 7 |
| ATOM | 3377 | CA | ALA | B | 157 | 59.149 | 7.006 | 21.699 | 1.00 | 23.16 | 6 |

TABLE 1-continued

| ATOM | 3378 | C | ALA | B | 157 | 58.684 | 7.366 | 20.300 | 1.00 | 21.84 | 6 |
|---|---|---|---|---|---|---|---|---|---|---|---|
| ATOM | 3379 | O | ALA | B | 157 | 57.504 | 7.836 | 20.225 | 1.00 | 22.95 | 8 |
| ATOM | 3380 | CB | ALA | B | 157 | 59.953 | 8.235 | 22.216 | 1.00 | 21.48 | 6 |
| ATOM | 3381 | N | LEU | B | 158 | 59.510 | 7.286 | 19.278 | 1.00 | 20.55 | 7 |
| ATOM | 3382 | CA | LEU | B | 158 | 59.209 | 7.601 | 17.902 | 1.00 | 24.17 | 6 |
| ATOM | 3383 | C | LEU | B | 158 | 58.018 | 6.737 | 17.408 | 1.00 | 24.35 | 6 |
| ATOM | 3384 | O | LEU | B | 158 | 57.063 | 7.345 | 16.896 | 1.00 | 21.76 | 8 |
| ATOM | 3385 | CB | LEU | B | 158 | 60.387 | 7.347 | 16.959 | 1.00 | 23.67 | 6 |
| ATOM | 3386 | CG | LEU | B | 158 | 60.332 | 7.840 | 15.511 | 1.00 | 25.33 | 6 |
| ATOM | 3387 | CD1 | LEU | B | 158 | 60.910 | 9.254 | 15.385 | 1.00 | 25.04 | 6 |
| ATOM | 3388 | CD2 | LEU | B | 158 | 61.078 | 6.855 | 14.633 | 1.00 | 24.59 | 6 |
| ATOM | 3389 | N | ILE | B | 159 | 58.085 | 5.451 | 17.683 | 1.00 | 21.94 | 7 |
| ATOM | 3390 | CA | ILE | B | 159 | 56.938 | 4.578 | 17.235 | 1.00 | 22.18 | 6 |
| ATOM | 3391 | C | ILE | B | 159 | 55.685 | 4.727 | 18.032 | 1.00 | 24.01 | 6 |
| ATOM | 3392 | O | ILE | B | 159 | 54.587 | 4.804 | 17.414 | 1.00 | 21.79 | 8 |
| ATOM | 3393 | CB | ILE | B | 159 | 57.436 | 3.108 | 17.263 | 1.00 | 21.63 | 6 |
| ATOM | 3394 | CG1 | ILE | B | 159 | 58.615 | 3.036 | 16.314 | 1.00 | 21.10 | 6 |
| ATOM | 3395 | CG2 | ILE | B | 159 | 56.305 | 2.118 | 16.906 | 1.00 | 21.29 | 6 |
| ATOM | 3396 | CD1 | ILE | B | 159 | 58.290 | 3.361 | 14.848 | 1.00 | 27.17 | 6 |
| ATOM | 3397 | N | ARG | B | 160 | 55.764 | 5.016 | 19.357 | 1.80 | 21.20 | 7 |
| ATOM | 3398 | CA | ARG | B | 160 | 54.563 | 5.304 | 20.113 | 1.00 | 23.22 | 6 |
| ATOM | 3399 | C | ARG | B | 160 | 53.911 | 6.620 | 19.579 | 1.00 | 20.84 | 6 |
| ATOM | 3400 | O | ARG | B | 160 | 52.688 | 6.684 | 19.482 | 1.00 | 22.99 | 8 |
| ATOM | 3401 | CB | ARG | B | 160 | 54.786 | 5.438 | 21.627 | 1.00 | 22.64 | 6 |
| ATOM | 3402 | CG | ARG | B | 160 | 54.975 | 4.035 | 22.266 | 1.00 | 25.40 | 6 |
| ATOM | 3403 | CD | ARG | B | 160 | 55.364 | 4.303 | 23.720 | 0.50 | 28.99 | 6 |
| ATOM | 3404 | NE | ARG | B | 160 | 55.627 | 3.143 | 24.540 | 0.50 | 32.14 | 7 |
| ATOM | 3405 | CZ | ARG | B | 160 | 54.843 | 2.116 | 24.819 | 0.50 | 32.06 | 6 |
| ATOM | 3406 | NH1 | ARG | B | 160 | 53.609 | 1.993 | 24.361 | 0.50 | 31.32 | 7 |
| ATOM | 3407 | NH2 | ARG | B | 160 | 55.288 | 1.143 | 25.624 | 0.50 | 32.40 | 7 |
| ATOM | 3408 | N | LYS | B | 161 | 54.699 | 7.617 | 19.257 | 1.00 | 20.06 | 7 |
| ATOM | 3409 | CA | LYS | B | 161 | 54.121 | 8.866 | 18.707 | 1.00 | 19.89 | 6 |
| ATOM | 3410 | C | LYS | B | 161 | 53.502 | 8.570 | 17.331 | 1.00 | 20.88 | 6 |
| ATOM | 3411 | O | LYS | B | 161 | 52.418 | 9.085 | 17.017 | 1.00 | 20.38 | 8 |
| ATOM | 3412 | CB | LYS | B | 161 | 55.172 | 9.998 | 18.633 | 1.00 | 21.42 | 6 |
| ATOM | 3413 | CG | LYS | B | 161 | 54.474 | 11.290 | 18.133 | 1.00 | 23.56 | 6 |
| ATOM | 3414 | CD | LYS | B | 161 | 55.345 | 12.508 | 18.131 | 1.00 | 27.88 | 6 |
| ATOM | 3415 | CE | LYS | B | 161 | 54.736 | 13.692 | 17.336 | 1.00 | 31.75 | 6 |
| ATOM | 3416 | NZ | LYS | B | 161 | 53.349 | 13.890 | 17.879 | 1.00 | 29.32 | 7 |
| ATOM | 3417 | N | MET | B | 162 | 54.244 | 7.875 | 16.465 | 1.00 | 19.25 | 7 |
| ATOM | 3418 | CA | MET | B | 162 | 53.744 | 7.586 | 15.106 | 1.00 | 20.25 | 6 |
| ATOM | 3419 | C | MET | B | 162 | 52.443 | 6.849 | 15.190 | 1.00 | 20.77 | 6 |
| ATOM | 3420 | O | MET | B | 162 | 51.432 | 7.100 | 14.451 | 1.00 | 20.50 | 8 |
| ATOM | 3421 | CB | MET | B | 162 | 54.864 | 6.798 | 14.378 | 1.00 | 20.27 | 6 |
| ATOM | 3422 | CG | MET | B | 162 | 54.438 | 6.504 | 12.918 | 1.00 | 20.30 | 6 |
| ATOM | 3423 | SD | MET | B | 162 | 55.575 | 5.209 | 12.231 | 1.00 | 23.99 | 16 |
| ATOM | 3424 | CE | MET | B | 162 | 54.976 | 3.754 | 13.066 | 1.00 | 22.75 | 6 |
| ATOM | 3425 | N | VAL | B | 163 | 52.331 | 5.858 | 16.110 | 1.00 | 19.38 | 7 |
| ATOM | 3426 | CA | VAL | B | 163 | 51.106 | 5.095 | 16.243 | 1.00 | 20.12 | 6 |
| ATOM | 3427 | C | VAL | B | 163 | 49.926 | 5.955 | 16.693 | 1.00 | 22.03 | 6 |
| ATOM | 3428 | O | VAL | B | 163 | 48.820 | 5.841 | 16.163 | 1.00 | 19.78 | 8 |
| ATOM | 3429 | CB | VAL | B | 163 | 51.310 | 3.926 | 17.212 | 1.00 | 19.66 | 6 |
| ATOM | 3430 | CG1 | VAL | B | 163 | 50.044 | 3.269 | 17.672 | 1.00 | 20.89 | 6 |
| ATOM | 3431 | CG2 | VAL | B | 163 | 52.253 | 2.958 | 16.455 | 1.00 | 20.73 | 6 |
| ATOM | 3432 | N | ALA | B | 164 | 50.127 | 6.771 | 17.688 | 1.00 | 20.47 | 7 |
| ATOM | 3433 | CA | ALA | B | 164 | 49.065 | 7.634 | 18.189 | 1.00 | 21.69 | 6 |
| ATOM | 3434 | C | ALA | B | 164 | 48.642 | 8.624 | 17.101 | 1.00 | 20.50 | 6 |
| ATOM | 3435 | O | ALA | B | 164 | 47.419 | 8.750 | 16.892 | 1.00 | 23.25 | 8 |
| ATOM | 3436 | CB | ALA | B | 164 | 49.604 | 8.359 | 19.418 | 1.00 | 20.80 | 6 |
| ATOM | 3437 | N | ASP | B | 165 | 49.612 | 9.237 | 16.440 | 1.00 | 19.12 | 7 |
| ATOM | 3438 | CA | ASP | B | 165 | 49.190 | 10.233 | 15.409 | 1.00 | 18.46 | 6 |
| ATOM | 3439 | C | ASP | B | 165 | 48.550 | 9.577 | 14.207 | 1.00 | 22.82 | 6 |
| ATOM | 3440 | O | ASP | B | 165 | 47.594 | 10.145 | 13.660 | 1.00 | 22.60 | 8 |
| ATOM | 3441 | CB | ASP | B | 165 | 50.392 | 10.996 | 14.943 | 1.00 | 18.70 | 6 |
| ATOM | 3442 | CG | ASP | B | 165 | 51.018 | 12.009 | 15.941 | 1.00 | 18.80 | 6 |
| ATOM | 3443 | OD1 | ASP | B | 165 | 50.354 | 12.300 | 16.916 | 1.00 | 21.84 | 8 |
| ATOM | 3444 | OD2 | ASP | B | 165 | 52.112 | 12.486 | 15.692 | 1.00 | 21.56 | 8 |
| ATOM | 3445 | N | MET | B | 166 | 49.185 | 8.526 | 13.694 | 1.00 | 19.28 | 7 |
| ATOM | 3446 | CA | MET | B | 166 | 48.660 | 7.953 | 12.411 | 1.00 | 20.68 | 6 |
| ATOM | 3447 | C | MET | B | 166 | 47.436 | 7.082 | 12.604 | 1.00 | 21.52 | 6 |
| ATOM | 3448 | O | MET | B | 166 | 46.935 | 6.605 | 11.577 | 1.00 | 22.25 | 8 |
| ATOM | 3449 | CB | MET | B | 166 | 49.878 | 7.292 | 11.723 | 1.00 | 17.15 | 6 |
| ATOM | 3450 | CG | MET | B | 166 | 50.905 | 8.348 | 11.281 | 1.00 | 21.78 | 6 |
| ATOM | 3451 | SD | MET | B | 166 | 50.266 | 9.743 | 10.357 | 1.00 | 21.48 | 16 |
| ATOM | 3452 | CE | MET | B | 166 | 49.315 | 9.048 | 8.969 | 1.00 | 22.58 | 6 |
| ATOM | 3453 | N | GLY | B | 167 | 46.947 | 6.745 | 13.792 | 1.00 | 22.34 | 7 |
| ATOM | 3454 | CA | GLY | B | 167 | 45.725 | 5.983 | 14.001 | 1.00 | 21.60 | 6 |
| ATOM | 3455 | C | GLY | B | 167 | 45.804 | 4.480 | 13.881 | 1.00 | 21.23 | 6 |
| ATOM | 3456 | O | GLY | B | 167 | 44.803 | 3.783 | 13.677 | 1.00 | 19.88 | 8 |

TABLE 1-continued

| | | | | | | | | | | |
|---|---|---|---|---|---|---|---|---|---|---|
| ATOM | 3457 | N | PHE | B | 168 | 47.043 | 3.939 | 13.961 | 1.00 | 21.11 | 7 |
| ATOM | 3458 | CA | PHE | B | 168 | 47.170 | 2.494 | 13.958 | 1.00 | 20.42 | 6 |
| ATOM | 3459 | C | PHE | B | 168 | 46.553 | 1.828 | 15.193 | 1.00 | 20.83 | 6 |
| ATOM | 3460 | O | PHE | B | 168 | 46.842 | 2.233 | 16.321 | 1.00 | 22.53 | 8 |
| ATOM | 3461 | CB | PHE | B | 168 | 48.653 | 2.079 | 13.921 | 1.00 | 21.51 | 6 |
| ATOM | 3462 | CG | PHE | B | 168 | 49.420 | 2.244 | 12.648 | 1.00 | 21.26 | 6 |
| ATOM | 3463 | CD1 | PHE | B | 168 | 50.305 | 3.310 | 12.535 | 1.00 | 21.28 | 6 |
| ATOM | 3464 | CD2 | PHE | B | 168 | 49.352 | 1.351 | 11.604 | 1.00 | 21.16 | 6 |
| ATOM | 3465 | CE1 | PHE | B | 168 | 51.095 | 3.489 | 11.409 | 1.00 | 22.13 | 6 |
| ATOM | 3466 | CE2 | PHE | B | 168 | 50.080 | 1.550 | 10.442 | 1.00 | 24.10 | 6 |
| ATOM | 3467 | CZ | PHE | B | 168 | 50.978 | 2.592 | 10.348 | 1.00 | 20.59 | 6 |
| ATOM | 3468 | N | ASP | B | 169 | 45.751 | 0.812 | 14.997 | 1.00 | 22.55 | 7 |
| ATOM | 3469 | CA | ASP | B | 169 | 45.089 | 0.089 | 16.054 | 1.00 | 23.63 | 6 |
| ATOM | 3470 | C | ASP | B | 169 | 46.010 | −1.072 | 16.556 | 1.00 | 23.14 | 6 |
| ATOM | 3471 | O | ASP | B | 169 | 45.637 | −2.215 | 16.493 | 1.00 | 23.77 | 8 |
| ATOM | 3472 | CB | ASP | B | 169 | 43.773 | −0.497 | 15.594 | 1.00 | 27.60 | 6 |
| ATOM | 3473 | CG | ASP | B | 169 | 42.879 | −1.031 | 16.711 | 1.00 | 30.74 | 6 |
| ATOM | 3474 | OD1 | ASP | B | 169 | 43.197 | −0.784 | 17.892 | 1.00 | 34.41 | 8 |
| ATOM | 3475 | OD2 | ASP | B | 169 | 41.884 | −1.685 | 16.342 | 1.00 | 34.81 | 8 |
| ATOM | 3476 | N | ILE | B | 170 | 47.137 | −0.643 | 17.058 | 1.00 | 20.48 | 7 |
| ATOM | 3477 | CA | ILE | B | 170 | 48.196 | −1.584 | 17.457 | 1.00 | 19.43 | 6 |
| ATOM | 3478 | C | ILE | B | 170 | 48.725 | −1.236 | 18.834 | 1.00 | 21.42 | 6 |
| ATOM | 3479 | O | ILE | B | 170 | 49.048 | −0.083 | 19.071 | 1.00 | 22.91 | 8 |
| ATOM | 3480 | CB | ILE | B | 170 | 49.351 | −1.526 | 16.434 | 1.00 | 19.13 | 6 |
| ATOM | 3481 | CG1 | ILE | B | 170 | 48.940 | −1.849 | 14.994 | 1.00 | 21.06 | 6 |
| ATOM | 3482 | CG2 | ILE | B | 170 | 50.464 | −2.519 | 16.854 | 1.00 | 20.00 | 6 |
| ATOM | 3483 | CD1 | ILE | B | 170 | 50.054 | −1.568 | 13.974 | 1.00 | 23.10 | 6 |
| ATOM | 3484 | N | GLU | B | 171 | 48.847 | −2.233 | 19.720 | 1.00 | 20.51 | 7 |
| ATOM | 3485 | CA | GLU | B | 171 | 49.415 | −1.968 | 21.050 | 1.00 | 22.48 | 6 |
| ATOM | 3486 | C | GLU | B | 171 | 50.925 | −1.992 | 20.961 | 1.00 | 23.14 | 6 |
| ATOM | 3487 | O | GLU | B | 171 | 51.470 | −3.024 | 20.518 | 1.00 | 23.79 | 8 |
| ATOM | 3488 | CB | GLU | B | 171 | 48.824 | −2.974 | 22.034 | 1.00 | 24.29 | 6 |
| ATOM | 3489 | CG | GLU | B | 171 | 49.506 | −2.861 | 23.391 | 1.00 | 28.59 | 6 |
| ATOM | 3490 | CD | GLU | B | 171 | 49.089 | −3.843 | 24.453 | 1.00 | 33.66 | 6 |
| ATOM | 3491 | OE1 | GLU | B | 171 | 48.310 | −4.782 | 24.246 | 1.00 | 34.21 | 8 |
| ATOM | 3492 | OE2 | GLU | B | 171 | 49.580 | −3.608 | 25.609 | 1.00 | 37.13 | 8 |
| ATOM | 3493 | N | ILE | B | 172 | 51.637 | −0.956 | 21.410 | 1.00 | 21.22 | 7 |
| ATOM | 3494 | CA | ILE | B | 172 | 53.093 | −0.965 | 21.349 | 1.00 | 19.30 | 6 |
| ATOM | 3495 | C | ILE | B | 172 | 53.656 | −1.362 | 22.720 | 1.00 | 24.29 | 6 |
| ATOM | 3496 | O | ILE | B | 172 | 53.145 | −0.847 | 23.730 | 1.00 | 25.41 | 8 |
| ATOM | 3497 | CB | ILE | B | 172 | 53.631 | 0.401 | 20.893 | 1.00 | 20.79 | 6 |
| ATOM | 3498 | CG1 | ILE | B | 172 | 53.086 | 0.809 | 19.509 | 1.00 | 22.57 | 6 |
| ATOM | 3499 | CG2 | ILE | B | 172 | 55.162 | 0.435 | 20.888 | 1.00 | 22.05 | 6 |
| ATOM | 3500 | CD1 | ILE | B | 172 | 53.459 | −0.175 | 18.386 | 1.00 | 21.95 | 6 |
| ATOM | 3501 | N | VAL | B | 173 | 54.392 | −2.471 | 22.752 | 1.00 | 21.27 | 7 |
| ATOM | 3502 | CA | VAL | B | 173 | 54.895 | −3.034 | 24.024 | 1.00 | 25.99 | 6 |
| ATOM | 3503 | C | VAL | B | 173 | 56.363 | −2.785 | 24.113 | 1.00 | 25.58 | 6 |
| ATOM | 3504 | O | VAL | B | 173 | 57.087 | −3.255 | 23.240 | 1.00 | 22.50 | 8 |
| ATOM | 3505 | CB | VAL | B | 173 | 54.583 | −4.552 | 24.123 | 1.00 | 25.82 | 6 |
| ATOM | 3506 | CG1 | VAL | B | 173 | 55.242 | −5.122 | 25.406 | 1.00 | 26.85 | 6 |
| ATOM | 3507 | CG2 | VAL | B | 173 | 53.094 | −4.779 | 24.096 | 1.00 | 27.94 | 6 |
| ATOM | 3508 | N | GLY | B | 174 | 56.820 | −2.085 | 25.189 | 1.00 | 24.62 | 7 |
| ATOM | 3509 | CA | GLY | B | 174 | 58.270 | −1.862 | 25.313 | 1.00 | 23.53 | 6 |
| ATOM | 3510 | C | GLY | B | 174 | 58.740 | −3.002 | 26.282 | 1.00 | 23.91 | 6 |
| ATOM | 3511 | O | GLY | B | 174 | 57.998 | −3.288 | 27.218 | 1.00 | 26.78 | 8 |
| ATOM | 3512 | N | VAL | B | 175 | 59.801 | −3.641 | 25.849 | 1.00 | 22.58 | 7 |
| ATOM | 3513 | CA | VAL | B | 175 | 60.234 | −4.783 | 26.676 | 1.00 | 24.09 | 6 |
| ATOM | 3514 | C | VAL | B | 175 | 61.523 | −4.341 | 27.430 | 1.00 | 23.90 | 6 |
| ATOM | 3515 | O | VAL | B | 175 | 62.502 | −4.011 | 26.762 | 1.00 | 24.10 | 8 |
| ATOM | 3516 | CB | VAL | B | 175 | 60.476 | −6.015 | 25.853 | 1.00 | 24.37 | 6 |
| ATOM | 3517 | CG1 | VAL | B | 175 | 60.852 | −7.180 | 26.767 | 1.00 | 28.33 | 6 |
| ATOM | 3518 | CG2 | VAL | B | 175 | 59.219 | −6.353 | 24.984 | 1.00 | 24.52 | 6 |
| ATOM | 3519 | N | PRO | B | 176 | 61.469 | −4.464 | 28.728 | 1.00 | 28.58 | 7 |
| ATOM | 3520 | CA | PRO | B | 176 | 62.648 | −4.211 | 29.574 | 1.00 | 32.47 | 6 |
| ATOM | 3521 | C | PRO | B | 176 | 63.888 | −4.974 | 29.180 | 1.00 | 32.41 | 6 |
| ATOM | 3522 | O | PRO | B | 176 | 63.831 | −6.135 | 28.746 | 1.00 | 28.92 | 8 |
| ATOM | 3523 | CB | PRO | B | 176 | 62.159 | −4.588 | 30.980 | 1.00 | 33.03 | 6 |
| ATOM | 3524 | CG | PRO | B | 176 | 60.685 | −4.380 | 30.922 | 1.00 | 34.15 | 6 |
| ATOM | 3525 | CD | PRO | B | 176 | 60.320 | −4.916 | 29.543 | 1.00 | 28.09 | 6 |
| ATOM | 3526 | N | ILE | B | 177 | 65.121 | −4.418 | 29.353 | 1.00 | 31.48 | 7 |
| ATOM | 3527 | CA | ILE | B | 177 | 66.307 | −5.079 | 28.865 | 1.00 | 32.30 | 6 |
| ATOM | 3528 | C | ILE | B | 177 | 66.572 | −6.407 | 29.607 | 1.00 | 30.07 | 6 |
| ATOM | 3529 | O | ILE | B | 177 | 66.054 | −6.698 | 30.686 | 1.00 | 32.04 | 8 |
| ATOM | 3530 | CB | ILE | B | 177 | 67.641 | −4.292 | 28.903 | 1.00 | 33.70 | 6 |
| ATOM | 3531 | CG1 | ILE | B | 177 | 68.066 | −3.943 | 30.331 | 1.00 | 33.12 | 6 |
| ATOM | 3532 | CG2 | ILE | B | 177 | 67.518 | −3.039 | 28.030 | 1.00 | 34.28 | 6 |
| ATOM | 3533 | CD1 | ILE | B | 177 | 69.430 | −3.243 | 30.349 | 1.00 | 34.81 | 6 |
| ATOM | 3534 | N | MET | B | 178 | 67.408 | −7.204 | 28.952 | 1.00 | 32.08 | 7 |
| ATOM | 3535 | CA | MET | B | 178 | 67.674 | −8.503 | 29.572 | 1.00 | 35.37 | 6 |

TABLE 1-continued

| ATOM | 3536 | C | MET | B | 178 | 68.620 | −8.292 | 30.772 | 1.00 | 34.12 | 6 |
|---|---|---|---|---|---|---|---|---|---|---|---|
| ATOM | 3537 | O | MET | B | 178 | 69.597 | −7.573 | 30.642 | 1.00 | 31.98 | 8 |
| ATOM | 3538 | CB | MET | B | 178 | 68.295 | −9.532 | 28.641 | 1.00 | 40.27 | 6 |
| ATOM | 3539 | CG | MET | B | 178 | 67.437 | −10.819 | 28.679 | 1.00 | 44.21 | 6 |
| ATOM | 3540 | SD | MET | B | 178 | 68.203 | −12.124 | 27.749 | 1.00 | 51.85 | 16 |
| ATOM | 3541 | CE | MET | B | 178 | 69.561 | −11.316 | 26.916 | 1.00 | 48.86 | 6 |
| ATOM | 3542 | N | ARG | B | 179 | 68.313 | −8.994 | 31.814 | 1.00 | 35.69 | 7 |
| ATOM | 3543 | CA | ARG | B | 179 | 69.085 | −8.847 | 33.060 | 1.00 | 36.43 | 6 |
| ATOM | 3544 | C | ARG | B | 179 | 69.292 | −10.188 | 33.715 | 1.00 | 37.86 | 6 |
| ATOM | 3545 | O | ARG | B | 179 | 68.430 | −11.054 | 33.618 | 1.00 | 38.23 | 8 |
| ATOM | 3546 | CB | ARG | B | 179 | 68.260 | −7.887 | 33.870 | 1.00 | 36.62 | 6 |
| ATOM | 3547 | CG | ARG | B | 179 | 68.473 | −7.248 | 35.163 | 1.00 | 38.40 | 6 |
| ATOM | 3548 | CD | ARG | B | 179 | 67.373 | −6.311 | 35.598 | 1.00 | 34.70 | 6 |
| ATOM | 3549 | NE | ARG | B | 179 | 67.202 | −5.122 | 34.808 | 1.00 | 31.82 | 7 |
| ATOM | 3550 | CZ | ARG | B | 179 | 68.057 | −4.149 | 34.534 | 1.00 | 32.71 | 6 |
| ATOM | 3551 | NH1 | ARG | B | 179 | 69.308 | −4.167 | 34.984 | 1.00 | 30.99 | 7 |
| ATOM | 3552 | NH2 | ARG | B | 179 | 67.715 | −3.067 | 33.831 | 1.00 | 33.25 | 7 |
| ATOM | 3553 | N | ALA | B | 180 | 70.363 | −10.335 | 34.477 | 1.00 | 36.11 | 7 |
| ATOM | 3554 | CA | ALA | B | 180 | 70.602 | −11.562 | 35.235 | 1.00 | 36.60 | 6 |
| ATOM | 3555 | C | ALA | B | 180 | 69.640 | −11.614 | 36.404 | 1.00 | 36.37 | 6 |
| ATOM | 3556 | O | ALA | B | 180 | 68.929 | −10.685 | 36.743 | 1.00 | 36.44 | 8 |
| ATOM | 3557 | CB | ALA | B | 180 | 72.048 | −11.541 | 35.689 | 1.00 | 36.08 | 6 |
| ATOM | 3558 | N | LYS | B | 181 | 69.621 | −12.775 | 37.102 | 1.00 | 37.25 | 7 |
| ATOM | 3559 | CA | LYS | B | 181 | 68.797 | −12.903 | 38.292 | 1.00 | 38.41 | 6 |
| ATOM | 3560 | C | LYS | B | 181 | 69.223 | −11.942 | 39.395 | 1.00 | 37.82 | 6 |
| ATOM | 3561 | O | LYS | B | 181 | 68.366 | −11.482 | 40.158 | 1.00 | 40.11 | 8 |
| ATOM | 3562 | CB | LYS | B | 181 | 68.862 | −14.317 | 38.895 | 1.00 | 39.54 | 6 |
| ATOM | 3563 | N | ASP | B | 182 | 70.495 | −11.584 | 39.503 | 1.00 | 36.65 | 7 |
| ATOM | 3564 | CA | ASP | B | 182 | 70.935 | −10.663 | 40.548 | 1.00 | 35.51 | 6 |
| ATOM | 3565 | C | ASP | B | 182 | 70.714 | −9.206 | 40.091 | 1.00 | 35.06 | 6 |
| ATOM | 3566 | O | ASP | B | 182 | 71.004 | −8.303 | 40.868 | 1.00 | 33.11 | 8 |
| ATOM | 3567 | CB | ASP | B | 182 | 72.392 | −10.861 | 40.981 | 1.00 | 37.04 | 6 |
| ATOM | 3568 | CG | ASP | B | 182 | 73.414 | −10.661 | 39.890 | 1.00 | 38.43 | 6 |
| ATOM | 3569 | OD1 | ASP | B | 182 | 73.047 | −10.265 | 38.753 | 1.00 | 38.66 | 8 |
| ATOM | 3570 | OD2 | ASP | B | 182 | 74.624 | −10.938 | 40.116 | 1.00 | 38.45 | 8 |
| ATOM | 3571 | N | GLY | B | 183 | 70.283 | −8.992 | 38.840 | 1.00 | 35.23 | 7 |
| ATOM | 3572 | CA | GLY | B | 183 | 69.907 | −7.618 | 38.467 | 1.00 | 32.81 | 6 |
| ATOM | 3573 | C | GLY | B | 183 | 70.883 | −7.003 | 37.494 | 1.00 | 33.61 | 6 |
| ATOM | 3574 | O | GLY | B | 183 | 70.523 | −5.956 | 36.928 | 1.00 | 33.06 | 8 |
| ATOM | 3575 | N | LEU | B | 184 | 72.029 | −7.592 | 37.220 | 1.00 | 31.99 | 7 |
| ATOM | 3576 | CA | LEU | B | 184 | 72.977 | −7.004 | 36.286 | 1.00 | 32.29 | 6 |
| ATOM | 3577 | C | LEU | B | 184 | 72.517 | −7.011 | 34.826 | 1.00 | 33.46 | 6 |
| ATOM | 3578 | O | LEU | B | 184 | 72.300 | −8.130 | 34.314 | 1.00 | 32.16 | 8 |
| ATOM | 3579 | CB | LEU | B | 184 | 74.325 | −7.737 | 36.370 | 1.00 | 32.38 | 6 |
| ATOM | 3580 | CG | LEU | B | 184 | 75.481 | −7.019 | 35.655 | 1.00 | 32.34 | 6 |
| ATOM | 3581 | CD1 | LEU | B | 184 | 75.643 | −5.559 | 36.125 | 1.00 | 34.61 | 6 |
| ATOM | 3582 | CD2 | LEU | B | 184 | 76.748 | −7.838 | 35.853 | 1.00 | 34.57 | 6 |
| ATOM | 3583 | N | ALA | B | 185 | 72.466 | −5.818 | 34.204 | 1.00 | 32.96 | 7 |
| ATOM | 3584 | CA | ALA | B | 185 | 72.099 | −5.821 | 32.780 | 1.00 | 33.17 | 6 |
| ATOM | 3585 | C | ALA | B | 185 | 73.053 | −6.670 | 31.950 | 1.00 | 35.69 | 6 |
| ATOM | 3586 | O | ALA | B | 185 | 74.281 | −6.510 | 32.057 | 1.00 | 35.57 | 8 |
| ATOM | 3587 | CB | ALA | B | 185 | 72.076 | −4.368 | 32.316 | 1.00 | 29.95 | 6 |
| ATOM | 1443 | N | LEU | B | 186 | 72.752 | −7.823 | 31.203 | 1.00 | 16.87 | |
| ATOM | 1444 | CA | LEU | B | 186 | 73.699 | −8.676 | 30.476 | 1.00 | 16.99 | |
| ATOM | 1445 | O | LEU | B | 186 | 74.354 | −7.793 | 29.406 | 1.00 | 17.67 | |
| ATOM | 1446 | O | LEU | B | 186 | 73.662 | −7.050 | 28.666 | 1.00 | 20.34 | |
| ATOM | 1447 | CB | LEU | B | 186 | 73.001 | −9.890 | 29.872 | 1.00 | 16.87 | |
| ATOM | 1448 | CG | LEU | B | 186 | 72.315 | −10.841 | 30.851 | 1.00 | 18.67 | |
| ATOM | 1449 | CD1 | LEU | B | 186 | 71.803 | −12.062 | 30.097 | 1.00 | 20.67 | |
| ATOM | 1450 | CD2 | LEU | B | 186 | 73.289 | −11.257 | 31.936 | 1.00 | 17.31 | |
| ATOM | 1451 | N | SER | B | 187 | 75.650 | −7.991 | 29.285 | 1.00 | 18.83 | |
| ATOM | 1452 | CA | SER | B | 187 | 76.407 | −7.179 | 28.327 | 1.00 | 17.18 | |
| ATOM | 1453 | C | SER | B | 187 | 77.754 | −7.771 | 28.079 | 1.00 | 17.64 | |
| ATOM | 1454 | O | SER | B | 187 | 78.405 | −8.305 | 28.987 | 1.00 | 18.63 | |
| ATOM | 1455 | CB | SER | B | 187 | 76.597 | −5.762 | 28.933 | 1.00 | 20.23 | |
| ATOM | 1456 | OG | SER | B | 187 | 77.485 | −4.989 | 28.093 | 1.00 | 20.91 | |
| ATOM | 1457 | N | SER | B | 188 | 78.290 | −7.564 | 26.832 | 1.00 | 17.55 | |
| ATOM | 1458 | CA | SER | B | 188 | 79.706 | −7.917 | 26.649 | 1.00 | 17.70 | |
| ATOM | 1459 | C | SER | B | 188 | 80.653 | −7.182 | 27.579 | 1.00 | 17.74 | |
| ATOM | 1460 | O | SER | B | 188 | 81.764 | −7.648 | 27.944 | 1.00 | 18.92 | |
| ATOM | 1461 | CB | SER | B | 188 | 80.127 | −7.598 | 25.196 | 1.00 | 19.73 | |
| ATOM | 1462 | OG | SER | B | 188 | 79.893 | −6.208 | 24.915 | 1.00 | 20.84 | |
| ATOM | 1463 | N | ARG | B | 189 | 80.298 | −6.012 | 28.096 | 1.00 | 18.16 | |
| ATOM | 1464 | CA | ARG | B | 189 | 81.104 | −5.205 | 28.988 | 1.00 | 19.85 | |
| ATOM | 1465 | C | ARG | B | 189 | 81.386 | −5.989 | 30.311 | 1.00 | 20.33 | |
| ATOM | 1466 | O | ARG | B | 189 | 82.356 | −5.612 | 30.969 | 1.00 | 21.91 | |
| ATOM | 1467 | CB | ARG | B | 189 | 80.426 | −3.848 | 29.284 | 1.00 | 20.55 | |
| ATOM | 1468 | CG | ARG | B | 189 | 80.245 | −3.075 | 27.973 | 1.00 | 22.89 | |
| ATOM | 1469 | CD | ARG | B | 189 | 79.609 | −1.707 | 28.273 | 1.00 | 23.21 | |

TABLE 1-continued

| ATOM | 1470 | NE  | ARG | B | 189 | 79.461 | -1.073  | 26.939 | 1.00 | 25.97 |   |
|------|------|-----|-----|---|-----|--------|---------|--------|------|-------|---|
| ATOM | 1471 | CZ  | ARG | B | 189 | 79.880 | 0.157   | 26.683 | 1.00 | 28.29 |   |
| ATOM | 1472 | NH1 | ARG | B | 189 | 80.387 | 0.915   | 27.617 | 1.00 | 26.60 |   |
| ATOM | 1473 | NH2 | ARG | B | 189 | 79.714 | 0.627   | 25.429 | 1.00 | 28.41 |   |
| ATOM | 1474 | N   | ASN | B | 190 | 80.441 | -6.790  | 30.763 | 1.00 | 19.42 |   |
| ATOM | 1475 | CA  | ASN | B | 190 | 80.639 | -7.442  | 32.041 | 1.00 | 19.64 |   |
| ATOM | 1476 | C   | ASN | B | 190 | 81.891 | -8.271  | 32.059 | 1.00 | 22.61 |   |
| ATOM | 1477 | O   | ASN | B | 190 | 82.467 | -8.717  | 33.097 | 1.00 | 23.27 |   |
| ATOM | 1478 | CB  | ASN | B | 190 | 79.437 | -8.347  | 32.355 | 1.00 | 19.54 |   |
| ATOM | 1479 | CG  | ASN | B | 190 | 78.168 | -7.518  | 32.494 | 1.00 | 21.41 |   |
| ATOM | 1480 | OD1 | ASN | B | 190 | 77.045 | -8.077  | 32.323 | 1.00 | 21.40 |   |
| ATOM | 1481 | ND2 | ASN | B | 190 | 78.310 | -6.244  | 32.814 | 1.00 | 19.16 |   |
| ATOM | 1497 | N   | GLY | B | 191 | 82.333 | -8.712  | 30.735 | 1.00 | 27.44 |   |
| ATOM | 1498 | CA  | GLY | B | 191 | 83.554 | -9.514  | 30.632 | 1.00 | 28.04 |   |
| ATOM | 1499 | C   | GLY | B | 191 | 84.823 | -8.796  | 31.035 | 1.00 | 29.70 |   |
| ATOM | 1500 | O   | GLY | B | 191 | 85.815 | -9.487  | 31.266 | 1.00 | 31.47 |   |
| ATOM | 1482 | N   | TYR | B | 192 | 84.825 | -7.581  | 31.228 | 1.00 | 26.92 |   |
| ATOM | 1483 | CA  | TYR | B | 192 | 86.032 | -6.786  | 31.629 | 1.00 | 29.88 |   |
| ATOM | 1484 | C   | TYR | B | 192 | 86.854 | -6.581  | 33.125 | 1.00 | 29.91 |   |
| ATOM | 1485 | O   | TYR | B | 192 | 87.053 | -5.998  | 33.601 | 1.00 | 34.28 |   |
| ATOM | 1486 | CB  | TYR | B | 192 | 86.154 | -5.424  | 30.922 | 1.00 | 30.32 |   |
| ATOM | 1487 | CG  | TYR | B | 192 | 86.340 | -5.687  | 29.438 | 1.00 | 32.17 |   |
| ATOM | 1488 | CD1 | TYR | B | 192 | 85.211 | -5.943  | 28.667 | 1.00 | 32.38 |   |
| ATOM | 1489 | CD2 | TYR | B | 192 | 87.596 | -5.764  | 28.842 | 1.00 | 34.00 |   |
| ATOM | 1490 | CE1 | TYR | B | 192 | 85.313 | -6.234  | 27.337 | 1.00 | 35.21 |   |
| ATOM | 1491 | CE2 | TYR | B | 192 | 87.703 | -6.056  | 27.486 | 1.00 | 34.55 |   |
| ATOM | 1492 | CZ  | TYR | B | 192 | 86.578 | -6.276  | 26.747 | 1.00 | 36.66 |   |
| ATOM | 1493 | OH  | TYR | B | 192 | 86.631 | -6.577  | 25.395 | 1.00 | 38.33 |   |
| ATOM | 1494 | N   | LEU | B | 193 | 85.033 | -7.028  | 33.865 | 1.00 | 28.20 |   |
| ATOM | 1495 | CA  | LEU | B | 193 | 85.075 | -6.900  | 35.299 | 1.00 | 26.63 |   |
| ATOM | 1496 | C   | LEU | B | 193 | 85.870 | -7.994  | 35.986 | 1.00 | 27.15 |   |
| ATOM | 1497 | O   | LEU | B | 193 | 85.690 | -9.155  | 35.614 | 1.00 | 28.28 |   |
| ATOM | 1498 | CB  | LEU | B | 193 | 83.651 | -6.979  | 35.888 | 1.00 | 26.20 |   |
| ATOM | 1499 | CG  | LEU | B | 193 | 82.648 | -5.971  | 35.339 | 1.00 | 25.58 |   |
| ATOM | 1500 | CD1 | LEU | B | 193 | 81.223 | -6.375  | 35.649 | 1.00 | 24.08 |   |
| ATOM | 1501 | CD2 | LEU | B | 193 | 82.909 | -4.563  | 35.910 | 1.00 | 27.77 |   |
| ATOM | 1502 | N   | THR | B | 194 | 86.596 | -7.704  | 37.090 | 1.00 | 28.42 |   |
| ATOM | 1503 | CA  | THR | B | 194 | 87.177 | -8.819  | 37.838 | 1.00 | 27.62 |   |
| ATOM | 1504 | C   | THR | B | 194 | 86.087 | -9.564  | 38.585 | 1.00 | 25.74 |   |
| ATOM | 1505 | O   | THR | B | 194 | 84.983 | -8.990  | 38.712 | 1.00 | 26.48 |   |
| ATOM | 1506 | CB  | THR | B | 194 | 88.236 | -8.313  | 38.835 | 1.00 | 29.34 |   |
| ATOM | 1507 | OG1 | THR | B | 194 | 87.611 | -7.354  | 39.693 | 1.00 | 38.55 |   |
| ATOM | 1508 | CG2 | THR | B | 194 | 89.370 | -7.647  | 38.064 | 1.00 | 32.65 |   |
| ATOM | 3620 | N   | ALA | B | 195 | 86.095 | -11.397 | 38.739 | 1.00 | 45.01 | 7 |
| ATOM | 3621 | CA  | ALA | B | 195 | 85.137 | -12.052 | 39.619 | 1.00 | 45.61 | 6 |
| ATOM | 3622 | C   | ALA | B | 195 | 84.702 | -11.095 | 40.732 | 1.00 | 46.90 | 6 |
| ATOM | 3623 | O   | ALA | B | 195 | 83.510 | -11.093 | 41.082 | 1.00 | 45.91 | 8 |
| ATOM | 3624 | CB  | ALA | B | 195 | 85.717 | -13.336 | 48.196 | 1.00 | 46.79 | 6 |
| ATOM | 3625 | N   | GLU | B | 196 | 85.603 | -18.288 | 41.278 | 1.00 | 47.33 | 7 |
| ATOM | 3626 | CA  | GLU | B | 196 | 85.242 | -9.350  | 42.330 | 1.00 | 48.34 | 6 |
| ATOM | 3627 | C   | GLU | B | 196 | 84.313 | -8.252  | 41.828 | 1.00 | 46.99 | 6 |
| ATOM | 3628 | O   | GLU | B | 196 | 83.325 | -7.912  | 42.497 | 1.00 | 47.72 | 8 |
| ATOM | 3629 | CB  | GLU | B | 196 | 86.459 | -8.634  | 42.959 | 1.00 | 52.20 | 6 |
| ATOM | 3630 | CG  | GLU | B | 196 | 86.011 | -7.646  | 44.018 | 1.00 | 56.19 | 6 |
| ATOM | 3631 | CD  | GLU | B | 196 | 86.989 | -6.639  | 44.543 | 1.00 | 59.41 | 6 |
| ATOM | 3632 | OE1 | GLU | B | 196 | 88.104 | -6.474  | 43.993 | 1.00 | 61.45 | 8 |
| ATOM | 3633 | OE2 | GLU | B | 196 | 86.639 | -5.966  | 45.555 | 1.00 | 61.84 | 8 |
| ATOM | 3634 | N   | GLN | B | 197 | 84.641 | -7.664  | 40.687 | 1.00 | 44.75 | 7 |
| ATOM | 3635 | CA  | GLN | B | 197 | 83.801 | -6.624  | 40.095 | 1.00 | 43.46 | 6 |
| ATOM | 3636 | C   | GLN | B | 197 | 82.428 | -7.188  | 39.782 | 1.00 | 42.72 | 6 |
| ATOM | 3637 | O   | GLN | B | 197 | 81.425 | -6.478  | 39.983 | 1.00 | 41.97 | 8 |
| ATOM | 3638 | CB  | GLN | B | 197 | 84.430 | -6.018  | 38.832 | 1.00 | 43.86 | 6 |
| ATOM | 3639 | CG  | GLN | B | 197 | 85.754 | -5.346  | 39.203 | 1.00 | 46.24 | 6 |
| ATOM | 3640 | CD  | GLN | B | 197 | 86.485 | -4.709  | 38.047 | 1.00 | 48.63 | 6 |
| ATOM | 3641 | OE1 | GLN | B | 197 | 86.387 | -5.148  | 36.902 | 1.00 | 50.12 | 8 |
| ATOM | 3642 | NE2 | GLN | B | 197 | 87.247 | -3.655  | 38.397 | 1.00 | 49.65 | 7 |
| ATOM | 3643 | N   | ARG | B | 198 | 82.339 | -8.436  | 39.342 | 1.00 | 40.11 | 7 |
| ATOM | 3644 | CA  | ARG | B | 198 | 81.024 | -9.023  | 39.025 | 1.00 | 40.65 | 6 |
| ATOM | 3645 | C   | ARG | B | 198 | 80.231 | -9.134  | 40.321 | 1.00 | 40.50 | 6 |
| ATOM | 3646 | O   | ARG | B | 198 | 79.001 | -9.070  | 40.226 | 1.00 | 40.26 | 8 |
| ATOM | 3647 | CB  | ARG | B | 198 | 81.196 | -10.331 | 38.255 | 1.00 | 38.75 | 6 |
| ATOM | 3648 | CG  | ARG | B | 198 | 79.950 | -11.169 | 37.980 | 1.00 | 40.23 | 6 |
| ATOM | 3649 | CD  | ARG | B | 198 | 78.984 | -10.360 | 37.114 | 1.00 | 38.56 | 6 |
| ATOM | 3650 | NE  | ARG | B | 198 | 77.712 | -10.999 | 36.860 | 1.00 | 40.33 | 7 |
| ATOM | 3651 | CZ  | ARG | B | 198 | 76.685 | -10.913 | 37.703 | 1.00 | 38.73 | 6 |
| ATOM | 3652 | NH1 | ARG | B | 198 | 76.828 | -10.212 | 38.843 | 1.00 | 37.38 | 7 |
| ATOM | 3653 | NH2 | ARG | B | 198 | 75.530 | -11.506 | 37.383 | 1.00 | 39.11 | 7 |
| ATOM | 3654 | N   | LYS | B | 199 | 80.821 | -9.198  | 41.506 | 1.00 | 40.18 | 7 |
| ATOM | 3655 | CA  | LYS | B | 199 | 80.067 | -9.237  | 42.738 | 1.00 | 41.84 | 6 |

TABLE 1-continued

| ATOM | 3656 | C | LYS | B | 199 | 79.519 | −7.843 | 43.083 | 1.00 | 39.14 | 6 |
|---|---|---|---|---|---|---|---|---|---|---|---|
| ATOM | 3657 | O | LYS | B | 199 | 78.440 | −7.806 | 43.660 | 1.00 | 39.85 | 8 |
| ATOM | 3658 | CB | LYS | B | 199 | 80.852 | −9.706 | 43.969 | 1.00 | 44.70 | 6 |
| ATOM | 3659 | CG | LYS | B | 199 | 81.675 | −10.963 | 43.783 | 1.00 | 48.43 | 6 |
| ATOM | 3660 | CD | LYS | B | 199 | 82.186 | −11.540 | 45.087 | 1.00 | 50.67 | 6 |
| ATOM | 3661 | CE | LYS | B | 199 | 82.837 | −10.559 | 46.037 | 1.00 | 52.79 | 6 |
| ATOM | 3662 | NZ | LYS | B | 199 | 84.285 | −10.286 | 45.751 | 1.00 | 55.36 | 7 |
| ATOM | 3663 | N | ILE | B | 200 | 80.245 | −6.791 | 42.754 | 1.00 | 36.48 | 7 |
| ATOM | 3664 | CA | ILE | B | 200 | 79.815 | −5.425 | 43.013 | 1.00 | 36.30 | 6 |
| ATOM | 3665 | C | ILE | B | 200 | 78.867 | −4.836 | 41.964 | 1.00 | 34.09 | 6 |
| ATOM | 3666 | O | ILE | B | 200 | 77.970 | −4.048 | 42.300 | 1.00 | 31.98 | 8 |
| ATOM | 3667 | CB | ILE | B | 200 | 81.036 | −4.477 | 43.052 | 1.00 | 37.30 | 6 |
| ATOM | 3668 | CG1 | ILE | B | 200 | 81.938 | −4.835 | 44.261 | 1.00 | 39.39 | 6 |
| ATOM | 3669 | CG2 | ILE | B | 200 | 80.668 | −2.995 | 43.087 | 1.00 | 38.32 | 6 |
| ATOM | 3670 | CD1 | ILE | B | 200 | 83.228 | −4.024 | 44.171 | 1.00 | 39.23 | 6 |
| ATOM | 3671 | N | ALA | B | 201 | 78.923 | −5.343 | 40.749 | 1.00 | 31.89 | 7 |
| ATOM | 3672 | CA | ALA | B | 201 | 78.199 | −4.790 | 39.605 | 1.00 | 30.33 | 6 |
| ATOM | 3673 | C | ALA | B | 201 | 76.683 | −4.738 | 39.757 | 1.00 | 30.26 | 6 |
| ATOM | 3674 | O | ALA | B | 201 | 76.126 | −3.736 | 39.270 | 1.00 | 28.19 | 8 |
| ATOM | 3675 | CB | ALA | B | 201 | 78.588 | −5.549 | 38.327 | 1.00 | 31.33 | 6 |
| ATOM | 3676 | N | PRO | B | 202 | 75.978 | −5.632 | 40.395 | 1.00 | 29.89 | 7 |
| ATOM | 3677 | CA | PRO | B | 202 | 74.538 | −5.483 | 40.618 | 1.00 | 31.17 | 6 |
| ATOM | 3678 | C | PRO | B | 202 | 74.130 | −4.220 | 41.350 | 1.00 | 30.89 | 6 |
| ATOM | 3679 | O | PRO | B | 202 | 72.942 | −3.842 | 41.356 | 1.00 | 33.70 | 8 |
| ATOM | 3680 | CB | PRO | B | 202 | 74.171 | −6.714 | 41.422 | 1.00 | 31.80 | 6 |
| ATOM | 3681 | CG | PRO | B | 202 | 75.203 | −7.727 | 41.041 | 1.00 | 32.51 | 6 |
| ATOM | 3682 | CD | PRO | B | 202 | 76.485 | −6.926 | 40.935 | 1.00 | 30.92 | 6 |
| ATOM | 3683 | N | GLY | B | 203 | 75.003 | −3.520 | 42.079 | 1.00 | 30.61 | 7 |
| ATOM | 3684 | CA | GLY | B | 203 | 74.724 | −2.274 | 42.775 | 1.00 | 29.71 | 6 |
| ATOM | 3685 | C | GLY | B | 203 | 74.185 | −1.180 | 41.844 | 1.00 | 29.14 | 6 |
| ATOM | 3686 | O | GLY | B | 203 | 73.382 | −0.333 | 42.278 | 1.00 | 27.39 | 8 |
| ATOM | 3687 | N | LEU | B | 204 | 74.569 | −1.208 | 40.562 | 1.00 | 26.29 | 7 |
| ATOM | 3688 | CA | LEU | B | 204 | 74.116 | −0.193 | 39.634 | 1.00 | 27.87 | 6 |
| ATOM | 3689 | C | LEU | B | 204 | 72.595 | −0.279 | 39.482 | 1.00 | 26.50 | 6 |
| ATOM | 3690 | O | LEU | B | 204 | 71.878 | 0.736 | 39.532 | 1.00 | 26.32 | 8 |
| ATOM | 3691 | CB | LEU | B | 204 | 74.789 | −0.294 | 38.259 | 1.00 | 28.45 | 6 |
| ATOM | 3692 | CG | LEU | B | 204 | 74.362 | 0.731 | 37.212 | 1.00 | 29.87 | 6 |
| ATOM | 3693 | CD1 | LEU | B | 204 | 74.600 | 2.168 | 37.697 | 1.00 | 31.40 | 6 |
| ATOM | 3694 | CD2 | LEU | B | 204 | 75.087 | 0.559 | 35.887 | 1.00 | 32.44 | 6 |
| ATOM | 3695 | N | TYR | B | 205 | 72.132 | −1.509 | 39.245 | 1.00 | 26.81 | 7 |
| ATOM | 3696 | CA | TYR | B | 205 | 70.667 | −1.619 | 39.081 | 1.00 | 28.26 | 6 |
| ATOM | 3697 | C | TYR | B | 205 | 69.946 | −1.322 | 40.382 | 1.00 | 28.28 | 6 |
| ATOM | 3698 | O | TYR | B | 205 | 68.816 | −0.829 | 40.340 | 1.00 | 27.87 | 8 |
| ATOM | 3699 | CB | TYR | B | 205 | 70.328 | −2.995 | 38.524 | 1.00 | 27.88 | 6 |
| ATOM | 3700 | CG | TYR | B | 205 | 68.848 | −3.144 | 38.265 | 1.00 | 30.23 | 6 |
| ATOM | 3701 | CD1 | TYR | B | 205 | 68.193 | −2.323 | 37.360 | 1.00 | 30.41 | 6 |
| ATOM | 3702 | CD2 | TYR | B | 205 | 68.111 | −4.106 | 38.935 | 1.00 | 32.30 | 6 |
| ATOM | 3703 | CE1 | TYR | B | 205 | 66.838 | −2.493 | 37.115 | 1.00 | 31.17 | 6 |
| ATOM | 3704 | CE2 | TYR | B | 205 | 66.743 | −4.304 | 38.698 | 1.00 | 32.16 | 6 |
| ATOM | 3705 | CZ | TYR | B | 205 | 66.134 | −3.480 | 37.784 | 1.00 | 33.79 | 6 |
| ATOM | 3706 | OH | TYR | B | 205 | 64.774 | −3.587 | 37.529 | 1.00 | 36.69 | 8 |
| ATOM | 3707 | N | LYS | B | 206 | 70.554 | −1.567 | 41.568 | 1.00 | 27.79 | 7 |
| ATOM | 3708 | CA | LYS | B | 206 | 69.949 | −1.137 | 42.812 | 1.00 | 28.48 | 6 |
| ATOM | 3709 | C | LYS | B | 206 | 69.794 | 0.379 | 42.849 | 1.00 | 26.89 | 6 |
| ATOM | 3710 | O | LYS | B | 206 | 68.729 | 0.847 | 43.295 | 1.00 | 26.06 | 8 |
| ATOM | 3711 | CB | LYS | B | 206 | 70.814 | −1.650 | 44.005 | 1.00 | 31.12 | 6 |
| ATOM | 3712 | CG | LYS | B | 206 | 70.702 | −3.191 | 44.056 | 1.00 | 35.12 | 6 |
| ATOM | 3713 | CD | LYS | B | 206 | 71.439 | −3.803 | 45.235 | 1.00 | 38.80 | 6 |
| ATOM | 3714 | CE | LYS | B | 206 | 71.267 | −5.329 | 45.230 | 1.00 | 41.11 | 6 |
| ATOM | 3715 | NZ | LYS | B | 206 | 72.055 | −5.939 | 46.361 | 1.00 | 44.45 | 7 |
| ATOM | 3716 | N | VAL | B | 207 | 70.786 | 1.151 | 42.450 | 1.00 | 24.10 | 7 |
| ATOM | 3717 | CA | VAL | B | 207 | 70.698 | 2.623 | 42.437 | 1.00 | 23.57 | 6 |
| ATOM | 3718 | C | VAL | B | 207 | 69.692 | 3.075 | 41.353 | 1.00 | 25.00 | 6 |
| ATOM | 3719 | O | VAL | B | 207 | 68.785 | 3.854 | 41.709 | 1.00 | 25.30 | 8 |
| ATOM | 3720 | CB | VAL | B | 207 | 72.075 | 3.263 | 42.273 | 1.00 | 25.80 | 6 |
| ATOM | 3721 | CG1 | VAL | B | 207 | 71.998 | 4.765 | 42.088 | 1.00 | 24.61 | 6 |
| ATOM | 3722 | CG2 | VAL | B | 207 | 72.941 | 2.900 | 43.507 | 1.00 | 26.07 | 6 |
| ATOM | 3723 | N | LEU | B | 208 | 69.679 | 2.455 | 40.200 | 1.00 | 25.37 | 7 |
| ATOM | 3724 | CA | LEU | B | 208 | 68.640 | 2.782 | 39.185 | 1.00 | 25.10 | 6 |
| ATOM | 3725 | C | LEU | B | 208 | 67.243 | 2.553 | 39.694 | 1.00 | 24.92 | 6 |
| ATOM | 3726 | O | LEU | B | 208 | 66.280 | 3.338 | 39.468 | 1.00 | 25.42 | 8 |
| ATOM | 3727 | CB | LEU | B | 208 | 68.989 | 1.910 | 37.985 | 1.00 | 26.66 | 6 |
| ATOM | 3728 | CG | LEU | B | 208 | 68.261 | 2.079 | 36.661 | 1.00 | 30.34 | 6 |
| ATOM | 3729 | CD1 | LEU | B | 208 | 68.389 | 3.525 | 36.163 | 1.00 | 32.04 | 6 |
| ATOM | 3730 | CD2 | LEU | B | 208 | 68.793 | 1.084 | 35.646 | 1.00 | 31.70 | 6 |
| ATOM | 3731 | N | SER | B | 209 | 67.019 | 1.416 | 40.355 | 1.00 | 26.22 | 7 |
| ATOM | 3732 | CA | SER | B | 209 | 65.726 | 1.035 | 40.907 | 1.00 | 29.64 | 6 |
| ATOM | 3733 | C | SER | B | 209 | 65.293 | 2.025 | 41.988 | 1.00 | 30.28 | 6 |
| ATOM | 3734 | O | SER | B | 209 | 64.107 | 2.380 | 42.055 | 1.00 | 30.20 | 8 |

TABLE 1-continued

| | | | | | | | | | | |
|---|---|---|---|---|---|---|---|---|---|---|
| ATOM | 3735 | CB | SER | B | 209 | 65.710 | −0.386 | 41.480 | 1.00 | 30.00 | 6 |
| ATOM | 3736 | OG | SER | B | 209 | 65.923 | −1.312 | 40.425 | 1.00 | 32.79 | 8 |
| ATOM | 3737 | N | SER | B | 210 | 66.262 | 2.526 | 42.772 | 1.00 | 29.87 | 7 |
| ATOM | 3738 | CA | SER | B | 210 | 65.938 | 3.533 | 43.764 | 1.00 | 30.73 | 6 |
| ATOM | 3739 | C | SER | B | 210 | 65.469 | 4.839 | 43.141 | 1.00 | 28.63 | 6 |
| ATOM | 3740 | O | SER | B | 210 | 64.551 | 5.481 | 43.694 | 1.00 | 30.02 | 8 |
| ATOM | 3741 | CB | SER | B | 210 | 67.171 | 3.837 | 44.652 | 1.00 | 33.65 | 6 |
| ATOM | 3742 | OG | SER | B | 210 | 66.847 | 4.965 | 45.451 | 1.00 | 38.88 | 8 |
| ATOM | 3743 | N | ILE | B | 211 | 66.115 | 5.259 | 42.067 | 1.00 | 26.67 | 7 |
| ATOM | 3744 | CA | ILE | B | 211 | 65.727 | 6.462 | 41.337 | 1.00 | 26.97 | 6 |
| ATOM | 3745 | C | ILE | B | 211 | 64.283 | 6.278 | 40.860 | 1.00 | 29.84 | 6 |
| ATOM | 3746 | O | ILE | B | 211 | 63.426 | 7.151 | 41.011 | 1.00 | 29.98 | 8 |
| ATOM | 3747 | CB | ILE | B | 211 | 66.584 | 6.759 | 40.124 | 1.00 | 26.70 | 6 |
| ATOM | 3748 | CC1 | ILE | B | 211 | 68.031 | 7.036 | 40.607 | 1.00 | 26.03 | 6 |
| ATOM | 3749 | CG2 | ILE | B | 211 | 66.046 | 7.935 | 39.290 | 1.00 | 27.20 | 6 |
| ATOM | 3750 | CD1 | ILE | B | 211 | 69.081 | 7.179 | 39.551 | 1.00 | 25.43 | 6 |
| ATOM | 3751 | N | ALA | B | 212 | 64.062 | 5.111 | 40.250 | 1.00 | 29.63 | 7 |
| ATOM | 3752 | CA | ALA | B | 212 | 62.703 | 4.840 | 39.732 | 1.00 | 31.76 | 6 |
| ATOM | 3753 | C | ALA | B | 212 | 61.680 | 4.874 | 40.827 | 1.00 | 33.70 | 6 |
| ATOM | 3754 | O | ALA | B | 212 | 60.601 | 5.488 | 40.669 | 1.00 | 35.70 | 8 |
| ATOM | 3755 | CB | ALA | B | 212 | 62.713 | 3.477 | 39.041 | 1.00 | 30.18 | 6 |
| ATOM | 3756 | N | ASP | B | 213 | 61.985 | 4.267 | 41.976 | 1.00 | 35.57 | 7 |
| ATOM | 3757 | CA | ASP | B | 213 | 61.051 | 4.267 | 43.097 | 1.00 | 37.44 | 6 |
| ATOM | 3758 | C | ASP | B | 213 | 60.766 | 5.705 | 43.541 | 1.00 | 38.51 | 6 |
| ATOM | 3759 | O | ASP | B | 213 | 59.588 | 5.981 | 43.821 | 1.00 | 39.54 | 8 |
| ATOM | 3760 | CB | ASP | B | 213 | 61.540 | 3.469 | 44.294 | 1.00 | 40.83 | 6 |
| ATOM | 3761 | CG | ASP | B | 213 | 61.594 | 1.978 | 44.075 | 1.00 | 43.42 | 6 |
| ATOM | 3762 | OD1 | ASP | B | 213 | 60.952 | 1.468 | 43.127 | 1.00 | 44.23 | 8 |
| ATOM | 3763 | OD2 | ASP | B | 213 | 62.266 | 1.294 | 44.889 | 1.00 | 45.13 | 8 |
| ATOM | 3764 | N | LYS | B | 214 | 61.739 | 6.605 | 43.622 | 1.00 | 36.89 | 7 |
| ATOM | 3765 | CA | LYS | B | 214 | 61.439 | 7.980 | 44.023 | 1.00 | 37.14 | 6 |
| ATOM | 3766 | C | LYS | B | 214 | 60.553 | 8.695 | 43.015 | 1.00 | 38.10 | 6 |
| ATOM | 3767 | O | LYS | B | 214 | 59.689 | 9.521 | 43.354 | 1.00 | 38.08 | 8 |
| ATOM | 3768 | CB | LYS | B | 214 | 62.734 | 8.783 | 44.210 | 1.00 | 35.35 | 6 |
| ATOM | 3769 | CG | LYS | B | 214 | 63.592 | 8.274 | 45.353 | 1.00 | 34.18 | 6 |
| ATOM | 3770 | CD | LYS | B | 214 | 64.924 | 9.016 | 45.447 | 1.00 | 33.76 | 6 |
| ATOM | 3771 | CE | LYS | B | 214 | 65.708 | 8.660 | 46.703 | 1.00 | 35.46 | 6 |
| ATOM | 3772 | NZ | LYS | B | 214 | 66.968 | 9.471 | 46.836 | 1.00 | 33.81 | 7 |
| ATOM | 3773 | N | LEU | B | 215 | 60.824 | 8.468 | 41.720 | 1.00 | 37.41 | 7 |
| ATOM | 3774 | CA | LEU | B | 215 | 60.005 | 9.116 | 40.679 | 1.00 | 38.52 | 6 |
| ATOM | 3775 | C | LEU | B | 215 | 58.575 | 8.587 | 40.776 | 1.00 | 41.72 | 6 |
| ATOM | 3776 | O | LEU | B | 215 | 57.606 | 9.372 | 40.631 | 1.00 | 41.98 | 8 |
| ATOM | 3777 | CB | LEU | B | 215 | 60.604 | 8.904 | 39.310 | 1.00 | 37.43 | 6 |
| ATOM | 3778 | CG | LEU | B | 215 | 61.897 | 9.594 | 38.900 | 1.00 | 36.45 | 6 |
| ATOM | 3779 | CD1 | LEU | B | 215 | 62.313 | 9.105 | 37.529 | 1.00 | 36.60 | 6 |
| ATOM | 3780 | CD2 | LEU | B | 215 | 61.767 | 11.119 | 38.869 | 1.00 | 37.66 | 6 |
| ATOM | 3781 | N | GLN | B | 216 | 58.409 | 7.300 | 41.061 | 1.00 | 42.52 | 7 |
| ATOM | 3782 | CA | CLN | B | 216 | 57.077 | 6.739 | 41.231 | 1.00 | 46.61 | 6 |
| ATOM | 3783 | C | GLN | B | 216 | 56.353 | 7.337 | 42.439 | 1.00 | 47.19 | 6 |
| ATOM | 3784 | O | GLN | B | 216 | 55.125 | 7.438 | 42.427 | 1.00 | 48.78 | 8 |
| ATOM | 3785 | CB | GLN | B | 216 | 57.069 | 5.232 | 41.449 | 1.00 | 48.29 | 6 |
| ATOM | 3786 | CG | GLN | B | 216 | 57.290 | 4.444 | 40.180 | 1.00 | 53.02 | 6 |
| ATOM | 3787 | CD | GLN | B | 216 | 56.839 | 3.002 | 40.322 | 1.00 | 54.94 | 6 |
| ATOM | 3788 | OE1 | GLN | B | 216 | 55.736 | 2.658 | 39.896 | 1.00 | 57.54 | 8 |
| ATOM | 3789 | NE2 | GLN | B | 216 | 57.710 | 2.210 | 40.927 | 1.00 | 55.50 | 7 |
| ATOM | 3790 | N | ALA | B | 217 | 57.092 | 7.678 | 43.486 | 1.00 | 46.68 | 7 |
| ATOM | 3791 | CA | ALA | B | 217 | 56.502 | 8.282 | 44.665 | 1.00 | 47.12 | 6 |
| ATOM | 3792 | C | ALA | B | 217 | 56.114 | 9.746 | 44.444 | 1.00 | 46.63 | 6 |
| ATOM | 3793 | O | ALA | B | 217 | 55.403 | 10.274 | 45.308 | 1.00 | 47.81 | 8 |
| ATOM | 3794 | CB | ALA | B | 217 | 57.460 | 8.177 | 45.853 | 1.00 | 46.15 | 6 |
| ATOM | 3795 | N | GLY | B | 218 | 56.519 | 10.406 | 43.374 | 1.00 | 45.52 | 7 |
| ATOM | 3796 | CA | GLY | B | 218 | 56.156 | 11.790 | 43.127 | 1.00 | 45.00 | 6 |
| ATOM | 3797 | C | GLY | B | 218 | 57.308 | 12.764 | 43.230 | 1.00 | 45.03 | 6 |
| ATOM | 3798 | O | GLY | B | 218 | 57.199 | 13.970 | 42.964 | 1.00 | 45.86 | 8 |
| ATOM | 3799 | N | GLU | B | 219 | 58.491 | 12.255 | 43.605 | 1.00 | 43.84 | 7 |
| ATOM | 3800 | CA | GLU | B | 219 | 59.664 | 13.121 | 43.708 | 1.00 | 43.09 | 6 |
| ATOM | 3801 | C | GLU | B | 219 | 60.052 | 13.746 | 42.388 | 1.00 | 40.95 | 6 |
| ATOM | 3802 | O | GLU | B | 219 | 60.141 | 13.088 | 41.333 | 1.00 | 39.42 | 8 |
| ATOM | 3803 | CB | GLU | B | 219 | 60.804 | 12.270 | 44.287 | 1.00 | 45.88 | 6 |
| ATOM | 3804 | CG | GLU | B | 219 | 61.238 | 12.787 | 45.633 | 1.00 | 50.50 | 6 |
| ATOM | 3805 | CD | GLU | B | 219 | 62.401 | 12.048 | 46.269 | 1.00 | 52.33 | 6 |
| ATOM | 3806 | OE1 | GLU | B | 219 | 62.065 | 11.125 | 47.052 | 1.00 | 54.16 | 8 |
| ATOM | 3807 | OE2 | GLU | B | 219 | 63.564 | 12.388 | 46.016 | 1.00 | 53.19 | 8 |
| ATOM | 3808 | N | ARG | B | 220 | 60.247 | 15.065 | 42.373 | 1.00 | 38.26 | 7 |
| ATOM | 3809 | CA | ARG | B | 220 | 60.572 | 15.785 | 41.151 | 1.00 | 38.87 | 6 |
| ATOM | 3810 | C | ARG | B | 220 | 61.803 | 16.664 | 41.272 | 1.00 | 38.94 | 6 |
| ATOM | 3811 | O | ARG | B | 220 | 62.119 | 17.358 | 40.305 | 1.00 | 39.85 | 8 |
| ATOM | 3812 | CB | ARG | B | 220 | 59.396 | 16.676 | 40.670 | 1.00 | 39.03 | 6 |
| ATOM | 3813 | CG | ARG | B | 220 | 58.187 | 15.871 | 40.179 | 1.00 | 39.62 | 6 |

TABLE 1-continued

| ATOM | 3814 | CD  | ARG | B | 220 | 58.562 | 15.016 | 38.972 | 1.00 | 39.07 | 6 |
|------|------|-----|-----|---|-----|--------|--------|--------|------|-------|---|
| ATOM | 3815 | NE  | ARG | B | 220 | 57.490 | 14.110 | 38.632 | 1.00 | 39.25 | 7 |
| ATOM | 3816 | CZ  | ARG | B | 220 | 57.184 | 12.886 | 39.019 | 1.00 | 39.75 | 6 |
| ATOM | 3817 | NH1 | ARG | B | 220 | 57.946 | 12.211 | 39.893 | 1.00 | 39.07 | 7 |
| ATOM | 3818 | NH2 | ARG | B | 220 | 56.073 | 12.331 | 38.529 | 1.00 | 38.25 | 7 |
| ATOM | 3819 | N   | ASP | B | 221 | 62.564 | 16.577 | 42.361 | 1.00 | 38.00 | 7 |
| ATOM | 3820 | CA  | ASP | B | 221 | 63.792 | 17.372 | 42.433 | 1.00 | 38.21 | 6 |
| ATOM | 3821 | C   | ASP | B | 221 | 64.911 | 16.557 | 41.791 | 1.00 | 36.88 | 6 |
| ATOM | 3822 | O   | ASP | B | 221 | 65.691 | 15.899 | 42.474 | 1.00 | 36.84 | 8 |
| ATOM | 3823 | CB  | ASP | B | 221 | 64.146 | 17.760 | 43.866 | 1.00 | 40.08 | 6 |
| ATOM | 3824 | CG  | ASP | B | 221 | 65.276 | 18.775 | 43.867 | 1.00 | 40.98 | 6 |
| ATOM | 3825 | OD1 | ASP | B | 221 | 66.189 | 18.865 | 43.017 | 1.00 | 40.33 | 8 |
| ATOM | 3826 | OD2 | ASP | B | 221 | 65.237 | 19.583 | 44.824 | 1.00 | 45.27 | 8 |
| ATOM | 3827 | N   | LEU | B | 222 | 64.940 | 16.559 | 40.472 | 1.00 | 36.51 | 7 |
| ATOM | 3828 | CA  | LEU | B | 222 | 65.839 | 15.703 | 39.697 | 1.00 | 35.37 | 6 |
| ATOM | 3829 | C   | LEU | B | 222 | 67.312 | 15.852 | 40.004 | 1.00 | 34.02 | 6 |
| ATOM | 3830 | O   | LEU | B | 222 | 68.053 | 14.855 | 40.041 | 1.00 | 31.24 | 8 |
| ATOM | 3831 | CB  | LEU | B | 222 | 65.575 | 15.983 | 38.203 | 1.00 | 35.83 | 6 |
| ATOM | 3832 | CG  | LEU | B | 222 | 64.144 | 15.686 | 37.720 | 1.00 | 38.11 | 6 |
| ATOM | 3833 | CD1 | LEU | B | 222 | 64.187 | 15.314 | 36.239 | 1.00 | 38.86 | 6 |
| ATOM | 3834 | CD2 | LEU | B | 222 | 63.430 | 14.608 | 38.526 | 1.00 | 36.91 | 6 |
| ATOM | 3835 | N   | ASP | B | 223 | 67.763 | 17.101 | 40.153 | 1.00 | 33.49 | 7 |
| ATOM | 3836 | CA  | ASP | B | 223 | 69.154 | 17.349 | 40.442 | 1.00 | 33.63 | 6 |
| ATOM | 3837 | C   | ASP | B | 223 | 69.524 | 16.656 | 41.751 | 1.00 | 31.73 | 6 |
| ATOM | 3838 | O   | ASP | B | 223 | 70.620 | 16.132 | 41.870 | 1.00 | 31.34 | 8 |
| ATOM | 3839 | CB  | ASP | B | 223 | 69.494 | 18.827 | 40.653 | 1.00 | 34.33 | 6 |
| ATOM | 3840 | N   | GLU | B | 224 | 68.635 | 16.790 | 42.733 | 1.00 | 31.71 | 7 |
| ATOM | 3841 | CA  | GLU | B | 224 | 68.909 | 16.161 | 44.035 | 1.00 | 31.51 | 6 |
| ATOM | 3842 | C   | GLU | B | 224 | 68.836 | 14.656 | 43.974 | 1.00 | 29.02 | 6 |
| ATOM | 3843 | O   | GLU | B | 224 | 69.667 | 13.945 | 44.502 | 1.00 | 28.00 | 8 |
| ATOM | 3844 | CB  | GLU | B | 224 | 67.907 | 16.696 | 45.089 | 1.00 | 34.56 | 6 |
| ATOM | 3845 | CG  | GLU | B | 224 | 68.123 | 16.063 | 46.454 | 1.00 | 37.72 | 6 |
| ATOM | 3846 | CD  | GLU | B | 224 | 69.389 | 16.542 | 47.140 | 1.00 | 42.79 | 6 |
| ATOM | 3847 | OE1 | GLU | B | 224 | 70.120 | 17.403 | 46.574 | 1.00 | 43.28 | 8 |
| ATOM | 3848 | OE2 | GLU | B | 224 | 69.660 | 16.051 | 48.273 | 1.00 | 43.45 | 8 |
| ATOM | 3849 | N   | ILE | B | 225 | 67.863 | 14.079 | 43.231 | 1.00 | 27.24 | 7 |
| ATOM | 3850 | CA  | ILE | B | 225 | 67.835 | 12.642 | 43.056 | 1.00 | 26.19 | 6 |
| ATOM | 3851 | C   | ILE | B | 225 | 69.109 | 12.145 | 42.417 | 1.00 | 25.15 | 6 |
| ATOM | 3852 | O   | ILE | B | 225 | 69.651 | 11.121 | 42.828 | 1.00 | 26.25 | 8 |
| ATOM | 3853 | CB  | ILE | B | 225 | 66.632 | 12.214 | 42.152 | 1.00 | 28.29 | 6 |
| ATOM | 3854 | CG1 | ILE | B | 225 | 65.340 | 12.494 | 42.878 | 1.00 | 29.03 | 6 |
| ATOM | 3855 | CG2 | ILE | B | 225 | 66.803 | 10.740 | 41.776 | 1.00 | 25.65 | 6 |
| ATOM | 3856 | CD1 | ILE | B | 225 | 64.109 | 12.596 | 42.001 | 1.00 | 31.93 | 6 |
| ATOM | 3857 | N   | ILE | B | 226 | 69.578 | 12.801 | 41.373 | 1.00 | 26.43 | 7 |
| ATOM | 3858 | CA  | ILE | B | 226 | 70.786 | 12.406 | 40.641 | 1.00 | 25.84 | 6 |
| ATOM | 3859 | C   | ILE | B | 226 | 72.040 | 12.551 | 41.500 | 1.00 | 27.10 | 6 |
| ATOM | 3860 | O   | ILE | B | 226 | 72.923 | 11.716 | 41.451 | 1.00 | 24.94 | 8 |
| ATOM | 3861 | CB  | ILE | B | 226 | 70.923 | 13.170 | 39.304 | 1.00 | 27.17 | 6 |
| ATOM | 3862 | CG1 | ILE | B | 226 | 69.753 | 12.662 | 38.429 | 1.00 | 27.18 | 6 |
| ATOM | 3863 | CG2 | ILE | B | 226 | 72.280 | 12.981 | 38.632 | 1.00 | 27.48 | 6 |
| ATOM | 3864 | CD1 | ILE | B | 226 | 69.562 | 13.504 | 37.159 | 1.00 | 27.31 | 6 |
| ATOM | 3865 | N   | THR | B | 227 | 72.095 | 13.642 | 42.283 | 1.00 | 25.81 | 7 |
| ATOM | 3866 | CA  | THR | B | 227 | 73.300 | 13.811 | 43.112 | 1.00 | 25.80 | 6 |
| ATOM | 3867 | C   | THR | B | 227 | 73.368 | 12.725 | 44.157 | 1.00 | 24.81 | 6 |
| ATOM | 3868 | O   | THR | B | 227 | 74.457 | 12.188 | 44.484 | 1.00 | 23.72 | 8 |
| ATOM | 3869 | CB  | THR | B | 227 | 73.230 | 15.226 | 43.714 | 1.00 | 25.87 | 6 |
| ATOM | 3870 | OG1 | THR | B | 227 | 73.461 | 16.226 | 42.719 | 1.00 | 27.10 | 8 |
| ATOM | 3871 | CG2 | THR | B | 227 | 74.317 | 15.419 | 44.776 | 1.00 | 30.13 | 6 |
| ATOM | 3872 | N   | ILE | B | 228 | 72.202 | 12.447 | 44.753 | 1.00 | 21.50 | 7 |
| ATOM | 3873 | CA  | ILE | B | 228 | 72.230 | 11.384 | 45.756 | 1.00 | 21.63 | 6 |
| ATOM | 3874 | C   | ILE | B | 228 | 72.645 | 10.046 | 45.160 | 1.00 | 23.87 | 6 |
| ATOM | 3875 | O   | ILE | B | 228 | 73.410 | 9.242  | 45.679 | 1.00 | 22.19 | 8 |
| ATOM | 3876 | CB  | ILE | B | 228 | 70.892 | 11.236 | 46.481 | 1.00 | 21.84 | 6 |
| ATOM | 3877 | CG1 | ILE | B | 228 | 70.746 | 12.501 | 47.397 | 1.00 | 24.08 | 6 |
| ATOM | 3878 | CG2 | ILE | B | 228 | 70.762 | 9.964  | 47.278 | 1.00 | 22.76 | 6 |
| ATOM | 3879 | CD1 | ILE | B | 228 | 69.295 | 12.583 | 47.901 | 1.00 | 26.19 | 6 |
| ATOM | 3880 | N   | ALA | B | 229 | 72.035 | 9.747  | 43.962 | 1.00 | 23.45 | 7 |
| ATOM | 3881 | CA  | ALA | B | 229 | 72.386 | 8.510  | 43.308 | 1.00 | 24.32 | 6 |
| ATOM | 3882 | C   | ALA | B | 229 | 73.835 | 8.419  | 42.943 | 1.00 | 21.10 | 6 |
| ATOM | 3883 | O   | ALA | B | 229 | 74.403 | 7.325  | 43.107 | 1.00 | 23.01 | 8 |
| ATOM | 3884 | CB  | ALA | B | 229 | 71.481 | 8.404  | 42.050 | 1.00 | 22.78 | 6 |
| ATOM | 3885 | N   | GLY | B | 230 | 74.533 | 9.496  | 42.596 | 1.00 | 22.98 | 7 |
| ATOM | 3886 | CA  | GLY | B | 230 | 75.940 | 9.540  | 42.325 | 1.00 | 25.69 | 6 |
| ATOM | 3887 | C   | GLY | B | 230 | 76.731 | 9.266  | 43.636 | 1.00 | 25.98 | 6 |
| ATOM | 3888 | O   | GLY | B | 230 | 77.669 | 8.455  | 43.656 | 1.00 | 23.67 | 8 |
| ATOM | 3889 | N   | GLN | B | 231 | 76.233 | 9.789  | 44.748 | 1.00 | 25.92 | 7 |
| ATOM | 3890 | CA  | GLN | B | 231 | 76.907 | 9.478  | 46.035 | 1.00 | 27.99 | 6 |
| ATOM | 3891 | C   | GLN | B | 231 | 76.700 | 8.048  | 46.427 | 1.00 | 26.47 | 6 |
| ATOM | 3892 | O   | GLN | B | 231 | 77.666 | 7.384  | 46.850 | 1.00 | 25.84 | 8 |

TABLE 1-continued

| ATOM | 3893 | CB  | GLN | B | 231 | 76.407 | 10.471 | 47.120 | 1.00 | 28.03 | 6 |
| ATOM | 3894 | CG  | GLN | B | 231 | 76.834 | 10.043 | 48.531 | 1.00 | 32.38 | 6 |
| ATOM | 3895 | CD  | GLN | B | 231 | 78.316 | 10.219 | 48.756 | 1.00 | 32.95 | 6 |
| ATOM | 3896 | OE1 | GLN | B | 231 | 79.045 | 10.701 | 47.905 | 1.00 | 33.95 | 8 |
| ATOM | 3897 | NE2 | GLN | B | 231 | 78.780 | 9.786  | 49.922 | 1.00 | 36.62 | 7 |
| ATOM | 3898 | N   | GLU | B | 232 | 75.516 | 7.434  | 46.178 | 1.00 | 26.86 | 7 |
| ATOM | 3899 | CA  | GLU | B | 232 | 75.285 | 6.024  | 46.475 | 1.00 | 25.40 | 6 |
| ATOM | 3900 | C   | GLU | B | 232 | 76.193 | 5.139  | 45.605 | 1.00 | 27.57 | 6 |
| ATOM | 3901 | O   | GLU | B | 232 | 76.802 | 4.178  | 46.110 | 1.00 | 28.11 | 8 |
| ATOM | 3902 | CB  | GLU | B | 232 | 73.827 | 5.559  | 46.287 | 1.00 | 27.07 | 6 |
| ATOM | 3903 | CG  | GLU | B | 232 | 72.820 | 6.282  | 47.171 | 1.00 | 30.63 | 6 |
| ATOM | 3904 | CD  | GLU | B | 232 | 71.375 | 5.946  | 46.930 | 1.00 | 34.51 | 6 |
| ATOM | 3905 | OE1 | GLU | B | 232 | 71.033 | 5.379  | 45.860 | 1.00 | 37.23 | 8 |
| ATOM | 3906 | OE2 | GLU | B | 232 | 70.510 | 6.232  | 47.794 | 1.00 | 35.98 | 8 |
| ATOM | 3907 | N   | LEU | B | 233 | 76.346 | 5.489  | 44.313 | 1.00 | 26.60 | 7 |
| ATOM | 3908 | CA  | LEU | B | 233 | 77.272 | 4.700  | 43.490 | 1.00 | 26.30 | 6 |
| ATOM | 3909 | C   | LEU | B | 233 | 78.710 | 4.784  | 44.024 | 1.00 | 28.83 | 6 |
| ATOM | 3910 | O   | LEU | B | 233 | 79.402 | 3.781  | 44.040 | 1.00 | 28.19 | 8 |
| ATOM | 3911 | CB  | LEU | B | 233 | 77.171 | 5.171  | 42.025 | 1.00 | 27.72 | 6 |
| ATOM | 3912 | CG  | LEU | B | 233 | 75.816 | 4.809  | 41.372 | 1.00 | 26.70 | 6 |
| ATOM | 3913 | CD1 | LEU | B | 233 | 75.511 | 5.576  | 40.104 | 1.00 | 27.51 | 6 |
| ATOM | 3914 | CD2 | LEU | B | 233 | 75.819 | 3.312  | 41.048 | 1.00 | 28.08 | 6 |
| ATOM | 3915 | N   | ASN | B | 234 | 79.166 | 6.006  | 44.330 | 1.00 | 31.21 | 7 |
| ATOM | 3916 | CA  | ASN | B | 234 | 80.540 | 6.248  | 44.790 | 1.00 | 32.86 | 6 |
| ATOM | 3917 | C   | ASN | B | 234 | 80.761 | 5.404  | 46.020 | 1.00 | 32.80 | 6 |
| ATOM | 3918 | O   | ASN | B | 234 | 81.764 | 4.675  | 46.099 | 1.00 | 34.18 | 8 |
| ATOM | 3919 | CB  | ASN | B | 234 | 80.775 | 7.750  | 45.048 | 1.00 | 33.46 | 6 |
| ATOM | 3920 | CG  | ASN | B | 234 | 82.187 | 8.099  | 45.503 | 1.00 | 38.46 | 6 |
| ATOM | 3921 | OD1 | ASN | B | 234 | 82.545 | 7.889  | 46.687 | 1.00 | 39.27 | 8 |
| ATOM | 3922 | ND2 | ASN | B | 234 | 83.042 | 8.646  | 44.636 | 1.00 | 38.37 | 7 |
| ATOM | 3923 | N   | GLU | B | 235 | 79.781 | 5.385  | 46.942 | 1.00 | 32.30 | 7 |
| ATOM | 3924 | CA  | GLU | B | 235 | 79.995 | 4.556  | 48.156 | 1.00 | 34.69 | 6 |
| ATOM | 3925 | C   | GLU | B | 235 | 80.036 | 3.082  | 47.880 | 1.00 | 35.00 | 6 |
| ATOM | 3926 | O   | GLU | B | 235 | 80.783 | 2.325  | 48.548 | 1.00 | 34.91 | 8 |
| ATOM | 3927 | CB  | GLU | B | 235 | 78.927 | 4.941  | 49.210 | 1.00 | 35.01 | 6 |
| ATOM | 3928 | N   | LYS | B | 236 | 79.431 | 2.541  | 46.819 | 1.00 | 32.85 | 7 |
| ATOM | 3929 | CA  | LYS | B | 236 | 79.476 | 1.161  | 46.438 | 1.00 | 32.12 | 6 |
| ATOM | 3930 | C   | LYS | B | 236 | 80.733 | 0.795  | 45.662 | 1.00 | 31.23 | 6 |
| ATOM | 3931 | O   | LYS | B | 236 | 81.027 | −0.387 | 45.442 | 1.00 | 32.24 | 8 |
| ATOM | 3932 | CB  | LYS | B | 236 | 78.257 | 0.838  | 45.530 | 1.00 | 31.56 | 6 |
| ATOM | 3933 | CG  | LYS | B | 236 | 76.968 | 0.739  | 46.321 | 1.00 | 33.04 | 6 |
| ATOM | 3934 | CD  | LYS | B | 236 | 75.825 | 0.425  | 45.347 | 1.00 | 34.58 | 6 |
| ATOM | 3935 | CE  | LYS | B | 236 | 74.486 | 0.657  | 46.017 | 1.00 | 38.11 | 6 |
| ATOM | 3936 | NZ  | LYS | B | 236 | 74.152 | −0.406 | 47.008 | 1.00 | 41.00 | 7 |
| ATOM | 3937 | N   | GLY | B | 237 | 81.463 | 1.790  | 45.196 | 1.00 | 31.15 | 7 |
| ATOM | 3938 | CA  | GLY | B | 237 | 82.701 | 1.595  | 44.467 | 1.00 | 32.69 | 6 |
| ATOM | 3939 | C   | GLY | B | 237 | 82.728 | 2.025  | 43.030 | 1.00 | 33.87 | 6 |
| ATOM | 3940 | O   | GLY | B | 237 | 83.730 | 1.798  | 42.345 | 1.00 | 36.00 | 8 |
| ATOM | 3941 | N   | PHE | B | 238 | 81.635 | 2.625  | 42.522 | 1.00 | 30.77 | 7 |
| ATOM | 3942 | CA  | PHE | B | 238 | 81.579 | 3.079  | 41.154 | 1.00 | 31.26 | 6 |
| ATOM | 3943 | C   | PHE | B | 238 | 82.111 | 4.488  | 41.041 | 1.00 | 32.04 | 6 |
| ATOM | 3944 | O   | PHE | B | 238 | 82.216 | 5.186  | 42.067 | 1.00 | 32.73 | 8 |
| ATOM | 3945 | CB  | PHE | B | 238 | 80.125 | 3.016  | 40.628 | 1.00 | 31.33 | 6 |
| ATOM | 3946 | CG  | PHE | B | 238 | 79.481 | 1.668  | 40.628 | 1.00 | 29.12 | 6 |
| ATOM | 3947 | CD1 | PHE | B | 238 | 78.935 | 1.079  | 41.736 | 1.00 | 29.70 | 6 |
| ATOM | 3948 | CD2 | PHE | B | 238 | 79.401 | 0.975  | 39.390 | 1.00 | 29.67 | 6 |
| ATOM | 3949 | CE1 | PHE | B | 238 | 78.325 | −0.181 | 41.661 | 1.00 | 30.02 | 6 |
| ATOM | 3950 | CE2 | PHE | B | 238 | 78.805 | −0.265 | 39.328 | 1.09 | 28.39 | 6 |
| ATOM | 3951 | CZ  | PHE | B | 238 | 78.268 | −0.858 | 40.457 | 1.00 | 29.71 | 6 |
| ATOM | 3952 | N   | ARG | B | 239 | 82.539 | 4.918  | 39.876 | 1.00 | 32.94 | 7 |
| ATOM | 3953 | CA  | ARG | B | 239 | 83.050 | 6.269  | 39.716 | 1.00 | 35.99 | 6 |
| ATOM | 3954 | C   | ARG | B | 239 | 82.426 | 6.906  | 38.487 | 1.00 | 38.53 | 6 |
| ATOM | 3955 | O   | ARG | B | 239 | 81.735 | 6.244  | 37.694 | 1.00 | 38.62 | 8 |
| ATOM | 3956 | CB  | ARG | B | 239 | 84.581 | 6.280  | 39.597 | 1.00 | 35.70 | 6 |
| ATOM | 3957 | CG  | ARG | B | 239 | 85.340 | 5.894  | 40.856 | 1.00 | 36.08 | 6 |
| ATOM | 3958 | CD  | ARG | B | 239 | 85.108 | 6.926  | 41.956 | 1.00 | 35.58 | 6 |
| ATOM | 3959 | NE  | ARG | B | 239 | 85.710 | 6.612  | 43.215 | 1.00 | 36.21 | 7 |
| ATOM | 3960 | CZ  | ARG | B | 239 | 85.280 | 5.815  | 44.190 | 1.00 | 37.41 | 6 |
| ATOM | 3961 | NH1 | ARG | B | 239 | 84.113 | 5.159  | 44.129 | 1.00 | 35.39 | 7 |
| ATOM | 3962 | NH2 | ARG | B | 239 | 86.015 | 5.707  | 45.288 | 1.00 | 35.70 | 7 |
| ATOM | 3963 | N   | ALA | B | 240 | 82.667 | 8.199  | 38.339 | 1.00 | 38.40 | 7 |
| ATOM | 3964 | CA  | ALA | B | 240 | 82.310 | 8.977  | 37.152 | 1.00 | 39.45 | 6 |
| ATOM | 3965 | C   | ALA | B | 240 | 80.954 | 8.630  | 36.553 | 1.00 | 39.96 | 6 |
| ATOM | 3966 | O   | ALA | B | 240 | 80.846 | 8.388  | 35.348 | 1.00 | 41.59 | 8 |
| ATOM | 3967 | CB  | ALA | B | 240 | 83.408 | 8.761  | 36.103 | 1.00 | 39.64 | 6 |
| ATOM | 3968 | N   | ASP | B | 241 | 79.899 | 8.687  | 37.369 | 1.00 | 39.86 | 7 |
| ATOM | 3969 | CA  | ASP | B | 241 | 78.567 | 8.382  | 36.881 | 1.00 | 37.91 | 6 |
| ATOM | 3970 | C   | ASP | B | 241 | 78.087 | 9.495  | 35.947 | 1.00 | 39.44 | 6 |
| ATOM | 3971 | O   | ASP | B | 241 | 78.464 | 10.658 | 36.063 | 1.00 | 38.78 | 8 |

TABLE 1-continued

| | | | | | | | | | | |
|---|---|---|---|---|---|---|---|---|---|---|
| ATOM | 3972 | CB | ASP | B | 241 | 77.554 | 8.232 | 38.028 | 1.00 | 39.68 | 6 |
| ATOM | 3973 | CG | ASP | B | 241 | 77.464 | 9.573 | 38.758 | 1.00 | 42.34 | 6 |
| ATOM | 3974 | OD1 | ASP | B | 241 | 76.577 | 10.419 | 38.447 | 1.00 | 44.14 | 8 |
| ATOM | 3975 | OD2 | ASP | B | 241 | 78.353 | 9.828 | 39.610 | 1.00 | 41.04 | 8 |
| ATOM | 3976 | N | ASP | B | 242 | 77.220 | 9.122 | 35.028 | 1.00 | 36.17 | 7 |
| ATOM | 3977 | CA | ASP | B | 242 | 76.543 | 10.050 | 34.122 | 1.00 | 36.78 | 6 |
| ATOM | 3978 | C | ASP | B | 242 | 75.102 | 9.548 | 34.108 | 1.00 | 32.97 | 6 |
| ATOM | 3979 | O | ASP | B | 242 | 74.890 | 8.412 | 33.654 | 1.00 | 32.78 | 8 |
| ATOM | 3980 | CB | ASP | B | 242 | 77.160 | 10.107 | 32.755 | 1.00 | 41.35 | 6 |
| ATOM | 3981 | CG | ASP | B | 242 | 76.317 | 10.792 | 31.704 | 1.00 | 46.81 | 6 |
| ATOM | 3982 | OD1 | ASP | B | 242 | 76.414 | 10.318 | 30.543 | 1.00 | 50.98 | 8 |
| ATOM | 3983 | OD2 | ASP | B | 242 | 75.539 | 11.741 | 31.944 | 1.00 | 49.34 | 8 |
| ATOM | 3984 | N | ILE | B | 243 | 74.204 | 10.301 | 34.710 | 1.00 | 29.36 | 7 |
| ATOM | 3985 | CA | ILE | B | 243 | 72.817 | 9.893 | 34.861 | 1.00 | 27.87 | 6 |
| ATOM | 3986 | C | ILE | B | 243 | 71.890 | 10.907 | 34.213 | 1.00 | 28.93 | 6 |
| ATOM | 3987 | O | ILE | B | 243 | 71.986 | 12.098 | 34.489 | 1.00 | 28.18 | 8 |
| ATOM | 3988 | CB | ILE | B | 243 | 72.407 | 9.746 | 36.339 | 1.00 | 28.09 | 6 |
| ATOM | 3989 | CG1 | ILE | B | 243 | 73.240 | 8.680 | 37.065 | 1.00 | 28.98 | 6 |
| ATOM | 3990 | CG2 | ILE | B | 243 | 70.934 | 9.373 | 36.477 | 1.00 | 26.56 | 6 |
| ATOM | 3991 | CD1 | ILE | B | 243 | 73.044 | 8.655 | 38.575 | 1.00 | 28.71 | 6 |
| ATOM | 3992 | N | GLN | B | 244 | 70.912 | 10.442 | 33.437 | 1.00 | 27.35 | 7 |
| ATOM | 3993 | CA | GLN | B | 244 | 69.944 | 11.390 | 32.837 | 1.00 | 29.56 | 6 |
| ATOM | 3994 | C | GLN | B | 244 | 68.550 | 10.906 | 33.126 | 1.00 | 28.63 | 6 |
| ATOM | 3995 | O | GLN | B | 244 | 68.328 | 9.670 | 33.170 | 1.00 | 28.44 | 8 |
| ATOM | 3996 | CB | GLN | B | 244 | 70.154 | 11.546 | 31.342 | 1.00 | 32.37 | 6 |
| ATOM | 3997 | CG | GLN | B | 244 | 71.494 | 11.871 | 30.754 | 1.00 | 33.10 | 6 |
| ATOM | 3998 | N | ILE | B | 245 | 67.580 | 11.792 | 33.287 | 1.00 | 28.47 | 7 |
| ATOM | 3999 | CA | ILE | B | 245 | 66.194 | 11.454 | 33.560 | 1.00 | 27.98 | 6 |
| ATOM | 4000 | C | ILE | B | 245 | 65.367 | 12.295 | 32.544 | 1.00 | 29.53 | 6 |
| ATOM | 4001 | O | ILE | B | 245 | 65.647 | 13.473 | 32.427 | 1.00 | 28.72 | 8 |
| ATOM | 4002 | CB | ILE | B | 245 | 65.647 | 11.723 | 34.955 | 1.00 | 30.08 | 6 |
| ATOM | 4003 | CG1 | ILE | B | 245 | 66.275 | 10.837 | 36.048 | 1.00 | 31.65 | 6 |
| ATOM | 4004 | CG2 | ILE | B | 245 | 64.136 | 11.475 | 34.988 | 1.00 | 30.80 | 6 |
| ATOM | 4005 | CD1 | ILE | B | 245 | 65.994 | 11.415 | 37.433 | 1.00 | 33.41 | 6 |
| ATOM | 4006 | N | ARG | B | 246 | 64.608 | 11.578 | 31.703 | 1.00 | 28.63 | 7 |
| ATOM | 4007 | CA | ARG | B | 246 | 63.903 | 12.319 | 30.635 | 1.00 | 29.40 | 6 |
| ATOM | 4008 | C | ARG | B | 246 | 62.475 | 11.841 | 30.597 | 1.00 | 29.33 | 6 |
| ATOM | 4009 | O | ARG | B | 246 | 62.198 | 10.775 | 31.136 | 1.00 | 29.29 | 8 |
| ATOM | 4010 | CB | ARG | B | 246 | 64.481 | 12.084 | 29.252 | 1.00 | 33.51 | 6 |
| ATOM | 4011 | CG | ARG | B | 246 | 65.896 | 12.479 | 29.026 | 1.00 | 37.29 | 6 |
| ATOM | 4012 | CD | ARG | B | 246 | 66.517 | 12.212 | 27.672 | 1.00 | 42.16 | 6 |
| ATOM | 4013 | NE | ARG | B | 246 | 67.527 | 13.251 | 27.472 | 1.00 | 47.11 | 7 |
| ATOM | 4014 | CZ | ARG | B | 246 | 68.770 | 13.142 | 27.056 | 1.00 | 50.44 | 6 |
| ATOM | 4015 | NH1 | ARG | B | 246 | 69.318 | 11.970 | 26.737 | 1.00 | 53.10 | 7 |
| ATOM | 4016 | NH2 | ARG | B | 246 | 69.502 | 14.252 | 26.974 | 1.00 | 51.57 | 7 |
| ATOM | 4017 | N | ASP | B | 247 | 61.544 | 12.634 | 30.039 | 1.00 | 28.70 | 7 |
| ATOM | 4018 | CA | ASP | B | 247 | 60.185 | 12.189 | 29.792 | 1.00 | 29.87 | 6 |
| ATOM | 4019 | C | ASP | B | 247 | 60.289 | 11.146 | 28.656 | 1.00 | 25.96 | 6 |
| ATOM | 4020 | O | ASP | B | 247 | 60.989 | 11.431 | 27.671 | 1.00 | 27.47 | 8 |
| ATOM | 4021 | CB | ASP | B | 247 | 59.303 | 13.349 | 29.389 | 1.00 | 31.15 | 6 |
| ATOM | 4022 | CG | ASP | B | 247 | 57.894 | 13.014 | 28.997 | 1.00 | 33.47 | 6 |
| ATOM | 4023 | OD1 | ASP | B | 247 | 57.667 | 12.084 | 28.184 | 1.00 | 32.45 | 6 |
| ATOM | 4024 | OD2 | ASP | B | 247 | 56.982 | 13.703 | 29.524 | 1.00 | 33.36 | 6 |
| ATOM | 4025 | N | ALA | B | 248 | 59.759 | 9.981 | 28.873 | 1.00 | 27.20 | 7 |
| ATOM | 4026 | CA | ALA | B | 248 | 59.987 | 8.893 | 27.906 | 1.00 | 28.58 | 6 |
| ATOM | 4027 | C | ALA | B | 248 | 59.141 | 9.055 | 26.643 | 1.00 | 29.88 | 6 |
| ATOM | 4028 | O | ALA | B | 248 | 59.444 | 8.315 | 25.702 | 1.00 | 29.99 | 8 |
| ATOM | 4029 | CB | ALA | B | 248 | 59.652 | 7.572 | 28.566 | 1.00 | 28.03 | 6 |
| ATOM | 4030 | N | ASP | B | 249 | 58.121 | 9.877 | 26.724 | 1.00 | 28.08 | 7 |
| ATOM | 4031 | CA | ASP | B | 249 | 57.293 | 10.116 | 25.513 | 1.00 | 30.80 | 6 |
| ATOM | 4032 | C | ASP | B | 249 | 57.764 | 11.262 | 24.667 | 1.00 | 29.85 | 6 |
| ATOM | 4033 | O | ASP | B | 249 | 57.690 | 11.217 | 23.402 | 1.00 | 30.23 | 8 |
| ATOM | 4034 | CB | ASP | B | 249 | 55.853 | 10.392 | 25.955 | 1.00 | 32.78 | 6 |
| ATOM | 4035 | CG | ASP | B | 249 | 55.226 | 9.204 | 26.623 | 1.00 | 37.46 | 6 |
| ATOM | 4036 | OD1 | ASP | B | 249 | 55.538 | 8.084 | 26.164 | 1.00 | 39.14 | 8 |
| ATOM | 4037 | OD2 | ASP | B | 249 | 54.448 | 9.329 | 27.595 | 1.00 | 39.72 | 8 |
| ATOM | 4038 | N | THR | B | 250 | 58.264 | 12.361 | 25.283 | 1.00 | 26.32 | 7 |
| ATOM | 4039 | CA | THR | B | 250 | 58.710 | 13.526 | 24.523 | 1.00 | 27.61 | 6 |
| ATOM | 4040 | C | THR | B | 250 | 60.191 | 13.683 | 24.413 | 1.00 | 26.93 | 6 |
| ATOM | 4041 | O | THR | B | 250 | 60.785 | 14.328 | 23.570 | 1.00 | 28.19 | 8 |
| ATOM | 4042 | CB | THR | B | 250 | 58.162 | 14.831 | 25.186 | 1.00 | 30.35 | 6 |
| ATOM | 4043 | OG1 | THR | B | 250 | 58.797 | 14.978 | 26.457 | 1.00 | 31.06 | 8 |
| ATOM | 4044 | CG2 | THR | B | 250 | 56.677 | 14.760 | 25.380 | 1.00 | 32.40 | 6 |
| ATOM | 4045 | N | LEU | B | 251 | 60.891 | 12.958 | 25.324 | 1.00 | 27.41 | 7 |
| ATOM | 4046 | CA | LEU | B | 251 | 62.336 | 12.857 | 25.461 | 1.00 | 30.17 | 6 |
| ATOM | 4047 | C | LEU | B | 251 | 62.928 | 14.204 | 25.968 | 1.00 | 31.32 | 6 |
| ATOM | 4048 | O | LEU | B | 251 | 64.110 | 14.434 | 25.775 | 1.00 | 33.84 | 8 |
| ATOM | 4049 | CB | LEU | B | 251 | 63.096 | 12.483 | 24.205 | 1.00 | 30.53 | 6 |
| ATOM | 4050 | CG | LEU | B | 251 | 62.568 | 11.151 | 23.560 | 1.00 | 30.23 | 6 |

TABLE 1-continued

| ATOM | 4051 | CD1 | LEU | B | 251 | 63.382 | 10.891 | 22.307 | 1.00 | 31.95 | 6 |
|---|---|---|---|---|---|---|---|---|---|---|---|
| ATOM | 4052 | CD2 | LEU | B | 251 | 62.575 | 10.004 | 24.541 | 1.00 | 30.44 | 6 |
| ATOM | 4053 | N | LEU | B | 252 | 62.054 | 15.017 | 26.483 | 1.00 | 33.09 | 7 |
| ATOM | 4054 | CA | LEU | B | 252 | 62.441 | 16.323 | 27.015 | 1.00 | 34.68 | 6 |
| ATOM | 4055 | C | LEU | B | 252 | 62.530 | 16.162 | 28.519 | 1.00 | 35.10 | 6 |
| ATOM | 4056 | O | LEU | B | 252 | 62.436 | 15.037 | 29.003 | 1.00 | 30.04 | 8 |
| ATOM | 4057 | CB | LEU | B | 252 | 61.439 | 17.401 | 26.633 | 1.00 | 35.48 | 6 |
| ATOM | 4058 | CG | LEU | B | 252 | 61.476 | 17.664 | 25.106 | 1.00 | 38.16 | 6 |
| ATOM | 4059 | CD1 | LEU | B | 252 | 60.219 | 18.416 | 24.715 | 1.00 | 38.56 | 6 |
| ATOM | 4060 | CD2 | LEU | B | 252 | 62.782 | 18.361 | 24.789 | 1.00 | 38.57 | 6 |
| ATOM | 4061 | N | GLU | B | 253 | 62.625 | 17.316 | 29.217 | 1.00 | 36.82 | 7 |
| ATOM | 4062 | CA | GLU | B | 253 | 62.731 | 17.220 | 30.668 | 1.00 | 39.59 | 6 |
| ATOM | 4063 | C | GLU | B | 253 | 61.417 | 16.777 | 31.259 | 1.00 | 39.50 | 6 |
| ATOM | 4064 | O | GLU | B | 253 | 60.403 | 17.042 | 30.591 | 1.00 | 40.91 | 8 |
| ATOM | 4065 | CB | GLU | B | 253 | 63.103 | 18.586 | 31.274 | 1.00 | 42.93 | 6 |
| ATOM | 4066 | CG | GLU | B | 253 | 64.342 | 19.202 | 30.643 | 1.00 | 48.27 | 6 |
| ATOM | 4067 | CD | GLU | B | 253 | 65.560 | 18.356 | 30.999 | 1.00 | 51.88 | 6 |
| ATOM | 4068 | OE1 | GLU | B | 253 | 65.758 | 18.143 | 32.226 | 1.00 | 54.42 | 8 |
| ATOM | 4069 | OE2 | GLU | B | 253 | 66.259 | 17.915 | 30.063 | 1.00 | 53.71 | 8 |
| ATOM | 4070 | N | VAL | B | 254 | 61.405 | 16.130 | 32.403 | 1.00 | 39.00 | 7 |
| ATOM | 4071 | CA | VAL | B | 254 | 60.167 | 15.751 | 33.062 | 1.00 | 40.35 | 6 |
| ATOM | 4072 | C | VAL | B | 254 | 59.384 | 16.991 | 33.488 | 1.00 | 43.05 | 6 |
| ATOM | 4073 | O | VAL | B | 254 | 59.955 | 17.997 | 33.903 | 1.00 | 42.79 | 8 |
| ATOM | 4074 | CB | VAL | B | 254 | 60.425 | 14.856 | 34.285 | 1.00 | 39.32 | 6 |
| ATOM | 4075 | CG1 | VAL | B | 254 | 59.162 | 14.614 | 35.088 | 1.00 | 37.70 | 6 |
| ATOM | 4076 | CG2 | VAL | B | 254 | 61.054 | 13.553 | 33.783 | 1.00 | 38.29 | 6 |
| ATOM | 4077 | N | SER | B | 255 | 58.070 | 16.937 | 33.293 | 1.00 | 46.50 | 7 |
| ATOM | 4078 | CA | SER | B | 255 | 57.178 | 18.041 | 33.641 | 1.00 | 47.57 | 6 |
| ATOM | 4079 | C | SER | B | 255 | 56.027 | 17.520 | 34.498 | 1.00 | 48.72 | 6 |
| ATOM | 4080 | O | SER | B | 255 | 56.063 | 16.436 | 35.062 | 1.00 | 49.33 | 8 |
| ATOM | 4081 | CB | SER | B | 255 | 56.663 | 18.739 | 32.379 | 1.00 | 47.97 | 6 |
| ATOM | 4082 | OG | SER | B | 255 | 55.566 | 18.022 | 31.814 | 1.00 | 50.04 | 8 |
| ATOM | 4083 | N | GLU | B | 256 | 54.990 | 18.358 | 34.593 | 1.00 | 48.58 | 7 |
| ATOM | 4084 | CA | GLU | B | 256 | 53.787 | 18.010 | 35.346 | 1.00 | 49.19 | 6 |
| ATOM | 4085 | C | GLU | B | 256 | 52.838 | 17.201 | 34.488 | 1.00 | 49.15 | 6 |
| ATOM | 4086 | O | GLU | B | 256 | 51.953 | 16.493 | 34.969 | 1.00 | 50.39 | 8 |
| ATOM | 4087 | CB | GLU | B | 256 | 53.154 | 19.321 | 35.844 | 1.00 | 49.68 | 6 |
| ATOM | 4088 | N | THR | B | 257 | 53.078 | 17.241 | 33.177 | 1.00 | 48.71 | 7 |
| ATOM | 4089 | CA | THR | B | 257 | 52.306 | 16.471 | 32.211 | 1.00 | 49.54 | 6 |
| ATOM | 4090 | C | THR | B | 257 | 52.962 | 15.121 | 31.914 | 1.00 | 48.26 | 6 |
| ATOM | 4091 | O | THR | B | 257 | 52.333 | 14.259 | 31.285 | 1.00 | 48.37 | 8 |
| ATOM | 4092 | CB | THR | B | 257 | 52.146 | 17.265 | 30.913 | 1.00 | 50.65 | 6 |
| ATOM | 4093 | OG1 | THR | B | 257 | 53.430 | 17.717 | 30.454 | 1.00 | 52.73 | 8 |
| ATOM | 4094 | CG2 | THR | B | 257 | 51.277 | 18.496 | 31.154 | 1.00 | 52.44 | 6 |
| ATOM | 4095 | N | SER | B | 258 | 54.201 | 14.933 | 32.368 | 1.00 | 44.00 | 7 |
| ATOM | 4096 | CA | SER | B | 258 | 54.923 | 13.690 | 32.124 | 1.00 | 43.02 | 6 |
| ATOM | 4097 | C | SER | B | 258 | 54.197 | 12.470 | 32.665 | 1.00 | 41.05 | 6 |
| ATOM | 4098 | O | SER | B | 258 | 53.785 | 12.435 | 33.808 | 1.00 | 40.25 | 8 |
| ATOM | 4099 | CB | SER | B | 258 | 56.315 | 13.710 | 32.765 | 1.00 | 39.95 | 6 |
| ATOM | 4100 | OG | SER | B | 258 | 57.171 | 14.561 | 32.020 | 1.00 | 37.63 | 8 |
| ATOM | 4101 | N | LYS | B | 259 | 54.041 | 11.453 | 31.819 | 1.00 | 40.55 | 7 |
| ATOM | 4102 | CA | LYS | B | 259 | 53.347 | 10.253 | 32.275 | 1.00 | 40.93 | 6 |
| ATOM | 4103 | C | LYS | B | 259 | 54.339 | 9.094 | 32.390 | 1.00 | 38.96 | 6 |
| ATOM | 4104 | O | LYS | B | 259 | 54.036 | 8.130 | 33.071 | 1.00 | 39.56 | 8 |
| ATOM | 4105 | CB | LYS | B | 259 | 52.193 | 9.870 | 31.340 | 1.00 | 44.20 | 6 |
| ATOM | 4106 | CG | LYS | B | 259 | 51.223 | 11.038 | 31.184 | 1.00 | 47.43 | 6 |
| ATOM | 4107 | CD | LYS | B | 259 | 49.868 | 10.656 | 30.608 | 1.00 | 50.95 | 6 |
| ATOM | 4108 | CE | LYS | B | 259 | 48.814 | 11.646 | 31.143 | 1.00 | 52.15 | 6 |
| ATOM | 4109 | NZ | LYS | B | 259 | 47.678 | 11.728 | 30.177 | 1.00 | 54.34 | 7 |
| ATOM | 4110 | N | ARG | B | 260 | 55.446 | 9.187 | 31.695 | 1.00 | 38.03 | 7 |
| ATOM | 4111 | CA | ARG | B | 260 | 56.469 | 8.146 | 31.706 | 1.00 | 36.81 | 6 |
| ATOM | 4112 | C | ARG | B | 260 | 57.852 | 8.765 | 31.794 | 1.00 | 33.36 | 6 |
| ATOM | 4113 | O | ARG | B | 260 | 58.150 | 9.717 | 31.075 | 1.00 | 30.91 | 8 |
| ATOM | 4114 | CB | ARG | B | 260 | 56.438 | 7.267 | 30.445 | 1.00 | 38.22 | 6 |
| ATOM | 4115 | CG | ARG | B | 260 | 55.182 | 6.504 | 30.103 | 1.00 | 42.83 | 6 |
| ATOM | 4116 | CD | ARG | B | 260 | 55.389 | 5.584 | 28.896 | 1.00 | 43.79 | 6 |
| ATOM | 4117 | NE | ARG | B | 260 | 54.174 | 4.856 | 28.536 | 1.00 | 46.34 | 7 |
| ATOM | 4118 | N | ALA | B | 261 | 58.808 | 8.142 | 32.519 | 1.00 | 31.91 | 7 |
| ATOM | 4119 | CA | ALA | B | 261 | 60.182 | 8.623 | 32.486 | 1.00 | 28.39 | 6 |
| ATOM | 4120 | C | ALA | B | 261 | 61.176 | 7.524 | 32.106 | 1.00 | 25.89 | 6 |
| ATOM | 4121 | O | ALA | B | 261 | 60.882 | 6.354 | 32.381 | 1.00 | 29.01 | 8 |
| ATOM | 4122 | CB | ALA | B | 261 | 68.695 | 9.169 | 33.836 | 1.00 | 29.25 | 6 |
| ATOM | 4123 | N | VAL | B | 262 | 62.238 | 7.874 | 31.454 | 1.00 | 27.17 | 7 |
| ATOM | 4124 | CA | VAL | B | 262 | 63.325 | 6.947 | 31.122 | 1.00 | 29.12 | 6 |
| ATOM | 4125 | C | VAL | B | 262 | 64.544 | 7.432 | 31.944 | 1.00 | 28.50 | 6 |
| ATOM | 4126 | O | VAL | B | 262 | 64.860 | 8.605 | 31.932 | 1.00 | 27.83 | 8 |
| ATOM | 4127 | CB | VAL | B | 262 | 63.659 | 6.838 | 29.647 | 1.00 | 30.51 | 6 |
| ATOM | 4128 | CG1 | VAL | B | 262 | 63.902 | 8.231 | 29.043 | 1.00 | 30.91 | 6 |
| ATOM | 4129 | CG2 | VAL | B | 262 | 64.881 | 5.958 | 29.356 | 1.00 | 30.63 | 6 |

TABLE 1-continued

| | | | | | | | | | |
|---|---|---|---|---|---|---|---|---|---|
| ATOM | 4130 | N | ILE | B | 263 | 65.221 | 6.505 | 32.611 | 1.00 | 29.18 | 7 |
| ATOM | 4131 | CA | ILE | B | 263 | 66.406 | 6.792 | 33.454 | 1.00 | 27.39 | 6 |
| ATOM | 4132 | C | ILE | B | 263 | 67.590 | 6.119 | 32.790 | 1.00 | 25.94 | 6 |
| ATOM | 4133 | O | ILE | B | 263 | 67.437 | 4.906 | 32.507 | 1.00 | 25.04 | 8 |
| ATOM | 4134 | CB | ILE | B | 263 | 66.243 | 6.278 | 34.881 | 1.00 | 29.45 | 6 |
| ATOM | 4135 | CG1 | ILE | B | 263 | 64.898 | 6.687 | 35.497 | 1.00 | 29.18 | 6 |
| ATOM | 4136 | CG2 | ILE | B | 263 | 67.369 | 6.819 | 35.758 | 1.00 | 29.13 | 6 |
| ATOM | 4137 | CD1 | ILE | B | 263 | 64.395 | 5.672 | 36.508 | 1.00 | 32.09 | 6 |
| ATOM | 4138 | N | LEU | B | 264 | 68.626 | 6.784 | 32.377 | 1.00 | 25.66 | 7 |
| ATOM | 4139 | CA | LEU | B | 264 | 69.795 | 6.289 | 31.701 | 1.00 | 27.04 | 6 |
| ATOM | 4140 | C | LEU | B | 264 | 70.978 | 6.430 | 32.666 | 1.00 | 29.07 | 6 |
| ATOM | 4141 | O | LEU | B | 264 | 71.152 | 7.574 | 33.143 | 1.00 | 29.50 | 8 |
| ATOM | 4142 | CB | LEU | B | 264 | 70.153 | 7.070 | 30.438 | 1.00 | 29.75 | 6 |
| ATOM | 4143 | CG | LEU | B | 264 | 68.950 | 7.229 | 29.452 | 1.00 | 32.20 | 6 |
| ATOM | 4144 | CD1 | LEU | B | 264 | 69.399 | 8.095 | 28.298 | 1.00 | 33.01 | 6 |
| ATOM | 4145 | CD2 | LEU | B | 264 | 68.453 | 5.842 | 29.091 | 1.00 | 31.89 | 6 |
| ATOM | 4146 | N | VAL | B | 265 | 71.753 | 5.394 | 32.886 | 1.00 | 29.03 | 7 |
| ATOM | 4147 | CA | VAL | B | 265 | 72.864 | 5.494 | 33.821 | 1.00 | 32.13 | 6 |
| ATOM | 4148 | C | VAL | B | 265 | 74.099 | 4.822 | 33.213 | 1.00 | 34.01 | 6 |
| ATOM | 4149 | O | VAL | B | 265 | 74.044 | 3.750 | 32.557 | 1.00 | 34.46 | 8 |
| ATOM | 4150 | CB | VAL | B | 265 | 72.642 | 4.856 | 35.202 | 1.00 | 32.74 | 6 |
| ATOM | 4151 | CG1 | VAL | B | 265 | 71.525 | 5.474 | 36.025 | 1.00 | 33.45 | 6 |
| ATOM | 4152 | CG2 | VAL | B | 265 | 72.331 | 3.361 | 35.046 | 1.00 | 33.30 | 6 |
| ATOM | 4153 | N | ALA | B | 266 | 75.219 | 5.485 | 33.397 | 1.00 | 33.41 | 7 |
| ATOM | 4154 | CA | ALA | B | 266 | 76.501 | 4.926 | 33.000 | 1.00 | 32.14 | 6 |
| ATOM | 4155 | C | ALA | B | 266 | 77.411 | 5.092 | 34.221 | 1.00 | 32.17 | 6 |
| ATOM | 4156 | O | ALA | B | 266 | 77.390 | 6.213 | 34.746 | 1.00 | 32.13 | 8 |
| ATOM | 4157 | CB | ALA | B | 266 | 77.139 | 5.570 | 31.794 | 1.00 | 32.99 | 6 |
| ATOM | 4158 | N | ALA | B | 267 | 78.175 | 4.058 | 34.569 | 1.00 | 31.42 | 7 |
| ATOM | 4159 | CA | ALA | B | 267 | 79.107 | 4.338 | 35.679 | 1.00 | 32.75 | 6 |
| ATOM | 4160 | C | ALA | B | 267 | 80.356 | 3.503 | 35.491 | 1.00 | 35.34 | 6 |
| ATOM | 4161 | O | ALA | B | 267 | 80.213 | 2.423 | 34.884 | 1.00 | 36.90 | 8 |
| ATOM | 4162 | CB | ALA | B | 267 | 78.446 | 4.006 | 36.993 | 1.00 | 31.22 | 6 |
| ATOM | 4163 | N | TRP | B | 268 | 81.511 | 3.868 | 36.036 | 1.00 | 36.69 | 7 |
| ATOM | 4164 | CA | TRP | B | 268 | 82.665 | 2.974 | 35.881 | 1.00 | 38.65 | 6 |
| ATOM | 4165 | C | TRP | B | 268 | 82.910 | 2.113 | 37.105 | 1.00 | 40.28 | 6 |
| ATOM | 4166 | O | TRP | B | 268 | 82.777 | 2.579 | 38.235 | 1.00 | 38.57 | 5 |
| ATOM | 4167 | CB | TRP | B | 268 | 83.927 | 3.805 | 35.609 | 1.00 | 40.65 | 6 |
| ATOM | 4168 | CG | TRP | B | 268 | 83.860 | 4.563 | 34.319 | 1.00 | 43.80 | 6 |
| ATOM | 4169 | CD1 | TRP | B | 268 | 83.114 | 5.662 | 34.040 | 1.00 | 44.47 | 6 |
| ATOM | 4170 | CD2 | TRP | B | 268 | 84.577 | 4.256 | 33.115 | 1.00 | 45.14 | 6 |
| ATOM | 4171 | NE1 | TRP | B | 268 | 83.311 | 6.063 | 32.729 | 1.00 | 45.41 | 7 |
| ATOM | 4172 | CE2 | TRP | B | 268 | 84.199 | 5.211 | 32.144 | 1.00 | 45.95 | 6 |
| ATOM | 4173 | CE3 | TRP | B | 268 | 85.470 | 3.244 | 32.757 | 1.00 | 45.65 | 6 |
| ATOM | 4174 | CZ2 | TRP | B | 268 | 84.703 | 5.199 | 30.836 | 1.00 | 46.17 | 6 |
| ATOM | 4175 | CZ3 | TRP | B | 268 | 85.984 | 3.242 | 31.463 | 1.00 | 46.00 | 6 |
| ATOM | 4176 | CH2 | TRP | B | 268 | 85.596 | 4.206 | 30.522 | 1.00 | 45.63 | 6 |
| ATOM | 4177 | N | LEU | B | 269 | 83.300 | 0.869 | 36.821 | 1.00 | 39.18 | 7 |
| ATOM | 4178 | CA | LEU | B | 269 | 83.691 | -0.026 | 37.916 | 1.00 | 43.86 | 6 |
| ATOM | 4179 | C | LEU | B | 269 | 85.093 | -0.471 | 37.522 | 1.00 | 46.33 | 6 |
| ATOM | 4180 | O | LEU | B | 269 | 85.247 | -0.946 | 36.400 | 1.00 | 47.07 | 5 |
| ATOM | 4181 | CB | LEU | B | 269 | 82.635 | -1.086 | 38.058 | 1.00 | 43.77 | 6 |
| ATOM | 4182 | CG | LEU | B | 269 | 82.651 | -2.072 | 39.212 | 1.00 | 44.62 | 6 |
| ATOM | 4183 | CD1 | LEU | B | 269 | 82.571 | -1.312 | 40.537 | 1.00 | 44.46 | 6 |
| ATOM | 4184 | CD2 | LEU | B | 269 | 81.518 | -3.080 | 39.046 | 1.00 | 42.39 | 6 |
| ATOM | 4185 | N | GLY | B | 270 | 86.102 | -0.049 | 38.293 | 1.00 | 48.41 | 7 |
| ATOM | 4186 | CA | GLY | B | 270 | 87.475 | -0.340 | 37.862 | 1.00 | 51.49 | 6 |
| ATOM | 4187 | C | GLY | B | 270 | 87.681 | 0.391 | 36.532 | 1.00 | 54.10 | 6 |
| ATOM | 4188 | O | GLY | B | 270 | 87.397 | 1.588 | 36.464 | 1.00 | 54.18 | 8 |
| ATOM | 4189 | N | ASP | B | 271 | 88.108 | -0.331 | 35.503 | 1.00 | 56.24 | 7 |
| ATOM | 4190 | CA | ASP | B | 271 | 88.288 | 0.320 | 34.199 | 1.00 | 56.89 | 6 |
| ATOM | 4191 | C | ASP | B | 271 | 87.142 | -0.096 | 33.280 | 1.00 | 54.99 | 6 |
| ATOM | 4192 | O | ASP | B | 271 | 87.162 | 0.231 | 32.097 | 1.00 | 55.57 | 8 |
| ATOM | 4193 | CB | ASP | B | 271 | 89.670 | 0.026 | 33.618 | 1.00 | 60.69 | 6 |
| ATOM | 4194 | CG | ASP | B | 271 | 90.400 | -1.175 | 34.164 | 1.00 | 64.16 | 6 |
| ATOM | 4195 | OD1 | ASP | B | 271 | 89.789 | -2.194 | 34.571 | 1.00 | 65.71 | 8 |
| ATOM | 4196 | OD2 | ASP | B | 271 | 91.657 | -1.179 | 34.206 | 1.00 | 66.40 | 8 |
| ATOM | 4197 | N | ALA | B | 272 | 86.129 | -0.780 | 33.807 | 1.00 | 52.97 | 7 |
| ATOM | 4198 | CA | ALA | B | 272 | 84.966 | -1.186 | 33.031 | 1.00 | 50.67 | 6 |
| ATOM | 4199 | C | ALA | B | 272 | 83.843 | -0.149 | 33.103 | 1.00 | 50.64 | 6 |
| ATOM | 4200 | O | ALA | B | 272 | 83.482 | 0.315 | 34.203 | 1.00 | 49.32 | 8 |
| ATOM | 4201 | CB | ALA | B | 272 | 84.389 | -2.501 | 33.520 | 1.00 | 50.42 | 6 |
| ATOM | 4202 | N | ARG | B | 273 | 83.255 | 0.166 | 31.958 | 1.00 | 47.60 | 7 |
| ATOM | 4203 | CA | ARG | B | 273 | 82.163 | 1.131 | 31.939 | 1.00 | 46.77 | 6 |
| ATOM | 4204 | C | ARG | B | 273 | 80.841 | 0.398 | 31.804 | 1.00 | 45.84 | 6 |
| ATOM | 4205 | O | ARG | B | 273 | 80.636 | -0.256 | 30.770 | 1.00 | 46.17 | 8 |
| ATOM | 4206 | CB | ARG | B | 273 | 82.312 | 2.144 | 30.804 | 1.00 | 48.87 | 6 |
| ATOM | 4207 | CG | ARG | B | 273 | 81.234 | 3.214 | 30.839 | 1.00 | 49.86 | 6 |
| ATOM | 4208 | CD | ARG | B | 273 | 81.436 | 4.283 | 29.773 | 1.00 | 52.81 | 6 |

TABLE 1-continued

| ATOM | 4209 | NE | ARG | B | 273 | 80.277 | 5.174 | 29.733 | 1.00 | 54.38 | 7 |
|------|------|-----|-----|---|-----|--------|-------|--------|------|-------|---|
| ATOM | 4210 | CZ | ARG | B | 273 | 79.665 | 5.669 | 28.671 | 1.00 | 55.34 | 6 |
| ATOM | 4211 | NH1 | ARG | B | 273 | 80.083 | 5.410 | 27.433 | 1.00 | 56.45 | 7 |
| ATOM | 4212 | NH2 | ARG | B | 273 | 78.606 | 6.455 | 28.819 | 1.00 | 54.66 | 7 |
| ATOM | 4213 | N | LEU | B | 274 | 79.992 | 0.448 | 32.821 | 1.00 | 41.38 | 7 |
| ATOM | 4214 | CA | LEU | B | 274 | 78.715 | −0.229 | 32.792 | 1.00 | 37.98 | 6 |
| ATOM | 4215 | C | LEU | B | 274 | 77.584 | 0.737 | 32.506 | 1.00 | 37.26 | 6 |
| ATOM | 4216 | O | LEU | B | 274 | 77.586 | 1.908 | 32.909 | 1.00 | 36.11 | 8 |
| ATOM | 4217 | CB | LEU | B | 274 | 78.395 | −0.939 | 34.118 | 1.00 | 38.68 | 6 |
| ATOM | 4218 | CG | LEU | B | 274 | 79.554 | −1.797 | 34.654 | 1.00 | 41.26 | 6 |
| ATOM | 4219 | CD1 | LEU | B | 274 | 79.161 | −2.469 | 35.960 | 1.00 | 41.73 | 6 |
| ATOM | 4220 | CD2 | LEU | B | 274 | 79.999 | −2.827 | 33.625 | 1.00 | 42.85 | 6 |
| ATOM | 4221 | N | ILE | B | 275 | 76.603 | 0.270 | 31.724 | 1.00 | 35.74 | 7 |
| ATOM | 4222 | CA | ILE | B | 275 | 75.493 | 1.141 | 31.372 | 1.00 | 33.53 | 6 |
| ATOM | 4223 | C | ILE | B | 275 | 74.202 | 0.402 | 31.685 | 1.00 | 32.45 | 6 |
| ATOM | 4224 | O | ILE | B | 275 | 74.121 | −0.836 | 31.733 | 1.00 | 31.50 | 8 |
| ATOM | 4225 | CB | ILE | B | 275 | 75.466 | 1.658 | 29.914 | 1.00 | 36.92 | 6 |
| ATOM | 4226 | CG1 | ILE | B | 275 | 75.105 | 0.527 | 28.946 | 1.00 | 37.93 | 6 |
| ATOM | 4227 | CG2 | ILE | B | 275 | 76.794 | 2.331 | 29.537 | 1.00 | 36.91 | 6 |
| ATOM | 4228 | CD1 | ILE | B | 275 | 74.962 | 1.004 | 27.506 | 1.00 | 38.53 | 6 |
| ATOM | 4229 | N | ASP | B | 276 | 73.124 | 1.174 | 31.933 | 1.00 | 28.46 | 7 |
| ATOM | 4230 | CA | ASP | B | 276 | 71.866 | 0.517 | 32.262 | 1.00 | 30.30 | 6 |
| ATOM | 4231 | C | ASP | B | 276 | 70.716 | 1.517 | 32.068 | 1.00 | 29.63 | 6 |
| ATOM | 4232 | O | ASP | B | 276 | 71.081 | 2.666 | 31.835 | 1.00 | 27.88 | 8 |
| ATOM | 4233 | CB | ASP | B | 276 | 71.937 | −0.066 | 33.671 | 1.00 | 32.97 | 6 |
| ATOM | 4234 | CG | ASP | B | 276 | 70.851 | −1.058 | 33.987 | 1.00 | 34.63 | 6 |
| ATOM | 4235 | OD1 | ASP | B | 276 | 69.857 | −1.272 | 33.231 | 1.00 | 37.08 | 8 |
| ATOM | 4236 | OD2 | ASP | B | 276 | 70.931 | −1.716 | 35.054 | 1.00 | 35.37 | 8 |
| ATOM | 4237 | N | ASN | B | 277 | 69.478 | 1.072 | 32.012 | 1.00 | 30.76 | 7 |
| ATOM | 4238 | CA | ASN | B | 277 | 68.339 | 1.963 | 31.738 | 1.00 | 31.92 | 6 |
| ATOM | 4239 | C | ASN | B | 277 | 67.121 | 1.388 | 32.426 | 1.00 | 29.27 | 6 |
| ATOM | 4240 | O | ASN | B | 277 | 67.035 | 0.187 | 32.641 | 1.00 | 30.64 | 8 |
| ATOM | 4241 | CB | ASN | B | 277 | 68.041 | 2.214 | 30.258 | 1.00 | 37.99 | 6 |
| ATOM | 4242 | CG | ASN | B | 277 | 66.700 | 1.999 | 29.601 | 1.00 | 41.20 | 6 |
| ATOM | 4243 | OD1 | ASN | B | 277 | 65.702 | 1.397 | 30.046 | 1.00 | 41.98 | 8 |
| ATOM | 4244 | ND2 | ASN | B | 277 | 66.503 | 2.495 | 28.345 | 1.00 | 41.86 | 7 |
| ATOM | 4245 | N | LYS | B | 278 | 66.149 | 2.219 | 32.760 | 1.00 | 28.29 | 7 |
| ATOM | 4246 | CA | LYS | B | 278 | 64.891 | 1.736 | 33.328 | 1.00 | 30.58 | 6 |
| ATOM | 4247 | C | LYS | B | 278 | 63.822 | 2.756 | 32.929 | 1.00 | 33.32 | 6 |
| ATOM | 4248 | O | LYS | B | 278 | 64.130 | 3.940 | 32.793 | 1.00 | 32.01 | 8 |
| ATOM | 4249 | CB | LYS | B | 278 | 64.919 | 1.486 | 34.834 | 1.00 | 31.32 | 6 |
| ATOM | 4250 | CG | LYS | B | 278 | 63.617 | 0.953 | 35.422 | 1.00 | 35.08 | 6 |
| ATOM | 4251 | CD | LYS | B | 278 | 63.793 | 0.340 | 36.790 | 1.00 | 38.13 | 6 |
| ATOM | 4252 | CE | LYS | B | 278 | 63.031 | −0.950 | 37.108 | 1.00 | 39.29 | 6 |
| ATOM | 4253 | NZ | LYS | B | 278 | 63.193 | −1.103 | 38.612 | 1.00 | 44.44 | 7 |
| ATOM | 4254 | N | MET | B | 279 | 62.625 | 2.256 | 32.594 | 1.00 | 33.66 | 7 |
| ATOM | 4255 | CA | MET | B | 279 | 61.488 | 3.102 | 32.303 | 1.00 | 36.39 | 6 |
| ATOM | 4256 | C | MET | B | 279 | 60.543 | 3.014 | 33.483 | 1.00 | 35.26 | 6 |
| ATOM | 4257 | O | MET | B | 279 | 60.470 | 1.929 | 34.090 | 1.00 | 38.21 | 8 |
| ATOM | 4258 | CB | MET | B | 279 | 60.797 | 2.708 | 30.965 | 1.00 | 38.06 | 6 |
| ATOM | 4259 | CG | MET | B | 279 | 61.358 | 3.604 | 29.846 | 1.00 | 42.01 | 6 |
| ATOM | 4260 | SD | MET | B | 279 | 61.219 | 2.888 | 28.222 | 1.00 | 48.77 | 16 |
| ATOM | 4261 | CE | MET | B | 279 | 62.632 | 3.595 | 27.392 | 1.00 | 46.06 | 6 |
| ATOM | 4262 | N | VAL | B | 280 | 59.853 | 4.082 | 33.859 | 1.00 | 34.69 | 7 |
| ATOM | 4263 | CA | VAL | B | 280 | 58.937 | 4.046 | 34.991 | 1.00 | 37.86 | 6 |
| ATOM | 4264 | C | VAL | B | 280 | 57.655 | 4.778 | 34.624 | 1.00 | 39.91 | 6 |
| ATOM | 4265 | O | VAL | B | 280 | 57.722 | 5.842 | 33.971 | 1.00 | 39.57 | 8 |
| ATOM | 4266 | CB | VAL | B | 280 | 59.605 | 4.627 | 36.262 | 1.00 | 40.03 | 6 |
| ATOM | 4267 | CG1 | VAL | B | 280 | 60.582 | 5.734 | 35.894 | 1.00 | 40.43 | 6 |
| ATOM | 4268 | CG2 | VAL | B | 280 | 58.595 | 5.132 | 37.286 | 1.00 | 41.28 | 6 |
| ATOM | 4269 | N | GLU | B | 281 | 56.521 | 4.221 | 35.046 | 1.00 | 42.47 | 7 |
| ATOM | 4270 | CA | GLU | B | 281 | 55.243 | 4.911 | 34.809 | 1.00 | 45.74 | 6 |
| ATOM | 4271 | C | GLU | B | 281 | 54.973 | 5.919 | 35.910 | 1.00 | 47.07 | 6 |
| ATOM | 4272 | O | GLU | B | 281 | 55.370 | 5.595 | 37.039 | 1.00 | 46.25 | 8 |
| ATOM | 4273 | CB | GLU | B | 281 | 54.152 | 3.848 | 34.719 | 1.00 | 47.41 | 6 |
| ATOM | 4274 | CG | GLU | B | 281 | 54.308 | 2.918 | 33.516 | 1.00 | 48.19 | 6 |
| ATOM | 4275 | CD | GLU | B | 281 | 53.705 | 3.562 | 32.275 | 1.00 | 50.10 | 6 |
| ATOM | 4276 | OE1 | GLU | B | 281 | 52.718 | 4.312 | 32.460 | 1.00 | 51.21 | 8 |
| ATOM | 4277 | OE2 | GLU | B | 281 | 54.203 | 3.330 | 31.153 | 1.00 | 50.72 | 8 |
| ATOM | 4278 | N | LEU | B | 282 | 54.358 | 7.077 | 35.662 | 1.00 | 49.43 | 7 |
| ATOM | 4279 | CA | LEU | B | 282 | 54.144 | 8.043 | 36.731 | 1.00 | 52.69 | 6 |
| ATOM | 4280 | C | LEU | B | 282 | 52.714 | 8.211 | 37.222 | 1.00 | 56.10 | 6 |
| ATOM | 4281 | O | LEU | B | 282 | 51.741 | 8.259 | 36.479 | 1.00 | 57.86 | 8 |
| ATOM | 4282 | CB | LEU | B | 282 | 54.654 | 9.413 | 36.232 | 1.00 | 51.33 | 6 |
| ATOM | 4283 | CG | LEU | B | 282 | 56.153 | 9.442 | 35.898 | 1.00 | 51.16 | 6 |
| ATOM | 4284 | CD1 | LEU | B | 282 | 56.568 | 10.774 | 35.313 | 1.00 | 49.90 | 6 |
| ATOM | 4285 | CD2 | LEU | B | 282 | 56.959 | 9.109 | 37.146 | 1.00 | 50.87 | 6 |
| ATOM | 4286 | N | ALA | B | 283 | 52.591 | 8.404 | 38.527 | 1.00 | 58.60 | 7 |
| ATOM | 4287 | CA | ALA | B | 283 | 51.340 | 8.572 | 39.260 | 1.00 | 61.51 | 6 |

TABLE 1-continued

| ATOM | 4288 | C | ALA | B | 283 | 50.222 | 7.659 | 38.748 | 1.00 | 62.69 | 6 |
|---|---|---|---|---|---|---|---|---|---|---|---|
| ATOM | 4289 | O | ALA | B | 283 | 49.365 | 7.240 | 39.565 | 1.00 | 64.21 | 8 |
| ATOM | 4290 | CB | ALA | B | 283 | 50.878 | 10.031 | 39.215 | 1.00 | 61.28 | |
| Water | | | | | | | | | | | |
| ATOM | 4303 | O | WAT | W | 1 | 33.957 | 17.885 | −21.689 | 1.00 | 20.48 | |
| ATOM | 4304 | O | WAT | W | 2 | 37.847 | 13.185 | 4.982 | 1.00 | 21.45 | |
| ATOM | 4305 | O | WAT | W | 3 | 63.980 | −1.350 | 11.191 | 1.00 | 28.46 | |
| ATOM | 4306 | O | WAT | W | 4 | 56.095 | −1.331 | −2.328 | 1.00 | 33.26 | |
| ATOM | 4307 | O | WAT | W | 5 | 33.170 | 18.137 | −24.293 | 1.00 | 23.96 | |
| ATOM | 4308 | O | WAT | W | 6 | 37.215 | 10.622 | −2.497 | 1.00 | 25.23 | |
| ATOM | 4309 | O | WAT | W | 7 | 34.408 | 20.030 | −20.099 | 1.00 | 22.90 | |
| ATOM | 4310 | O | WAT | W | 8 | 44.843 | 0.417 | 12.211 | 1.00 | 25.44 | |
| ATOM | 4311 | O | WAT | W | 9 | 32.057 | 20.794 | −18.723 | 1.00 | 21.33 | |
| ATOM | 4312 | O | WAT | W | 10 | 39.891 | 15.086 | 5.128 | 1.00 | 21.17 | |
| ATOM | 4313 | O | WAT | W | 11 | 60.554 | 9.975 | 11.882 | 1.00 | 23.86 | |
| ATOM | 4314 | O | WAT | W | 12 | 47.956 | 16.767 | 16.754 | 1.00 | 25.70 | |
| ATOM | 4315 | O | WAT | W | 13 | 26.013 | 19.028 | 0.123 | 1.00 | 29.25 | |
| ATOM | 4316 | O | WAT | W | 14 | 41.289 | 15.802 | −0.016 | 1.00 | 29.45 | |
| ATOM | 4317 | O | WAT | W | 15 | 26.238 | 26.828 | −12.429 | 1.00 | 26.43 | |
| ATOM | 4318 | O | WAT | W | 16 | 42.677 | −8.069 | 14.438 | 1.00 | 49.57 | |
| ATOM | 4319 | O | WAT | W | 17 | 44.205 | −22.405 | 7.937 | 1.00 | 26.54 | |
| ATOM | 4320 | O | WAT | W | 18 | 41.204 | 15.438 | 2.596 | 1.00 | 28.73 | |
| ATOM | 4321 | O | WAT | W | 19 | 50.665 | 6.851 | −9.161 | 1.00 | 28.82 | |
| ATOM | 4322 | O | WAT | W | 20 | 45.856 | 11.020 | 16.763 | 1.00 | 28.19 | |
| ATOM | 4323 | O | WAT | W | 21 | 56.240 | 9.146 | 22.228 | 1.00 | 29.25 | |
| ATOM | 4324 | O | WAT | W | 22 | 34.167 | 22.025 | −17.131 | 1.00 | 24.52 | |
| ATOM | 4325 | O | WAT | W | 23 | 46.937 | −3.706 | 12.756 | 1.00 | 34.74 | |
| ATOM | 4326 | O | WAT | W | 24 | 42.413 | 2.422 | 14.402 | 1.00 | 33.61 | |
| ATOM | 4327 | O | WAT | W | 25 | 41.229 | −21.204 | 14.206 | 1.00 | 24.13 | |
| ATOM | 4328 | O | WAT | W | 26 | 41.221 | 12.093 | −6.937 | 1.00 | 25.26 | |
| ATOM | 4329 | O | WAT | W | 27 | 24.372 | 15.958 | −5.041 | 1.00 | 27.65 | |
| ATOM | 4330 | O | WAT | W | 28 | 35.615 | −12.052 | 11.939 | 1.00 | 30.34 | |
| ATOM | 4331 | O | WAT | W | 29 | 37.895 | 12.192 | −4.849 | 1.00 | 26.69 | |
| ATOM | 4332 | O | WAT | W | 30 | 52.106 | 20.252 | −2.182 | 1.00 | 28.30 | |
| ATOM | 4333 | O | WAT | W | 31 | 68.369 | 9.094 | 44.468 | 1.00 | 25.44 | |
| ATOM | 4334 | O | WAT | W | 32 | 56.344 | 0.572 | −4.129 | 1.00 | 43.47 | |
| ATOM | 4335 | O | WAT | W | 33 | 23.101 | 20.797 | −4.005 | 1.00 | 36.59 | |
| ATOM | 4336 | O | WAT | W | 34 | 49.261 | −5.331 | 2.868 | 1.00 | 26.99 | |
| ATOM | 4337 | O | WAT | W | 35 | 47.984 | −9.414 | 25.007 | 1.00 | 26.83 | |
| ATOM | 4338 | O | WAT | W | 36 | 42.604 | −1.487 | 5.352 | 1.00 | 30.62 | |
| ATOM | 4339 | O | WAT | W | 37 | 62.274 | −5.597 | 10.141 | 1.00 | 27.42 | |
| ATOM | 4340 | O | WAT | W | 38 | 26.216 | 16.962 | −12.131 | 1.00 | 28.51 | |
| ATOM | 4341 | O | WAT | W | 39 | 30.958 | 20.957 | −10.945 | 1.00 | 28.67 | |
| ATOM | 4342 | O | WAT | W | 40 | 34.816 | 15.313 | 17.023 | 1.00 | 30.79 | |
| ATOM | 4343 | O | WAT | W | 41 | 49.918 | 15.022 | 17.578 | 1.00 | 28.50 | |
| ATOM | 4344 | O | WAT | W | 42 | 51.910 | 5.889 | 8.625 | 1.00 | 38.44 | |
| ATOM | 4345 | O | WAT | W | 43 | 62.846 | −1.187 | 14.226 | 1.00 | 46.50 | |
| ATOM | 4346 | O | WAT | W | 44 | 25.403 | 26.593 | −16.292 | 1.00 | 39.06 | |
| ATOM | 4347 | O | WAT | W | 45 | 30.520 | 20.301 | 5.385 | 1.00 | 32.49 | |
| ATOM | 4348 | O | WAT | W | 46 | 45.010 | −17.167 | 2.635 | 1.00 | 34.22 | |
| ATOM | 4349 | O | WAT | W | 47 | 47.032 | −2.770 | 5.031 | 1.00 | 22.23 | |
| ATOM | 4350 | O | WAT | W | 48 | 48.414 | 1.477 | −5.713 | 1.00 | 29.51 | |
| ATOM | 4351 | O | WAT | W | 49 | 31.672 | 7.463 | −13.621 | 1.00 | 36.04 | |
| ATOM | 4352 | O | WAT | W | 50 | 62.969 | 0.366 | 20.839 | 1.00 | 25.12 | |
| ATOM | 4353 | O | WAT | W | 51 | 52.181 | 16.341 | 18.209 | 1.00 | 33.67 | |
| ATOM | 4354 | O | WAT | W | 52 | 34.216 | 17.207 | 10.342 | 1.00 | 25.68 | |
| ATOM | 4355 | O | WAT | W | 53 | 52.739 | 13.892 | −0.142 | 1.00 | 24.81 | |
| ATOM | 4356 | O | WAT | W | 54 | 48.513 | −7.403 | 4.595 | 1.00 | 33.10 | |
| ATOM | 4357 | O | WAT | W | 55 | 50.165 | 3.786 | 7.424 | 1.00 | 31.96 | |
| ATOM | 4358 | O | WAT | W | 56 | 61.601 | −10.884 | −3.900 | 1.00 | 38.55 | |
| ATOM | 4359 | O | WAT | W | 57 | 40.862 | −13.477 | 5.834 | 1.00 | 26.78 | |
| ATOM | 4360 | O | WAT | W | 58 | 73.540 | −3.703 | 38.069 | 1.00 | 28.56 | |
| ATOM | 4361 | O | WAT | W | 59 | 53.267 | 18.858 | −0.006 | 1.00 | 28.15 | |
| ATOM | 4362 | O | WAT | W | 60 | 47.896 | −10.104 | 11.452 | 1.00 | 29.42 | |
| ATOM | 4363 | O | WAT | W | 61 | 32.210 | 13.233 | −12.282 | 1.00 | 31.94 | |
| ATOM | 4364 | O | WAT | W | 62 | 48.007 | 11.908 | 18.269 | 1.00 | 37.69 | |
| ATOM | 4365 | O | WAT | W | 63 | 29.173 | 9.259 | −17.716 | 1.00 | 30.38 | |
| ATOM | 4366 | O | WAT | W | 64 | 35.297 | 19.389 | 9.031 | 1.00 | 29.80 | |
| ATOM | 4367 | O | WAT | W | 65 | 40.504 | 2.299 | −10.545 | 1.00 | 32.49 | |
| ATOM | 4368 | O | WAT | W | 66 | 41.958 | −10.772 | 13.351 | 1.00 | 42.64 | |
| ATOM | 4369 | O | WAT | W | 67 | 36.143 | 16.525 | −1.066 | 1.00 | 34.59 | |
| ATOM | 4370 | O | WAT | W | 68 | 62.385 | −11.067 | −1.312 | 1.00 | 33.16 | |
| ATOM | 4371 | O | WAT | W | 69 | 65.110 | 11.392 | 10.350 | 1.00 | 28.97 | |
| ATOM | 4372 | O | WAT | W | 70 | 63.427 | −3.415 | 19.364 | 1.00 | 27.45 | |
| ATOM | 4373 | O | WAT | W | 71 | 68.617 | 14.525 | 33.511 | 1.00 | 37.55 | |
| ATOM | 4374 | O | WAT | W | 72 | 61.639 | −4.893 | 17.918 | 1.00 | 24.98 | |
| ATOM | 4375 | O | WAT | W | 73 | 66.736 | 4.204 | 19.794 | 1.00 | 30.21 | |
| ATOM | 4376 | O | WAT | W | 74 | 55.982 | 12.796 | 22..001 | 1.00 | 36.21 | |

TABLE 1-continued

| | | | | | | | | | |
|---|---|---|---|---|---|---|---|---|---|
| ATOM | 4377 | O | WAT | W | 75 | 64.346 | 6.123 | −5.386 | 1.00 40.37 |
| ATOM | 4378 | O | WAT | W | 76 | 65.025 | −2.313 | 32.956 | 1.00 37.41 |
| ATOM | 4379 | O | WAT | W | 77 | 44.448 | −0.359 | −6.294 | 1.00 29.00 |
| ATOM | 4380 | O | WAT | W | 78 | 48.675 | −0.966 | −4.566 | 1.00 35.26 |
| ATOM | 4381 | O | WAT | W | 79 | 31.748 | 14.620 | −27.469 | 1.00 30.01 |
| ATOM | 4382 | O | WAT | W | 80 | 22.272 | 14.300 | −4.370 | 1.00 33.41 |
| ATOM | 4383 | O | WAT | W | 81 | 61.185 | 6.162 | 25.319 | 1.00 33.42 |
| ATOM | 4384 | O | WAT | W | 82 | 25.793 | 11.693 | −9.261 | 1.00 32.09 |
| ATOM | 4385 | O | WAT | W | 83 | 44.087 | 16.403 | −7.636 | 1.00 30.17 |
| ATOM | 4386 | O | WAT | W | 84 | 42.576 | −4.126 | 6.016 | 1.00 55.25 |
| ATOM | 4387 | O | WAT | W | 85 | 68.891 | 7.733 | 20.798 | 1.00 37.85 |
| ATOM | 4388 | O | WAT | W | 86 | 70.712 | −5.611 | 41.295 | 1.00 34.04 |
| ATOM | 4389 | O | WAT | W | 87 | 43.384 | −22.647 | 14.391 | 1.00 41.78 |
| ATOM | 4390 | O | WAT | W | 88 | 70.983 | −8.966 | 9.646 | 1.00 33.63 |
| ATOM | 4391 | O | WAT | W | 89 | 75.957 | −17.895 | 11.852 | 1.00 47.71 |
| ATOM | 4392 | O | WAT | W | 90 | 63.730 | −0.759 | 18.432 | 1.00 34.78 |
| ATOM | 4393 | O | WAT | W | 91 | 31.689 | 15.534 | −14.467 | 1.00 32.23 |
| ATOM | 4394 | O | WAT | W | 92 | 44.527 | −11.830 | 12.755 | 1.00 34.17 |
| ATOM | 4395 | O | WAT | W | 93 | 20.677 | 30.620 | −24.626 | 1.00 31.71 |
| ATOM | 4396 | O | WAT | W | 94 | 44.639 | 17.338 | −10.200 | 1.00 34.48 |
| ATOM | 4397 | O | WAT | W | 95 | 75.731 | 12.312 | 36.456 | 1.00 43.57 |
| ATOM | 4398 | O | WAT | W | 96 | 44.412 | 10.904 | 19.269 | 1.00 42.19 |
| ATOM | 4399 | O | WAT | W | 97 | 22.294 | 30.665 | −27.831 | 1.00 34.67 |
| ATOM | 4400 | O | WAT | W | 98 | 61.020 | 1.839 | −4.047 | 1.00 32.70 |
| ATOM | 4401 | O | WAT | W | 99 | 63.564 | −3.241 | 9.033 | 1.00 26.37 |
| ATOM | 4402 | O | WAT | W | 100 | 58.754 | 3.167 | −4.838 | 1.00 32.36 |
| ATOM | 4403 | O | WAT | W | 101 | 65.772 | −9.474 | 4.700 | 1.00 28.90 |
| ATOM | 4404 | O | WAT | W | 102 | 68.154 | 15.020 | 30.966 | 1.00 48.55 |
| ATOM | 4405 | O | WAT | W | 103 | 69.423 | 3.142 | 26.541 | 1.00 37.38 |
| ATOM | 4406 | O | WAT | W | 104 | 46.011 | 16.393 | −32.096 | 1.00 35.12 |
| ATOM | 4407 | O | WAT | W | 105 | 29.379 | 18.412 | −31.086 | 1.00 39.01 |
| ATOM | 4408 | O | WAT | W | 106 | 45.917 | −11.276 | 10.149 | 1.00 27.62 |
| ATOM | 4409 | O | WAT | W | 107 | 24.739 | 28.644 | −17.280 | 1.00 32.77 |
| ATOM | 4410 | O | WAT | W | 108 | 79.205 | 12.257 | 45.859 | 1.00 41.16 |
| ATOM | 4411 | O | WAT | W | 109 | 73.058 | −3.265 | 35.431 | 1.00 33.63 |
| ATOM | 4412 | O | WAT | W | 110 | 46.854 | −9.240 | 3.826 | 1.00 36.79 |
| ATOM | 4413 | O | WAT | W | 111 | 25.850 | 9.001 | −9.625 | 1.00 34.69 |
| ATOM | 4414 | O | WAT | W | 112 | 62.047 | 8.655 | 0.423 | 1.00 33.56 |
| ATOM | 4415 | O | WAT | W | 113 | 37.663 | 10.928 | −18.842 | 1.00 34.05 |
| ATOM | 4416 | O | WAT | W | 114 | 34.619 | 21.383 | −14.295 | 1.00 30.74 |
| ATOM | 4417 | O | WAT | W | 115 | 58.523 | 21.835 | −8.875 | 1.00 37.34 |
| ATOM | 4418 | O | WAT | W | 116 | 28.178 | 28.182 | −10.656 | 1.00 43.64 |
| ATOM | 4419 | O | WAT | W | 117 | 66.395 | −3.417 | 24.653 | 1.00 32.24 |
| ATOM | 4420 | O | WAT | W | 118 | 51.651 | 21.138 | 16.503 | 1.00 35.04 |
| ATOM | 4421 | O | WAT | W | 119 | 46.184 | −9.790 | 13.725 | 1.00 38.61 |
| ATOM | 4422 | O | WAT | W | 120 | 77.317 | −2.960 | 44.894 | 1.00 29.27 |
| ATOM | 4423 | O | WAT | W | 121 | 53.189 | 17.937 | 10.605 | 1.00 29.73 |
| ATOM | 4424 | O | WAT | W | 122 | 36.010 | 12.829 | −10.679 | 1.00 33.47 |
| ATOM | 4425 | O | WAT | W | 123 | 34.086 | 3.401 | −11.327 | 1.00 50.83 |
| ATOM | 4426 | O | WAT | W | 124 | 67.551 | −6.941 | −3.458 | 1.00 40.00 |
| ATOM | 4427 | O | WAT | W | 125 | 22.839 | 14.210 | −21.134 | 1.00 33.56 |
| ATOM | 4428 | O | WAT | W | 126 | 46.144 | 1.450 | −7.279 | 1.00 34.78 |
| ATOM | 4429 | O | WAT | W | 127 | 44.101 | 21.525 | 16.698 | 1.00 39.31 |
| ATOM | 4430 | O | WAT | W | 128 | 53.306 | 5.434 | −16.838 | 1.00 54.57 |
| ATOM | 4431 | O | WAT | W | 129 | 50.250 | 1.205 | 22.740 | 1.00 28.98 |
| ATOM | 4432 | O | WAT | W | 130 | 26.485 | 19.155 | −29.949 | 1.00 29.98 |
| ATOM | 4433 | O | WAT | W | 131 | 24.707 | 18.542 | −27.822 | 1.00 37.35 |
| ATOM | 4434 | O | WAT | W | 132 | 67.710 | 5.567 | 21.896 | 1.00 29.04 |
| ATOM | 4435 | O | WAT | W | 133 | 45.674 | −4.052 | 19.840 | 1.00 36.16 |
| ATOM | 4436 | O | WAT | W | 134 | 24.220 | 25.124 | −21.068 | 1.00 34.59 |
| ATOM | 4437 | O | WAT | W | 135 | 61.598 | 17.680 | 13.540 | 1.00 42.71 |
| ATOM | 4438 | O | WAT | W | 136 | 49.468 | −7.110 | 25.310 | 1.00 38.94 |
| ATOM | 4439 | O | WAT | W | 137 | 66.911 | 11.234 | 12.429 | 1.00 37.05 |
| ATOM | 4440 | O | WAT | W | 138 | 57.148 | 2.737 | 30.896 | 1.00 48.38 |
| ATOM | 4441 | O | WAT | W | 139 | 34.489 | 9.771 | −18.467 | 1.00 30.91 |
| ATOM | 4442 | O | WAT | W | 140 | 32.760 | 21.132 | 4.304 | 1.00 29.66 |
| ATOM | 4443 | O | WAT | W | 141 | 49.857 | −2.000 | −1.297 | 1.00 39.89 |
| ATOM | 4444 | O | WAT | W | 142 | 54.890 | −1.411 | 27.207 | 1.00 47.87 |
| ATOM | 4445 | O | WAT | W | 143 | 64.172 | 15.675 | 32.993 | 1.00 36.07 |
| ATOM | 4446 | O | WAT | W | 144 | 55.868 | −7.470 | −4.555 | 1.00 42.27 |
| ATOM | 4447 | O | WAT | W | 145 | 44.776 | 21.855 | −19.009 | 1.00 46.18 |
| ATOM | 4448 | O | WAT | W | 146 | 81.842 | 9.124 | 42.112 | 1.00 41.17 |
| ATOM | 4449 | O | WAT | W | 147 | 65.891 | 12.184 | 46.900 | 1.00 41.27 |
| ATOM | 4450 | O | WAT | W | 148 | 61.870 | −0.694 | 32.618 | 1.00 36.54 |
| ATOM | 4451 | O | WAT | W | 149 | 53.665 | −22.423 | 14.114 | 1.00 45.13 |
| ATOM | 4452 | O | WAT | W | 150 | 78.486 | −11.509 | 9.153 | 1.00 39.16 |
| ATOM | 4453 | O | WAT | W | 151 | 57.272 | 24.770 | −5.465 | 1.00 53.97 |
| ATOM | 4454 | O | WAT | W | 152 | 76.932 | 13.052 | 43.714 | 1.00 34.28 |
| ATOM | 4455 | O | WAT | W | 153 | 46.722 | −10.271 | 21.629 | 1.00 39.60 |

TABLE 1-continued

| ATOM | 4456 | O | WAT | W | 154 | 71.871 | −14.779 | 14.884 | 1.00 | 41.12 |
|---|---|---|---|---|---|---|---|---|---|---|
| ATOM | 4457 | O | WAT | W | 155 | 75.221 | −2.490 | 33.675 | 1.00 | 36.01 |
| ATOM | 4458 | O | WAT | W | 156 | 79.538 | 8.216 | 41.312 | 1.00 | 39.15 |
| ATOM | 4459 | O | WAT | W | 157 | 37.416 | −3.706 | 5.762 | 1.00 | 38.40 |
| ATOM | 4460 | O | WAT | W | 158 | 35.517 | 15.310 | 19.620 | 1.00 | 36.39 |
| ATOM | 4461 | O | WAT | W | 159 | 51.237 | 5.731 | 5.785 | 1.00 | 34.79 |
| ATOM | 4462 | O | WAT | W | 160 | 51.381 | −1.632 | 26.211 | 1.00 | 44.45 |
| ATOM | 4463 | O | WAT | W | 161 | 43.466 | 16.232 | −32.007 | 1.00 | 52.60 |
| ATOM | 4464 | O | WAT | W | 162 | 75.662 | 12.257 | 40.222 | 1.00 | 38.37 |
| ATOM | 4465 | O | WAT | W | 163 | 32.057 | −13.826 | 10.708 | 1.00 | 39.45 |
| ATOM | 4466 | O | WAT | W | 164 | 44.346 | 0.072 | 6.468 | 1.00 | 36.40 |
| ATOM | 4467 | O | WAT | W | 165 | 52.324 | −2.560 | −1.704 | 1.00 | 46.60 |
| ATOM | 4468 | O | WAT | W | 166 | 57.861 | 8.649 | −15.458 | 1.00 | 41.61 |
| ATOM | 4469 | O | WAT | W | 167 | 67.132 | −5.044 | 15.257 | 1.00 | 40.23 |
| ATOM | 4470 | O | WAT | W | 168 | 59.264 | −1.197 | 31.588 | 1.00 | 51.30 |
| ATOM | 4471 | O | WAT | W | 169 | 51.835 | 3.346 | 23.021 | 1.00 | 39.67 |
| ATOM | 4472 | O | WAT | W | 170 | 57.419 | −5.177 | −4.443 | 1.00 | 35.72 |
| ATOM | 4473 | O | WAT | W | 171 | 48.627 | 11.775 | 20.770 | 1.00 | 47.02 |
| ATOM | 4474 | O | WAT | W | 172 | 64.778 | −5.263 | 25.321 | 1.00 | 34.04 |
| ATOM | 4475 | O | WAT | W | 173 | 21.644 | 11.926 | −2.423 | 1.00 | 35.54 |
| ATOM | 4476 | O | WAT | W | 174 | 40.345 | 0.581 | 13.671 | 1.00 | 59.11 |
| ATOM | 4477 | O | WAT | W | 175 | 65.019 | −5.440 | 32.798 | 1.00 | 40.87 |
| ATOM | 4478 | O | WAT | W | 176 | 44.228 | −7.202 | 4.474 | 1.00 | 39.61 |
| ATOM | 4479 | O | WAT | W | 177 | 83.719 | 10.000 | 40.277 | 1.00 | 42.80 |
| ATOM | 4480 | O | WAT | W | 178 | 68.408 | −7.591 | −0.478 | 1.00 | 38.18 |
| ATOM | 4481 | O | WAT | W | 179 | 63.973 | −9.992 | −4.755 | 1.00 | 51.42 |
| ATOM | 4482 | O | WAT | W | 180 | 39.726 | 7.902 | −27.189 | 1.00 | 49.92 |
| ATOM | 4483 | O | WAT | W | 181 | 55.044 | 0.850 | −6.811 | 1.00 | 51.09 |
| ATOM | 4484 | O | WAT | W | 182 | 25.424 | 1.610 | −6.315 | 1.00 | 30.30 |
| ATOM | 4485 | O | WAT | W | 183 | 25.655 | 20.392 | −3.870 | 1.00 | 43.57 |
| ATOM | 4486 | O | WAT | W | 184 | 43.760 | −10.333 | 15.054 | 1.00 | 39.92 |
| ATOM | 4487 | O | WAT | W | 185 | 46.383 | 19.180 | −9.597 | 1.00 | 33.30 |
| ATOM | 4488 | O | WAT | W | 186 | 57.924 | 9.404 | −18.128 | 1.00 | 44.22 |
| ATOM | 4489 | O | WAT | W | 187 | 58.234 | −16.451 | 0.308 | 1.00 | 36.17 |
| ATOM | 4490 | O | WAT | W | 188 | 38.059 | −19.859 | 11.817 | 1.00 | 32.02 |
| ATOM | 4491 | O | WAT | W | 189 | 42.349 | 23.603 | 0.069 | 1.00 | 55.22 |
| ATOM | 4492 | O | WAT | W | 190 | 62.117 | 0.301 | 41.059 | 1.00 | 47.46 |
| ATOM | 4493 | O | WAT | W | 191 | 39.146 | 34.096 | 6.333 | 1.00 | 35.61 |
| ATOM | 4494 | O | WAT | W | 192 | 52.021 | −17.641 | 1.723 | 1.00 | 36.52 |
| ATOM | 4495 | O | WAT | W | 193 | 30.405 | 15.315 | −12.140 | 1.00 | 40.90 |
| ATOM | 4496 | O | WAT | W | 194 | 56.589 | 6.376 | −25.137 | 1.00 | 50.29 |
| ATOM | 4497 | O | WAT | W | 195 | 32.292 | 21.747 | −31.418 | 1.00 | 30.10 |
| ATOM | 4498 | O | WAT | W | 196 | 25.932 | 26.262 | −31.876 | 1.00 | 33.19 |
| ATOM | 4499 | O | WAT | W | 197 | 44.253 | 27.169 | 0.607 | 1.00 | 41.25 |
| ATOM | 4500 | O | WAT | W | 198 | 31.985 | 18.702 | 10.898 | 1.00 | 43.36 |
| ATOM | 4501 | O | WAT | W | 199 | 66.104 | 14.551 | 9.666 | 1.00 | 42.15 |
| ATOM | 4502 | O | WAT | W | 200 | 65.400 | 14.447 | 48.384 | 1.00 | 54.11 |
| ATOM | 4503 | O | WAT | W | 201 | 23.164 | 26.745 | −32.350 | 1.00 | 43.78 |
| ATOM | 4504 | O | WAT | W | 202 | 36.449 | −19.529 | 9.775 | 1.00 | 56.52 |
| ATOM | 4505 | O | WAT | W | 203 | 37.955 | 9.830 | −30.717 | 1.00 | 42.18 |
| ATOM | 4506 | O | WAT | W | 204 | 80.612 | −6.612 | 30.354 | 1.00 | 58.09 |
| ATOM | 4507 | O | WAT | W | 205 | 42.193 | −5.177 | 3.641 | 1.00 | 53.40 |
| ATOM | 4508 | O | WAT | W | 206 | 34.846 | 19.253 | −0.441 | 1.00 | 43.51 |
| ATOM | 4509 | O | WAT | W | 207 | 55.615 | −2.982 | −4.231 | 1.00 | 46.41 |
| ATOM | 4510 | O | WAT | W | 208 | 51.625 | 4.220 | −8.519 | 1.00 | 45.10 |
| ATOM | 4511 | O | WAT | W | 209 | 25.739 | 8.524 | −24.942 | 1.00 | 36.13 |
| ATOM | 4512 | O | WAT | W | 210 | 68.747 | 17.314 | 21.066 | 1.00 | 43.56 |
| ATOM | 4513 | O | WAT | W | 211 | 84.666 | 3.989 | 47.339 | 1.00 | 56.35 |
| ATOM | 4514 | O | WAT | W | 212 | 39.125 | 28.472 | 0.851 | 1.00 | 43.49 |
| ATOM | 4515 | O | WAT | W | 213 | 40.758 | −6.436 | 1.126 | 1.00 | 43.08 |
| ATOM | 4516 | O | WAT | W | 214 | 65.742 | −7.673 | 25.260 | 1.00 | 39.84 |
| ATOM | 4517 | O | WAT | W | 215 | 68.113 | 7.014 | 26.268 | 1.00 | 44.06 |
| ATOM | 4518 | O | WAT | W | 216 | 50.292 | 24.666 | −37.803 | 1.00 | 47.27 |
| ATOM | 4519 | O | WAT | W | 217 | 76.215 | −4.709 | 32.421 | 1.00 | 35.98 |
| ATOM | 4520 | O | WAT | W | 218 | 28.732 | 31.945 | −22.056 | 1.00 | 33.29 |
| ATOM | 4521 | O | WAT | W | 219 | 74.218 | 14.100 | 34.912 | 1.00 | 76.11 |
| ATOM | 4522 | O | WAT | W | 220 | 57.961 | 0.451 | 28.074 | 1.00 | 47.45 |
| ATOM | 4523 | O | WAT | W | 221 | 32.590 | 10.932 | −11.111 | 1.00 | 49.96 |
| ATOM | 4524 | O | WAT | W | 222 | 51.203 | −19.722 | 11.498 | 1.00 | 41.52 |
| ATOM | 4525 | O | WAT | W | 223 | 55.448 | −14.143 | −4.633 | 1.00 | 36.90 |
| ATOM | 4526 | O | WAT | W | 224 | 21.981 | 23.670 | −26.954 | 1.00 | 35.03 |
| ATOM | 4527 | O | WAT | W | 225 | 38.572 | −13.668 | 7.579 | 1.00 | 39.66 |
| ATOM | 4528 | O | WAT | W | 226 | 56.707 | −16.581 | 26.316 | 1.00 | 35.78 |
| ATOM | 4529 | O | WAT | W | 227 | 70.225 | 2.519 | 46.317 | 1.00 | 45.99 |
| ATOM | 4530 | O | WAT | W | 228 | 36.498 | 21.585 | 14.126 | 1.00 | 33.98 |
| ATOM | 4531 | O | WAT | W | 229 | 61.790 | −13.520 | −4.514 | 1.00 | 50.15 |
| ATOM | 4532 | O | WAT | W | 230 | 64.989 | −1.584 | 30.303 | 1.00 | 36.47 |
| ATOM | 4533 | O | WAT | W | 231 | 38.229 | 27.188 | 10.218 | 1.00 | 45.56 |
| ATOM | 4534 | O | WAT | W | 232 | 67.835 | −7.729 | 5.083 | 1.00 | 34.03 |

TABLE 1-continued

| ATOM | 4535 | O | WAT | W | 233 | 45.674 | 22.663 | 18.801 | 1.00 | 65.84 |
|---|---|---|---|---|---|---|---|---|---|---|
| ATOM | 4536 | O | WAT | W | 234 | 43.579 | −5.428 | 17.882 | 1.00 | 43.49 |
| ATOM | 4537 | O | WAT | W | 235 | 64.221 | 5.067 | 46.860 | 1.00 | 41.97 |
| ATOM | 4538 | O | WAT | W | 236 | 72.469 | 18.804 | 43.000 | 1.00 | 36.08 |
| ATOM | 4539 | O | WAT | W | 237 | 43.180 | 3.609 | 16.574 | 1.00 | 59.75 |
| ATOM | 4540 | O | WAT | W | 238 | 34.121 | 16.290 | −13.499 | 1.00 | 46.11 |
| ATOM | 4541 | O | WAT | W | 239 | 62.037 | 17.693 | 20.122 | 1.00 | 50.69 |
| ATOM | 4542 | O | WAT | W | 240 | 37.376 | 10.472 | −16.234 | 1.00 | 45.81 |
| ATOM | 4543 | O | WAT | W | 241 | 26.431 | 22.009 | −0.233 | 1.00 | 46.92 |
| ATOM | 4544 | O | WAT | W | 242 | 25.310 | 12.750 | −11.978 | 1.00 | 50.59 |
| ATOM | 4545 | O | WAT | W | 243 | 19.671 | 9.916 | −3.708 | 1.00 | 49.70 |
| ATOM | 4546 | O | WAT | W | 244 | 38.186 | 21.703 | 16.967 | 1.00 | 35.43 |
| ATOM | 4547 | O | WAT | W | 245 | 40.977 | −0.520 | −8.992 | 1.00 | 51.53 |
| ATOM | 4548 | O | WAT | W | 246 | 17.264 | 17.138 | 1.436 | 1.00 | 65.65 |
| ATOM | 4549 | O | WAT | W | 247 | 59.212 | −16.788 | −2.401 | 1.00 | 43.21 |
| ATOM | 4550 | O | WAT | W | 248 | 77.330 | −11.434 | 7.852 | 1.00 | 51.89 |
| ATOM | 4551 | O | WAT | W | 249 | 22.908 | 25.131 | −34.628 | 1.00 | 44.65 |
| ATOM | 4552 | O | WAT | W | 250 | 37.272 | 2.059 | 20.950 | 1.00 | 42.62 |
| ATOM | 4553 | O | WAT | W | 251 | 78.365 | −12.406 | 10.087 | 1.00 | 55.28 |
| ATOM | 4554 | O | WAT | W | 252 | 31.173 | 17.182 | −10.252 | 1.00 | 47.60 |
| ATOM | 4555 | O | WAT | W | 253 | 48.516 | −12.376 | −1.883 | 1.00 | 33.36 |
| ATOM | 4556 | O | WAT | W | 254 | 43.940 | 18.919 | −6.022 | 1.00 | 54.48 |
| ATOM | 4557 | O | WAT | W | 255 | 30.610 | 3.062 | 18.104 | 1.00 | 46.62 |
| ATOM | 4558 | O | WAT | W | 256 | 72.364 | 2.032 | 11.881 | 1.00 | 60.78 |
| ATOM | 4559 | O | WAT | W | 257 | 36.491 | −6.172 | 6.630 | 1.00 | 48.36 |
| ATOM | 4560 | O | WAT | W | 258 | 65.789 | −10.191 | 31.731 | 1.00 | 42.15 |
| ATOM | 4561 | O | WAT | W | 259 | 59.438 | 15.957 | 21.720 | 1.00 | 40.75 |
| ATOM | 4562 | O | WAT | W | 260 | 31.766 | 20.345 | 7.940 | 1.00 | 41.46 |
| ATOM | 4563 | O | WAT | W | 261 | 38.175 | 22.668 | 9.740 | 1.00 | 36.51 |
| ATOM | 4564 | O | WAT | W | 262 | 69.731 | 20.766 | 38.855 | 1.00 | 45.16 |
| ATOM | 4565 | O | WAT | W | 263 | 25.834 | 32.385 | −27.930 | 1.00 | 39.41 |
| ATOM | 4566 | O | WAT | W | 264 | 70.140 | −4.383 | 3.316 | 1.00 | 42.01 |
| ATOM | 4567 | O | WAT | W | 265 | 17.686 | 28.637 | −27.597 | 1.00 | 36.50 |
| ATOM | 4568 | O | WAT | W | 266 | 38.498 | 10.397 | 17.979 | 1.00 | 38.49 |
| ATOM | 4569 | O | WAT | W | 267 | 41.552 | 17.448 | −14.793 | 1.00 | 45.70 |
| ATOM | 4570 | O | WAT | W | 268 | 43.965 | −4.267 | 15.684 | 1.00 | 47.33 |
| ATOM | 4571 | O | WAT | W | 269 | 24.247 | 23.631 | −0.377 | 1.00 | 52.61 |
| ATOM | 4572 | O | WAT | W | 270 | 39.439 | 16.949 | −2.045 | 1.00 | 40.49 |
| ATOM | 4573 | O | WAT | W | 271 | 49.374 | 23.294 | 3.413 | 1.00 | 46.56 |
| ATOM | 4574 | O | WAT | W | 272 | 39.872 | 8.421 | −18.197 | 1.00 | 45.41 |
| ATOM | 4575 | O | WAT | W | 273 | 46.466 | −1.275 | 7.239 | 1.00 | 47.88 |
| ATOM | 4576 | O | WAT | W | 274 | 29.019 | 38.205 | −20.300 | 1.00 | 61.46 |
| ATOM | 4577 | O | WAT | W | 275 | 69.375 | 1.409 | 13.444 | 1.00 | 43.48 |
| ATOM | 4578 | O | WAT | W | 276 | 72.207 | 3.732 | 29.386 | 1.00 | 40.43 |
| ATOM | 4579 | O | WAT | W | 277 | 39.712 | 37.170 | 0.051 | 1.00 | 39.08 |
| ATOM | 4580 | O | WAT | W | 278 | 48.094 | −1.929 | 10.639 | 1.00 | 35.23 |
| ATOM | 4581 | O | WAT | W | 279 | 46.176 | −0.007 | 10.070 | 1.00 | 57.82 |
| ATOM | 4582 | O | WAT | W | 280 | 34.060 | 14.226 | −7.694 | 1.00 | 47.69 |
| ATOM | 4583 | O | WAT | W | 281 | 66.985 | −1.458 | 15.223 | 1.00 | 40.31 |
| ATOM | 4584 | O | WAT | W | 282 | 69.909 | −11.226 | 6.382 | 1.00 | 54.99 |
| ATOM | 4585 | O | WAT | W | 283 | 27.681 | 22.895 | 8.733 | 1.00 | 41.91 |
| ATOM | 4586 | O | WAT | W | 284 | 44.274 | −3.092 | 9.331 | 1.00 | 47.80 |
| ATOM | 4587 | O | WAT | W | 285 | 35.726 | 14.777 | −5.459 | 1.00 | 63.96 |
| ATOM | 4588 | O | WAT | W | 286 | 36.355 | 13.676 | −2.214 | 1.00 | 51.47 |
| ATOM | 4589 | O | WAT | W | 287 | 45.262 | 7.207 | 17.415 | 1.00 | 54.68 |
| ATOM | 4590 | O | WAT | W | 288 | 68.185 | 20.756 | 43.230 | 1.00 | 51.92 |
| ATOM | 4591 | O | WAT | W | 289 | 61.045 | 16.189 | 10.892 | 1.00 | 47.39 |
| ATOM | 4592 | O | WAT | W | 290 | 37.948 | 29.641 | −14.217 | 1.00 | 51.54 |
| ATOM | 4593 | O | WAT | W | 291 | 25.752 | 1.732 | 16.571 | 1.00 | 50.52 |
| ATOM | 4594 | O | WAT | W | 292 | 21.651 | 4.509 | 5.878 | 1.00 | 55.37 |
| ATOM | 4595 | O | WAT | W | 293 | 57.826 | 3.992 | 44.663 | 1.00 | 46.21 |
| ATOM | 4596 | O | WAT | W | 294 | 66.103 | 19.731 | 40.130 | 1.00 | 39.58 |
| ATOM | 4597 | O | WAT | W | 295 | 46.479 | 4.707 | 17.542 | 1.00 | 44.15 |
| ATOM | 4598 | O | WAT | W | 296 | 71.219 | −3.422 | 0.474 | 1.00 | 42.17 |
| ATOM | 4599 | O | WAT | W | 297 | 39.881 | 2.904 | 14.591 | 1.00 | 39.80 |
| ATOM | 4600 | O | WAT | W | 298 | 56.543 | 16.797 | 18.584 | 1.00 | 46.72 |
| ATOM | 4601 | O | WAT | W | 299 | 61.789 | −18.999 | 2.206 | 1.00 | 57.02 |
| ATOM | 4602 | O | WAT | W | 300 | 42.705 | 10.878 | −13.312 | 1.00 | 41.71 |
| ATOM | 4603 | O | WAT | W | 301 | 69.432 | 7.509 | 6.399 | 1.00 | 56.46 |
| ATOM | 4604 | O | WAT | W | 302 | 50.399 | 1.771 | −8.208 | 1.00 | 46.36 |
| ATOM | 4605 | O | WAT | W | 303 | 80.707 | 8.597 | 32.436 | 1.00 | 57.84 |
| ATOM | 4606 | O | WAT | W | 304 | 35.950 | −3.190 | −6.617 | 1.00 | 47.01 |
| ATOM | 4607 | O | WAT | W | 305 | 63.191 | 13.663 | 10.338 | 1.00 | 47.69 |
| ATOM | 4608 | O | WAT | W | 306 | 32.746 | 17.045 | 16.882 | 1.00 | 38.37 |
| ATOM | 4609 | O | WAT | W | 307 | 55.795 | 22.081 | −3.121 | 1.00 | 45.39 |
| ATOM | 4610 | O | WAT | W | 308 | 52.917 | −15.266 | −5.084 | 1.00 | 58.04 |
| ATOM | 4611 | O | WAT | W | 309 | 32.990 | 20.281 | −2.705 | 1.00 | 41.15 |
| ATOM | 4612 | O | WAT | W | 310 | 65.221 | −0.521 | 13.373 | 1.00 | 50.04 |
| ATOM | 4613 | O | WAT | W | 311 | 31.445 | 8.146 | −16.640 | 1.00 | 47.12 |

TABLE 1-continued

| | | | | | | | | | |
|---|---|---|---|---|---|---|---|---|---|
| ATOM | 4614 | O | WAT | W | 312 | 70.526 | −1.084 | −1.047 | 1.00 | 43.90 |
| ATOM | 4615 | O | WAT | W | 313 | 67.588 | −6.363 | 21.900 | 1.00 | 57.15 |
| ATOM | 4616 | O | WAT | W | 314 | 66.096 | −4.686 | 20.242 | 1.00 | 69.24 |
| ATOM | 4617 | O | WAT | W | 315 | 47.292 | 23.337 | 13.967 | 1.00 | 42.45 |
| ATOM | 4618 | O | WAT | W | 316 | 77.697 | −6.690 | 46.864 | 1.00 | 61.61 |
| ATOM | 4619 | O | WAT | W | 317 | 57.134 | 18.189 | −19.802 | 1.00 | 61.48 |
| ATOM | 4620 | O | WAT | W | 318 | 56.615 | 6.099 | −16.259 | 1.00 | 55.28 |
| ATOM | 4621 | O | WAT | W | 319 | 70.759 | 17.127 | 50.284 | 1.00 | 46.60 |
| ATOM | 4622 | O | WAT | W | 320 | 72.021 | −17.283 | 5.694 | 1.00 | 53.07 |
| ATOM | 4623 | O | WAT | W | 321 | 23.729 | 4.269 | −4.449 | 1.00 | 58.06 |
| ATOM | 4624 | O | WAT | W | 322 | 22.138 | 20.117 | −24.492 | 1.00 | 37.83 |
| ATOM | 4625 | O | WAT | W | 323 | 40.526 | 13.448 | −0.063 | 1.00 | 54.95 |
| ATOM | 4626 | O | WAT | W | 324 | 28.034 | −4.586 | 23.421 | 1.00 | 50.98 |
| ATOM | 4627 | O | WAT | W | 325 | 38.920 | 16.623 | −33.391 | 1.00 | 53.48 |
| ATOM | 4628 | O | WAT | W | 326 | 77.040 | −7.476 | 27.616 | 1.00 | 73.56 |
| ATOM | 4629 | O | WAT | W | 327 | 68.678 | −0.075 | 28.998 | 1.00 | 51.90 |
| ATOM | 4630 | O | WAT | W | 328 | 46.505 | 7.743 | −11.664 | 1.00 | 43.38 |
| ATOM | 4631 | O | WAT | W | 329 | 43.657 | 18.299 | −3.514 | 1.00 | 20.00 |
| ATOM | 4632 | O | WAT | W | 330 | 40.596 | 13.269 | −4.354 | 1.00 | 20.00 |
| ATOM | 4633 | O | WAT | W | 331 | 66.428 | −1.404 | 17.847 | 1.00 | 20.00 |
| ATOM | 4634 | O | WAT | W | 332 | 41.584 | 19.897 | −1.703 | 1.00 | 20.00 |
| ATOM | 4635 | O | WAT | W | 333 | 41.694 | 22.971 | −4.274 | 1.00 | 20.00 |
| ATOM | 4636 | O | WAT | W | 334 | 67.997 | 3.764 | 15.541 | 1.00 | 20.00 |
| ATOM | 4637 | O | WAT | W | 335 | 60.537 | 18.286 | 2.068 | 1.00 | 20.00 |
| ATOM | 4638 | O | WAT | W | 336 | 56.447 | 20.428 | 10.716 | 1.00 | 20.00 |
| ATOM | 4639 | O | WAT | W | 337 | 55.557 | 22.546 | 9.246 | 1.00 | 20.00 |
| ATOM | 4640 | O | WAT | W | 338 | 58.179 | 16.183 | −0.749 | 1.00 | 20.00 |
| ATOM | 4641 | O | WAT | W | 339 | 58.887 | 16.112 | −3.916 | 1.00 | 20.00 |
| ATOM | 4642 | O | WAT | W | 340 | 63.509 | 11.351 | 2.806 | 1.00 | 20.00 |
| ATOM | 4643 | O | WAT | W | 341 | 62.716 | 14.296 | 1.151 | 1.00 | 20.00 |
| ATOM | 4644 | O | WAT | W | 342 | 39.563 | −4.272 | 12.971 | 1.00 | 20.00 |
| ATOM | 4645 | O | WAT | W | 343 | 39.743 | −6.346 | 11.592 | 1.00 | 20.00 |
| ATOM | 4646 | O | WAT | W | 344 | 44.345 | −8.782 | 9.282 | 1.00 | 20.00 |
| ATOM | 4647 | O | WAT | W | 345 | 38.126 | −6.949 | 4.925 | 1.00 | 20.00 |
| ATOM | 4648 | O | WAT | W | 346 | 41.558 | −9.568 | 2.423 | 1.00 | 20.00 |
| ATOM | 4649 | O | WAT | W | 347 | 46.133 | −8.864 | −1.132 | 1.00 | 20.00 |
| ATOM | 4650 | O | WAT | W | 348 | 42.431 | 12.582 | 19.513 | 1.00 | 20.00 |
| ATOM | 4651 | O | WAT | W | 349 | 39.817 | 3.709 | 21.589 | 1.00 | 20.00 |
| ATOM | 4652 | O | WAT | W | 350 | 40.535 | 5.544 | 20.119 | 1.00 | 20.00 |
| ATOM | 4653 | O | WAT | W | 351 | 41.467 | 8.090 | 20.981 | 1.00 | 20.00 |
| ATOM | 4654 | O | WAT | W | 352 | 61.469 | 16.879 | −5.628 | 1.00 | 20.00 |
| ATOM | 4655 | O | WAT | W | 353 | 57.522 | 13.280 | −9.676 | 1.00 | 20.00 |
| ATOM | 4656 | O | WAT | W | 354 | 57.275 | 9.042 | −5.426 | 1.00 | 20.00 |
| ATOM | 4657 | O | WAT | W | 355 | 59.327 | 5.417 | −6.085 | 1.00 | 20.00 |
| ATOM | 4658 | O | WAT | W | 356 | 52.962 | −4.323 | −3.179 | 1.00 | 20.00 |
| ATOM | 4659 | O | WAT | W | 357 | 36.344 | −8.909 | 7.979 | 1.00 | 20.00 |
| ATOM | 4660 | O | WAT | W | 358 | 42.391 | 30.320 | −15.418 | 1.00 | 20.00 |
| ATOM | 4661 | O | WAT | W | 359 | 52.354 | 18.876 | −21.657 | 1.00 | 20.00 |
| ATOM | 4662 | O | WAT | W | 360 | 85.510 | 2.059 | 39.934 | 1.00 | 20.00 |
| ATOM | 4663 | O | WAT | W | 361 | 86.895 | 4.068 | 37.822 | 1.00 | 20.00 |
| ATOM | 4664 | O | WAT | W | 362 | 81.610 | 8.015 | 30.106 | 1.00 | 20.00 |
| ATOM | 4665 | O | WAT | W | 363 | 81.600 | 7.773 | 49.392 | 1.00 | 20.00 |
| ATOM | 4666 | O | WAT | W | 364 | 76.414 | 9.988 | 52.505 | 1.00 | 20.00 |
| ATOM | 4667 | O | WAT | W | 365 | 67.897 | 8.778 | 49.346 | 1.00 | 20.00 |
| ATOM | 4668 | O | WAT | W | 366 | 63.858 | 2.436 | 46.800 | 1.00 | 20.00 |
| ATOM | 4669 | O | WAT | W | 367 | 71.953 | 1.096 | 48.138 | 1.00 | 20.00 |
| ATOM | 4670 | O | WAT | W | 368 | 89.873 | −11.648 | 35.808 | 1.00 | 20.00 |
| ATOM | 4671 | O | WAT | W | 369 | 88.460 | −12.813 | 38.004 | 1.00 | 20.00 |
| ATOM | 4672 | O | WAT | W | 370 | 91.761 | −9.669 | 35.928 | 1.00 | 20.00 |
| ATOM | 4673 | O | WAT | W | 371 | 88.580 | −15.367 | 38.475 | 1.00 | 20.00 |
| ATOM | 4674 | O | WAT | W | 372 | 76.861 | −9.543 | 44.348 | 1.00 | 20.00 |
| ATOM | 4675 | O | WAT | W | 373 | 74.471 | −6.743 | 45.210 | 1.00 | 20.00 |
| ATOM | 4676 | O | WAT | W | 374 | 79.402 | −2.424 | 46.754 | 1.00 | 20.00 |
| ATOM | 4677 | O | WAT | W | 375 | 75.647 | −0.122 | 49.778 | 1.00 | 20.00 |
| ATOM | 4678 | O | WAT | W | 376 | 77.752 | 1.584 | 49.411 | 1.00 | 20.00 |
| ATOM | 4679 | O | WAT | W | 377 | 37.468 | −4.589 | 21.373 | 1.00 | 20.00 |
| ATOM | 4680 | O | WAT | W | 378 | 45.334 | −7.735 | 21.716 | 1.00 | 20.00 |
| ATOM | 4681 | O | WAT | W | 379 | 46.136 | −5.299 | 22.588 | 1.00 | 20.00 |
| ATOM | 4682 | O | WAT | W | 380 | 43.144 | −7.232 | 20.423 | 1.00 | 20.00 |
| ATOM | 4683 | O | WAT | W | 381 | 42.129 | −4.775 | 20.988 | 1.00 | 20.00 |
| ATOM | 4684 | O | WAT | W | 382 | 47.659 | −14.000 | 24.499 | 1.00 | 20.00 |
| ATOM | 4685 | O | WAT | W | 383 | 41.892 | −6.834 | 15.632 | 1.00 | 20.00 |
| ATOM | 4686 | O | WAT | W | 384 | 42.961 | −8.398 | 13.868 | 1.00 | 20.00 |

TABLE 2

Composition of defined minimal culture medium for selenium-containing PS. All components were filter-sterilized through 0.22 μm filters, except where indicated.

| Compound | Stock conc. | Volume | Comments |
|---|---|---|---|
| M9 medium[a] | 1' | 250 ml | Autoclaved. |
| MgSO$_4$ | 1 M | 250 μl | Autoclaved separately from M9 medium to avoid precipitation. |
| D-glucose | 4% w/v | 25 ml | Not autoclaved, since that caused glucose to caramelize (yellow colour); filter sterilized instead. |
| Thiamine | 0.5% w/v | 25 μl | Prepared stock and stored at −20° C.; since repeated cycles of freeze and thaw do not damage it. |
| FeSO$_4$ | 4.2 g/l | 250 μl | Prepared stock and stored at −20° C., to prevent oxidation. |
| Ampicillin | 100 mg/ml | 250 μl | Filter sterilized and stored as aliquots - cycles of freeze and thaw were avoided. |
| IPTG | 70 mg/ml | 250 μl | |
| L-arginine | 2.53% w/v | 5 ml | Supplemented for AT1371 deficiency; prepared together as single stock. |
| L-histidine | 0.31% w/v | | |
| L-proline | 4.6% w/v | | |
| Adenine | 1.35% w/v | | |
| L-lysine | 12.5 g/l | 2 ml | Cocktail for methionine pathway inhibition; prepared as one stock. Final concentrations were 100 and 50 mg/l respectively. |
| L-phenylalanine | 12.5 g/l | | |
| L-threonine | 12.5 g/l | | |
| L-isoleucine | 6.25 g/l | | |
| L-leucine | 6.25 g/l | | |
| L-valine | 6.25 g/l | | |
| L-seleno-methionine | Final conc: 50 mg/l | | No need to sterilise, to minimise risk of oxidation. Dissolved in water directly in bottle in which supplied, then added. |

[a]Sambrook, J., Fritsch, E. F. & Maniatis, T. (1989). Molecular cloning: a laboratory manual, 2nd ed. Cold Spring Harbour Laboratory Press, Cold Spring Harbor, N.Y.

TABLE 3

Crystallographic refinement

| | | |
|---|---|---|
| No. reflexions (test set) | 77294 (4062) | Test set is excluded from refinement for cross-validation Restraints in TNT with a weight assigned |
| No. restraints | 15730 | |
| No. parameters | 20236 | |
| Weight for geom. restraints (TNT) | 3 | |
| Final model parameters | | |

TABLE 3-continued

| | | |
|---|---|---|
| Residues | 566 | |
| Hetero | 1 Tris, 2 ethanediol | |
| No. water molecules | 622 | |
| No. non-hydrogen atoms | 5059 | |
| Resolution range (Å) | 45–1.7 | |
| Refinement convergence | | |
| R$_{free}$ | 24.9 | R$_{factor}$ calculated using test reflexions |
| R$_{factor}$ | 22.6 | R$_{factor}$ = $\Sigma_h \|\|F_{obs}\| - \|F_{calc}\|\| / \Sigma_h \|F_{obs}\|$, w/o test reflexions. |
| DDQ (score, ranking) | | |
| UFO | 0.71 (bottom 25%) | "Unassigned positive Feature left-Over score" |
| DDQ-R | 15.2 (bottom 25%) | Ratio of Shift and Water peak contributions. |
| Average B-factor, | | |
| subunit A (Å$^2$) | 33.9 | |
| subunit B (Å$^2$) | 36.4 | |
| waters (Å$^2$) | 47.8 | |
| Wilson distribution B$_{factor}$ (Å$^2$) | 28.0 | |
| Model quality | | |
| Ramachandran plot | % residues in most favoured region | 92.2 |
| | % residues in generously-allowed region | 7.4 |
| | No. residues in dis-allowed region | 0 |
| Rms deviation from ideal ("root mean square") | Covalent bond lengths (Å) | 0.018 |
| | Bond angles (°) | 1.41 |
| | Planar groups (Å) | 0.007 |
| Procheck criteria | % bond lengths outside expected limits | 2.6 |
| | % bond angles outside expected limits | 3.1 |
| | % planar groups outside expected limits | 1.0 |
| WhatCheck criteria | No. unsaturated H-bonds | 2 |
| | No. residues in unusual environments | 14 |

What is claimed is:

1. A crystal of pantothenate synthetase (PS) having a monoclinic space group P2$_1$, and unit cell dimensions of a=66.0±0.2 Å, b=78.1±0.2 Å, c=77.1±0.2 Å and f=103.7±0.2°.

2. A crystal of PS having the three dimensional atomic coordinates of Table 1.

\* \* \* \* \*

UNITED STATES PATENT AND TRADEMARK OFFICE
CERTIFICATE OF CORRECTION

PATENT NO.   : 6,484,103 B1
DATED        : November 19, 2002
INVENTOR(S)  : Blundell et al.

It is certified that error appears in the above-identified patent and that said Letters Patent is hereby corrected as shown below:

Column 134,
Line 50, delete "f" and insert -- β -- therefor.

Signed and Sealed this

Ninth Day of September, 2003

JAMES E. ROGAN
*Director of the United States Patent and Trademark Office*